US011071745B2

(12) United States Patent
Checcone et al.

(10) Patent No.: US 11,071,745 B2
(45) Date of Patent: *Jul. 27, 2021

(54) VIRAL PROPHYLAXIS TREATMENT METHODS AND PRE-EXPOSURE PROPHYLAXIS KITS

(71) Applicant: ELIAN LLC, Monrovia, CA (US)

(72) Inventors: Emidio A. Checcone, Monrovia, CA (US); Christina Ramirez, Monrovia, CA (US)

(73) Assignee: ELIAN LLC, Monrovia, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/044,276

(22) Filed: Jul. 24, 2018

(65) Prior Publication Data

US 2020/0030345 A1 Jan. 30, 2020
US 2020/0147110 A9 May 14, 2020

Related U.S. Application Data

(63) Continuation of application No. 14/793,550, filed on Jul. 7, 2015, now Pat. No. 10,052,329.

(60) Provisional application No. 62/021,589, filed on Jul. 7, 2014.

(51) Int. Cl.
A61P 31/22 (2006.01)
A61P 31/12 (2006.01)
A61P 31/18 (2006.01)
A61K 31/52 (2006.01)
A61K 31/522 (2006.01)
A61K 31/675 (2006.01)
A61P 15/18 (2006.01)
A61K 9/00 (2006.01)

(52) U.S. Cl.
CPC .......... A61K 31/675 (2013.01); A61K 9/0036 (2013.01); A61P 15/18 (2018.01); A61P 31/18 (2018.01)

(58) Field of Classification Search
CPC .......... A61P 31/18; A61P 31/22; A61P 31/12; A61K 31/675; A61K 31/7076; A61K 31/708; A61K 31/522; A61K 31/52
See application file for complete search history.

(56) References Cited

U.S. PATENT DOCUMENTS

| 4,719,235 | A  | * | 1/1988  | Kern ..................... A61K 31/225 424/443 |
| 5,795,721 | A  |   | 8/1998  | Rabin et al. |
| 6,180,634 | B1 | * | 1/2001  | Vacca ................... A61K 31/495 514/254.11 |
| 2001/0031737 | A1 | * | 10/2001 | Richardson ........... A61K 9/0034 514/42 |
| 2002/0091097 | A1 |   | 7/2002  | Bratzler |
| 2011/0184003 | A1 |   | 7/2011  | Margolis et al. |
| 2012/0071498 | A1 | * | 3/2012  | Whitten ............... A61K 9/0014 514/263.32 |
| 2012/0296315 | A1 |   | 11/2012 | Moench |
| 2013/0216590 | A1 |   | 8/2013  | Karim |
| 2014/0209100 | A1 |   | 7/2014  | Kiser |
| 2016/0000797 | A1 | * | 1/2016  | Checcone ............ A61K 31/522 424/432 |

FOREIGN PATENT DOCUMENTS

| JP | 2009-530316 A | 8/2009 |
| JP | 2013-528219 A | 7/2013 |
| WO | 99/53897 | 10/1999 |
| WO | 00/15255 | 3/2000 |
| WO | 2007/106944 A1 | 9/2007 |
| WO | 2011/156416 A1 | 12/2011 |
| WO | WO2013013172 | 1/2013 |
| WO | 2013/173590 | 11/2013 |
| WO | WO2016007538 A1 | 1/2016 |

OTHER PUBLICATIONS

Dickerson et al. "Reduction of symptoms by valacyclovir in cytomegalovirus-seropositive individuals with schizophrenia." Am J Psychiatry. Dec. 2003;160(12):2234-6). (Year: 2003).*
Cerruti et al. ("Synergistic interaction between interferon-alpha and acyclovir in the treatment of herpes simplex virus type 1 infection in mice." Antiviral Res. 1985;Suppl 1:217-23.) (Year: 1985).*
Apri™ Tablets (desogestrel and ethinyl estradiol) (Application No. 75256_S7 (1999); Center for Drug Evaluation and Research). (Year: 1999).*
Lessina™ Tablets (levonorgestrel and ethinyl estradiol) (Application No. 75803 (2002); Center for Drug Evaluation and Research). (Year: 2002).*
Norethindrone Tablets (norethindrone and ethinyl estradiol) (Reference ID: 3305612 (May 2013); Warner Chilcott Company, LLC). (Year: 2013).*
Ortho-Cyclen® (norgestimate and ethinyl estradiol) (Reference ID: 3383539 (Oct. 2013); Janssen Pharmaceuticals, Inc.) (Year: 2013).*
Andrei et al., Topical tenofovir, a microbicide effective against HIV, inhibits herpes simplex virus-2 replication. Cell Host Microbe, 10(4):379-389 (2011).
Antigentics.com. Agenus' HerpV therapeutic vaccine for genital herpes meets primary endpoint in randomized phase 2 trial. 4 pages (2013) Available from: http://www.antigenics.com/docs/press-releases/2013/herpv-vaccine-for-genital-herpes-meets-primary-enpoint.php.
Bacon, T., et al., Herpes Simplex Virus resistance to acyclovir and penciclovir after two decades of antiviral therapy. Clin. Microbiol. Rev, 16(1):114-128 (2003).

(Continued)

Primary Examiner — Jeffrey S Lundgren
Assistant Examiner — Chris E Simmons
(74) Attorney, Agent, or Firm — Duane Morris LLP; Thomas J. Kowalski; Deborah L. Lu

(57) ABSTRACT

The present disclosure provides compositions and methods for the prevention of HSV infection in an HSV seronegative individual.

42 Claims, No Drawings

(56) References Cited

OTHER PUBLICATIONS

Baeten, J., et al., *Antiretroviral prophylaxis for HIV prevention in heterosexual men and women.* N Engl J Med, 367(5):399-410 (2012).
Baker, D., et al., *Nine-year effectiveness of continuous suppressive therapy with aciclovir in patients with recurrent genital herpes.* J Eur Acad Dermatol Venereol, 5(S1):S169 (1995) Abstract only.
Beutner, K., Valacyclovir: a review of its antiviral and pharmacokinetic properties, and clinical efficacy. *Antiviral Research*, 28:281-290 (1995).
Genocea reports positive initial Phase1/2A results for Gen-003, its pioneering therapeutic vaccine candidate for the treatment of herpes simplex virus-2 (HSV-2), at ICAAC 2013. Press Release, 3 pages, Sep. 12, 2013.
Birth control now with antiviral capabilities. http://guardianlv.com/2014/03/birth-control-now-with-antiviral-capabilities/ downloaded from the internet on Jun. 24, 2015, 4 pages.
Bradley, H., et al., Seroprevalence of herpes simplex virus types 1 and 2—United States, 1999-2010. *J Infect Dis*, 209(3):325-333 (2013).
Burrel, S., C. et al., Helicase-primase inhibitor Pritelivir for HSV-2 infection. *N Engl J Med*, 2014. 370:1663-1664 (2014).
Centers for Disease Control and Prevention, Monitoring selected national HIV prevention and care objectives by using HIV surveillance data—United States and 6 U.S. dependent areas-2010. *HIV Surveillance Supplemental Report*, 2012. 17 (No. 3, part A), 27 pages.
Centers for Disease Control and Prevention. *Preexposure prophylaxis for the prevention of HIV infection in the United States.* 2014, Jun. 16, 2014, 67 pages. Available from: http://www.cdc.gov/hiv/pdf/guidelines/PrEPguidelines2014.pdf.
Centers for Disease Control and Prevention, *Incidence, prevalence, and cost of sexual transmitted infections in the United States.* 2013, 4 pages.
Centers for Disease Control and Prevention, Seroprevalence of herpes simplex virus type 2 among persons aged 14-49 years—United States, 2005-2008, 1 page Handout.
Choopanya, K., et al., *Antiretroviral prophylaxis for HIV infection in injecting drug users in Bangkok, Thailand (the Bangkok Tenofovir Study): a randomised, double-blind, placebo-controlled phase 3 trial.* Lancet, 381(9883): 2083-90 (2013) (Abstract only).
Christophers, J., et al., *Survey of resistance of herpes simlex virus to acyclovir in northwest England.* Antimicrob Agents Chemother, 42: 868-72 (1998).
Clark et al., Engineering a segmented dual-reservoir polyurethane intravaginal ring for simultaneous prevention of HIV transmission and unwanted pregnancy. PLOS/One, 9(3):e88509 (2014).
ClinicalTrials.gov. Study of the safety of a particular herpes vaccine in adults with or without herpes infection. 2013, 5 pages. Available from: clinicaltrials.gov/ct2/show/NCT01915212.
Corey, L., et al., Once-daily valacyclovir to reduce the risk of transmission of genital Herpes. *N Engl J Med*, 350(1):11-20 (2004).
Corey, L., et al., *The effects of herpes simplex virus-2 on HIV-1 acquistion and transmission: a review of two overlapping epidemics.* J Acquir Immune Defic Syndr, 35(5):435-445 (2004).
Crespi, C., et al., Longitudinal study of herpes simplex virus type 2 infection using viral dynamic modeling. *Sex Transm Infect*, 83(6):359-364 (2007).
Cunningham, A. et. al, The cycle of human herpes simplex virus infection: virus transport and immune control. *J Infect Dis*, 194(S1):S11-S18 (2006).
Degreef, H. and Famciclovir Herpes Zoster Clinical Study Group, Famciclovir, a new antiherpes drug: results of the first controlled clinical study demonstrating its efficacy in the treatment of uncomplicated herpes zoster in immunocompetent patients. *Int. J. Antimicrob. Agents*, 4: 241-246 (1994).
Earnshaw, D., et al., Mode of antiviral action of penciclovir in MRC-5 cells infected with herpes simplex virus type 1 (HSV-1), HSV-2, and varicella-zoster virus. Antimicrob. *Agents Chemother*, 36:2747-2757 (1992).
Fleming, D., et al., Herpes simplex virus type 2 in the Unites States, 1976 to 1994. *N Engl J Med*, 337:1105-1111 (1997).
Freeman, E. et. al., Herpes simplex virus 2 infection increases HIV acquisition in men and women: a systematic review and meta analysis of longitudinal studies. *AIDS*, 20:73-83 (2006).
Gershengorn, H., G. Darby, and S. Blower, *Predicting the emergence of drug-resistant HSV-2: new predictions.* BMC Infectious Diseases, 3(1):5 pages (2003).
Grant, R., et al., *Preexposure chemoprophylaxis for HIV prevention in men who have sex with men.* N Engl J Med, 363(27):2587-2599 (2010).
Grant, R., et al., *Uptake of pre-exposure prophylaxis, sexual practices, and HIV incidence in men and transgender women who have sex with men: a cohort study.* Lancet Infect Dis, 14(9):820-829 (2014) Abstract only.
Grobskopf, L., et al., *Randomized trial of clinical safety of daily oral tenofovir disoproxil fumarate among HIV-uninfected men who have sex with men in the United States.* J Acquired Immune Defic Syndr, 64(1):79-86 (2013).
Gupta, R. et. al, Valacyclovir and acyclovir for suppression of shedding of herpes simplex virus in the genital tract. *J Infect Dis*, 190:1374-1381 (2004).
Herriman, Vaginal ring delivers herpes, HIV antivirals, contraceptives for months of protection: Northwestern researcher. http://www.theglobaldispatch.com/vaginal-ring-delivers-herpes-hiv-antivirals-contraceptives-for-months-of-protection-northwetprn-researcher-24618/ downloaded from the internet on Jun. 24, 2015, published Mar. 11, 2014, 4 pages.
Ilsley, D., et al., Acyclic guanosine analogs inhibit DNA polymerases, $\alpha$, $\delta$, and $\epsilon$ with very different potencies and have unique mechanisms of action. *Biochemistry*, 34:2504-2510 (1995).
Johnston, et al., Ineffectiveness of daily standard and high-dose antiviral therapy in preventing short episodes of genital HSV-2 reactivation: three randomized, open-label cross-over trials. *Lancet*, 379:641-647 (2012).
Johnston, et al., HSV-2: In pursuit of a vaccine. *J Clin. Invest*, 121:12 (2011).
Le Meur, Y., et al., *The renal safety of high doses of valacyclovir for prevention of cytomegalovirus infection after renal transplantation.* Nephrol. Dial. Transplant., 15(3): 442 (2000).
Ljungman, P., et al., *Randomized study of valacyclovir as prophylaxis against cytomegalovirus reactivation in recipients of allogeneic bone marrow transplants.* Blood, 99(8):3050-3056 (2002).
Lowance, D., et al., *Valacyclovir for the prevention of cytomegalovirus disease after renal transplantation . International Valacyclovir Cytomegalovirus phrophylaxis transplantation study group.* N Engl J Med, 340(19):1462-70 (1999).
Lowe, D., et al., Mode of action of ( R)-9-[4-hydroxy-2-(hydroxymethyl)butyl]guanine against herpesviruses. Antimicrob. *Agents Chemother*, 39(8):1802-1808 (1995).
Mark, K. et. al, Rapidly cleared episodes of herpes simplex virus reactivation in immunocompetent adults. *J Infect Dis*, 198(8):1141-1149 (2008).
Mertz, G., et al., *Prolonged continuous versus intermittent oral acyclovir treatment in normal adults with frequently recurring genital herpes simplex virus infection.* Am J Med, 85(Supp 2A):14-19 (1988).
Mertz, G., et al., Risk factors for the sexual transmission of genital herpes. *Ann Intern Med*, 116(3):197-202 (1992).
Mesquita et al., Intravaginal ring delivery of tenofovir disoproxil fumarate for prevention of HIV and herpes simplex virus infection. J.Antimicrob Chemother, 67:1730-1738 (2012).
PCT/US2015/039417 International Search Report and Written Opinion dated Oct. 2, 2015.
Pottage, D. and H. Kessler, Herpes simplex virus variants resistance to acyclovir: clinical relevance. *Infect. Agents Dis*, 4:115-124 (1995) (Abstract only).
Reyes, M., et al., *Acyclovir-resistant herpes simplex virus: preliminary results from a national surveillance system.* Antiviral Research, 37: A44 (1998).
Reynolds, S., et al., Recent herpes simplex virus type 2 infection and the risk of human immunodeficiency virus type 1 acquisition in India. *J Infect Dis*, 187:1513-21(2003).

(56) References Cited

OTHER PUBLICATIONS

RxList.com. *Famvir (famciclovir) Drug information: Indications, Dosage, and how supplied—Prescribing information at RxList.* 2014, 3 pages. Available from: http://www.rxlist.com/famvir-drug/indications-dosage.htm.

RxList.com. *Valtrex (Valacyclovir hydrochloride) Drug information: Indications, dosage and how supplied—Prescribing information at RxList.* 2014, 4 pages. Available from: http://www.rxlist.com/valtrex-drug/indications-dosage.htm.

RxList.com. *Zovirax (acyclovir) drug information: indications, dosage, and how supplied—Prescribing information at RxList.* 2014 Jun. 18, 2014, 2 pages. Available from: http://www.rxlist.com/zovirax-drug/indications-dosage.htm.

Schiffer, J. et. al, Frequent release of low amounts of herpes simplex virus from neurons: results from a mathematical model. *Sci Transl Med,* 1(7): 7ra16 (2009).

Sheffield et al., Valacyclovir prophylaxis to prevent recurrent herpes at delivery. Obstet. Gynecol., 108(1):141-147 (2006).

Smith et al., Intravaginal ring eluting tenofovir disoproxil fumarate completely protects macaques from multiple vaginal simian-HIV challenges. PNAS, 110(40):16145-16150 (2013).

Smith, J. and N. Robinson, Age-specific prevalence of infection with herpes simplex virus types 2 and 1: A global review. *J Infect Dis,* 186(S1):S3-S28 (2002).

Thigpen, M., et al., *Antiretroviral preexposure prophylaxis for heterosexual HIV transmission in Botswana.* N Engl J Med, 367(5):423-434 (2012).

Thurman et al., Multipurpose prevention technologies: Biomedical tools to prevent HIV-1, HSV-2, and unintended pregnancies. Infectious Diseases in Obstetrics and Gynecology, 1-10 (2011).

Tobian, A., et al., Factors associated with the prevalence and incidence of herpes simplex virus type 2 infection among men in Rakai, Uganda. J Infect Dis, 199:945-9 (2009).

Truvada approved to reduce the risk of sexually transmitted HIV in people who are not infected by the virus. 2012, 2 pages. Available from: http://www.fda.gov/forconsumers/byaudience/forpatientadvocates/hivandaidsactivities/ucm312264.html.

Tyring, S., D. Baker, and W. Snowden, *Valacyclovir for Herpes Simplex Virus infection: long-term safety and sustained efficacy after 20 years' experience.* J Infect Dis, 186(S1): S40-S46 (2001).

Vere Hodge, R. and Y.-C. Chen, The mode of action of penciclovir. *Antiviral Chem Chemother,* 4(S1):13-24 (1993).

Wald, A. and K. Link, Risk of human immunodeficiency virus infection in herpes simplex virus type-2 seropositive persons: A meta-analysis. J Infect Dis, 185:45-52 (2002).

Wald, A., et al., Effect of condoms on reducing the transmission of herpes simplex virus type 2 from men to women. *JAMA,* 285(24):3100-6 (2001).

Wald, A., et al., Frequent genital herpes simplex virus shedding in immunocompetent women: Effect of acyclovir treatment. *J Clin. Invest,* 99(5):1092-1097 (1997).

Watson-Jones, D. et. al, Effect of herpes simplex suppression on incidence of HIV among women in Tanzania. N Engl J Med, 358:1560-1571 (2008).

World Health Organization, *Consolidated guidelines on HIV prevention, diagnosis, treatment, and care for key populations.* 2014, WHO, 3 pages. http://www.who.int/hiv/pub/guidelines/keypopulations/en/ (accessed Jul. 12, 2014).

Zhu, J., et al., Persistence of HIV-1 receptor-positive cells after HSV-2 reactivation: a potential mechanism for increased HIV-1 acquisition. Nat Med, 15(8): 886-892 (2009).

Hodge and Field, Antiviral agents for Herpes Simplex virus. IN: *Advances in Pharmacology,* edited by S.J. Enna, Elsevier Inc., San Diego, CA, vol. 67, Chapter 1, p. 1-38, 2013.

Written Opinion of the Intellectual Property Office of Singapore dated Jul. 17, 2017 which issued during prosecution of Singapore Application No. 11201700061P.

Supplementary European Search Report dated Dec. 20, 2017, which issued during prosecution of European Application No. 15818554.6.

Marcus et al. "Daily oral emtricitabine/tenofovir preexposure prophylaxis and herpes simplex virus type 2 among men who have sex with men" PLOS, Mar. 2014, vol. 9, No. 3, pp. 1-8.

Celum et al. ("Daily oral tenofovir and Emitricitabine/tenofovir preexposure prophylaxis reduces herpes simplex virus type 2 acquisition among heterosexual HIV-1-uninfected men and women" Annals of Internal Medicine, Jul. 1, 2014, vol. 161, No. 1, pp. 11-19).

"Sexually Transmitted Diseases Treatment Guidelines, 201 O" WWW.CDC.gov/mmwr.

"Bangkok Tenofovir Study: PrEP for HIV prevention among people who inject drug," CDC, Jul. 2013.

Holmes, "FDA paves the way for pre-exposure HIV prophylaxis," The Lancet, vol. 380, 2012, p. 325.

Sheffield et al. "Valacyclovir Perophylaxis to prevent recurrent herpes at Delivery," Obstetrics & Gynecology, 2006, vol. 108, No. 1, pp. 141-147.

Robert Snoeck, et al., New Treatments for Genital Herpes, Current Opinion in Infectious Diseases (2002) vol. 15, No. 1, p. 49-55.

\* cited by examiner

VIRAL PROPHYLAXIS TREATMENT METHODS AND PRE-EXPOSURE PROPHYLAXIS KITS

CROSS-REFERENCE TO RELATED APPLICATIONS

This application claims the benefit of U.S. Provisional Application No. 62/021,589 filed Jul. 7, 2014, which is incorporated by reference herein in its entirety.

BACKGROUND OF THE INVENTION

Herpes simplex virus (HSV) causes life-long viral disease in those infected and there is currently no cure. HSV infection typically leads to establishment of latent viral infection in nerve cells, with consequences of this infection covering a spectrum from no symptoms to repeated and/or severe episodes of active form of the disease. Active forms of the disease can manifest as cold sores and/or genital herpes.

Worldwide, there are over 500 million people infected with HSV type 2 (HIV-2), with an estimated 23 million new infections annually. It has been estimated by the Centers for Disease Control and Prevention that in the United States alone in 2008, 16 percent of the population was infected with HSV-2 and in excess of 90% of U.S. citizens were possibly HSV-1 positive. It is estimated that about 776,000 people in the United States acquire genital herpes (HSV-1 or HSV-2) infections each year.

SUMMARY OF THE INVENTION

Herpes simplex virus (HSV) is associated in many infected individuals with recurrences that manifest themselves as cold sores and/or genital herpes, both of which are often painful and embarrassing. HSV is also of significant public health consequence in that infection with HSV increases the risk of a person acquiring human immunodeficiency virus (HIV) by 2-3 fold, with an 8-fold increased risk if the person is exposed to HIV soon after HSV is acquired. Therefore, in order to address the HIV epidemic, it is also necessary to address the HSV epidemic.

During primary infection, HSV infects epithelial cells at the skin and mucosal surfaces. The virus then travels along nerve axons to the dorsal root ganglia. It is there that latency is established, as the virus can lie dormant and hidden from the immune system in this location. Thus, these neuronal cells act as the reservoir for the latent virus. When the virus is reactivated, the virus travels from the dorsal root ganglia back to the skin, referred to as viral shedding, where the virus is detectable from the epithelial surfaces. Viral reactivation is sometimes asymptomatic or may create a lesion or ulcer. In either case, the virus may be transmitted to a new host. Most HSV-2 transmissions occur during asymptomatic shedding.

A traditional approach to reduce HSV transmission through sexual contact involves the use of physical barriers between HSV seropositive and HSV seronegative individuals, for example, condoms. While condom usage is effective in the prevention of some sexually transmitted infections, in the case of HSV, the site of infection may lie outside of the region where the condom provides protection. If there exists viral shedding in sites outside of the condom area, transmission can still occur even with proper condom usage as skin-to-skin contact during viral shedding is sufficient for HSV transmission.

Clinical treatment of HSV has shifted from focusing on acute treatment of symptomatic outbreaks (e.g., treatment of lesions) to reducing the frequency of symptomatic outbreaks, thus reducing the viremia and amount of viral shedding in the seropositive individual. This has led to the development of suppressive therapy, in which the seropositive individual attempts to maintain a low-level concentration of an HSV antiviral drug in the bloodstream so that the number of outbreaks is potentially reduced, and to reduce viral shedding, potentially lowering the risk of transmission. However, suppressive treatment with antiviral drugs does not completely eliminate all viral shedding, providing a possible transmission pathway for infection of seronegative individuals.

Even with suppressive treatments proliferating, HSV infections have exploded and are elevating the risk of HIV infection, making the spread of HSV a serious public health risk and pandemic. There are a number of deficiencies in current suppressive therapy that hinder the effectiveness of decreasing HSV transmission from the HSV seropositive to the HSV seronegative individual. Treatment focused solely on seropositive individuals can create a single point of failure with respect to reducing the likelihood of transmission. For example, if the seropositive individual is non-compliant with the drug regimen, if the viral strain is resistant to the antiviral agent, and/or if the dosage is inadequate, then a sufficient amount of virus to produce a sustainable infection may be transferred to the seronegative person. Under this single-subject treatment approach, controlling the spread of HSV is solely dependent on the effectiveness of a single layer, the treatment of a seropositive subject. This has failed to adequately reduce the spread of HSV. Traditional suppressive therapies also generally involve administering a single antiviral drug. This single-drug approach exacerbates the single point of failure problem, as cumulative effects of multiple drugs are not realized, and the probability of exposing the virus to the optimal drug option can be reduced. In addition, as a result of non-compliance, a viral strain may evolve and develop resistance to the single drug in use, weakening or even possibly neutralizing the single layer protection. A further important issue is that many people are unaware that they are infected with HSV or are in denial of their HSV seropositive status, and therefore they may not be aware of or provided with suppressive therapy. In a National Health and Nutrition Examination Survey performed in 1997 and published in the New England Journal of Medicine, 91% of people seropositive for HSV-2 were unaware that they were infected. Furthermore, suppressive therapy does not offer an HSV seronegative individual who may be at risk of exposure to HSV a method of protection outside of avoiding direct physical contact with an HSV seropositive individual. For many individuals, especially those in situations where consent or knowledge of the other persons true sero-status is not established prior to physical activity, such protection is not available. The present disclosure addresses the need for providing compositions and methods for the prevention of HSV infection in a seronegative individual by treating the seronegative individual with one or more antiviral agents. Further provided, are methods and compositions for treating both HSV seropositive and HSV seronegative individuals with one or more antivirals to further reduce the risk of HSV transmission and infection.

In one aspect, provided herein is a method of preventing HSV infection in an HSV seronegative subject, the method comprising administering to the subject a therapeutically effective amount of a first antiviral agent prior to physical contact with a partner who is seropositive for HSV. In some embodiments, the subject is or will be in an ongoing mutually-monogamous sexual relationship with the HSV seropositive partner. In some embodiments, the subject is not or will not be in a mutually-monogamous sexual relationship with the HSV seropositive partner. In some embodiments, the method further comprises administering to the HSV seropositive partner a therapeutically effective amount of a second antiviral agent. In some embodiments, the method further comprises determining if the subject is at risk for exposure to HSV prior to administering the first antiviral agent. In some embodiments, the method further comprises determining the therapeutically effective amount of the first antiviral agent. In some embodiments, administering comprises delivering the first antiviral agent to the subject using a long-acting drug delivery device. In some embodiments, the long-acting drug delivery device is an intravaginal ring.

In some embodiments, the first antiviral agent comprises valacyclovir, acyclovir, famciclovir, pritelivir, tenofovir, ganciclovir, glycyrrhizic acid, *Sambucus nigra*, valganciclovir, or a salt, solvate or combination thereof. In some embodiments, the therapeutically effective amount of the first antiviral agent is from about 5 mg to about 1000 mg.

In some embodiments, the method further comprises administering to the subject a therapeutically effective amount of an additional antiviral agent. In some embodiments, the additional antiviral agent is an HIV antiviral agent. In some embodiments, the HIV antiviral agent comprises tenofovir, emtricitabine, lamivudine, efavirenz, raltegravir, dolutegravir, maravoric, rilpirivine, or a salt, solvate or combination thereof.

In some embodiments, the method further comprises administering to the subject an effective amount of a contraceptive. In some embodiments, the contraceptive comprises levonorgestrel, estradiol, dosogestrel, ethinyl estradiol, norethindrone acetate, norgestimate, or a salt, solvate or combination thereof.

In another aspect, provided herein is a method of preventing HSV infection in an HSV seronegative subject, the method comprising administering to the subject a therapeutically effective amount of a first antiviral agent after physical contact with a partner who is seropositive for HSV. In some embodiments, the method further comprises administering to the subject a therapeutically effective amount of an additional antiviral agent prior to physical contact with the HSV seropositive partner. In some embodiments, the method further comprises administering to the HSV seropositive partner a therapeutically effective amount of a second antiviral agent. In some embodiments, the method further comprises determining the therapeutically effective amount of the first antiviral agent.

In some embodiments, administering comprises delivering the first antiviral agent to the subject using a long-acting drug delivery device. In some embodiments, the long-acting drug delivery device is an intravaginal ring.

In some embodiments, the first antiviral agent comprises valacyclovir, acyclovir, famciclovir, pritelivir, tenofovir, ganciclovir, glycyrrhizic acid, *Sambucus nigra*, valganciclovir, or a salt, solvate or combination thereof. In some embodiments, the therapeutically effective amount of the first antiviral agent is from about 500 mg to about 2000 mg.

In some embodiments, the method further comprises administering to the subject a therapeutically effective amount of an HIV antiviral agent. In some embodiments, the HIV antiviral agent comprises tenofovir, emtricitabine, lamivudine, efavirenz, raltegravir, dolutegravir, maravoric, rilpirivine, or a salt, solvate or combination thereof.

In some embodiments, the method further comprises administering to the subject an effective amount of a contraceptive. In some embodiments, the contraceptive comprises levonorgestrel, estradiol, dosogestrel, ethinyl estradiol, norethindrone acetate, norgestimate, or a salt, solvate or combination thereof. In some embodiments, the contraceptive is an emergency contraceptive. In some embodiments, the emergency contraceptive comprises levonorgestrel.

In another aspect, provided herein is an HSV treatment kit comprising a) a therapeutically effective amount of a first antiviral agent; b) a delivery device for delivering the first antiviral agent to an HSV seronegative subject; and c) instructions comprising information on how to administer the first antiviral agent using the delivery device to prevent HSV infection in the HSV seronegative subject.

In some embodiments, the therapeutically effective amount of the first antiviral agent is an amount useful for the prevention of HSV infection in the HSV seronegative subject when administered to the HSV seronegative subject prior to exposure to HSV. In some embodiments, the therapeutically effective amount of the first antiviral agent is an amount useful for suppression of HSV in a seropositive subject; provided that the delivery device further provides a method for delivering the first antiviral agent to the HSV seropositive subject; and provided that the instructions further comprise information on how to administer the first antiviral agent using the delivery device to suppress HSV reactivation in the HSV seropositive subject.

In some embodiments, the therapeutically effective amount of the first antiviral agent is an amount useful for the prevention of HSV infection in the HSV seronegative subject when administered after the HSV seronegative subject is exposed to HSV. In some embodiments, the therapeutically effective amount of the first antiviral agent is an amount useful for treatment of an outbreak of HSV in a seropositive subject; provided that the delivery device further provides a method for delivering the first antiviral agent to the HSV seropositive subject; and provided that the instructions further comprise information on how to administer the first antiviral agent using the delivery device to treat an HSV outbreak in the HSV seropositive subject.

In some embodiments, the delivery device is a long-acting drug delivery device. In some embodiments, the long-acting delivery device is an intravaginal ring.

In some embodiments, the first antiviral agent comprises valacyclovir, acyclovir, famciclovir, pritelivir, tenofovir, ganciclovir, glycyrrhizic acid, *Sambucus nigra*, valganciclovir, or a salt, solvate or combination thereof.

In some embodiments, the kit further comprises one or more additional antiviral agents. In some embodiments, the one or more additional antiviral agents comprises an HSV antiviral agent, an HIV antiviral agent, or both HSV and HIV antiviral agents. In some embodiments, the HIV antiviral agent comprises tenofovir, emtricitabine, lamivudine, efavirenz, raltegravir, dolutegravir, maravoric, rilpirivine, or a salt, solvate or combination thereof.

In some embodiments, the kit further comprises an effective dose of a contraceptive. In some embodiments, the contraceptive comprises levonorgestrel, estradiol, dosogestrel, ethinyl estradiol, norethindrone acetate, norgestimate, or a salt, solvate or combination thereof.

In another aspect, provided herein is a method of preventing HSV infection in an HSV seronegative subject, the method comprising administering to the subject a composition comprising a low dose of a first antiviral agent prior to physical contact with a partner who is seropositive for HSV.

In some embodiments, the physical contact occurs during one occasion. In some embodiments, the physical contact occurs during two or more separate occasions. In some embodiments, the physical contact occurs with the HSV seropositive partner and one or more additional partners. In some embodiments, the physical contact is sexual contact. In some embodiments, the subject and the HSV seropositive partner use a physical barrier during sexual contact, as non-limiting examples, a male or female condom. In some embodiments, the subject is or will be in an ongoing mutually-monogamous sexual relationship with the HSV seropositive partner. In some embodiments, the subject is not or will not be in a mutually-monogamous sexual relationship with the HSV seropositive partner. In some embodiments, the HSV seropositive partner is aware of their HSV sero-status. In some embodiments, the HSV seropositive partner is unaware of their HSV sero-status.

In some embodiments, the HSV seropositive partner is undergoing HSV suppression therapy comprising the administration of a second low dose of a second antiviral agent to the HSV seropositive partner. In some embodiments, the method further comprises administering to the HSV seropositive partner a second low dose of a second antiviral agent. In some embodiments, the second antiviral agent comprises a same active agent as the first antiviral agent. In some embodiments, the second antiviral agent comprises a different active agent than the first antiviral agent.

In some embodiments, the subject is exposed to HSV from the HSV seropositive partner during physical contact. In some embodiments, the administered composition suppresses HSV replication in the subject. In some embodiments, the administered composition suppresses HSV activation in the subject. In some embodiments, the administered composition reduces the risk of HSV infection in the subject. In some embodiments, the risk of HSV infection in the subject is reduced by at least about 50%, 60%, 70%, 80%, 90% or 95%.

In some embodiments, the method further comprises determining if the subject is at risk for exposure to HSV prior to administering the composition. In some embodiments, the subject has been determined to be at risk for exposure to HSV.

In some embodiments, the method further comprises determining the low dose of the first antiviral agent. In some embodiments, the method further comprises determining a delivery mechanism for administering the composition to the subject. In some embodiments, the delivery mechanism comprises a long-acting drug delivery device. In some embodiments, the long-acting drug delivery device comprises an injection device, intravaginal ring, transdermal patch, or a combination thereof. In some embodiments, the low dose of the first antiviral agent is from about 5 mg to about 1 g. As non-limiting examples, the composition comprises about 5 mg, 10 mg, 20 mg, 25 mg, 30 mg, 40 mg, 50 mg, 60 mg, 70 mg, 80 mg, 90 mg, 100 mg, 125 mg, 150 mg, 175 mg, 200 mg, 225 mg, 250 mg, 275 mg, 300 mg, 350 mg, 400 mg, 500 mg, 600 mg, 650 mg, 700 mg, 750 mg, 800 mg, 850 mg, 900 mg, 950 mg, or 1000 mg of the first antiviral agent.

In some embodiments, the first antiviral agent comprises valacyclovir, acyclovir, famciclovir, pritelivir, penciclovir, ganciclovir, valganciclovi, cidofovir, foscarnet, darunavir, glycyrrhizic acid, *Sambucus nigra*, glutamine, FV-100, ASP2151, me-609, ASP2151, topical VDO, PEG-formulation (Devirex AG), vidarabine, cidofovir, crofelemer (SP-303T), EPB-348, CMX001, V212, NB-001, squaric acid, ionic zinc, sorivudine (ARYS-01), trifluridine, 882C87, merlin (ethanol and glycolic acid mixture), vitamin C, AIC316, versabase gel with *Sarracenia purpurea*, UB-621, lysine, edoxudine, brivudine, cytarabine, docosanol, tromantadine, resiquimod (R-848), imiquimod, resiquimod, tenofovir, tenofovir disoproxil fumarate, tenofovir alafenamide fumarate, or a salt, solvate or combination thereof.

In some embodiments, the first antiviral agent comprises an HSV vaccine and optionally an adjuvant. In some embodiments, the HSV vaccine comprises GSK208141 (gD2t, GSK glycoprotein D (gD)-Alum/3-deacylated form of monophosphoryl lipid A), Herpes Zoster GSK 1437173A, gD2-AS04, Havrix™, gD-Alum, Zostavax/Zoster vaccine (V211, V212, V210), HSV529, HerpV (AG-707 rh-Hsc70 polyvalent peptide complex), VCL-HB01, VCL-HM01, pPJV7630, GEN-003, SPL7013 gel (VivaGel™), GSK324332A, or a salt, solvate or combination thereof.

In some embodiments, the composition further comprises an additional antiviral agent. In some embodiments, the method further comprises administering to the subject an additional antiviral agent. In some embodiments, the additional antiviral agent is administered to the subject at a dosage from about 50 mg to about 1 g, for example, 5 mg, 10 mg, 20 mg, 25 mg, 30 mg, 40 mg, 50 mg, 60 mg, 70 mg, 80 mg, 90 mg, 100 mg, 125 mg, 150 mg, 175 mg, 200 mg, 225 mg, 250 mg, 275 mg, 300 mg, 350 mg, 400 mg, 500 mg, 600 mg, 650 mg, 700 mg, 750 mg, 800 mg, 850 mg, 900 mg, 950 mg, or 1000 mg. In some embodiments, the additional antiviral agent is an HIV antiviral agent. In some embodiments, the HIV antiviral agent comprises abacavir, didanosine, emtricitabine, lamivudine, stavudine, tenofovir, tenofovir disoporoxil fumarate, zidovudine, apricitabine, stampidine, elvucitabine, racivir, amdoxovir, stavudine, zalcitabine, festinavir, dideoxycytidine ddC, azidothymidine, tenofovir alafenamide fumarate, entecavir, delavirdine, efavirenz, etravirine, nevirapine, rilpivirine, doravirine, calanolide A, capravirine, epivir, TMC125, adefovir, dapivirine, lersivirine, atazanavir, darunavir, fosamprenavir, indinavir, nelfinavir, ritonavir, saquinavir, tipranavir, lopinavir, amprenavir, telinavir, droxinavir, emtriva, inviraze, agenerase, maraviroc, vicriviroc, cenicriviroc, lbalizumab, fostemsavir (BMS-663068), ibalizumab (TMB-355, TNX-355), PRO 140, b12 antibody, DCM205, DARPins, caprine antibody, VIR-576, enfuvirtide, AMD11070, PR0542, SCH-C, T-1249, cyanovirin, griffithsen, lectins, dolutegravir, elvitegravir, raltegravir, globoidnan A, MK-2048, BI224436, cabotegravir, GSK 1265744, GSK-572, or a salt, solvate or combination thereof.

In some embodiments, the composition further comprises a contraceptive. In some embodiments, the method further comprises administering to the subject an effective dose of a contraceptive. In some embodiments, the contraceptive comprises ethinyl estradiol, norethindrone, dosogestrel, levonorgestrel, ethynodiol diacetate, ethynodiol diacetate, RU486, N9, mifepristone, mifegyne, mifeprex, 17a-ethinyl-levongestrel, 17b-hydroxy-estra-4,9,11-trien-3-one, estradiol, medroxyprogesterone acetate, nestorone, norgestrienone, progesterone, etonogestril (3-keto-desogestrel), progestin, norgestimate, megestrol, etono-progestin alonegestrel, 17-acetoxy-16-methylene-19-norprogesterone, or a salt, solvate or combination thereof.

In another aspect, provided herein is an HSV treatment kit comprising a) a composition comprising a low dose of a first antiviral agent; b) a delivery device for delivering the composition to an HSV seronegative subject; and c) instructions comprising information on how to administer the composition using the delivery device to prevent HSV infection in the HSV seronegative subject. In some embodiments, HSV prevention comprises suppression of HSV replication in the HSV seronegative subject. In some embodiments, HSV prevention comprises suppression of HSV activation in the HSV seronegative subject.

In some embodiments, the low dose of the first antiviral agent is an amount useful for both prevention of HSV infection in the HSV seronegative subject and suppression of HSV in a seropositive subject. As non-limiting examples, the low dose is about 5 mg, 10 mg, 20 mg, 25 mg, 30 mg, 40 mg, 50 mg, 60 mg, 70 mg, 80 mg, 90 mg, 100 mg, 125 mg, 150 mg, 175 mg, 200 mg, 225 mg, 250 mg, 275 mg, 300 mg, 350 mg, 400 mg, 500 mg, 600 mg, 650 mg, 700 mg, 750 mg, 800 mg, 850 mg, 900 mg, 950 mg, or 1000 mg of the first antiviral agent. In some embodiments, the delivery device further provides a method for delivering the composition to the HSV seropositive subject. In some embodiments, the instructions further comprise information on how to administer the composition using the delivery device to suppress HSV reactivation in the HSV seropositive subject.

In some embodiments, the kit further comprises or is enclosed within a package. In some embodiments, the package comprises a label directed towards HSV seronegative subjects, HSV seropositive subjects and subjects of unknown HSV sero-status.

In some embodiments, the delivery device comprises an oral tablet, oral capsule, or oral solution. In some embodiments, the delivery device is a long-acting drug delivery device. In some embodiments, the long-acting delivery device comprises an injection device, intravaginal ring, transdermal patch, or a combination thereof.

In some embodiments, the first antiviral agent comprises valacyclovir, acyclovir, famciclovir, pritelivir, penciclovir, ganciclovir, valganciclovi, cidofovir, foscarnet, darunavir, glycyrrhizic acid, *Sambucus nigra*, glutamine, FV-100, ASP2151, me-609, ASP2151, topical VDO, PEG-formulation (Devirex AG), vidarabine, cidofovir, crofelemer (SP-303T), EPB-348, CMX001, V212, NB-001, squaric acid, ionic zinc, sorivudine (ARYS-01), trifluridine, 882C87, merlin (ethanol and glycolic acid mixture), vitamin C, AIC316, versabase gel with *Sarracenia purpurea*, UB-621, lysine, edoxudine, brivudine, cytarabine, docosanol, tromantadine, resiquimod (R-848), imiquimod, resiquimod, tenofovir, tenofovir disoproxil fumarate, tenofovir alafenamide fumarate, or a salt, solvate or combination thereof.

In some embodiments, the low dose of the first antiviral agent is from about 5 mg to about 1 g, for example, about 5 mg, 10 mg, 20 mg, 25 mg, 30 mg, 40 mg, 50 mg, 60 mg, 70 mg, 80 mg, 90 mg, 100 mg, 125 mg, 150 mg, 175 mg, 200 mg, 225 mg, 250 mg, 275 mg, 300 mg, 350 mg, 400 mg, 500 mg, 600 mg, 650 mg, 700 mg, 750 mg, 800 mg, 850 mg, 900 mg, 950 mg, or 1000 mg.

In some embodiments, the kit further comprises a second antiviral agent. In some embodiments, the second antiviral agent is present in the composition at a second low dose. In some embodiments, the second low dose is from about 5 mg to about 1 g, for example, about 5 mg, 10 mg, 20 mg, 25 mg, 30 mg, 40 mg, 50 mg, 60 mg, 70 mg, 80 mg, 90 mg, 100 mg, 125 mg, 150 mg, 175 mg, 200 mg, 225 mg, 250 mg, 275 mg, 300 mg, 350 mg, 400 mg, 500 mg, 600 mg, 650 mg, 700 mg, 750 mg, 800 mg, 850 mg, 900 mg, 950 mg, or 1000 mg. In some embodiments, the second antiviral agent is an HSV antiviral agent. In some embodiments, the second antiviral agent is an HIV antiviral agent. In some embodiments, the HIV antiviral agent comprises abacavir, didanosine, emtricitabine, lamivudine, stavudine, tenofovir, tenofovir disoproxil fumarate, zidovudine, apricitabine, stampidine, elvucitabine, racivir, amdoxovir, stavudine, zalcitabine, festinavir, dideoxycytidine ddC, azidothymidine, tenofovir alafenamide fumarate, entecavir, delavirdine, efavirenz, etravirine, nevirapine, rilpivirine, doravirine, calanolide A, capravirine, epivir, TMC125, adefovir, dapivirine, lersivirine, atazanavir, darunavir, fosamprenavir, indinavir, nelfinavir, ritonavir, saquinavir, tipranavir, lopinavir, amprenavir, telinavir, droxinavir, emtriva, invirase, agenerase, maraviroc, vicriviroc, cenicriviroc, lbalizumab, fostemsavir (BMS-663068), ibalizumab (TMB-355, TNX-355), PRO 140, b12 antibody, DCM205, DARPins, caprine antibody, VIR-576, enfuvirtide, AMD11070, PR0542, SCH-C, T-1249, cyanovirin, griffithsen, lectins, dolutegravir, elvitegravir, raltegravir, globoidnan A, MK-2048, BI224436, cabotegravir, GSK 1265744, GSK-572, or a salt, solvate or combination thereof.

In some embodiments, the kit further comprises a contraceptive. In some embodiments, the contraceptive comprises ethinyl estradiol, norethindrone, dosogestrel, levonorgestrel, ethynodiol diacetate, ethynodiol diacetate, RU486, N9, mifepristone, mifegyne, mifeprex, 17a-ethinyl-levongestrel, 17b-hydroxy-estra-4,9,11-trien-3-one, estradiol, medroxyprogesterone acetate, nestorone, norgestrienone, progesterone, etonogestril (3-keto-desogestrel), progestin, norgestimate, megestrol, etono-progestin alonegestrel, 17-acetoxy-16-methylene-19-norprogesterone, or a salt, solvate or combination thereof.

In another aspect, provided herein is a method of preventing HSV infection in an HSV seronegative subject, the method comprising administering to the subject a composition comprising a very high dose of a first antiviral agent after physical contact with a partner who is seropositive for HSV. In some embodiments, the method further comprises administering to the subject a low dose of a second antiviral agent prior to physical contact with the HSV seropositive partner. In some embodiments, the second antiviral agent comprises a same active agent as the first antiviral agent. In some embodiments, the second antiviral agent comprises a different active agent than the first antiviral agent. In some embodiments, the physical contact occurs during one occasion. In some embodiments, the physical contact occurs during two or more separate occasions.

In some embodiments, the physical contact occurs with the HSV seropositive partner and one or more additional partners. In some embodiments, the subject is or will be in an ongoing mutually-monogamous sexual relationship with the HSV seropositive partner. In some embodiments, the subject is not or will not be in a mutually-monogamous sexual relationship with the HSV seropositive partner. In some embodiments, the HSV seropositive partner is aware of their HSV sero-status. In some embodiments, the HSV seropositive partner is unaware of their HSV sero-status. In some embodiments, the HSV seropositive partner is undergoing HSV suppression therapy comprising the administration of a suppressive antiviral agent to the HSV seropositive partner. In some embodiments, the method further comprises administering to the HSV seropositive partner a suppressive antiviral agent. In some embodiments, the suppressive antiviral agent comprises a same active agent as the first antiviral agent. In some embodiments, the suppressive antiviral agent comprises a different active agent than the first antiviral agent.

In some embodiments, the physical contact is sexual contact. In some embodiments, the subject and the HSV seropositive partner use a physical barrier during sexual contact.

In some embodiments, the subject is exposed to HSV from the HSV seropositive partner during physical contact.

In some embodiments, the administered composition suppresses HSV replication in the subject. In some embodiments, the administered composition suppresses HSV activation in the subject. In some embodiments, the administered composition reduces the risk of HSV infection in the subject. In some embodiments, the risk of HSV infection in the subject is reduced by at least about 50%, 60%, 70%, 80%, 90%, or 95%.

In some embodiments, the method further comprises determining the very high dose of the first antiviral agent. In some embodiments, the method further comprises determining a delivery mechanism for administering the composition to the subject. In some embodiments, the delivery mechanism comprises a long-acting drug delivery device. In some embodiments, the long-acting drug delivery device comprises an injection device, intravaginal ring, transdermal patch, or a combination thereof.

In some embodiments, the first antiviral agent comprises valacyclovir, acyclovir, famciclovir, pritelivir, penciclovir, ganciclovir, valganciclovi, cidofovir, foscarnet, darunavir, glycyrrhizic acid, *Sambucus nigra*, glutamine, FV-100, ASP2151, me-609, ASP2151, topical VDO, PEG-formulation (Devirex AG), vidarabine, cidofovir, crofelemer (SP-303T), EPB-348, CMX001, V212, NB-001, squaric acid, ionic zinc, sorivudine (ARYS-01), trifluridine, 882C87, merlin (ethanol and glycolic acid mixture), vitamin C, AIC316, versabase gel with *Sarracenia purpurea*, UB-621, lysine, edoxudine, brivudine, cytarabine, docosanol, tromantadine, resiquimod (R-848), imiquimod, resiquimod, tenofovir, tenofovir disoproxil fumarate, tenofovir alafenamide fumarate, or a salt, solvate or combination thereof.

In some embodiments, the first antiviral agent comprises an HSV vaccine and optionally an adjuvant. In some embodiments, the HSV vaccine comprises GSK208141 (gD2t, GSK glycoprotein D (gD)-Alum/3-deacylated form of monophosphoryl lipid A), Herpes Zoster GSK 1437173A, gD2-AS04, Havrix™, gD-Alum, Zostavax/Zoster vaccine (V211, V212, V210), HSV529, HerpV (AG-707 rh-Hsc70 polyvalent peptide complex), VCL-HB01, VCL-HM01, pPJV7630, GEN-003, SPL7013 gel (VivaGel™), GSK324332A, or a salt, solvate or combination thereof.

In some embodiments, the very high dose of the first antiviral agent is from about 500 mg to about 2500 mg, for example, about 500 mg, 600 mg, 700 mg, 800 mg, 900 mg, 1000 mg, 1100 mg, 1200 mg, 1300 mg, 1400 mg, 1500 mg, 1600 mg, 1700 mg, 1800 mg, 1900 mg, 2000 mg, 2100 mg, 2200 mg, 2300 mg, 2400 mg, or 2500 mg. In some embodiments, the very high dose of the first antiviral agent is an amount greater than an amount useful for treating an initial outbreak of HSV in a seropositive patient.

In some embodiments, the composition further comprises an additional antiviral agent. In some embodiments, the method further comprises administering to the subject an additional antiviral agent. In some embodiments, the additional antiviral agent is administered to the subject at a dosage from about 500 mg to about 2500 mg, for example, about 500 mg, 600 mg, 700 mg, 800 mg, 900 mg, 1000 mg, 1100 mg, 1200 mg, 1300 mg, 1400 mg, 1500 mg, 1600 mg, 1700 mg, 1800 mg, 1900 mg, 2000 mg, 2100 mg, 2200 mg, 2300 mg, 2400 mg, or 2500 mg. In some embodiments, the additional antiviral agent is an HIV antiviral agent. In some embodiments, the HIV antiviral agent comprises abacavir, didanosine, emtricitabine, lamivudine, stavudine, tenofovir, tenofovir disoporoxil fumarate, zidovudine, apricitabine, stampidine, elvucitabine, racivir, amdoxovir, stavudine, zalcitabine, festinavir, dideoxycytidine ddC, azidothymidine, tenofovir alafenamide fumarate, entecavir, delavirdine, efavirenz, etravirine, nevirapine, rilpivirine, doravirine, calanolide A, capravirine, epivir, TMC125, adefovir, dapivirine, lersivirine, atazanavir, darunavir, fosamprenavir, indinavir, nelfinavir, ritonavir, saquinavir, tipranavir, lopinavir, amprenavir, telinavir, droxinavir, emtriva, invirase, agenerase, maraviroc, enfuvirtide, vicriviroc, cenicriviroc, lbalizumab, fostemsavir (BMS-663068), ibalizumab (TMB-355, TNX-355), PRO 140, b12 antibody, DCM205, DARPins, caprine antibody, VIR-576, AMD11070, PR0542, SCH-C, T-1249, cyanovirin, griffithsen, lectins, dolutegravir, elvitegravir, raltegravir, globoidnan A, MK-2048, BI224436, cabotegravir, GSK 1265744, GSK-572, or a salt, solvate or combination thereof.

In some embodiments, the composition further comprises a contraceptive. In some embodiments, the method further comprises administering to the subject an effective dose of a contraceptive. In some embodiments, the contraceptive comprises ethinyl estradiol, norethindrone, dosogestrel, levonorgestrel, ethynodiol diacetate, ethynodiol diacetate, RU486, N9, mifepristone, mifegyne, mifeprex, 17a-ethinyl-levongestrel, 17b-hydroxy-estra-4,9,11-trien-3-one, estradiol, medroxyprogesterone acetate, nestorone, norgestrienone, progesterone, etonogestril (3-keto-desogestrel), progestin, norgestimate, megestrol, etono-progestin alonegestrel, 17-acetoxy-16-methylene-19-norprogesterone, or a salt, solvate or combination thereof. In some embodiments, the contraceptive is an emergency contraceptive.

In another aspect, provided herein is an HSV treatment kit comprising a) a composition comprising a very high dose of a first antiviral agent; b) a delivery device for delivering the composition to an HSV seronegative subject; and c) instructions comprising information on how to administer the composition using the delivery device to prevent HSV infection in the HSV seronegative subject after the HSV seronegative subject is exposed to HSV. In some embodiments, HSV prevention comprises suppression of HSV replication in the HSV seronegative subject. In some embodiments, HSV prevention comprises suppression of HSV activation in the HSV seronegative subject.

In some embodiments, the very high dose of the first antiviral agent is an amount useful for both prevention of HSV infection in the HSV seronegative subject after exposure to HSV and treatment of an initial outbreak of HSV in an HSV seropositive subject. In some embodiments, the very high dose of the first antiviral agent is an amount greater than an amount useful for treating an initial outbreak of HSV in an HSV seropositive subject.

In some embodiments, the delivery device further provides a method for delivering the composition to the HSV seropositive subject. In some embodiments, the instructions further comprise information on how to administer the composition using the delivery device to treat an HSV outbreak in the HSV seropositive subject.

In some embodiments, the kit further comprises or is enclosed within a package. In some embodiments, the package comprises a label directed towards HSV seronegative subjects, HSV seropositive subjects and subjects of unknown HSV sero-status.

In some embodiments, the delivery device comprises an oral tablet, oral capsule, or oral solution. In some embodiments, the delivery device is a long-acting drug delivery device. In some embodiments, the long-acting delivery device comprises an injection device, intravaginal ring, transdermal patch, or a combination thereof.

In some embodiments, the first antiviral agent comprises valacyclovir, acyclovir, famciclovir, pritelivir, penciclovir, ganciclovir, valganciclovi, cidofovir, foscarnet, darunavir, glycyrrhizic acid, *Sambucus nigra*, glutamine, FV-100, ASP2151, me-609, ASP2151, topical VDO, PEG-formulation (Devirex AG), vidarabine, cidofovir, crofelemer (SP-303T), EPB-348, CMX001, V212, NB-001, squaric acid, ionic zinc, sorivudine (ARYS-01), trifluridine, 882C87, merlin (ethanol and glycolic acid mixture), vitamin C, AIC316, versabase gel with *Sarracenia purpurea*, UB-621, lysine, edoxudine, brivudine, cytarabine, docosanol, tromantadine, resiquimod (R-848), imiquimod, resiquimod, tenofovir, tenofovir disoproxil fumarate, tenofovir alafenamide fumarate, or a salt, solvate or combination thereof.

In some embodiments, the very high dose of the first antiviral agent is from about 500 mg to about 2500 mg, for example, about 500 mg, 600 mg, 700 mg, 800 mg, 900 mg, 1000 mg, 1100 mg, 1200 mg, 1300 mg, 1400 mg, 1500 mg, 1600 mg, 1700 mg, 1800 mg, 1900 mg, 2000 mg, 2100 mg, 2200 mg, 2300 mg, 2400 mg, or 2500 mg.

In some embodiments, the kit further comprises a second antiviral agent. In some embodiments, the second antiviral agent is an HSV antiviral agent. In some embodiments, the second antiviral agent is an HIV antiviral agent. In some embodiments, the HIV antiviral agent comprises abacavir, didanosine, emtrictabine, lamivudine, stavudine, tenofovir, tenofovir disoporoxil fumarate, zidovudine, apricitabine, stampidine, elvucitabine, racivir, amdoxovir, stavudine, zalcitabine, festinavir, dideoxycytidine ddC, azidothymidine, tenofovir alafenamide fumarate, entecavir, delavirdine, efavirenz, etravirine, nevirapine, rilpivirine, doravirine, calanolide A, capravirine, epivir, TMC125, adefovir, dapivirine, lersivirine, atazanavir, darunavir, fosamprenavir, indinavir, nelfinavir, ritonavir, saquinavir, tipranavir, lopinavir, amprenavir, telinavir, droxinavir, emtriva, invirase, agenerase, maraviroc, enfuvirtide, vicriviroc, cenicriviroc, lbalizumab, fostemsavir (BMS-663068), ibalizumab (TMB-355, TNX-355), PRO 140, b12 antibody, DCM205, DARPins, caprine antibody, VIR-576, AMD11070, PR0542, SCH-C, T-1249, cyanovirin, griffithsen, lectins, dolutegravir, elvitegravir, raltegravir, globoidnan A, MK-2048, BI224436, cabotegravir, GSK 1265744, GSK-572, or a salt, solvate or combination thereof.

In some embodiments, the kit further comprises a contraceptive. In some embodiments, the contraceptive comprises ethinyl estradiol, norethindrone, dosogestrel, levonorgestrel, ethynodiol diacetate, ethynodiol diacetate, RU486, N9, mifepristone, mifegyne, mifeprex, 17a-ethinyl-levongestrel, 17b-hydroxy-estra-4,9,11-trien-3-one, estradiol, medroxyprogesterone acetate, nestorone, norgestrienone, progesterone, etonogestril (3-keto-desogestrel), progestin, norgestimate, megestrol, etono-progestin alonegestrel, 17-acetoxy-16-methylene-19-norprogesterone, or a salt, solvate or combination thereof. In some embodiments, the kit comprises an emergency contraceptive.

INCORPORATION BY REFERENCE

All publications, patents, and patent applications mentioned in this specification are herein incorporated by reference to the same extent as if each individual publication, patent, or patent application was specifically and individually indicated to be incorporated by reference.

DETAILED DESCRIPTION OF THE INVENTION

The current standard practice for preventing HSV infection involves suppressive treatment of an HSV seropositive individual to reduce transmission of the virus to an HSV seronegative individual. As described previously, these methods rely on the compliance of an HSV seropositive individual and often do not provide adequate protection for the HSV seronegative individual. Described herein, in various aspects, are methods for the prevention of HSV infection in a seronegative individual comprising administering to the seronegative individual a composition comprising one or more antiviral agents. If the HSV seronegative individual is in a relationship with an HSV seropositive partner (i.e., an HSV discordant relationship), the methods optionally further comprise suppressive treatment of the HSV seropositive individual, providing a second layer of protection for the seronegative individual. In one aspect, provided are compositions comprising one or more antiviral agents useful for the prevention of HSV infection in an HSV seronegative individual, wherein the compositions protect the seronegative individual against the transmission of shedding virus from the seropositive individual. These antiviral compositions for protecting HSV seronegative individuals are optionally also useful in suppressive treatment of HSV seropositive individuals. In some aspects of the methods described herein, the HSV compositions further comprise and/or are administered with, one or more additional antiviral agents. For example, the compositions described herein comprise one or more HSV antiviral agents and one or more human immunodeficiency virus (HIV) antiviral agents. In some cases, the HSV antiviral agent also treats or prevents infection by another virus, such as HIV. In additional embodiments, a composition comprising an HSV antiviral, and optionally one or more additional antiviral agents, further comprises and/or is administered with a contraceptive agent. As such, the present disclosure, in various embodiments, provides compositions and methods for the prevention of HSV infection in an HSV seronegative individual, while optionally further preventing pregnancy and/or infection by additional viruses.

In one aspect of the disclosure, described herein are compositions and methods for the prevention of HSV infection in an HSV seronegative individual at risk for exposure to HSV. In some cases, these compositions are referred to as pre-exposure compositions or HSV pre-exposure compositions. In some embodiments, the HSV seronegative individual is at risk for exposure to HSV through one or more incidents of sexual contact with one or more partners, where the one or more partners is HSV seropositive or has an unknown HSV sero-status. As one example, the HSV seronegative individual at risk for exposure to HSV is likely to engage in one or more incidents of sexual contact with the same partner. In some cases, the seronegative individual and the partner are in a monogamous relationship. In other cases, the seronegative individual and the partner are not in a monogamous relationship. As another example, the HSV seronegative individual at risk for exposure to HSV is likely to engage in one or more incidents of sexual contact with one or more different partners. In various embodiments, the pre-exposure compositions described herein comprise one or more antiviral agents at a low dose, for example, a dose that is the same or 10%, 20%, 30%, 40%, 50%, 60%, 70%, 80%, or 90% smaller than the dose typically administered to an HSV seropositive individual for suppression therapy.

In another aspect, described herein are compositions and methods for the prevention of HSV infection in an HSV seronegative individual after exposure to HSV. In some cases, these compositions are referred to as post-exposure compositions or HSV post-exposure compositions. In some embodiments, the HSV seronegative individual is exposed to HSV through one or more incidents of sexual contact with one or more partners, where the one or more partners is HSV seropositive. In some cases, the HSV seropositive partner is aware of their seropositive status. In other cases, the HSV seropositive partner is unaware of their seropositive status. As one example, the HSV seronegative individual is exposed HSV through one or more incidents of sexual contact with the same HSV seropositive partner. In some cases, the seronegative individual and the partner are in a monogamous relationship. In other cases, the seronegative individual and the partner are not in a monogamous relationship. As another example, the HSV seronegative individual is exposed to HSV through one or more incidents of sexual contact with one or more different partners. In various embodiments, the post-exposure compositions described herein comprise one or more antiviral agents at a high dose, for example, a dose that is the same or 10%, 20%, 30%, 40%, 50%, 60%, 70%, 80%, or 90% greater than the dose typically administered to an HSV seropositive individual for therapy after an initial outbreak.

In some embodiments, an HSV composition or an antiviral composition refers to a pre-exposure composition. In some embodiments, an HSV composition or an antiviral composition refers to a post-exposure composition. In some embodiments, an HSV composition or an antiviral composition refers to a composition comprising one or more antivirals for suppressive therapy of an HSV seropositive individual. In some embodiments, an HSV composition or an antiviral composition refers to both pre-exposure and post-exposure compositions. In further embodiments, an HSV composition or an antiviral composition refers to pre-exposure compositions, post-exposure compositions, and compositions for suppressive therapy.

In one aspect of the disclosure, provided herein are compositions and methods for the prevention of HSV infection in an HSV seronegative subject in an HSV discordant relationship with an HSV seropositive subject. In some embodiments, an HSV seronegative subject is administered a first composition comprising one or more first antiviral agents and the HSV seropositive subject is administered a second composition comprising one or more second antiviral agents. In some cases, a first antiviral agent, or a pharmaceutically acceptable salt or solvate thereof, comprises the same active agent as a second antiviral agent, or a pharmaceutically acceptable salt of solvate thereof. In some cases, a first antiviral agent comprises a different active agent than a second antiviral agent. In some cases, a first antiviral agent is administered in a dosage that is the same or different as the dosage of the second antiviral agent. In some cases, the first composition is delivered using the same delivery mechanism as the second composition. In other cases, the first composition is delivered using a different delivery mechanism as the second composition. In some cases, these methods further provide enhanced HSV infection prevention in seronegative individuals by improving delivery of antiviral agents to the seropositive individual and/or the seronegative individual, for example, by using long-acting drug delivery mechanism. In some embodiments, the compositions administered to the HSV seronegative individual are pre-exposure compositions for prophylactic treatment. In some embodiments, the compositions administered to the HSV seronegative individual are post-exposure compositions for prophylactic treatment. Prophylactic treatment of an HSV seronegative individual, when used in combination with suppressive treatment of the HSV seropositive individual, provides a second opportunity to inactivate any virus that has been shed by the seropositive individual so that there are insufficient quantities of HSV to create a productive, sustainable infection in the new host and thus creates an added layer of protection against HSV infection. In some embodiments, this enhanced HSV infection prevention is further amplified when the methods further comprise safe sex practices. In addition, treating the seronegative as well as the seropositive person can increases the likelihood of compliance and removes the stigma of HSV infection, thereby improving the likelihood of self-diagnosis and treatment in seropositive individuals. Under a scenario in which both seropositive and seronegative individuals are taking antivirals, seropositive individuals no longer face a stigma and all individuals are acting in a way that greatly reduces transmission of HSV. This can significantly improve HSV treatment and transmission prevention and, by extension, HIV transmission prevention.

In some embodiments, provided herein are methods for administering an antiviral composition to an HSV seronegative individual, provided that the HSV seronegative individual is associated with a risk category for infection with HSV. In some aspects of the methods described herein, the methods for preventing HSV infection in an HSV seronegative individual comprise determining a risk category of the HSV seronegative individual. In some embodiments, an individual associates with a different HSV risk category over a period of time. In such instances, the methods of administering an antiviral composition are optionally modulated to align with this change in risk category. For example, in some instances, an individual no longer in an HSV risk category discontinues use of an antiviral composition. In some cases, an HSV seronegative individual is at risk for infection with HSV through exposure from an HSV seropositive partner, wherein the HSV seronegative and HSV seropositive individuals are in a monogamous, HSV discordant relationship. In some cases, an HSV seronegative individual is at risk for infection with HSV through exposure from an HSV seropositive partner, wherein the two individuals are not in a monogamous relationship. In this instance, the risk for infection can occur during a single or multiple physical encounters with the HSV seropositive partner. In some cases, an HSV seronegative individual is at risk for infection with HSV through exposure from multiple HSV seropositive partners, wherein the individuals are not in a monogamous relationship. In this instance, the risk for infection can occur during a single or multiple physical encounters with the HSV seropositive partners. In some cases, an HSV seronegative individual is at risk for infection with HSV through exposure from one or more partners of unknown HSV status, wherein the individuals are not in a monogamous relationship. In this instance, the risk for infection can occur during a single or multiple physical encounters with the one or more partners. In some embodiments, an HSV individual at risk for exposure to HSV is administered a pre-exposure composition comprising a low dose of at least one antiviral agent. In some embodiments, an HSV individual suspected of or having been exposed to HSV is administered a post-exposure composition comprising a high dose of at least one antiviral agent.

In some embodiments, provided herein are methods for administering an antiviral composition to an individual of unknown HSV sero-status. In some cases, the individual is HSV seropositive and does not know their sero-status. In other cases, the individual is HSV seropositive and does not admit to others that they are HSV seropositive. In some cases, the individual is HSV seronegative and does not know their sero-status. Not knowing their sero-status or being in denial of it, can prevent individuals from warning seronegative persons of the risk of transmission. In some embodiments, the methods described herein comprise administering an antiviral agent to an individual of unknown status in an amount that is both effective for prevention of HSV infection in an HSV seronegative subject and effective for HSV suppression therapy in an HSV seropositive subject. In some cases, the effective amount is a low dose of an antiviral agent. In such instances, HSV testing is not required for administering an antiviral composition. Common methods for testing for HSV sero-status include immunoassays, cell culturing and nucleic acid detection, for example, using polymerase chain reaction. As the standard of care does not currently provide test kits readily performed without assistance of a laboratory and health care personal, HSV sero-status is not easily ascertained. In various aspects, the methods and compositions provided eliminate the need for determining sero-status.

In some embodiments, provided herein are methods for administering an antiviral composition to an individual of known HSV seropositive status. The stigma associated with HSV infection can cause individuals to avoid the uncomfortable conversation with a doctor that is necessary for HSV testing and/or obtaining antiviral drugs. In some cases, the HSV seropositive individual is administered a same dosage of an antiviral that an HSV seronegative individual would be administered to prevent HSV infection, eliminating the need for the HSV seropositive individual to admit their sero-status.

The methods for preventing HSV infection in an HSV seronegative individual, in various embodiments, comprise administering to the HSV seronegative individual a composition comprising one or more antiviral agents. In some embodiments, the methods comprise determining a mechanism of administering the HSV composition. In some embodiments, the methods comprise determining a risk category of the HSV seronegative individual. In some embodiments, the methods comprise determining an antiviral agent dosage amount effective to suppress HSV replication, HSV re-activation, or both HSV replication and HSV re-activation. In some embodiments, the methods comprise determining a route of administration of the composition and a delivery mechanism, for example, oral tablet, transdermal patch or intravaginal ring. In some embodiments, the methods comprise determining an anatomical location on the individual for engagement of an antiviral composition delivery mechanism. In some embodiments, the methods comprise maintaining delivery of an antiviral composition to an individual for a therapeutically effective amount of time, for example, the delivery mechanism provides sustained or long-acting delivery of an active agent of the composition. Long-acting drug delivery mechanisms include, without limitation, injection devices, intravaginal rings, and transdermal patches. As a non-limiting example, the delivery mechanism is an intravaginal ring which is maintained within the subject and releases an active agent of a composition to the subject for a therapeutically effective amount of time.

In one aspect, provided herein are compositions comprising one or more antiviral agents and methods of administering one or more antiviral agents, wherein the compositions are administered using a long-acting delivery mechanism via a long-acting delivery device. In some embodiments, the antiviral compositions are administered to HSV seronegative individuals. In some embodiments, the antiviral compositions are administered to HSV seropositive individuals. In further embodiments, the compositions are administered to both HSV seropositive and HSV seronegative individuals, wherein the compositions may have the same or different active antiviral agents. In some embodiments, the long-acting delivery device is an intravaginal ring. In some embodiments, the long-acting delivery device is an injectable device. In some embodiments, the long-acting delivery device is a transdermal patch. Long-acting delivery mechanisms, in many cases, provide a higher average, more consistent, and/or more reliable concentration of the antiviral drug within the bloodstream of a subject over a longer period time, as compared to oral administration of the same antiviral drug dosage. In some instances, administration of an antiviral composition described herein via a long-acting delivery mechanism reduces the risk of non-compliance in the subject. For example, compliance in subjects administered an antiviral composition via a long-acting drug delivery device is at least about 10%, 20%, 30%, 40%, 50%, 60%, 70%, 80%, 90%, 100% or greater than compliance in subjects administered an antiviral composition via an oral formulation. Subjects may be less likely to forget to take a dosage when it is automatically administered through a long-acting drug delivery device. In some embodiments, the long-acting drug delivery device delivers an antiviral agent, such as an HSV antiviral, and another antiviral agent, such as one that prevents HIV. In other or additional embodiments, the long-acting drug delivery device delivers an antiviral agent and a contraceptive.

In further embodiments, provided herein are methods and compositions for reducing the incidence of HSV infection in a seronegative individual and therefore the incidence of HIV infection. In some cases, reducing the incidence of HSV infection can indirectly reduce the incidence of HIV infection. As previously discussed, the risk of contracting HIV is higher when there is an HSV co-infection. This is true not only because HSV infection creates scarring and other flaws in the skin that reduce the skin's effectiveness as a barrier to HIV, but also because the presence of HSV activates the immune system in such a way that it becomes more vulnerable to invasion by HIV. In addition, HSV has been shown to upregulate the chemokine receptor CCR5, the primary co-receptor for HIV, which is a suspected mechanism for the increased risk of transmission of HIV in HSV positive people. Hence, reducing the incidence of HSV can greatly reduce the risk of HIV infection, thus reducing a severe medical risk and significant public health cost.

Viruses and Viral Diseases

Provided herein, in various aspects, are methods for the prevention of viral infection in a subject comprising administering to the subject a composition comprising an effective dose of at least one antiviral agent. The methods and compositions described herein relate to any infective virus. In some embodiments, reference to a virus is not limited to a single virus and is inclusive of one or more infective viruses. In exemplary embodiments, a virus is at least one herpes simplex virus (HSV). In various instances, reference to HSV is inclusive of all infectious viruses and is not limited to herpes simplex virus. In some embodiments, a virus is at least one human immunodeficiency virus (HIV). In some cases, the methods prevent infection by both HSV and HIV viruses. In non-limiting examples, at least one virus includes at least one of herpes virus, HIV-I, HIV-2, simian immunodeficiency virus (SIV), feline leukemia virus, picornavirus family, respiratory syncytial virus (RSV), influenza, adenovirus, rhinovirus, enterovirus, poliovirus, rubella virus, paramyxovirus, rotavirus, neurotropic virus, or oncovirus. In some embodiments, the picornavirus family includes but is not limited to picornavirus, poliovirus, rhinovirus, enterovirus (coxsackie virus), hepatitis (hepatitis virus type A, hepatitis virus type B, hepatitis virus type C), aphthovirus, parechovirus, and encephalomyocarditis virus.

In some embodiments, the herpes virus includes, but is not limited to, herpes simplex virus-1, herpes simplex virus-2, varicella-zoster (chicken pox, shingles, human herpes virus 3), Epstein-Ban (human herpes virus 4), cytomegalovirus (human herpes virus 5), roseolovirus (human herpes virus 6 and 7), and Karposi's sarcoma-associated herpes virus (human herpes virus 8). HSV-1 typically produces cold sores and in some instances, genital herpes in infected persons. HSV-2 typically produces genital herpes in infected persons. Significant manifestations of HSV-1 and HSV-2 include oropharyngeal infections, skin infections, ocular infections, and central nervous system disorders such as meningitis and encephalitis.

In some embodiments, HIV includes HIV-1 (HIV type-1), HIV-2 (HIV type-2) and SIV. HIV-1 includes, but is not limited to, extracellular virus particles and the forms of HIV-1 associated with HIV-1 infected cells. In some instances, HIV-1 represents any of the known major subtypes (Classes A, B, C, D E, F, G and H), recombinant strains or outlying subtype (Group 0), including laboratory strains and primary isolates. HIV-2 includes, but is not limited to, extracellular virus particles and the forms of HIV-2 associated with HIV-2 infected cells. SIV is an HIV-like virus that infects monkeys, chimpanzees, and other nonhuman primates.

In some embodiments, a viral infection refers to a verified presence of a viral antibody, viral antigen, and/or viral nucleic acid in a subject using viral diagnostic tests known to those skilled in the art (e.g. immunoassays such as ELISAs, Western blot, and lateral flow assays; and PCR). In exemplary embodiments, an HSV infection refers to the verified presence of anti-HSV antibody or HSV nucleic acid. In some instances, an HSV seropositive individual is an individual who has detectable anti-HSV antibody in their blood. In some instances, an HSV seronegative individual is an individual who does not have detectable anti-HSV antibody in their blood. In some cases, an HSV seronegative individual has been exposed to HSV, but HSV has not established an infection and/or the individual has not yet seroconverted so that anti-HSV antibodies are not yet detectable.

Antiviral Compositions

Provided herein, in various aspects, are compositions and methods for the prevention of HSV infection in an HSV seronegative subject from an HSV seropositive subject, the methods comprising administering to the HSV seronegative subject a composition comprising an effective dose of a first antiviral agent. In various embodiments, the composition prevents the establishment of a new persistent infection in the seronegative individual after exposure to HSV. In some embodiments, the composition is administered prior to HSV exposure from a seropositive individual, e.g., the composition is a pre-exposure composition. In some embodiments, the composition is administered after HSV exposure from a seropositive individual, e.g., the composition is a post-exposure composition. In some embodiments, the composition is administered prior to and after HSV exposure to the seronegative individual.

In additional aspects, provided herein are methods for the prevention of HSV infection in an HSV seronegative subject from an HSV seropositive individual, the methods comprising administering to the HSV seronegative subject a composition comprising a first effective dose of a first antiviral agent and further comprising administering to the HSV seropositive individual a second composition comprising a second effective dose of a second antiviral agent. In some embodiments, the first antiviral agent and the second antiviral agent comprise the same active agent. In some embodiments, the first antiviral agent and the second antiviral agent comprise different active agents. In some embodiments, the composition comprising an effective dose of a first antiviral agent is useful for the prevention of HSV and one or more additional viral infections. In some embodiments, the composition comprising the first antiviral agent further comprises or is administered with an additional antiviral agent, wherein the additional antiviral agent is useful for the prevention of HSV and/or one or more additional viral infections. Additional viral infections include, without limitation, HIV, HPV, hepatitis, influenza, and diseases and conditions resulting therefrom.

In some embodiments, an antiviral agent in a composition for administration to an HSV seronegative individual inactivates HSV shed by a seropositive individual and transferred to the HSV seronegative individual. In some cases, the antiviral agent administered to an HSV seronegative individual that has been exposed to HSV reduces the amount of viable virus so that the virus is not able to produce a sustainable infection in the individual. In some cases, a further layer of protection is achieved when an HSV seropositive partner of the HSV seronegative individual is in suppressive therapy, which reduces the amount of virus transferred to the HSV seronegative individual.

In some embodiments, the compositions useful for the methods of reducing HSV viral infection in seronegative individuals comprise two or more antivirals. In some cases, at least two of the two or more antivirals employ different mechanisms for inhibiting viral infection. In some cases, an antiviral administered to a seronegative subject is the same as an antiviral administered to a seropositive subject. In some cases, an antiviral administered to a seronegative subject is different than an antiviral administered to a seropositive subject. In some cases, two or more antivirals are administered within the same composition, or two or more antivirals are administered within two or more different compositions, to create a cumulative effect incorporating the efficacy of the various drugs against the target virus. For example, a combination of antivirals (within the same composition or co-administered within different compositions) reduces the rate of viral infection to a greater degree than employing one of the antivirals in the combination. As another example, a combination of antivirals reduces the rate of viral shedding and transmission rate to a greater degree than employing only one of the antivirals within the combination. In some cases, combination therapy is effective in situations where a single agent may be ineffective due to, for example, drug resistance, dosing mistakes, and/or non-compliance. In some cases, combinations of antivirals having different mechanisms of action provide enhanced therapeutic effectiveness over a single antiviral.

Provided herein, in some embodiments, are compositions comprising one or more antiviral agents and methods of treating an HSV and HIV seronegative individual with said compositions to prevent HSV and/or HIV infection. In some instances, at least one of the one or more antiviral agents is an HSV antiviral agent. In some instances, at least one of the one or more antiviral agents is an HIV antiviral agent. In some cases, at least one of the one or more antiviral agents is useful for the treatment of both HSV and HIV.

Further provided herein, in various aspects, are compositions and methods for the prevention of pregnancy and HSV infection in an HSV seronegative subject. In some embodiments, the methods comprise administering to the subject a composition comprising a first antiviral agent and a contraceptive agent. In some embodiments, the methods comprise administering to the subject a first composition comprising a first antiviral agent and a second composition comprising a contraceptive agent. In various cases, the first antiviral agent further prevents HIV infection. In some cases, the compositions further comprise a second antiviral agent that prevents viral infection, such as HSV and/or HIV infection.

Antiviral Agents

A variety of antiviral agents are useful in the methods and compositions described herein for both the prevention of viral transmission from seropositive individuals to seronegative individuals and the prevention of viral infection in seronegative individuals exposed to virus. In some embodiments, a seronegative individual is treated with a composition comprising an antiviral for the prevention of viral infection in the seronegative individual. In exemplary embodiments, antiviral agents administered to a seronegative individual for infection prevention include those useful for acute and/or suppressive therapy in seropositive individuals. In some embodiments, antiviral agents are useful in the methods and compositions described herein for the prevention of HSV transmission from HSV seropositive individuals to HSV seronegative individuals. In some embodiments, an HSV seronegative individual is treated with a composition comprising an antiviral for the prevention of HSV infection in the seronegative individual. In exemplary embodiments, antiviral agents administered to an HSV seronegative individual for infection prevention include those useful for acute and/or suppressive therapy in HSV seropositive individuals.

Antiviral agents useful in the compositions and methods described herein include, without limitation, any compound or a pharmaceutically acceptable salt or solvate thereof, which is capable of inhibiting replication of a virus in a cell, such as a cell in a subject, or which is effective in treating, preventing, or delaying the onset or progression of viral infection or viral diseases or conditions arising from viral infection. In some embodiments, an antiviral agent prevents or delays initial infection of an individual exposed to a virus. In some embodiments, an antiviral agent reduces the viral burden in an individual infected with a virus. In some embodiments, an antiviral agent prolongs an asymptomatic phase of a viral infection. In some embodiments, an antiviral agent maintains low viral loads of virus in infected patients. In some embodiments, an antiviral agent increases overall health or quality of life in an individual infected with a virus. In some embodiments, an antiviral agent prolongs life expectancy of an individual infected with a virus. In a non-limiting example, the effect(s) of an antiviral agent on a subject are determined by comparing a subject treated with an antiviral with a subject not treated with an antiviral, for instance, in a clinical trial to determine whether treatment with an antiviral agent is effective in treating, preventing or delaying the onset or progression of viral infection or viral diseases or conditions arising from viral infection. In some instances, the virus is a herpes virus. In some instances, the virus is HIV. In some instances, a virus refers to more than one virus, for example, an antiviral agent administered to a subject prevents or delays infection by two or more viruses after the subject is exposed to the two or more viruses. In some cases, the two or more viruses comprise HSV and HIV.

Suitable antiviral agents useful for the compositions and methods herein include, without limitation, HSV antivirals, HIV antivirals, "off-label" drugs useful for treating viral diseases or conditions, hepatitis antivirals, human papillomavirus (HPV) antivirals, and influenza antivirals. "Off-label" drugs include drugs such as cancer agents which are useful for the treatment of a viral infection or diseases or conditions resulting therefrom, which are not currently approved for viral treatment. Antiviral agents include viral protease inhibitors, viral reverse transcriptase inhibitors, viral entry inhibitors viral co-receptor inhibitors, viral fusion inhibitors, viral maturation inhibitors, viral integrase inhibitors and viral immunogens. In some embodiments, an antiviral agent comprises RNA, e.g., siRNA, that target viral nucleic acids. In some embodiments, an antiviral agent comprises a microbicide. In some embodiments, an antiviral agent is a component of a viral patch, for example, Hansaplast® herpes patch SOS or Compeed® herpes vesicle patch.

In some embodiments, an antiviral agent useful for the prevention of a viral disease comprises an antiviral agent that when administered to an individual seronegative for infection with the viral disease, the seronegative individual has a decreased chance of becoming infected and seropositive for the virus. For example, an effective amount of an antiviral agent administered alone or in combination with one or more additional antiviral agents to a seronegative subject or population of subjects, reduces the risk of the subject or population of subjects becoming infected with a virus by at least about 10%, 20%, 30%, 40%, 50%, 60%, 70%, 80%, 90%, 95%, or 100%. In some embodiments, an antiviral agent useful for the prevention of one viral disease is also useful for the prevention of a second viral disease. For example, in some cases an HIV antiviral used to treat HIV seropositive individuals is also useful for the administration to an HSV seronegative individual to prevent the HSV seronegative individual from infection with HSV.

In some embodiments, an antiviral agent useful for the prevention of a viral disease is an HSV antiviral. In some cases, the viral disease is caused by a herpes virus, for example, HSV. In some cases, the viral disease is caused by infection with HIV. In some cases, the antiviral agent is useful for the prevention of two or more viral diseases. As a non-limiting example, the HSV antiviral is useful for the prevention of HSV and HIV. In some embodiments, an HSV antiviral includes an antiviral antibody, such as an anti-HSV antibody. Antibodies include monoclonal and polyclonal antibodies and include fragments and portions thereof, for example, Fab fragments.

In some embodiments, an antiviral agent useful for the prevention of a viral disease is an HIV antiviral. In some cases, the viral disease is caused by a herpes virus, for example, HSV. In some cases, the viral disease is caused by infection with HIV. In some cases, the viral disease is caused by a herpes virus, for example, HSV. In some cases, the antiviral agent is useful for the prevention of two or more viral diseases. As a non-limiting example, the HIV antiviral is useful for the prevention of HSV and HIV. In some embodiments, an HIV antiviral includes an antiviral antibody, such as an anti-HIV antibody.

HSV antiviral agents useful in the compositions and methods described herein include nucleoside analogs that selectively target viral DNA polymerase. In some cases, an HSV antiviral agent targets thymidine kinase. For example, HSV antiviral agents can be analogs of the natural nucleoside triphosphate dGTP, and are selectively phosphorylated in virus infected cells by viral thymidine kinase. The phosphorylation of these analogs is minimal in uninfected cells, and cellular DNA polymerases have lower affinities for the antiviral triphosphates compared with HSV polymerases. Viral DNA polymerase is selectively inhibited as viral incorporation of the analogue triphosphate into a growing DNA chain prevents continued chain elongation. Non-limiting examples of these nucleoside triphosphate analogs include acyclovir, valacyclovir, peniciclovir and famciclovir. In some cases, an HSV antiviral agent targets HSV protease. In some cases, an HSV antiviral agent inhibits viral helicase-primase complex. A non-limiting example of a helicase-primase inhibitor is pritelivir. In some cases wherein a virus is resistant to a nucleoside analog, the virus may be susceptible to a helicase-primase inhibitor or a combination of nucleoside analog and helicase-primase inhibitor. In some instances, a composition described herein comprises both a nucleoside analog and a helicase-primase inhibitor.

Non-limiting examples of HSV antiviral agents for use in the compositions and methods described herein include valacyclovir, acyclovir, famciclovir, pritelivir, penciclovir, ganciclovir, valganciclovir, cidofovir, foscarnet, darunavir, glycyrrhizic acid, glutamine, FV-100, ASP2151, me-609, ASP2151, topical VDO, PEG-formulation (Devirex AG), vidarabine, cidofovir, crofelemer (SP-303T), EPB-348, CMX001, V212, NB-001, squaric acid, ionic zinc, sorivudine (ARYS-01), trifluridine, 882C87, merlin (ethanol and glycolic acid mixture), vitamin C, AIC316, versabase gel with *Sarracenia purpurea*, UB-621, lysine, edoxudine, brivudine, cytarabine, docosanol, tromantadine, resiquimod (R-848), imiquimod, resiquimod, tenofovir, tenofovir disoproxil fumarate, tenofovir alafenamide fumarate, and salts, solvates, and/or combinations thereof.

In some embodiments, an antiviral agent of a composition described herein comprises a vaccine that provides acquired immunity to a disease caused by a virus. In some cases, the composition further comprises an adjuvant. In some embodiments, described herein are compositions comprising one or more viral vaccines useful for the prevention of HSV transmission. In some embodiments, described herein are compositions comprising one or more viral vaccines useful for the prevention of HIV transmission. In some embodiments, described herein are compositions comprising one or more viral vaccines useful for the prevention of HSV and HIV transmission. In some cases, the viral vaccine compositions further comprise or are administered with one or more additional antiviral agents. In some cases, the viral vaccine compositions further comprise or are administered with one or more birth control methods.

In some embodiments, a viral vaccine useful for the prevention of one viral disease is also useful for the prevention of a second viral disease. For example, in some cases an HSV vaccine is useful for the prevention of HIV infection in an HIV seronegative individual. As another example, an HIV vaccine is useful for the prevention of HSV infection in an HSV seronegative individual. In some cases, one or more viral vaccines are useful for the prevention of one or more viral diseases. As a non-limiting example, an HIV vaccine is useful for the prevention of HSV and HIV infection in a seronegative individual. As another example, an HSV vaccine is useful for the prevention of HSV and HIV infection in a seronegative individual.

Non-limiting examples of HSV vaccines useful as antiviral agents in compositions and methods described herein include GSK208141 (gD2t, GSK glycoprotein D (gD)-Alum/3-deacylated form of monophosphoryl lipid A), Herpes Zoster GSK 1437173A, gD2-AS04, Havrix™, gD-Alum, Zostavax/Zoster vaccine (V211, V212, V210), HSV529, HerpV (AG-707 rh-Hsc70 polyvalent peptide complex), VCL-HB01, VCL-HM01, pPJV7630, GEN-003, SPL7013 gel (VivaGel™) GSK324332A, and salts, solvates, and/or combinations thereof. Non-limiting examples of HIV vaccines useful as antiviral agents in compositions and methods described herein include GSK1492903A, VariZIG™, and Varivax. Non-limiting examples of adjuvants useful in antiviral compositions include QS-21, Matrix-M2, A1K(SO4)2, AlNa(SO4)2, AlNH4 (SO4), silica, alum, Al(OH)3, Ca3(PO4)2, kaolin, carbon, aluminum hydroxide, muramyl dipeptides, N-acetyl-muramyl-L-threonyl-D-isoglutamine (thr-DMP), N-acetyl-nornuramyl-L-alanyl-D-isoglutamine (CGP 11687, nor-MDP), N-acetylmuramyul-L-alanyl-D-isoglutaminyl-L-alanine-2-(1 '2'-dipalmitoyl-sn-glycero-3-hydroxphosphoryloxy)-ethylamine (CGP 19835A, MTP-PE), RIBI (MPL®+TDM+CWS) in a 2 percent squalene/Tween-80 emulsion, lipopolysaccharides, Freund's Complete Adjuvant (FCA), Freund's Incomplete Adjuvants, Merck Adjuvant 65, polynucleotides (e.g., poly IC and poly AU acids), wax D from *Mycobacterium tuberculosis*, substances found in *Corynebacterium parvum, Bordetella pertussis*, and members of the genus *Brucella*, Titermax, ISCOMS, Quil A, ALUN, Lipid A and derivatives, choleratoxin derivatives, HSP derivatives, LPS derivatives, synthetic peptide matrixes or GMDP, interleukin 1, interleukin 2, and Montanide ISA-51.

In some embodiments, an antiviral agent inhibits viral entry and/or viral fusion. Examples of entry and/or fusion inhibitors include, without limitation, maraviroc, enfuvirtide (T-20), vicriviroc, cenicriviroc, lbalizumab, fostemsavir (BMS-663068), ibalizumab (TMB-355, TNX-355), PRO 140, b12 antibody, DCM205, DARPins, caprine antibody, VIR-576, AMD11070, PR0542, SCH-C, T-1249, cyanovirin, griffithsen, lectins, pentafuside, and salts, solvates, and/or combinations thereof. In some embodiments, an antiviral agent is an HIV viral entry inhibitor. HIV viral entry inhibitors include, without limitation, CD4 receptor binding inhibitors, CD4 mimics, gp120 mimics, gp41 antagonists, anti-CD4 antibodies, CCR5 antagonists (e.g., zinc finger inhibitors), and CXCR4 co-receptor antagonists.

In some embodiments, an antiviral agent is an integrase inhibitor. Non-limiting examples of integrase inhibitors include dolutegravir, elvitegravir, raltegravir, globoidnan A, MK-2048, BI224436, cabotegravir, GSK 1265744, GSK-572, MK-0518, and salts, solvates, or combinations thereof.

In some embodiments, an antiviral agent is a reverse transcriptase inhibitor, for example, a nucleotide reverse transcriptase inhibitor and/or nucleoside reverse transcriptase inhibitor (NRTI). In some embodiments, an antiviral agent is a non-nucleoside reverse transcriptase inhibitor (NNRTI). NRTIs include, without limitation, abacavir, didanosine, emtrictabine, lamivudine, stavudine, tenofovir, tenofovir disoporoxil fumarate, zidovudine, apricitabine, stampidine, elvucitabine, racivir, amdoxovir, stavudine, zalcitabine, festinavir, dideoxycytidine ddC, azidothymidine, tenofovir alafenamide fumarate, entecavir, and salts, solvates, and/or combinations thereof. NNRTIs include, without limitation, delavirdine, efavirenz, etravirine (TMC-125), nevirapine, rilpivirine, doravirine, Calanolide A, capravirine, epivir, adefovir, dapivirine, lersivirine, and salts, solvates, and/or combinations thereof. Further non-limiting examples of reverse transcriptase inhibitors include alovudine, elvucitabine, TMC-278, DPC-083, amdoxovir, (−)-beta-D-2,6-diamino-purine dioxolane, MIV-210 (FLG), DFC (dexelvucitabine), dioxolane thymidine, L697639, atevirdine (U87201E), MIV-150, GSK-695634, GSK-678248, TMC-278, KP1461, KP-1212, lodenosine (FddA), 5-[(3,5-dichlorophenyl)thio]-4-isopropyl-1-(4-pyridylmethyl)imidazole-2-methanol carbamic acid, (−)-I2-D-2,6-diaminopurine dioxolane, AVX-754, BCH-13520, BMS- 56190 ((4S)-6-chloro-4-[(1E)-cyclopropylethenyl]-,-4-dihydro-4-trifluoromethyl-2 (1H)-quinazolinone), TMC-120, L697639, and salts, solvates, and/or combinations thereof.

In some embodiments, an antiviral agent is a protease inhibitor. Non-limiting examples of protease inhibitors include atazanavir, darunavir, fosamprenavir, indinavir, nelfinavir, ritonavir, saquinavir, tipranavir, lopinavir, amprenavir, telinavir (SC-52151), droxinavir, emtriva, invirase, agenerase, TMC-126, mozenavir (DMP-450), JE-2147 (AG1776), L-756423, KNI-272, DPC-681, DPC-684, BMS 186318, droxinavir (SC-55389a), DMP-323, KNI-227, 1-[(2-hydroxyethoxy)methyl]-6-(phenylthio)-thymine, AG-1859, RO-033-4649, R-944, DMP-850, DMP-851, brecanavir (GW640385), and salts, solvates, and/or combinations thereof.

In some embodiments, an antiviral agent is a microbicide. Non-limiting examples of microbicides include detergents such as nonoxynol-9, sodium dodecyl sulfate and Savvy (1.0% C31G). In some embodiments, the microbicide reduces the pH of vaginal secretions, for example, Buffer-Gel®. In some embodiments, an antiviral agent comprises a polyanion microbicide. Examples of polyanion microbicides are carrageenans. Carrageenans are linear sulfated polysaccharides which can be used by viruses for initial attachment to a cell membrane, thus acting as decoy receptors for viral binding. In some embodiments, a microbicide is a nanoscale dendrimeric molecule which binds to a virus. An example of a nanoscale dendrimeric molecule is the active component of VivaGel®. An additional example of a microbicide is PRO-2000, also known as PRO 2000/5, naphthalene 2-sulfonate polymer, or polynaphthalene sulphonate.

In some embodiments, a composition comprises an active agent that is used as an antiviral "off-label" drug for the treatment or prevention of viral infection. In some cases, a composition is administered with an "off-label" drug. Non-limiting examples of "off-label" drugs useful with or in the compositions provided herein include amphotericin B, sulfamethoxazole, trimethoprim, clarithromycin, daunorubicin, fluconazole, doxorubicin, anidulafungin, immune globulin, gamma globulin, dronabinol, megestrol acetate, atovaquone, rifabutin, pentamidine, trimetrexate glucuronate, leucovorin, alitretinoin gel, erythropoeetin, calcium hydroxylapatite, poly-L-lactic acid, somatropin rDNA, itraconazole, paclitaxel, voriconazole, cidofovir, fomivirsen, azithromycin, and salts, solvates, and/or combinations thereof. In some embodiments, an antiviral agent is a cancer drug, for example, ruxolitinib or tocilizumab.

In some embodiments, a composition for preventing or treating a viral infection comprises at least one of the following antiviral agents: bevirimat, TRIM5alpha, Tat antagonists, trichosanthin, abzyme, calanolide A, ceragenin, cyanovirin-N, diarylpyrimidines, epigallocatechin gallate (EGCG), foscarnet, griffithsin, hydroxycarbamide, miltefosine, portmanteau inhibitors, scytovirin, seliciclib, synergistic enhancers, tre recombinase, zinc finger protein transcription factor, KP-1461, BIT225, aplaviroc, atevirdine, brecanavir, capravirine, dexelvucitabine, emivirine, lersivirine, lodenosine, loviride, fomivirsen, glycyrrhizic acid (anti-inflammatory, inhibits 1 1beta-hydroxysteroid dehydrogenase), zinc salts, cellulose sulfate, cyclodextrins, dextrin-2-sulfate, NCP7 inhibitors, AMD-3100, BMS-806, BMS-793, C31G, carrageenan, CD4-IgG2, cellulose acetate phthalate, mAb 2G12, mAb b12, Merck 167, plant lectins, poly naphthalene sulfate, poly sulfo-styrene, PRO2000, PSC-Rantes, SCH-C, SCH-D, T-20, TMC-125, UC-781, UK-427, UK-857, or salts, solvates, or combinations thereof.

In some embodiments, a composition for preventing or treating a viral infection comprises at least one of the following antiviral agents: Carraguard (PC-515), brincidofovir (CMX001), zidovudine, virus-specific cytotoxic T cells, idoxuridine, podophyllotoxin, rifampicin, metisazone, interferon alfa 2b (Intron-A), peginterferon alfa-2a, ribavirin, moroxydine, pleconaril, BCX4430, taribavirin (viramidine, ICN 3142), favipiravir, rintatolimod, ibacitabine, (5-iodo-2'-deoxycytidine), methisazone (metisazone), ampligen, arbidol, Atripla®, combivir, imunovir, nexavir, trizivir, truvada, lamivudine, dideoxyadenosine, floxuridine, idozuridine, inosine pranobex, 2'-deoxy-5-(methylamino) uridine, digoxin, imiquimod, interferon type III, interferon type II, interferon type I, tea tree oil, or salts, solvates, or combinations thereof.

In some embodiments, a composition for preventing or treating a viral infection comprises a hepatitis antiviral agent comprising tenofovir, glycyrrhizic acid, fialuridine, telbivudine, adefovir, etecavir, lamivudine, clevudine, asunaprevir, boceprevir, faldaprevir, grazoprevir, paritaprevir, ritonavir, telaprevir, simeprevir, sofosbuvir, ACH-3102, daclatasvir, deleobuvir, elbasvir, ledipasvir, MK-3682, MK-8408, samatasvir, ombitasvir, entecavir, or salts, solvates, or combinations thereof.

In some embodiments, a composition for preventing or treating a viral infection comprises an influenza antiviral comprising elderberry *sambucus*, umifenovir, amantadine, rimantadine, oseltamivir, zanamivir, peramivir, laninamivir, or salts, solvates, or combinations thereof.

In some embodiments, a composition for preventing or treating a viral infection comprises an HPV antiviral comprising pyrrole polyamides, lopinavir, carrageenan, zinc, or salts, solvates, or combinations thereof.

In some aspects, provided are compositions comprising an antiviral agent in combination with at least one additional active agent, wherein a combination refers to a composition comprising a combination of two or more active agents or a composition comprising an antiviral agent administered in combination with one or more additional active agents. In some cases, a combination of active agents results in a synergistic effect in antiviral activity. A synergistic effect may be calculated, in one example, using the Sigmoid-Emax, Loewe, and median-effect equations.

In some embodiments, a composition comprising an antiviral agent useful for the prevention and/or treatment of a viral disease further comprises or is administered in combination with another drug or active agent for the prevention and/or treatment of the viral disease. In some cases, the composition comprises or is administered with a vaccine, gene therapy treatment, cytokine, TAT inhibitor, immunomodulator or combinations thereof. In some cases, the composition comprises or is administered with an anti-infective agent comprising an antifungal agent, an antibacterial, an antiprotozoal agent or combinations thereof. In some cases, the composition comprises or is administered with an immunomodulator, for example, pentamidine isethionate, autologous CD8+ infusion, gamma-interferon immunoglobulins, thymic peptides, IGF-I, anti-Leu3A, auto vaccination, biostimulation, extracorporeal photophoresis, cyclosporin, rapamycin, FK-565, FK-506, GCSF, GM-CSF, hyperthermia, isopinosine, rVIG, HIVIG, passive immunotherapy and polio vaccine hyperimmunization, or combinations thereof. In some embodiments, a composition comprises or is administered with a pharmacokinetic enhancer, for example, cobicistat. In some embodiments, a composition comprises or is administered with a synergistic enhancer, for example, chloroquine/quinoline enhancers of protease inhibitors, CYP3A4, hydroxyurea, leflunomide, mycophenolic acid, resveratrol, or combinations thereof.

In some embodiments, a composition useful in the methods described herein comprises a combination of active agents, at least one of which is an antiviral agent. Examples of combinations include, without limitation, maravoric and emtricitabine; maravoric, emtricitabine and raltegravir; raltegravir and emtricitabine; raltegravir and lamivudine; abacavir and lamivudine; abacavir, dolutegravir, and lamivudine; abacavir, lamivudine, and zidovudine; atazanavir and cobicistat; darunavir and cobicistat; efavirenz, emtricitabine, and tenofovir; elvitegravir, cobicistat, emtricitabine, and tenofovir; emtricitabine, rilpivirine, and tenofovir; lamivudine and raltegravir; lamivudine and zidovudine; lopinavir and ritonavir; emtricitabine and tenofovir disoproxil fumarate; lamivudine and zidovudine; lopinavir and ritonavir; inosine, acetamidobenzoic acid and dimethylaminoisopropanol; and salts, solvates, and/or combinations thereof.

In some embodiments, a composition useful in the methods described herein for the prevention of viral infection (e.g., HSV) in a seronegative subject and/or the treatment of a viral infection (e.g., HSV suppression treatment) in a seropositive subject comprises one or more of the following active agents: valacyclovir, acyclovir, famciclovir, pritelivir, penciclovir, ganciclovir, valganciclovi, cidofovir, foscarnet, darunavir, glycyrrhizic acid, glutamine, FV-100, ASP2151, me-609, ASP2151, topical VDO, PEG-formulation (Devirex AG), vidarabine, cidofovir, crofelemer (SP-303T), EPB-348, CMX001, V212, NB-001, squaric acid, ionic zinc, sorivudine (ARYS-01), trifluridine, 882C87, merlin (ethanol and glycolic acid mixture), vitamin C, AIC316, versabase gel with *Sarracenia purpurea*, UB-621, lysine, edoxudine, brivudine, cytarabine, docosanol, tromantadine, resiquimod (R-848), imiquimod, resiquimod, tenofovir, tenofovir disoproxil fumarate, tenofovir alafenamide fumarate, include GSK208141 (gD2t, GSK glycoprotein D (gD)-Alum/3-deacylated form of monophosphoryl lipid A), Herpes Zoster GSK 1437173A, gD2-AS04, Havrix™ gD-Alum, Zostavax/Zoster vaccine (V211, V212, V210), HSV529, HerpV (AG-707 rh-Hsc70 polyvalent peptide complex), VCL-HB01, VCL-HM01, pPJV7630, GEN-003, SPL7013 gel (VivaGel™), GSK324332A, GSK1492903A, VariZIG™, and Varivax, maraviroc, enfuvirtide, vicriviroc, cenicriviroc, lbalizumab, fostemsavir (BMS-663068), ibalizumab (TMB-355, TNX-355), PRO 140, b12 antibody, DCM205, DARPins, caprine antibody, VIR-576, enfuvirtide (T-20), AMD11070, PR0542, SCH-C, T-1249, cyanovirin, griffithsen, lectins, pentafuside, dolutegravir, elvitegravir, raltegravir, globoidnan A, MK-2048, BI224436, cabotegravir, GSK 1265744, GSK-572, MK-0518, abacavir, didanosine, emtrictabine, lamivudine, stavudine, tenofovir, tenofovir disoporoxil fumarate, zidovudine, apricitabine, stampidine, elvucitabine, racivir, amdoxovir, stavudine, zalcitabine, festinavir, dideoxycytidine ddC, azidothymidine, tenofovir alafenamide fumarate, entecavir, delavirdine, efavirenz, etravirine (TMC-125), nevirapine, rilpivirine, doravirine, Calanolide A, capravirine, epivir, adefovir, dapivirine, lersivirine, alovudine, elvucitabine, TMC-278, DPC-083, amdoxovir, (−)-beta-D-2,6-diamino-purine dioxolane, MIV-210 (FLG), DFC (dexelvucitabine), dioxolane thymidine, L697639, atevirdine (U87201E), MIV-150, GSK-695634, GSK-678248, TMC-278, KP1461, KP-1212, lodenosine (FddA), 5-[(3,5-dichlorophenyl)thio]-4-isopropyl-1-(4-pyridylmethyl)imidazole-2-methanol carbamic acid, (−)-I2-D-2,6-diaminopurine dioxolane, AVX-754, BCH-13520, BMS-56190 ((4S)-6-chloro-4-[(1E)-cyclopropylethenyl]-3,-4-dihydro-4-trifluoromethyl-2 (1H)-quinazolinone), TMC-120, L697639, atazanavir, darunavir, fosamprenavir, indinavir, nelfinavir, ritonavir, saquinavir, tipranavir, lopinavir, amprenavir, telinavir (SC-52151), droxinavir, emtriva, invirase, agenerase, TMC-126, mozenavir (DMP-450), JE-2147 (AG1776), L-756423, KNI-272, DPC-681, DPC-684, BMS 186318, droxinavir (SC-55389a), DMP-323, KNI-227, 1-[(2-hydroxyethoxy)methyl]-6-(phenylthio)-thymine, AG-1859, RO-033-4649, R-944, DMP-850, DMP-851, brecanavir (GW640385), nonoxynol-9, sodium dodecyl sulfate, Savvy (1.0% C31G), BufferGel®, carrageenans, Viva-Gel®, PRO-2000, also known as PRO 2000/5, naphthalene 2-sulfonate polymer, or polynaphthalene sulphonate, amphotericin B, sulfamethoxazole, trimethoprim, clarithromycin, daunorubicin, fluconazole, doxorubicin, anidulafungin, immune globulin, gamma globulin, dronabinol, megestrol acetate, atovaquone, rifabutin, pentamidine, trimetrexate glucuronate, leucovorin, alitretinoin gel, erythropoeetin, calcium hydroxylapatite, poly-L-lactic acid, somatropin rDNA, itraconazole, paclitaxel, voriconazole, cidofovir, fomivirsen, azithromycin, ruxolitinib, tocilizumab, bevirimat, TRIM5alpha, Tat antagonists, trichosanthin, abzyme, calanolide A, ceragenin, cyanovirin-N, diarylpyrimidines, epigallocatechin gallate (EGCG), foscarnet, griffithsin, hydroxycarbamide, miltefosine, portmanteau inhibitors, scytovirin, seliciclib, synergistic enhancers, tre recombinase, zinc finger protein transcription factor, KP-1461, BIT225, aplaviroc, atevirdine, brecanavir, capravirine, dexelvucitabine, emivirine, lersivirine, lodenosine, loviride, fomivirsen, glycyrrhizic acid (anti-inflammatory, inhibits 1 1beta-hydroxysteroid dehydrogenase), zinc salts, cellulose sulfate, cyclodextrins, dextrin-2-sulfate, NCP7 inhibitors, AMD-3100, BMS-806, BMS-793, C31G, carrageenan, CD4-IgG2, cellulose acetate phthalate, mAb 2G12, mAb b12, Merck 167, plant lectins, poly naphthalene sulfate, poly sulfo-styrene, PRO2000, PSC-Rantes, SCH-C, SCH-D, T-20, TMC-125, UC-781, UK-427, UK-857, Carraguard (PC-515), brincidofovir (CMX001), zidovudine, virus-specific cytotoxic T cells, idoxuridine, podophyllotoxin, rifampicin, metisazone, interferon alfa 2b (Intron-A), peginterferon alfa-2a, ribavirin, moroxydine, pleconaril, BCX4430, taribavirin (viramidine, ICN 3142), favipiravir, rintatolimod, ibacitabine, (5-iodo-2'-deoxycytidine), methisazone (metisazone), ampligen, arbidol, Atripla®, combivir, imunovir, nexavir, trizivir, truvada, lamivudine, dideoxyadenosine, floxuridine, idozuridine, inosine pranobex, 2'-deoxy-5-(methylamino)uridine, digoxin, imiquimod, interferon type III, interferon type II, interferon type I, tea tree oil, glycyrrhizic acid, fialuridine, telbivudine, adefovir, etecavir, lamivudine, clevudine, asunaprevir, boceprevir, faldaprevir, grazoprevir, paritaprevir, ritonavir, telaprevir, simeprevir, sofosbuvir, ACH-3102, daclatasvir, deleobuvir, elbasvir, ledipasvir, MK-3682, MK-8408, samatasvir, ombitasvir, entecavir, elderberry *sambucus*, umifenovir, amantadine, rimantadine, oseltamivir, zanamivir, peramivir, laninamivir, pyrrole polyamides, lopinavir, or salts, solvates, and/or combinations thereof. In some embodiments, the composition further comprises and/or is administered with one or more additional antiviral agents, such as an HSV and/or HIV antiviral. In some embodiments, the composition further comprises and/or is administered with one or more contraceptive agents.

In some embodiments, a composition useful in the methods described herein for the prevention of HSV infection in a seronegative subject and/or the treatment of HSV in a seropositive subject comprises one or more of the following antivirals: valacyclovir, acyclovir, famciclovir, pritelivir, penciclovir, ganciclovir, valganciclovi, cidofovir, foscarnet, darunavir, glycyrrhizic acid, glutamine, FV-100, ASP2151, me-609, ASP2151, topical VDO, PEG-formulation (Devirex AG), vidarabine, cidofovir, crofelemer (SP-303T), EPB-348, CMX001, V212, NB-001, squaric acid, ionic zinc, sorivudine (ARYS-01), trifluridine, 882C87, merlin (ethanol and glycolic acid mixture), vitamin C, AIC316, versabase gel with *Sarracenia purpurea*, UB-621, lysine, edoxudine, brivudine, cytarabine, docosanol, tromantadine, resiquimod (R-848), imiquimod, resiquimod, tenofovir, tenofovir disoproxil fumarate, tenofovir alafenamide fumarate, or salts, solvates, or combinations thereof. In some embodiments, the composition further comprises and/or is administered with one or more additional antiviral agents, such as an HSV and/or HIV antiviral. In some embodiments, the composition further comprises and/or is administered with one or more contraceptive agents.

In some embodiments, a composition useful in the methods described herein for the prevention of viral infection (e.g., HSV) in a seronegative subject and/or the treatment of viral infection (e.g., HSV suppression treatment) in a seropositive subject comprises 2, 3, 4, 5 or more of the following active agents valacyclovir, acyclovir, famciclovir, pritelivir, penciclovir, ganciclovir, valganciclovi, cidofovir, foscarnet, darunavir, glycyrrhizic acid, glutamine, FV-100, ASP2151, me-609, ASP2151, topical VDO, PEG-formulation (Devirex AG), vidarabine, cidofovir, crofelemer (SP-303T), EPB-348, CMX001, V212, NB-001, squaric acid, ionic zinc, sorivudine (ARYS-01), trifluridine, 882C87, merlin (ethanol and glycolic acid mixture), vitamin C, AIC316, versabase gel with *Sarracenia purpurea*, UB-621, lysine, edoxudine, brivudine, cytarabine, docosanol, tromantadine, resiquimod (R-848), imiquimod, resiquimod, tenofovir, tenofovir disoproxil fumarate, tenofovir alafenamide fumarate, include GSK208141 (gD2t, GSK glycoprotein D (gD)-Alum/3-deacylated form of monophosphoryl lipid A), Herpes Zoster GSK 1437173A, gD2-AS04, Havrix™ gD-Alum, Zostavax/Zoster vaccine (V211, V212, V210), HSV529, HerpV (AG-707 rh-Hsc70 polyvalent peptide complex), VCL-HB01, VCL-HM01, pPJV7630, GEN-003, SPL7013 gel (Viva-Gel™), GSK324332A, GSK1492903A, VariZIG™, and Varivax, maraviroc, enfuvirtide, vicriviroc, cenicriviroc, lbalizumab, fostemsavir (BMS-663068), ibalizumab (TMB-355, TNX-355), PRO 140, b12 antibody, DCM205, DARPins, caprine antibody, VIR-576, enfuvirtide (T-20), AMD11070, PR0542, SCH-C, T-1249, cyanovirin, griffithsen, lectins, pentafuside, dolutegravir, elvitegravir, raltegravir, globoidnan A, MK-2048, BI224436, cabotegravir, GSK 1265744, GSK-572, MK-0518, abacavir, didanosine, emtrictabine, lamivudine, stavudine, tenofovir, tenofovir disoporoxil fumarate, zidovudine, apricitabine, stampidine, elvucitabine, racivir, amdoxovir, stavudine, zalcitabine, festinavir, dideoxycytidine ddC, azidothymidine, tenofovir alafenamide fumarate, entecavir, delavirdine, efavirenz, etravirine (TMC-125), nevirapine, rilpivirine, doravirine, Calanolide A, capravirine, epivir, adefovir, dapivirine, lersivirine, alovudine, elvucitabine, TMC-278, DPC-083, amdoxovir, (−)-beta-D-2,6-diamino-purine dioxolane, MIV-210 (FLG), DFC (dexelvucitabine), dioxolane thymidine, L697639, atevirdine (U87201E), MIV-150, GSK-695634, GSK-678248, TMC-278, KP1461, KP-1212, lodenosine (FddA), 5-[(3,5-dichlorophenyl)thio]-4-isopropyl-1-(4-pyridylmethyl)imidazole-2-methanol carbamic acid, (−)-I2-D-2,6-diaminopurine dioxolane, AVX-754, BCH-13520, BMS-56190 ((4S)-6-chloro-4-[(1E)-cyclopropylethenyl]-3,-4-dihydro-4-trifluoromethyl-2 (1H)-quinazolinone), TMC-120, L697639, atazanavir, darunavir, fosamprenavir, indinavir, nelfinavir, ritonavir, saquinavir, tipranavir, lopinavir, amprenavir, telinavir (SC-52151), droxinavir, emtriva, invirase, agenerase, TMC-126, mozenavir (DMP-450), JE-2147 (AG1776), L-756423, KNI-272, DPC-681, DPC-684, BMS 186318, droxinavir (SC-55389a), DMP-323, KNI-227, 1-[(2-hydroxyethoxy)methyl]-6-(phenylthio)-thymine, AG-1859, RO-033-4649, R-944, DMP-850, DMP-851, brecanavir (GW640385), nonoxynol-9, sodium dodecyl sulfate, Savvy (1.0% C31G), BufferGel®, carrageenans, Viva-Gel®, PRO-2000, also known as PRO 2000/5, naphthalene 2-sulfonate polymer, or polynaphthalene sulphonate, amphotericin B, sulfamethoxazole, trimethoprim, clarithromycin, daunorubicin, fluconazole, doxorubicin, anidulafungin, immune globulin, gamma globulin, dronabinol, megestrol acetate, atovaquone, rifabutin, pentamidine, trimetrexate glucuronate, leucovorin, alitretinoin gel, erythropoeetin, calcium hydroxylapatite, poly-L-lactic acid, somatropin rDNA, itraconazole, paclitaxel, voriconazole, cidofovir, fomivirsen, azithromycin, ruxolitinib, tocilizumab, bevirimat, TRIM5alpha, Tat antagonists, trichosanthin, abzyme, calanolide A, ceragenin, cyanovirin-N, diarylpyrimidines, epigallocatechin gallate (EGCG), foscarnet, griffithsin, hydroxycarbamide, miltefosine, portmanteau inhibitors, scytovirin, seliciclib, synergistic enhancers, tre recombinase, zinc finger protein transcription factor, KP-1461, BIT225, aplaviroc, atevirdine, brecanavir, capravirine, dexelvucitabine, emivirine, lersivirine, lodenosine, loviride, fomivirsen, glycyrrhizic acid (anti-inflammatory, inhibits 1 1beta-hydroxysteroid dehydrogenase), zinc salts, cellulose sulfate, cyclodextrins, dextrin-2-sulfate, NCP7 inhibitors, AMD-3100, BMS-806, BMS-793, C31G, carrageenan, CD4-IgG2, cellulose acetate phthalate, mAb 2G12, mAb b12, Merck 167, plant lectins, poly naphthalene sulfate, poly sulfo-styrene, PRO2000, PSC-Rantes, SCH-C, SCH-D, T-20, TMC-125, UC-781, UK-427, UK-857, Carraguard (PC-515), brincidofovir (CMX001), zidovudine, virus-specific cytotoxic T cells, idoxuridine, podophyllotoxin, rifampicin, metisazone, interferon alfa 2b (Intron-A), peginterferon alfa-2a, ribavirin, moroxydine, pleconaril, BCX4430, taribavirin (viramidine, ICN 3142), favipiravir, rintatolimod, ibacitabine, (5-iodo-2'-deoxycytidine), methisazone (metisazone), ampligen, arbidol, Atripla®, combivir, imunovir, nexavir, trizivir, truvada, lamivudine, dideoxyadenosine, floxuridine, idozuridine, inosine pranobex, 2'-deoxy-5-(methylamino)uridine, digoxin, imiquimod, interferon type III, interferon type II, interferon type I, tea tree oil, glycyrrhizic acid, fialuridine, telbivudine, adefovir, etecavir, lamivudine, clevudine, asunaprevir, boceprevir, faldaprevir, grazoprevir, paritaprevir, ritonavir, telaprevir, simeprevir, sofosbuvir, ACH-3102, daclatasvir, deleobuvir, elbasvir, ledipasvir, MK-3682, MK-8408, samatasvir, ombitasvir, entecavir, elderberry *sambucus*, umifenovir, amantadine, rimantadine, oseltamivir, zanamivir, peramivir, laninamivir, pyrrole polyamides, lopinavir, or salts, solvates, and/or combinations thereof. In some embodiments, the composition further comprises and/or is administered with one or more additional antiviral agents, such as an HSV and/or HIV antiviral. In some embodiments, the composition further comprises and/or is administered with one or more contraceptive agents.

In some embodiments, a composition useful in the methods described herein for the prevention of HSV infection in a seronegative subject and/or the treatment of HSV in a seropositive subject comprises 2, 3, 4, 5 or more of the following antiviral agents: valacyclovir, acyclovir, famciclovir, pritelivir, penciclovir, ganciclovir, valganciclovi, cidofovir, foscarnet, darunavir, glycyrrhizic acid, glutamine, FV-100, ASP2151, me-609, ASP2151, topical VDO, PEG-formulation (Devirex AG), vidarabine, cidofovir, crofelemer (SP-303T), EPB-348, CMX001, V212, NB-001, squaric acid, ionic zinc, sorivudine (ARYS-01), trifluridine, 882C87, merlin (ethanol and glycolic acid mixture), vitamin C, AIC316, versabase gel with *Sarracenia purpurea*, UB-621, lysine, edoxudine, brivudine, cytarabine, docosanol, tromantadine, resiquimod (R-848), imiquimod, resiquimod, tenofovir, tenofovir disoproxil fumarate, tenofovir alafenamide fumarate, or salts, solvates, or combinations thereof. In some embodiments, the composition further comprises and/or is administered with one or more additional antiviral agents, such as an HSV and/or HIV antiviral. In some embodiments, the composition further comprises and/or is administered with one or more contraceptive agents.

In some embodiments, a composition useful in the methods described herein for the prevention of viral infection (e.g., HSV) in a seronegative subject and/or the treatment of viral infection (e.g., HSV suppression treatment) in a seropositive subject comprises one or more of the following active agents: valacyclovir, acyclovir, famciclovir, pritelivir, penciclovir, ganciclovir, valganciclovi, cidofovir, foscarnet, darunavir, glycyrrhizic acid, glutamine, FV-100, ASP2151, me-609, ASP2151, topical VDO, PEG-formulation (Devirex AG), vidarabine, cidofovir, crofelemer (SP-303T), EPB-348, CMX001, V212, NB-001, squaric acid, ionic zinc, sorivudine (ARYS-01), trifluridine, 882C87, merlin (ethanol and glycolic acid mixture), vitamin C, AIC316, versabase gel with *Sarracenia purpurea*, UB-621, lysine, edoxudine, brivudine, cytarabine, docosanol, tromantadine, resiquimod (R-848), imiquimod, resiquimod, tenofovir, tenofovir disoproxil fumarate, tenofovir alafenamide fumarate, or salts, solvates or combinations thereof, and one or more of the following active agents: maraviroc, enfuvirtide, vicriviroc, cenicriviroc, lbalizumab, fostemsavir (BMS-663068), ibalizumab (TMB-355, TNX-355), PRO 140, b12 antibody, DCM205, DARPins, caprine antibody, VIR-576, enfuvirtide (T-20), AMD11070, PR0542, SCH-C, T-1249, cyanovirin, griffithsen, lectins, pentafuside, dolutegravir, elvitegravir, raltegravir, globoidnan A, MK-2048, B1224436, cabotegravir, GSK 1265744, GSK-572, MK-0518, abacavir, didanosine, emtrictabine, lamivudine, stavudine, tenofovir, tenofovir disoporoxil fumarate, zidovudine, apricitabine, stampidine, elvucitabine, racivir, amdoxovir, stavudine, zalcitabine, festinavir, dideoxycytidine ddC, azidothymidine, tenofovir alafenamide fumarate, entecavir, delavirdine, efavirenz, etravirine (TMC-125), nevirapine, rilpivirine, doravirine, Calanolide A, capravirine, epivir, adefovir, dapivirine, lersivirine, alovudine, elvucitabine, TMC-278, DPC-083, amdoxovir, (−)-beta-D-2,6-diamino-purine dioxolane, MIV-210 (FLG), DFC (dexelvucitabine), dioxolane thymidine, L697639, atevirdine (U87201E), MIV-150, GSK-695634, GSK-678248, TMC-278, KP1461, KP-1212, lodenosine (FddA), 5-[(3,5-dichlorophenyl)thio]-4-isopropyl-1-(4-pyridylmethyl)imidazole-2-methanol carbamic acid, (−)-I2-D-2,6-diaminopurine dioxolane, AVX-754, BCH-13520, BMS-56190 ((4S)-6-chloro-4-[(1E)-cyclopropylethenyl]-3,-4-dihydro-4-trifluoromethyl-2 (1H)-quinazolinone), TMC-120, L697639, atazanavir, darunavir, fosamprenavir, indinavir, nelfinavir, ritonavir, saquinavir, tipranavir, lopinavir, amprenavir, telinavir (SC-52151), droxinavir, emtriva, invirase, agenerase, TMC-126, mozenavir (DMP-450), JE-2147 (AG1776), L-756423, KNI-272, DPC-681, DPC-684, BMS 186318, droxinavir (SC-55389a), DMP-323, KNI-227, 1-[(2-hydroxyethoxy)methyl]-6-(phenylthio)-thymine, AG-1859, RO-033-4649, R-944, DMP-850, DMP-851, brecanavir (GW640385), or salts, solvates, or combinations thereof. In some embodiments, the composition further comprises and/or is administered with one or more additional antiviral agents, such as an HSV and/or HIV antiviral. In some embodiments, the composition further comprises and/or is administered with one or more contraceptive agents.

In some embodiments, a composition useful in the methods described herein for the prevention of HSV infection in a seronegative subject and/or the treatment of HSV in a seropositive subject comprises 2, 3, 4, 5 or more of the following active agents: valacyclovir, acyclovir, famciclovir, pritelivir, penciclovir, ganciclovir, valganciclovi, cidofovir, foscarnet, darunavir, glycyrrhizic acid, glutamine, FV-100, ASP2151, me-609, ASP2151, topical VDO, PEG-formulation (Devirex AG), vidarabine, cidofovir, crofelemer (SP-303T), EPB-348, CMX001, V212, NB-001, squaric acid, ionic zinc, sorivudine (ARYS-01), trifluridine, 882C87, merlin (ethanol and glycolic acid mixture), vitamin C, AIC316, versabase gel with *Sarracenia purpurea*, UB-621, lysine, edoxudine, brivudine, cytarabine, docosanol, tromantadine, resiquimod (R-848), imiquimod, resiquimod, tenofovir, tenofovir disoproxil fumarate, tenofovir alafenamide fumarate, or salts, solvates, or combinations thereof; and 2, 3, 4, 5 or more of the following active agents: maraviroc, enfuvirtide, vicriviroc, cenicriviroc, lbalizumab, fostemsavir (BMS-663068), ibalizumab (TMB-355, TNX-355), PRO 140, b12 antibody, DCM205, DARPins, caprine antibody, VIR-576, enfuvirtide (T-20), AMD11070, PR0542, SCH-C, T-1249, cyanovirin, griffithsen, lectins, pentafuside, dolutegravir, elvitegravir, raltegravir, globoidnan A, MK-2048, B1224436, cabotegravir, GSK 1265744, GSK-572, MK-0518, abacavir, didanosine, emtrictabine, lamivudine, stavudine, tenofovir, tenofovir disoporoxil fumarate, zidovudine, apricitabine, stampidine, elvucitabine, racivir, amdoxovir, stavudine, zalcitabine, festinavir, dideoxycytidine ddC, azidothymidine, tenofovir alafenamide fumarate, entecavir, delavirdine, efavirenz, etravirine (TMC-125), nevirapine, rilpivirine, doravirine, Calanolide A, capravirine, epivir, adefovir, dapivirine, lersivirine, alovudine, elvucitabine, TMC-278, DPC-083, amdoxovir, (−)-beta-D-2,6-diamino-purine dioxolane, MIV-210 (FLG), DFC (dexelvucitabine), dioxolane thymidine, L697639, atevirdine (U87201E), MIV-150, GSK-695634, GSK-678248, TMC-278, KP1461, KP-1212, lodenosine (FddA), 5-[(3,5-dichlorophenyl)thio]-4-isopropyl-1-(4-pyridylmethyl)imidazole-2-methanol carbamic acid, (−)-I2-D-2,6-diaminopurine dioxolane, AVX-754, BCH-13520, BMS-56190 ((4S)-6-chloro-4-[(1E)-cyclopropylethenyl]-3,-4-dihydro-4-trifluoromethyl-2 (1H)-quinazolinone), TMC-120, L697639, atazanavir, darunavir, fosamprenavir, indinavir, nelfinavir, ritonavir, saquinavir, tipranavir, lopinavir, amprenavir, telinavir (SC-52151), droxinavir, emtriva, invirase, agenerase, TMC-126, mozenavir (DMP-450), JE-2147 (AG1776), L-756423, KNI-272, DPC-681, DPC-684, BMS 186318, droxinavir (SC-55389a), DMP-323, KNI-227, 1-[(2-hydroxyethoxy)methyl]-6-(phenylthio)-thymine, AG-1859, RO-033-4649, R-944, DMP-850, DMP-851, brecanavir (GW640385), or salts, solvates or combinations thereof. In some embodiments, the composition further comprises and/or is administered with one or more additional antiviral agents, such as an HSV and/or HIV antiviral. In some embodiments, the composition further comprises and/or is administered with one or more contraceptive agents.

Contraceptives

Provided herein, in various aspects, are compositions comprising one or more antiviral agents and methods for the prevention of viral infection in an individual seronegative for the virus, wherein the methods comprise administering to the seronegative individual the one or more antiviral agents in combination with one or more contraceptive agents. In some cases, the antiviral compositions further comprise one or more contraceptive agents. In some cases, the antiviral compositions are administered with one or more contraceptive agents. In some embodiments, provided herein are pre-exposure compositions comprising one or more contraceptive agents. In some cases, pre-exposure compositions are administered with one or more contraceptive agents. In some embodiments, provided herein are post-exposure compositions comprising one or more contraceptive agents. In some cases, post-exposure compositions are administered with one or more contraceptive agents. In further embodiments, provided herein are compositions for the treatment of individuals seropositive for a virus comprising one or more antiviral agents and one or more contraceptive agents. In yet further embodiments, provided herein are compositions for the treatment of individuals seropositive for a virus comprising one or more antiviral agents, wherein the one or more antiviral agents are administered with one or more contraceptive agents.

Provided herein, in various aspects, are compositions comprising one or more antiviral agents and methods for the prevention of HSV infection in an HSV seronegative individual, wherein the methods comprise administering to the seronegative individual the one or more antiviral agents in combination with one or more contraceptive agents. In some embodiments, one or more antiviral agents are HSV antiviral agents. In some embodiments, one or more antiviral agents are HIV antiviral agents. In some embodiments, one or more of the antiviral agents treat or prevent HSV, HIV, or both HSV and HIV. In some cases, the antiviral compositions further comprise one or more contraceptive agents. In some cases, the antiviral compositions are administered with one or more contraceptive agents. In some embodiments, provided herein are HSV pre-exposure compositions comprising one or more contraceptive agents. In some cases, HSV pre-exposure compositions are administered with one or more contraceptive agents. In some embodiments, provided herein are HSV post-exposure compositions comprising one or more contraceptive agents. In some cases, HSV post-exposure compositions are administered with one or more contraceptive agents. In further embodiments, provided herein are compositions for the treatment of HSV seropositive individuals comprising one or more antiviral agents and one or more contraceptive agents. In yet further embodiments, provided herein are compositions for the treatment HSV seropositive individuals comprising one or more antiviral agents, wherein the one or more antiviral agents are administered with one or more contraceptive agents.

In some embodiments, a composition useful in the methods described herein for the prevention of pregnancy and the prevention of HSV infection in a seronegative subject comprises 1, 2, 3, 4 or more antiviral agents and 1, 2, 3, 4, or more contraceptive agents. In some embodiments, a composition useful in the methods described herein for the prevention of pregnancy and the prevention of HSV and HIV infection in an HSV and HIV seronegative subject comprises 1, 2, 3, 4 or more antiviral agents and 1, 2, 3, 4, or more contraceptive agents. In some embodiments, a composition useful in the methods described herein for the prevention of pregnancy and the prevention of HSV infection in a seronegative subject comprises 1, 2, 3, 4, or more antiviral agents, wherein the composition is administered with 1, 2, 3, 4, or more contraceptive agents. In some embodiments, a composition useful in the methods described herein for the prevention of pregnancy and the prevention of HSV and HIV infection in an HSV and HIV seronegative subject comprises 1, 2, 3, 4, or more antiviral agents, wherein the composition is administered with 1, 2, 3, 4, or more contraceptive agents.

In some embodiments, a contraceptive agent refers to an active agent that prevents conception or pregnancy. Non-limiting examples of contraceptive agents useful in the compositions and methods provided herein include 17a-ethinyl-levonorgestrel-17b-hydroxy-estra-4,9,11-trien-3-one, estradiol, ethinyl estradiol, levonorgestrel, medroxyprogesterone acetate, nestorone, norethindrone, ethynodiol diacetate, RU486, N9, mifepristone, mifegyne, mifeprex, 17a-ethinyl-levongestrel, 17b-hydroxy-estra-4,9,11-trien-3-one, estradiol, norgestrienone, progesterone, etonogestril (3-keto-desogestrel), progestin, megestrol, etono-progestin alonegestrel, and 17-acetoxy-16-methylene-19-norprogesterone, and salts, solvates, and/or combinations thereof.

In some instances, reference to a contraceptive agent is inclusive of a physical barrier that prevents conception or pregnancy. In some instances, the physical barrier is a condom, cervical cap, female condom or diaphragm. In some cases, a contraceptive agent is an intrauterine device. In some cases, a contraceptive agent is a spermicide (e.g., nonoxynol, octoxynol). In some instances, a contraceptive agent is an emergency contraceptive agent that is administered after an incidence of unprotected sex, for example, in high doses. Non-limiting examples of emergency contraceptive agents include levonorgestrel, combinations of estrogen and progestin, progestin, antiprogestin (e.g., ulipristal acetate, mifepristone), and salts, solvates or combinations thereof. In some instances, a contraceptive agent is administered in combination with a post-exposure composition described herein, wherein the contraceptive agent and the post-exposure composition are configured to be administered after an incidence of unprotected sex.

In some embodiments, a composition useful in the methods described herein for the prevention of pregnancy and the prevention of viral infection (e.g., HSV) in a seronegative subject comprises a) one or more of the following active agents: valacyclovir, acyclovir, famciclovir, pritelivir, penciclovir, ganciclovir, valganciclovi, cidofovir, foscarnet, darunavir, glycyrrhizic acid, glutamine, FV-100, ASP2151, me-609, ASP2151, topical VDO, PEG-formulation (Devirex AG), vidarabine, cidofovir, crofelemer (SP-303T), EPB-348, CMX001, V212, NB-001, squaric acid, ionic zinc, sorivudine (ARYS-01), trifluridine, 882C87, merlin (ethanol and glycolic acid mixture), vitamin C, AIC316, versabase gel with *Sarracenia purpurea*, UB-621, lysine, edoxudine, brivudine, cytarabine, docosanol, tromantadine, resiquimod (R-848), imiquimod, resiquimod, tenofovir, tenofovir disoproxil fumarate, tenofovir alafenamide fumarate, include GSK208141 (gD2t, GSK glycoprotein D (gD)-Alum/3-deacylated form of monophosphoryl lipid A), Herpes Zoster GSK 1437173A, gD2-AS04, Havrix™, gD-Alum, Zostavax/Zoster vaccine (V211, V212, V210), HSV529, HerpV (AG-707 rh-Hsc70 polyvalent peptide complex), VCL-HB01, VCL-HM01, pPJV7630, GEN-003, SPL7013 gel (VivaGel™), GSK324332A, GSK1492903A, VariZIG™, and Varivax, maraviroc, enfuvirtide, vicriviroc, cenicriviroc, Ibalizumab, fostemsavir (BMS-663068), ibalizumab (TMB-355, TNX-355), PRO 140, b12 antibody, DCM205, DARPins, caprine antibody, VIR-576, enfuvirtide (T-20), AMD11070, PR0542, SCH-C, T-1249, cyanovirin, griffithsen, lectins, pentafuside, dolutegravir, elvitegravir, raltegravir, globoidnan A, MK-2048, BI224436, cabotegravir, GSK 1265744, GSK-572, MK-0518, abacavir, didanosine, emtricitabine, lamivudine, stavudine, tenofovir, tenofovir disoporoxil fumarate, zidovudine, apricitabine, stampidine, elvucitabine, racivir, amdoxovir, stavudine, zalcitabine, festinavir, dideoxycytidine ddC, azidothymidine, tenofovir alafenamide fumarate, entecavir, delavirdine, efavirenz, etravirine (TMC-125), nevirapine, rilpivirine, doravirine, Calanolide A, capravirine, epivir, adefovir, dapivirine, lersivirine, alovudine, elvucitabine, TMC-278, DPC-083, amdoxovir, (−)-beta-D-2,6-diamino-purine dioxolane, MIV-210 (FLG), DFC (dexelvucitabine), dioxolane thymidine, L697639, atevirdine (U87201E), MIV-150, GSK-695634, GSK-678248, TMC-278, KP1461, KP-1212, lodenosine (FddA), 5-[(3,5-dichlorophenyl)thio]-4-isopropyl-1-(4-pyridylmethyl)imidazole-2-methanol carbamic acid, (−)-I2-D-2,6-diaminopurine dioxolane, AVX-754, BCH-13520, BMS-56190 ((4S)-6-chloro-4-[(1E)-cyclopropylethenyl]-3,-4-dihydro-4-trifluoromethyl-2 (1H)-quinazolinone), TMC-120, L697639, atazanavir, darunavir, fosamprenavir, indinavir, nelfinavir, ritonavir, saquinavir, tipranavir, lopinavir, amprenavir, telinavir (SC-52151), droxinavir, emtriva, invirase, agenerase, TMC-126, mozenavir (DMP-450), JE-2147 (AG1776), L-756423, KNI-272, DPC-681, DPC-684, BMS 186318, droxinavir (SC-55389a), DMP-323, KNI-227, 1-[(2-hydroxyethoxy)methyl]-6-(phenylthio)-thymine, AG-1859, RO-033-4649, R-944, DMP-850, DMP-851, brecanavir (GW640385), nonoxynol-9, sodium dodecyl sulfate, Savvy (1.0% C31G), BufferGel®, carrageenans, VivaGel®, PRO-2000, also known as PRO 2000/5, naphthalene 2-sulfonate polymer, or polynaphthalene sulphonate, amphotericin B, sulfamethoxazole, trimethoprim, clarithromycin, daunorubicin, fluconazole, doxorubicin, anidulafungin, immune globulin, gamma globulin, dronabinol, megestrol acetate, atovaquone, rifabutin, pentamidine, trimetrexate glucuronate, leucovorin, alitretinoin gel, erythropoeetin, calcium hydroxylapatite, poly-L-lactic acid, somatropin rDNA, itraconazole, paclitaxel, voriconazole, cidofovir, fomivirsen, azithromycin, ruxolitinib, tocilizumab, bevirimat, TRIM5alpha, Tat antagonists, trichosanthin, abzyme, calanolide A, ceragenin, cyanovirin-N, diarylpyrimidines, epigallocatechin gallate (EGCG), foscarnet, griffithsin, hydroxycarbamide, miltefosine, portmanteau inhibitors, scytovirin, seliciclib, synergistic enhancers, tre recombinase, zinc finger protein transcription factor, KP-1461, BIT225, aplaviroc, atevirdine, brecanavir, capravirine, dexelvucitabine, emivirine, lersivirine, lodenosine, loviride, fomivirsen, glycyrrhizic acid (anti-inflammatory, inhibits 1 lbeta-hydroxysteroid dehydrogenase), zinc salts, cellulose sulfate, cyclodextrins, dextrin-2-sulfate, NCP7 inhibitors, AMD-3100, BMS-806, BMS-793, C31G, carrageenan, CD4-IgG2, cellulose acetate phthalate, mAb 2G12, mAb b12, Merck 167, plant lectins, poly naphthalene sulfate, poly sulfo-styrene, PRO2000, PSC-Rantes, SCH-C, SCH-D, T-20, TMC-125, UC-781, UK-427, UK-857, Carraguard (PC-515), brincidofovir (CMX001), zidovudine, virus-specific cytotoxic T cells, idoxuridine, podophyllotoxin, rifampicin, metisazone, interferon alfa 2b (Intron-A), peginterferon alfa-2a, ribavirin, moroxydine, pleconaril, BCX4430, taribavirin (viramidine, ICN 3142), favipiravir, rintatolimod, ibacitabine, (5-iodo-2'-deoxycytidine), methisazone (metisazone), ampligen, arbidol, Atripla®, combivir, imunovir, nexavir, trizivir, truvada, larnivudine, dideoxyadenosine, floxuridine, idozuridine, inosine pranobex, 2'-deoxy-5-(methylamino)uridine, digoxin, imiquimod, interferon type III, interferon type II, interferon type I, tea tree oil, glycyrrhizic acid, fialuridine, telbivudine, adefovir, etecavir, lamivudine, clevudine, asunaprevir, boceprevir, faldaprevir, grazoprevir, paritaprevir, ritonavir, telaprevir, simeprevir, sofosbuvir, ACH-3102, daclatasvir, deleobuvir, elbasvir, ledipasvir, MK-3682, MK-8408, samatasvir, ombitasvir, entecavir, elderberry *sambucus*, umifenovir, amantadine, rimantadine, oseltamivir, zanamivir, peramivir, laninamivir, pyrrole polyamides, lopinavir, or salts, solvates, and/or combinations thereof; and b) one or more of the following active agents: 17a-ethinyl-levonorgestrel-17b-hydroxy-estra-4,9,11-trien-3-one, estradiol, ethinyl estradiol, levonorgestrel, medroxyprogesterone acetate, nestorone, norethindrone, ethynodiol diacetate, RU486, N9, mifepristone, mifegyne, mifeprex, 17a-ethinyl-levongestrel, 17b-hydroxy-estra-4,9,11-trien-3-one, estradiol, norgestrienone, progesterone, etonogestril (3-keto-desogestrel), progestin, megestrol, etono-progestin alonegestrel, and 17-acetoxy-16-methylene-19-norprogesterone, or salts, solvates, or combinations thereof. In some embodiments, the composition is a pre-exposure composition comprising a low dose of the one or more active agents. In some embodiments, the composition is a post-exposure composition comprising a high dose of the one or more active agents. In some embodiments, the compositions further prevent and/or treat HIV infection. In some embodiments, the compositions are further administered with one or more HIV antivirals for the prevention and/or treatment of HIV. In some embodiments, the compositions further comprise or are administered with one or more additional contraceptive agents.

In some embodiments, a composition useful in the methods described herein for the prevention of pregnancy and the treatment of a viral infection (e.g., HSV suppression treatment) in a seropositive subject comprises a) one or more of the following active agents: valacyclovir, acyclovir, famciclovir, pritelivir, penciclovir, ganciclovir, valganciclovi, cidofovir, foscarnet, darunavir, glycyrrhizic acid, glutamine, FV-100, ASP2151, me-609, ASP2151, topical VDO, PEG-formulation (Devirex AG), vidarabine, cidofovir, crofelemer (SP-303T), EPB-348, CMX001, V212, NB-001, squaric acid, ionic zinc, sorivudine (ARYS-01), trifluridine, 882C87, merlin (ethanol and glycolic acid mixture), vitamin C, AIC316, versabase gel with *Sarracenia purpurea*, UB-621, lysine, edoxudine, brivudine, cytarabine, docosanol, tromantadine, resiquimod (R-848), imiquimod, resiquimod, tenofovir, tenofovir disoproxil fumarate, tenofovir alafenamide fumarate, include GSK208141 (gD2t, GSK glycoprotein D (gD)-Alum/3-deacylated form of monophosphoryl lipid A), Herpes Zoster GSK 1437173A, gD2-AS04, Havrix™, gD-Alum, Zostavax/Zoster vaccine (V211, V212, V210), HSV529, HerpV (AG-707 rh-Hsc70 polyvalent peptide complex), VCL-HB01, VCL-HM01, pPJV7630, GEN-003, SPL7013 gel (VivaGel™), GSK324332A, GSK1492903A, VariZIG™, and Varivax, maraviroc, enfuvirtide, vicriviroc, cenicriviroc, lbalizumab, fostemsavir (BMS-663068), ibalizumab (TMB-355, TNX-355), PRO 140, b12 antibody, DCM205, DARPins, caprine antibody, VIR-576, enfuvirtide (T-20), AMD11070, PR0542, SCH-C, T-1249, cyanovirin, griffithsen, lectins, pentafuside, dolutegravir, elvitegravir, raltegravir, globoidnan A, MK-2048, BI224436, cabotegravir, GSK 1265744, GSK-572, MK-0518, abacavir, didanosine, emtricitabine, lamivudine, stavudine, tenofovir, tenofovir disoporoxil fumarate, zidovudine, apricitabine, stampidine, elvucitabine, racivir, amdoxovir, stavudine, zalcitabine, festinavir, dideoxycytidine ddC, azidothymidine, tenofovir alafenamide fumarate, entecavir, delavirdine, efavirenz, etravirine (TMC-125), nevirapine, rilpivirine, doravirine, Calanolide A, capravirine, epivir, adefovir, dapivirine, lersivirine, alovudine, elvucitabine, TMC-278, DPC-083, amdoxovir, (−)-beta-D-2,6-diamino-purine dioxolane, MIV-210 (FLG), DFC (dexelvucitabine), dioxolane thymidine, L697639, atevirdine (U87201E), MIV-150, GSK-695634, GSK-678248, TMC-278, KP1461, KP-1212, lodenosine (FddA), 5-[(3,5-dichlorophenyl)thio]-4-isopropyl-1-(4-pyridylmethyl)imidazole-2-methanol carbamic acid, (−)-I2-D-2,6-diaminopurine dioxolane, AVX-754, BCH-13520, BMS-56190 ((4S)-6-chloro-4-[(1E)-cyclopropylethenyl]-3,-4-dihydro-4-trifluoromethyl-2 (1H)-quinazolinone), TMC-120, L697639, atazanavir, darunavir, fosamprenavir, indinavir, nelfinavir, ritonavir, saquinavir, tipranavir, lopinavir, amprenavir, telinavir (SC-52151), droxinavir, emtriva, invirase, agenerase, TMC-126, mozenavir (DMP-450), JE-2147 (AG1776), L-756423, KNI-272, DPC-681, DPC-684, BMS 186318, droxinavir (SC-55389a), DMP-323, KNI-227, 1-[(2-hydroxyethoxy)methyl]-6-(phenylthio)-thymine, AG-1859, RO-033-4649, R-944, DMP-850, DMP-851, brecanavir (GW640385), nonoxynol-9, sodium dodecyl sulfate, Savvy (1.0% C31G), BufferGel®, carrageenans, VivaGel®, PRO-2000, also known as PRO 2000/5, naphthalene 2-sulfonate polymer, or polynaphthalene sulphonate, amphotericin B, sulfamethoxazole, trimethoprim, clarithromycin, daunorubicin, fluconazole, doxorubicin, anidulafungin, immune globulin, gamma globulin, dronabinol, megestrol acetate, atovaquone, rifabutin, pentamidine, trimetrexate glucuronate, leucovorin, alitretinoin gel, erythropoeetin, calcium hydroxylapatite, poly-L-lactic acid, somatropin rDNA, itraconazole, paclitaxel, voriconazole, cidofovir, fomivirsen, azithromycin, ruxolitinib, tocilizumab, bevirimat, TRIM5alpha, Tat antagonists, trichosanthin, abzyme, calanolide A, ceragenin, cyanovirin-N, diarylpyrimidines, epigallocatechin gallate (EGCG), foscarnet, griffithsin, hydroxycarbamide, miltefosine, portmanteau inhibitors, scytovirin, seliciclib, synergistic enhancers, tre recombinase, zinc finger protein transcription factor, KP-1461, BIT225, aplaviroc, atevirdine, brecanavir, capravirine, dexelvucitabine, emivirine, lersivirine, lodenosine, loviride, fomivirsen, glycyrrhizic acid (anti-inflammatory, inhibits 1 lbeta-hydroxysteroid dehydrogenase), zinc salts, cellulose sulfate, cyclodextrins, dextrin-2-sulfate, NCP7 inhibitors, AMD-3100, BMS-806, BMS-793, C31G, carrageenan, CD4-IgG2, cellulose acetate phthalate, mAb 2G12, mAb b12, Merck 167, plant lectins, poly naphthalene sulfate, poly sulfo-styrene, PRO2000, PSC-Rantes, SCH-C, SCH-D, T-20, TMC-125, UC-781, UK-427, UK-857, Carraguard (PC-515), brincidofovir (CMX001), zidovudine, virus-specific cytotoxic T cells, idoxuridine, podophyllotoxin, rifampicin, metisazone, interferon alfa 2b (Intron-A), peginterferon alfa-2a, ribavirin, moroxydine, pleconaril, BCX4430, taribavirin (viramidine, ICN 3142), favipiravir, rintatolimod, ibacitabine, (5-iodo-2'-deoxycytidine), methisazone (metisazone), ampligen, arbidol, Atripla®, combivir, imunovir, nexavir, trizivir, truvada, larnivudine, dideoxyadenosine, floxuridine, idozuridine, inosine pranobex, 2'-deoxy-5-(methylamino)uridine, digoxin, imiquimod, interferon type III, interferon type II, interferon type I, tea tree oil, glycyrrhizic acid, fialuridine, telbivudine, adefovir, etecavir, lamivudine, clevudine, asunaprevir, boceprevir, faldaprevir, grazoprevir, paritaprevir, ritonavir, telaprevir, simeprevir, sofosbuvir, ACH-3102, daclatasvir, deleobuvir, elbasvir, ledipasvir, MK-3682, MK-8408, samatasvir, ombitasvir, entecavir, elderberry *sambucus*, umifenovir, amantadine, rimantadine, oseltamivir, zanamivir, peramivir, laninamivir, pyrrole polyamides, lopinavir, or salts, solvates, and/or combinations thereof and b) one or more of the following active agents: 17a-ethinyl-levonorgestrel-17b-hydroxy-estra-4,9,11-trien-3-one, estradiol, ethinyl estradiol, levonorgestrel, medroxyprogesterone acetate, nestorone, norethindrone, ethynodiol diacetate, RU486, N9, mifepristone, mifegyne, mifeprex, 17a-ethinyl-levongestrel, 17b-hydroxy-estra-4,9,11-trien-3-one, estradiol, norgestrienone, progesterone, etonogestril (3-keto-desogestrel), progestin, megestrol, etono-progestin alonegestrel, and 17-acetoxy-16-methylene-19-norprogesterone, or salts, solvates, or combinations thereof. In some embodiments, the composition is a pre-exposure composition comprising a low dose of the one or more active agents. In some embodiments, the composition is a post-exposure composition comprising a high dose of the one or more active agents. In some embodiments, the compositions further prevent and/or treat HIV infection. In some embodiments, the compositions are further administered with one or more HIV antivirals for the prevention and/or treatment of HIV. In some embodiments, the compositions further comprise or are administered with one or more additional contraceptive agents.

In some embodiments, a composition useful in the methods described herein for the prevention of pregnancy and the prevention of HSV infection in a seronegative subject comprises a) 1, 2, 3, 4, 5 or more of the following active agents: valacyclovir, acyclovir, famciclovir, pritelivir, penciclovir, ganciclovir, valganciclovi, cidofovir, foscarnet, darunavir, glycyrrhizic acid, glutamine, FV-100, ASP2151, me-609, ASP2151, topical VDO, PEG-formulation (Devirex AG), vidarabine, cidofovir, crofelemer (SP-303T), EPB-348, CMX001, V212, NB-001, squaric acid, ionic zinc, sorivudine (ARYS-01), trifluridine, 882C87, merlin (ethanol and glycolic acid mixture), vitamin C, AIC316, versabase gel with *Sarracenia purpurea*, UB-621, lysine, edoxudine, brivudine, cytarabine, docosanol, tromantadine, resiquimod (R-848), imiquimod, resiquimod, tenofovir, tenofovir disoproxil fumarate, tenofovir alafenamide fumarate, or salts, solvates, or combinations thereof; b) 1, 2, 3, 4, 5 or more of the following active agents: maraviroc, enfuvirtide, vicriviroc, cenicriviroc, lbalizumab, fostemsavir (BMS-663068), ibalizumab (TMB-355, TNX-355), PRO 140, b12 antibody, DCM205, DARPins, caprine antibody, VIR-576, enfuvirtide (T-20), AMD11070, PR0542, SCH-C, T-1249, cyanovirin, griffithsen, lectins, pentafuside, dolutegravir, elvitegravir, raltegravir, globoidnan A, MK-2048, BI224436, cabotegravir, GSK 1265744, GSK-572, MK-0518, abacavir, didanosine, emtrictabine, lamivudine, stavudine, tenofovir, tenofovir disoporoxil fumarate, zidovudine, apricitabine, stampidine, elvucitabine, racivir, amdoxovir, stavudine, zalcitabine, festinavir, dideoxycytidine ddC, azidothymidine, tenofovir alafenamide fumarate, entecavir, delavirdine, efavirenz, etravirine (TMC-125), nevirapine, rilpivirine, doravirine, Calanolide A, capravirine, epivir, adefovir, dapivirine, lersivirine, alovudine, elvucitabine, TMC-278, DPC-083, amdoxovir, (−)-beta-D-2,6-diamino-purine dioxolane, MIV-210 (FLG), DFC (dexelvucitabine), dioxolane thymidine, L697639, atevirdine (U87201E), MIV-150, GSK-695634, GSK-678248, TMC-278, KP1461, KP-1212, lodenosine (FddA), 5-[(3,5-dichlorophenyl)thio]-4-isopropyl-1-(4-pyridylmethyl)imidazole-2-methanol carbamic acid, (−)-I2-D-2,6-diaminopurine dioxolane, AVX-754, BCH-13520, BMS-56190 ((4S)-6-chloro-4-[(1E)-cyclopropylethenyl]-3,-4-dihydro-4-trifluoromethyl-2 (1H)-quinazolinone), TMC-120, L697639, atazanavir, darunavir, fosamprenavir, indinavir, nelfinavir, ritonavir, saquinavir, tipranavir, lopinavir, amprenavir, telinavir (SC-52151), droxinavir, emtriva, invirase, agenerase, TMC-126, mozenavir (DMP-450), JE-2147

(AG1776), L-756423, KNI-272, DPC-681, DPC-684, BMS 186318, droxinavir (SC-55389a), DMP-323, KNI-227, 1-[(2-hydroxyethoxy)methyl]-6-(phenylthio)-thymine, AG-1859, RO-033-4649, R-944, DMP-850, DMP-851, brecanavir (GW640385), or salts, solvates or combinations thereof; and c) 1, 2, 3, 4, or more of the following active agents: 17a-ethinyl-levonorgestrel-17b-hydroxy-estra-4,9,11-trien-3-one, estradiol, ethinyl estradiol, levonorgestrel, medroxyprogesterone acetate, nestorone, norethindrone, ethynodiol diacetate, RU486, N9, mifepristone, mifegyne, mifeprex, 17a-ethinyl-levongestrel, 17b-hydroxy-estra-4,9,11-trien-3-one, estradiol, norgestrienone, progesterone, etonogestril (3-keto-desogestrel), progestin, megestrol, etono-progestin alonegestrel, and 17-acetoxy-16-methylene-19-norprogesterone, or salts, solvates or combinations thereof. In some embodiments, the composition is a pre-exposure composition comprising a low dose of the one or more active agents. In some embodiments, the composition is a post-exposure composition comprising a high dose of the one or more active agents. In some embodiments, the compositions further prevent and/or treat HIV infection. In some embodiments, the compositions are further administered with one or more HIV antivirals for the prevention and/or treatment of HIV. In some embodiments, the compositions further comprise or are administered with one or more additional contraceptive agents.

In some embodiments, a composition useful in the methods described herein for the prevention of pregnancy and the treatment of HSV in a seropositive subject comprises a) 1, 2, 3, 4, 5 or more of the following active agents: valacyclovir, acyclovir, famciclovir, pritelivir, penciclovir, ganciclovir, valganciclovi, cidofovir, foscarnet, darunavir, glycyrrhizic acid, glutamine, FV-100, ASP2151, me-609, ASP2151, topical VDO, PEG-formulation (Devirex AG), vidarabine, cidofovir, crofelemer (SP-303T), EPB-348, CMX001, V212, NB-001, squaric acid, ionic zinc, sorivudine (ARYS-01), trifluridine, 882C87, merlin (ethanol and glycolic acid mixture), vitamin C, AIC316, versabase gel with *Sarracenia purpurea*, UB-621, lysine, edoxudine, brivudine, cytarabine, docosanol, tromantadine, resiquimod (R-848), imiquimod, resiquimod, tenofovir, tenofovir disoproxil fumarate, tenofovir alafenamide fumarate, or salts, solvates, or combinations thereof; b) 1, 2, 3, 4, 5 or more of the following active agents: maraviroc, enfuvirtide, vicriviroc, cenicriviroc, lbalizumab, fostemsavir (BMS-663068), ibalizumab (TMB-355, TNX-355), PRO 140, b12 antibody, DCM205, DARPins, caprine antibody, VIR-576, enfuvirtide (T-20), AMD11070, PR0542, SCH-C, T-1249, cyanovirin, griffithsen, lectins, pentafuside, dolutegravir, elvitegravir, raltegravir, globoidnan A, MK-2048, BI224436, cabotegravir, GSK 1265744, GSK-572, MK-0518, abacavir, didanosine, emtrictabine, lamivudine, stavudine, tenofovir, tenofovir disoporoxil fumarate, zidovudine, apricitabine, stampidine, elvucitabine, racivir, amdoxovir, stavudine, zalcitabine, festinavir, dideoxycytidine ddC, azidothymidine, tenofovir alafenamide fumarate, entecavir, delavirdine, efavirenz, etravirine (TMC-125), nevirapine, rilpivirine, doravirine, Calanolide A, capravirine, epivir, adefovir, dapivirine, lersivirine, alovudine, elvucitabine, TMC-278, DPC-083, amdoxovir, (–)-beta-D-2,6-diamino-purine dioxolane, MIV-210 (FLG), DFC (dexelvucitabine), dioxolane thymidine, L697639, atevirdine (U87201E), MIV-150, GSK-695634, GSK-678248, TMC-278, KP1461, KP-1212, lodenosine (FddA), 5-[(3,5-dichlorophenyl)thio]-4-isopropyl-1-(4-pyridylmethyl)imidazole-2-methanol carbamic acid, (–)-I2-D-2,6-diaminopurine dioxolane, AVX-754, BCH-13520, BMS-56190 ((4S)-6-chloro-4-[(1E)-cyclopropylethenyl]-3,-4-dihydro-4-trifluoromethyl-2 (1H)-quinazolinone), TMC-120, L697639, atazanavir, darunavir, fosamprenavir, indinavir, nelfinavir, ritonavir, saquinavir, tipranavir, lopinavir, amprenavir, telinavir (SC-52151), droxinavir, emtriva, invirase, agenerase, TMC-126, mozenavir (DMP-450), JE-2147 (AG1776), L-756423, KNI-272, DPC-681, DPC-684, BMS 186318, droxinavir (SC-55389a), DMP-323, KNI-227, 1-[(2-hydroxyethoxy)methyl]-6-(phenylthio)-thymine, AG-1859, RO-033-4649, R-944, DMP-850, DMP-851, brecanavir (GW640385), or salts, solvates or combinations thereof; and c) 1, 2, 3, 4, or more of the following active agents: 17a-ethinyl-levonorgestrel-17b-hydroxy-estra-4,9,11-trien-3-one, estradiol, ethinyl estradiol, levonorgestrel, medroxyprogesterone acetate, nestorone, norethindrone, ethynodiol diacetate, RU486, N9, mifepristone, mifegyne, mifeprex, 17a-ethinyl-levongestrel, 17b-hydroxy-estra-4,9,11-trien-3-one, estradiol, norgestrienone, progesterone, etonogestril (3-keto-desogestrel), progestin, megestrol, etono-progestin alonegestrel, and 17-acetoxy-16-methylene-19-norprogesterone, or salts, solvates or combinations thereof. In some embodiments, the composition is a pre-exposure composition comprising a low dose of the one or more active agents. In some embodiments, the composition is a post-exposure composition comprising a high dose of the one or more active agents. In some embodiments, the compositions further prevent and/or treat HIV infection. In some embodiments, the compositions are further administered with one or more HIV antivirals for the prevention and/or treatment of HIV. In some embodiments, the compositions further comprise or are administered with one or more additional contraceptive agents.

Valacyclovir Compositions

Provided herein, in various aspects, are compositions useful for the prevention of HSV infection in an HSV seronegative subject, the compositions comprising the active agent valacyclovir, or a salt or solvate thereof, wherein the compositions further comprise and/or are administered with one or more additional active agents. Further provided herein, in various aspects, are methods of preventing HSV infection in an HSV seronegative subject comprising administering to the subject a combination of valacyclovir, or a salt or solvate thereof, and one or more additional active agents. In some cases, the combination of valacyclovir and the one or more additional active agents further prevents infection by one or more additional infectious diseases, for example, HIV. In some instances, the combination of valacyclovir and the one or more additional active agents is administered together in one composition. In some instances, valacyclovir and the one or more additional active agents are co-administered in different compositions. In some embodiments, at least one of the one or more additional active agents is an antiviral agent, for example, an HSV antiviral agent, HIV antiviral agent, and/or any antiviral agent described elsewhere herein. In some embodiments, at least one of the one or more additional active agents is a contraceptive. In some embodiments, at least one of the one or more additional active agents is an antiviral agent and at least one of the one or more additional active agents is a contraceptive agent. In some instances, one or more of the active agents are administered to the HSV seronegative subject to reduce the risk of acquiring HSV infection prior to exposure to HSV. In some instances, one or more active agents are administered to the HSV seronegative subject to reduce the risk of acquiring HSV infection after exposure to HSV. In some instances, one or more of the active agents are administered to the HSV seronegative subject prior to exposure to HSV and one or more of the active agents are administered to the HSV seronegative subject after exposure to HSV. In some of those cases, the dose of one or more active agents administered prior to exposure to HSV differs from the dose of one or more active agents administered after exposure to HSV. In some instances, a contraceptive agent is administered to the HSV seronegative subject to reduce the risk of pregnancy, prior to, and/or after, the subject engages in conduct that could result in pregnancy, e.g., the same conduct that results in exposure to HSV. In some embodiments, valacyclovir and/or one or more of the one or more additional active agents are administered using an oral formulation, for example, a pill, capsule, tablet or solution. In some embodiments, valacyclovir and/or one or more of the one or more additional active agents are administered using a long-acting delivery device, for example, an intravaginal ring. In some embodiments, the methods of preventing HSV infection in the HSV seronegative subject further comprise administering to an HSV seropositive partner of the HSV seronegative subject one or more antiviral agents, for example, as suppression therapy. In some cases, the HSV seropositive partner is administered an HSV antiviral.

Examples of HSV antiviral agents include, without limitation, valacyclovir, acyclovir, famciclovir, pritelivir, penciclovir, ganciclovir, valganciclovir, cidofovir, foscarnet, darunavir, glycyrrhizic acid, glutamine, FV-100, ASP2151, me-609, ASP2151, topical VDO, PEG-formulation (Devirex AG), vidarabine, cidofovir, crofelemer (SP-303T), EPB-348, CMX001, V212, NB-001, squaric acid, ionic zinc, sorivudine (ARYS-01), trifluridine, 882C87, merlin (ethanol and glycolic acid mixture), vitamin C, AIC316, versabase gel with *Sarracenia purpurea*, UB-621, lysine, edoxudine, brivudine, cytarabine, docosanol, tromantadine, resiquimod (R-848), imiquimod, resiquimod, tenofovir, tenofovir disoproxil fumarate, tenofovir alafenamide fumarate, or salts, solvates, or combinations thereof.

In some embodiments, the methods for preventing HSV infection in an HSV seronegative subject comprise administering to the HSV seronegative subject about or at least about 200 mg, 250 mg, 300 mg, 350 mg, 400 mg, 450 mg, 500 mg, 550 mg, 600 mg, 650 mg, 700 mg, 800 mg, 850 mg, 900 mg, 950 mg, 1000 mg, 1050 mg, 1100 mg, 1150 mg, 1200 mg, 1250 mg, 1300 mg, 1350 mg, 1400 mg, 1450 mg, 1500 mg, 1550 mg, 1600 mg, 1700 mg, or 1800 mg of valacyclovir, or a salt or solvate thereof. In some cases, valacyclovir, or a salt or solvate thereof, is administered in a dosage from about 500 mg to about 1500 mg, or from about 500 mg to about 1000 mg. In some cases, valacyclovir, or a salt or solvate thereof, is administered 1 time per week, 2 times per week, 3 times per week, 4 times per week, 5 times per week, 6 times per week, 1 time per day, 2 times per day, 3 times per day, 4 times per day, or continuously (e.g., using a long-acting delivery device).

In some embodiments, the compositions useful for preventing HSV infection in seronegative subjects comprising valacyclovir, or a salt or solvate thereof, further comprise emtricitabine. In some embodiments, the methods for preventing HSV infection in seronegative subjects comprising administering to the subject valacyclovir, or a salt or solvate thereof, further comprise administering to the subject emtricitabine, or a salt or solvate thereof. In some embodiments, the methods comprise administering to the HSV seronegative subject at least or about 50 mg, 100 mg, 150 mg, 200 mg, 250 mg, 300 mg, 350 mg, or 400 mg of emtricitabine, or a salt or solvate thereof. In some cases, emtricitabine is administered 1 time per week, 2 times per week, 3 times per week, 4 times per week, 5 times per week, 6 times per week, 1 time per day, 2 times per day, 3 times per day, 4 times per day, or continuously for a set duration of time. In some cases, the method of preventing HSV infection in the HSV seronegative subject comprises administering to the HSV seronegative subject from about 500 mg to about 1500 mg of valacyclovir, or a salt or solvate thereof, and from about 100 mg to about 300 mg of emtricitabine, or a salt or solvate thereof.

In some embodiments, the compositions useful for preventing HSV infection in seronegative subjects comprising valacyclovir, or a salt or solvate thereof, further comprise lamivudine. In some embodiments, the methods for preventing HSV infection in seronegative subjects comprising administering to the subject valacyclovir, or a salt or solvate thereof, further comprise administering to the subject lamivudine, or a salt or solvate thereof. In some embodiments, the methods comprise administering to the HSV seronegative subject at least or about 50 mg, 100 mg, 150 mg, 200 mg, 250 mg, 300 mg, 350 mg, or 400 mg of lamivudine, or a salt or solvate thereof. In some cases, lamivudine is administered 1 time per week, 2 times per week, 3 times per week, 4 times per week, 5 times per week, 6 times per week, 1 time per day, 2 times per day, 3 times per day, 4 times per day, or continuously for a set duration of time. In some cases, the method of preventing HSV infection in the HSV seronegative subject comprises administering to the HSV seronegative subject from about 500 mg to about 1500 mg of valacyclovir, or a salt or solvate thereof, and from about 100 mg to about 300 mg of lamivudine, or a salt or solvate thereof.

In some embodiments, the compositions useful for preventing HSV infection in seronegative subjects comprising valacyclovir, or a salt or solvate thereof, further comprise glycyrrhizic acid. In some embodiments, the methods for preventing HSV infection in seronegative subjects comprising administering to the subject valacyclovir, or a salt or solvate thereof, further comprise administering to the subject glycyrrhizic acid, or a salt or solvate thereof. In some embodiments, the methods comprise administering to the HSV seronegative subject at least or about 1 mg, 2 mg, 3 mg, 4 mg, 5 mg, 6 mg, 7 mg, or 8 mg, 9 mg, 10 mg, 11 mg, 12 mg, 13 mg, 14 mg, 15 mg, 20 mg of glycyrrhizic acid, or a salt or solvate thereof. In some cases, glycyrrhizic acid is administered 1 time per week, 2 times per week, 3 times per week, 4 times per week, 5 times per week, 6 times per week, 1 time per day, 2 times per day, 3 times per day, 4 times per day, or continuously for a set duration of time. In some cases, the method of preventing HSV infection in the HSV seronegative subject comprises administering to the HSV seronegative subject from about 500 mg to about 1500 mg of valacyclovir, or a salt or solvate thereof, and from about 1 mg to about 10 mg of glycyrrhizic acid, or a salt or solvate thereof.

In some embodiments, the compositions useful for preventing HSV infection in seronegative subjects comprising valacyclovir, or a salt or solvate thereof, further comprise *Sambucus nigra*. In some embodiments, the methods for preventing HSV infection in seronegative subjects comprising administering to the subject valacyclovir, or a salt or solvate thereof, further comprise administering to the subject *Sambucus nigra*, or a salt or solvate thereof. In some embodiments, the methods comprise administering to the HSV seronegative subject at least or about 50 mg, 100 mg, 150 mg, 200 mg, 250 mg, 300 mg, 350 mg, or 400 mg of *Sambucus nigra*, or a salt or solvate thereof. In some cases, *Sambucus nigra* is administered 1 time per week, 2 times per week, 3 times per week, 4 times per week, 5 times per week, 6 times per week, 1 time per day, 2 times per day, 3 times per day, 4 times per day, or continuously for a set duration of time. In some cases, the method of preventing HSV infection in the HSV seronegative subject comprises administering to the HSV seronegative subject from about 500 mg to about 1500 mg of valacyclovir, or a salt or solvate thereof, and from about 100 mg to about 200 mg of *Sambucus nigra*, or a salt or solvate thereof.

In some embodiments, the compositions useful for preventing HSV infection in seronegative subjects comprising valacyclovir, or a salt or solvate thereof, further comprise pritelivir. In some embodiments, the methods for preventing HSV infection in seronegative subjects comprising administering to the subject valacyclovir, or a salt or solvate thereof, further comprise administering to the subject pritelivir, or a salt or solvate thereof. In some embodiments, the methods comprise administering to the HSV seronegative subject at least or about 1 mg, 5 mg, 10 mg, 15 mg, 20 mg, 25 mg, 30 mg, 35 mg, 40 mg, 45 mg, 50 mg, 55 mg, 60 mg, 65 mg, 70 mg, 75 mg, 80 mg, 90 mg, or 100 mg of pritelivir, or a salt or solvate thereof. In some cases, pritelivir is administered 1 time per week, 2 times per week, 3 times per week, 4 times per week, 5 times per week, 6 times per week, 1 time per day, 2 times per day, 3 times per day, 4 times per day, or continuously for a set duration of time. In some cases, the method of preventing HSV infection in the HSV seronegative subject comprises administering to the HSV seronegative subject from about 500 mg to about 1500 mg of valacyclovir, or a salt or solvate thereof, and from about 5 mg to about 75 mg of pritelivir, or a salt or solvate thereof.

In some embodiments, the compositions useful for preventing HSV infection in seronegative subjects comprising valacyclovir, or a salt or solvate thereof, further comprise pritelivir and emtricitabine. In some embodiments, the methods for preventing HSV infection in seronegative subjects comprising administering to the subject valacyclovir, or a salt or solvate thereof, further comprise administering to the subject pritelivir, or a salt or solvate thereof and emtricitabine, or a salt or solvate thereof. In some embodiments, the methods comprise administering to the HSV seronegative subject at least or about 1 mg, 5 mg, 10 mg, 15 mg, 20 mg, 25 mg, 30 mg, 35 mg, 40 mg, 45 mg, 50 mg, 55 mg, 60 mg, 65 mg, 70 mg, 75 mg, 80 mg, 90 mg, or 100 mg of pritelivir, or a salt or solvate thereof. In some embodiments, the methods comprise administering to the HSV seronegative subject at least or about 50 mg, 100 mg, 150 mg, 200 mg, 250 mg, 300 mg, 350 mg, or 400 mg of emtricitabine, or a salt or solvate thereof. In some cases, pritelivir is administered 1 time per week, 2 times per week, 3 times per week, 4 times per week, 5 times per week, 6 times per week, 1 time per day, 2 times per day, 3 times per day, 4 times per day, or continuously for a set duration of time. In some cases, emtricitabine is administered 1 time per week, 2 times per week, 3 times per week, 4 times per week, 5 times per week, 6 times per week, 1 time per day, 2 times per day, 3 times per day, 4 times per day, or continuously for a set duration of time. In some cases, the method of preventing HSV infection in the HSV seronegative subject comprises administering to the HSV seronegative subject from about 500 mg to about 1500 mg of valacyclovir, or a salt or solvate thereof, from about 5 mg to about 75 mg of pritelivir, or a salt or solvate thereof, and from about 100 mg to about 300 mg of emtricitabine, or a salt or solvate thereof.

In some embodiments, the compositions useful for preventing HSV infection in seronegative subjects comprising valacyclovir, or a salt or solvate thereof, further comprise pritelivir and lamivudine. In some embodiments, the methods for preventing HSV infection in seronegative subjects comprising administering to the subject valacyclovir, or a salt or solvate thereof, further comprise administering to the subject pritelivir, or a salt or solvate thereof and lamivudine, or a salt or solvate thereof. In some embodiments, the methods comprise administering to the HSV seronegative subject at least or about 1 mg, 5 mg, 10 mg, 15 mg, 20 mg, 25 mg, 30 mg, 35 mg, 40 mg, 45 mg, 50 mg, 55 mg, 60 mg, 65 mg, 70 mg, 75 mg, 80 mg, 90 mg, or 100 mg of pritelivir, or a salt or solvate thereof. In some embodiments, the methods comprise administering to the HSV seronegative subject at least or about 50 mg, 100 mg, 150 mg, 200 mg, 250 mg, 300 mg, 350 mg, or 400 mg of lamivudine, or a salt or solvate thereof. In some cases, pritelivir is administered 1 time per week, 2 times per week, 3 times per week, 4 times per week, 5 times per week, 6 times per week, 1 time per day, 2 times per day, 3 times per day, 4 times per day, or continuously for a set duration of time. In some cases, lamivudine is administered 1 time per week, 2 times per week, 3 times per week, 4 times per week, 5 times per week, 6 times per week, 1 time per day, 2 times per day, 3 times per day, 4 times per day, or continuously for a set duration of time. In some cases, the method of preventing HSV infection in the HSV seronegative subject comprises administering to the HSV seronegative subject from about 500 mg to about 1500 mg of valacyclovir, or a salt or solvate thereof, from about 5 mg to about 75 mg of pritelivir, or a salt or solvate thereof, and from about 100 mg to about 300 mg of lamivudine, or a salt or solvate thereof.

In some embodiments, the compositions useful for preventing pregnancy and HSV infection in seronegative subjects comprising valacyclovir, or a salt or solvate thereof, further comprise emtricitabine and one or more contraceptive agents. In some embodiments, the methods for preventing pregnancy and HSV infection in seronegative subjects comprising administering to the subject valacyclovir, or a salt or solvate thereof, further comprise administering to the subject emtricitabine, or a salt or solvate thereof and one or more contraceptive agents. In some cases, the contraceptive agents comprise levonorgestrel and ethinyl estradiol. In some embodiments, the methods comprise administering to the HSV seronegative subject at least or about 50 mg, 100 mg, 150 mg, 200 mg, 250 mg, 300 mg, 350 mg, or 400 mg of emtricitabine, or a salt or solvate thereof. In some embodiments, the methods comprise administering to the HSV seronegative subject at least or about 0.05 mg, 0.10 mg, 0.15 mg, or 0.2 mg levonorgestrel, or a salt or solvate thereof. In some embodiments, the methods comprise administering to the HSV seronegative subject at least or about 0.01 mg, 0.015 mg, 0.02 mg, 0.025 mg, 0.03 mg, 0.035 mg, or 0.04 mg of ethinyl estradiol, or a salt or solvate thereof. In some cases, emtricitabine is administered 1 time per week, 2 times per week, 3 times per week, 4 times per week, 5 times per week, 6 times per week, 1 time per day, 2 times per day, 3 times per day, 4 times per day, or continuously for a set duration of time. In some cases, levonorgestrel and ethinyl estradiol are administered in cycles, each cycle comprising administering levonorgestrel and ethinyl estradiol daily for 21 days, followed by administering a placebo for 7 days. In some cases, a method of preventing pregnancy and HSV infection in the HSV seronegative subject comprises a) administering to the subject from about 500 to about 1500 mg of valacyclovir, or a salt or solvate thereof, once daily, b) administering to the subject from about 100 mg to about 300 mg of emtricitabine, or a salt or solvate thereof, once daily; and c) administering to the subject from about 0.05 mg to about 0.2 mg levonorgestrel, or a salt or solvate thereof, and from about 0.01 mg to about 0.03 mg ethinyl estradiol, or a salt or solvate thereof, once per day for about 21 days, followed by a placebo for about 7 days.

In some embodiments, the compositions useful for preventing pregnancy and HSV infection in seronegative subjects comprising valacyclovir, or a salt or solvate thereof, further comprise lamivudine and one or more contraceptive agents. In some embodiments, the methods for preventing pregnancy and HSV infection in seronegative subjects comprising administering to the subject valacyclovir, or a salt or solvate thereof, further comprise administering to the subject lamivudine, or a salt or solvate thereof and one or more contraceptive agents. In some cases, the contraceptive agents comprise levonorgestrel and ethinyl estradiol. In some embodiments, the methods comprise administering to the HSV seronegative subject at least or about 50 mg, 100 mg, 150 mg, 200 mg, 250 mg, 300 mg, 350 mg, or 400 mg of lamivudine, or a salt or solvate thereof. In some embodiments, the methods comprise administering to the HSV seronegative subject at least or about 0.05 mg, 0.10 mg, 0.15 mg, or 0.2 mg levonorgestrel, or a salt or solvate thereof. In some embodiments, the methods comprise administering to the HSV seronegative subject at least or about 0.01 mg, 0.015 mg, 0.02 mg, 0.025 mg, 0.03 mg, 0.035 mg, or 0.04 mg of ethinyl estradiol, or a salt or solvate thereof. In some cases, lamivudine is administered 1 time per week, 2 times per week, 3 times per week, 4 times per week, 5 times per week, 6 times per week, 1 time per day, 2 times per day, 3 times per day, 4 times per day, or continuously for a set duration of time. In some cases, levonorgestrel and ethinyl estradiol are administered in cycles, each cycle comprising administering levonorgestrel and ethinyl estradiol daily for 21 days, followed by administering a placebo for 7 days. In some cases, a method of preventing pregnancy and HSV infection in the HSV seronegative subject comprises a) administering to the subject from about 500 to about 1500 mg of valacyclovir, or a salt or solvate thereof, once daily, b) administering to the subject from about 100 mg to about 300 mg of lamivudine, or a salt or solvate thereof, once daily; and c) administering to the subject from about 0.05 mg to about 0.2 mg levonorgestrel, or a salt or solvate thereof, and from about 0.01 mg to about 0.03 mg ethinyl estradiol, or a salt or solvate thereof, once per day for about 21 days, followed by a placebo for about 7 days.

In some embodiments, the compositions useful for preventing pregnancy and HSV infection in seronegative subjects comprising valacyclovir, or a salt or solvate thereof, further comprise glycyrrhizic acid and one or more contraceptive agents. In some embodiments, the methods for preventing pregnancy and HSV infection in seronegative subjects comprising administering to the subject valacyclovir, or a salt or solvate thereof, further comprise administering to the subject glycyrrhizic acid, or a salt or solvate thereof and one or more contraceptive agents. In some cases, the contraceptive agents comprise levonorgestrel and ethinyl estradiol. In some embodiments, the methods comprise administering to the HSV seronegative subject at least or about 1 mg, 2 mg, 3 mg, 4 mg, 5 mg, 6 mg, 7 mg, or 8 mg, 9 mg, 10 mg, 11 mg, 12 mg, 13 mg, 14 mg, 15 mg, 20 mg of glycyrrhizic acid, or a salt or solvate thereof. In some embodiments, the methods comprise administering to the HSV seronegative subject at least or about 0.05 mg, 0.10 mg, 0.15 mg, or 0.2 mg levonorgestrel, or a salt or solvate thereof. In some embodiments, the methods comprise administering to the HSV seronegative subject at least or about 0.01 mg, 0.015 mg, 0.02 mg, 0.025 mg, 0.03 mg, 0.035 mg, or 0.04 mg of ethinyl estradiol, or a salt or solvate thereof. In some cases, glycyrrhizic acid is administered 1 time per week, 2 times per week, 3 times per week, 4 times per week, 5 times per week, 6 times per week, 1 time per day, 2 times per day, 3 times per day, 4 times per day, or continuously for a set duration of time. In some cases, levonorgestrel and ethinyl estradiol are administered in cycles, each cycle comprising administering levonorgestrel and ethinyl estradiol daily for 21 days, followed by administering a placebo for 7 days. In some cases, a method of preventing pregnancy and HSV infection in the HSV seronegative subject comprises a) administering to the subject from about 500 to about 1500 mg of valacyclovir, or a salt or solvate thereof, once daily, b) administering to the subject from about 1 mg to about 10 mg of glycyrrhizic acid, or a salt or solvate thereof, once daily; and c) administering to the subject from about 0.05 mg to about 0.2 mg levonorgestrel, or a salt or solvate thereof, and from about 0.01 mg to about 0.03 mg ethinyl estradiol, or a salt or solvate thereof, once per day for about 21 days, followed by a placebo for about 7 days.

In some embodiments, the compositions useful for preventing pregnancy and HSV infection in seronegative subjects comprising valacyclovir, or a salt or solvate thereof, further comprise *Sambucus nigra* and one or more contraceptive agents. In some embodiments, the methods for preventing pregnancy and HSV infection in seronegative subjects comprising administering to the subject valacyclovir, or a salt or solvate thereof, further comprise administering to the subject *Sambucus nigra*, or a salt or solvate thereof and one or more contraceptive agents. In some cases, the contraceptive agents comprise levonorgestrel and ethinyl estradiol. In some embodiments, the methods comprise administering to the HSV seronegative subject at least or about 50 mg, 100 mg, 150 mg, 200 mg, 250 mg, 300 mg, 350 mg, or 400 mg of *Sambucus nigra*, or a salt or solvate thereof. In some embodiments, the methods comprise administering to the HSV seronegative subject at least or about 0.05 mg, 0.10 mg, 0.15 mg, or 0.2 mg levonorgestrel, or a salt or solvate thereof. In some embodiments, the methods comprise administering to the HSV seronegative subject at least or about 0.01 mg, 0.015 mg, 0.02 mg, 0.025 mg, 0.03 mg, 0.035 mg, or 0.04 mg of ethinyl estradiol, or a salt or solvate thereof. In some cases, *Sambucus nigra* is administered 1 time per week, 2 times per week, 3 times per week, 4 times per week, 5 times per week, 6 times per week, 1 time per day, 2 times per day, 3 times per day, 4 times per day, or continuously for a set duration of time. In some cases, levonorgestrel and ethinyl estradiol are administered in cycles, each cycle comprising administering levonorgestrel and ethinyl estradiol daily for 21 days, followed by administering a placebo for 7 days. In some cases, a method of preventing pregnancy and HSV infection in the HSV seronegative subject comprises a) administering to the subject from about 500 to about 1500 mg of valacyclovir, or a salt or solvate thereof, once daily, b) administering to the subject from about 100 mg to about 200 mg of *Sambucus nigra*, or a salt or solvate thereof, once daily; and c) administering to the subject from about 0.05 mg to about 0.2 mg levonorgestrel, or a salt or solvate thereof, and from about 0.01 mg to about 0.03 mg ethinyl estradiol, or a salt or solvate thereof, once per day for about 21 days, followed by a placebo for about 7 days.

In some embodiments, the compositions useful for preventing pregnancy and HSV infection in seronegative subjects comprising valacyclovir, or a salt or solvate thereof, further comprise emtricitabine, tenofovir and one or more contraceptive agents. In some embodiments, the methods for preventing pregnancy and HSV infection in seronegative subjects comprising administering to the subject valacyclovir, or a salt or solvate thereof, further comprise administering to the subject emtricitabine, or a salt or solvate thereof; tenofovir, or a salt or solvate thereof; and one or more contraceptive agents. In some cases, the contraceptive agents comprise levonorgestrel and ethinyl estradiol. In some embodiments, the methods comprise administering to the HSV seronegative subject at least or about 50 mg, 100 mg, 150 mg, 200 mg, 250 mg, 300 mg, 350 mg, or 400 mg of emtricitabine, or a salt or solvate thereof. In some embodiments, the methods comprise administering to the HSV seronegative subject at least or about 50 mg, 100 mg, 150 mg, 200 mg, 250 mg, 300 mg, 350 mg, or 400 mg of tenofovir, or a salt or solvate thereof. In some embodiments, the methods comprise administering to the HSV seronegative subject at least or about 0.05 mg, 0.10 mg, 0.15 mg, or 0.2 mg levonorgestrel, or a salt or solvate thereof. In some embodiments, the methods comprise administering to the HSV seronegative subject at least or about 0.01 mg, 0.015 mg, 0.02 mg, 0.025 mg, 0.03 mg, 0.035 mg, or 0.04 mg of ethinyl estradiol, or a salt or solvate thereof. In some cases, emtricitabine is administered 1 time per week, 2 times per week, 3 times per week, 4 times per week, 5 times per week, 6 times per week, 1 time per day, 2 times per day, 3 times per day, 4 times per day, or continuously for a set duration of time. In some cases, tenofovir is administered 1 time per week, 2 times per week, 3 times per week, 4 times per week, 5 times per week, 6 times per week, 1 time per day, 2 times per day, 3 times per day, 4 times per day, or continuously for a set duration of time. In some cases, levonorgestrel and ethinyl estradiol are administered in cycles, each cycle comprising administering levonorgestrel and ethinyl estradiol daily for 21 days, followed by administering a placebo for 7 days. In some cases, a method of preventing pregnancy and HSV infection in the HSV seronegative subject comprises a) administering to the subject from about 500 to about 1500 mg of valacyclovir, or a salt or solvate thereof, once daily, b) administering to the subject from about 100 mg to about 300 mg of emtricitabine, or a salt or solvate thereof, once daily; c) administering to the subject from about 100 mg to about 400 mg of tenofovir, or a salt or solvate thereof, once daily; and d) administering to the subject from about 0.05 mg to about 0.2 mg levonorgestrel, or a salt or solvate thereof, and from about 0.01 mg to about 0.03 mg ethinyl estradiol, or a salt or solvate thereof, once per day for about 21 days, followed by a placebo for about 7 days.

In some embodiments, the compositions useful for preventing pregnancy and HSV infection in seronegative subjects comprising valacyclovir, or a salt or solvate thereof, further comprise lamivudine, tenofovir and one or more contraceptive agents. In some embodiments, the methods for preventing pregnancy and HSV infection in seronegative subjects comprising administering to the subject valacyclovir, or a salt or solvate thereof, further comprise administering to the subject lamivudine, or a salt or solvate thereof; tenofovir, or a salt or solvate thereof; and one or more contraceptive agents. In some cases, the contraceptive agents comprise levonorgestrel and ethinyl estradiol. In some embodiments, the methods comprise administering to the HSV seronegative subject at least or about 50 mg, 100 mg, 150 mg, 200 mg, 250 mg, 300 mg, 350 mg, or 400 mg of lamivudine, or a salt or solvate thereof. In some embodiments, the methods comprise administering to the HSV seronegative subject at least or about 50 mg, 100 mg, 150 mg, 200 mg, 250 mg, 300 mg, 350 mg, or 400 mg of tenofovir, or a salt or solvate thereof. In some embodiments, the methods comprise administering to the HSV seronegative subject at least or about 0.05 mg, 0.10 mg, 0.15 mg, or 0.2 mg levonorgestrel, or a salt or solvate thereof. In some embodiments, the methods comprise administering to the HSV seronegative subject at least or about 0.01 mg, 0.015 mg, 0.02 mg, 0.025 mg, 0.03 mg, 0.035 mg, or 0.04 mg of ethinyl estradiol, or a salt or solvate thereof. In some cases, lamivudine is administered 1 time per week, 2 times per week, 3 times per week, 4 times per week, 5 times per week, 6 times per week, 1 time per day, 2 times per day, 3 times per day, 4 times per day, or continuously for a set duration of time. In some cases, tenofovir is administered 1 time per week, 2 times per week, 3 times per week, 4 times per week, 5 times per week, 6 times per week, 1 time per day, 2 times per day, 3 times per day, 4 times per day, or continuously for a set duration of time. In some cases, levonorgestrel and ethinyl estradiol are administered in cycles, each cycle comprising administering levonorgestrel and ethinyl estradiol daily for 21 days, followed by administering a placebo for 7 days. In some cases, a method of preventing pregnancy and HSV infection in the HSV seronegative subject comprises a) administering to the subject from about 500 to about 1500 mg of valacyclovir, or a salt or solvate thereof, once daily, b) administering to the subject from about 100 mg to about 300 mg of lamivudine, or a salt or solvate thereof, once daily; c) administering to the subject from about 100 mg to about 400 mg of tenofovir, or a salt or solvate thereof, once daily; and d) administering to the subject from about 0.05 mg to about 0.2 mg levonorgestrel, or a salt or solvate thereof, and from about 0.01 mg to about 0.03 mg ethinyl estradiol, or a salt or solvate thereof, once per day for about 21 days, followed by a placebo for about 7 days.

In some embodiments, the compositions useful for preventing pregnancy and HSV infection in seronegative subjects comprising valacyclovir, or a salt or solvate thereof, further comprise glycyrrhizic acid, tenofovir, emtricitabine and one or more contraceptive agents. In some embodiments, the methods for preventing pregnancy and HSV infection in seronegative subjects comprising administering to the subject valacyclovir, or a salt or solvate thereof, further comprise administering to the subject glycyrrhizic acid, or a salt or solvate thereof; emtricitabine, or a salt or solvate thereof; tenofovir, or a salt or solvate thereof; and one or more contraceptive agents. In some cases, the contraceptive agents comprise levonorgestrel and ethinyl estradiol. In some embodiments, the methods comprise administering to the HSV seronegative subject at least or about 1 mg, 2 mg, 3 mg, 4 mg, 5 mg, 6 mg, 7 mg, 8 mg, 9 mg, 10 mg, 11 mg, 12 mg, 13 mg, 14 mg, 15 mg, or 20 mg of glycyrrhizic acid, or a salt or solvate thereof. In some embodiments, the methods comprise administering to the HSV seronegative subject at least or about 50 mg, 100 mg, 150 mg, 200 mg, 250 mg, 300 mg, 350 mg, or 400 mg of tenofovir, or a salt or solvate thereof. In some embodiments, the methods comprise administering to the HSV seronegative subject at least or about 50 mg, 100 mg, 150 mg, 200 mg, 250 mg, 300 mg, 350 mg, or 400 mg of emtricitabine, or a salt or solvate thereof. In some embodiments, the methods comprise administering to the HSV seronegative subject at least or about 0.05 mg, 0.10 mg, 0.15 mg, or 0.2 mg levonorgestrel, or a salt or solvate thereof. In some embodiments, the methods comprise administering to the HSV seronegative subject at least or about 0.01 mg, 0.015 mg, 0.02 mg, 0.025 mg, 0.03 mg, 0.035 mg, or 0.04 mg of ethinyl estradiol, or a salt or solvate thereof. In some cases, glycyrrhizic acid is administered 1 time per week, 2 times per week, 3 times per week, 4 times per week, 5 times per week, 6 times per week, 1 time per day, 2 times per day, 3 times per day, 4 times per day, or continuously for a set duration of time. In some cases, emtricitabine is administered 1 time per week, 2 times per week, 3 times per week, 4 times per week, 5 times per week, 6 times per week, 1 time per day, 2 times per day, 3 times per day, 4 times per day, or continuously for a set duration of time. In some cases, tenofovir is administered 1 time per week, 2 times per week, 3 times per week, 4 times per week, 5 times per week, 6 times per week, 1 time per day, 2 times per day, 3 times per day, 4 times per day, or continuously for a set duration of time. In some cases, levonorgestrel and ethinyl estradiol are administered in cycles, each cycle comprising administering levonorgestrel and ethinyl estradiol daily for 21 days, followed by administering a placebo for 7 days. In some cases, a method of preventing pregnancy and HSV infection in the HSV seronegative subject comprises a) administering to the subject from about 500 to about 1500 mg of valacyclovir, or a salt or solvate thereof, once daily, b) administering to the subject from about 1 mg to about 10 mg of glycyrrhizic acid, or a salt or solvate thereof, once daily; c) administering to the subject from about 100 mg to about 300 mg of emtricitabine, or a salt or solvate thereof, once daily; d) administering to the subject from about 100 mg to about 400 mg of tenofovir, or a salt or solvate thereof, once daily; and e) administering to the subject from about 0.05 mg to about 0.2 mg levonorgestrel, or a salt or solvate thereof, and from about 0.01 mg to about 0.03 mg ethinyl estradiol, or a salt or solvate thereof, once per day for about 21 days, followed by a placebo for about 7 days.

In some embodiments, the compositions useful for preventing pregnancy and HSV infection in seronegative subjects comprising valacyclovir, or a salt or solvate thereof, further comprise *Sambucus nigra*, tenofovir, emtricitabine and one or more contraceptive agents. In some embodiments, the methods for preventing pregnancy and HSV infection in seronegative subjects comprising administering to the subject valacyclovir, or a salt or solvate thereof, further comprise administering to the subject *Sambucus nigra*, or a salt or solvate thereof; emtricitabine, or a salt or solvate thereof; tenofovir, or a salt or solvate thereof; and one or more contraceptive agents. In some cases, the contraceptive agents comprise levonorgestrel and ethinyl estradiol. In some embodiments, the methods comprise administering to the HSV seronegative subject at least or about 50 mg, 100 mg, 150 mg, 200 mg, 250 mg, or 300 mg of *Sambucus nigra*, or a salt or solvate thereof. In some embodiments, the methods comprise administering to the HSV seronegative subject at least or about 50 mg, 100 mg, 150 mg, 200 mg, 250 mg, 300 mg, 350 mg, or 400 mg of tenofovir, or a salt or solvate thereof. In some embodiments, the methods comprise administering to the HSV seronegative subject at least or about 50 mg, 100 mg, 150 mg, 200 mg, 250 mg, 300 mg, 350 mg, or 400 mg of emtricitabine, or a salt or solvate thereof. In some embodiments, the methods comprise administering to the HSV seronegative subject at least or about 0.05 mg, 0.10 mg, 0.15 mg, or 0.2 mg levonorgestrel, or a salt or solvate thereof. In some embodiments, the methods comprise administering to the HSV seronegative subject at least or about 0.01 mg, 0.015 mg, 0.02 mg, 0.025 mg, 0.03 mg, 0.035 mg, or 0.04 mg of ethinyl estradiol, or a salt or solvate thereof. In some cases, *Sambucus nigra* is administered 1 time per week, 2 times per week, 3 times per week, 4 times per week, 5 times per week, 6 times per week, 1 time per day, 2 times per day, 3 times per day, 4 times per day, or continuously for a set duration of time. In some cases, emtricitabine is administered 1 time per week, 2 times per week, 3 times per week, 4 times per week, 5 times per week, 6 times per week, 1 time per day, 2 times per day, 3 times per day, 4 times per day, or continuously for a set duration of time. In some cases, tenofovir is administered 1 time per week, 2 times per week, 3 times per week, 4 times per week, 5 times per week, 6 times per week, 1 time per day, 2 times per day, 3 times per day, 4 times per day, or continuously for a set duration of time. In some cases, levonorgestrel and ethinyl estradiol are administered in cycles, each cycle comprising administering levonorgestrel and ethinyl estradiol daily for 21 days, followed by administering a placebo for 7 days. In some cases, a method of preventing pregnancy and HSV infection in the HSV seronegative subject comprises a) administering to the subject from about 500 to about 1500 mg of valacyclovir, or a salt or solvate thereof, once daily, b) administering to the subject from about 50 mg to about 200 mg of *Sambucus nigra*, or a salt or solvate thereof, once daily; c) administering to the subject from about 100 mg to about 300 mg of emtricitabine, or a salt or solvate thereof, once daily; d) administering to the subject from about 100 mg to about 400 mg of tenofovir, or a salt or solvate thereof, once daily; and e) administering to the subject from about 0.05 mg to about 0.2 mg levonorgestrel, or a salt or solvate thereof, and from about 0.01 mg to about 0.03 mg ethinyl estradiol, or a salt or solvate thereof, once per day for about 21 days, followed by a placebo for about 7 days.

In some embodiments, the compositions useful for preventing pregnancy and HSV infection in seronegative subjects comprising valacyclovir, or a salt or solvate thereof, further comprise tenofovir, emtricitabine and one or more contraceptive agents. In some embodiments, the methods for preventing pregnancy and HSV infection in seronegative subjects comprising administering to the subject valacyclovir, or a salt or solvate thereof, further comprise administering to the subject emtricitabine, or a salt or solvate thereof; tenofovir, or a salt or solvate thereof; and one or more contraceptive agents. In some cases, the contraceptive agents comprise dosogestrel and ethinyl estradiol. In some embodiments, the methods comprise administering to the HSV seronegative subject at least or about 50 mg, 100 mg, 150 mg, 200 mg, 250 mg, 300 mg, 350 mg, or 400 mg of tenofovir, or a salt or solvate thereof. In some embodiments, the methods comprise administering to the HSV seronegative subject at least or about 50 mg, 100 mg, 150 mg, 200 mg, 250 mg, 300 mg, 350 mg, or 400 mg of emtricitabine, or a salt or solvate thereof. In some embodiments, the methods comprise administering to the HSV seronegative subject at least or about 0.05 mg, 0.10 mg, 0.15 mg, 0.2 mg, 0.25 mg or 0.3 mg of dosogestrel, or a salt or solvate thereof. In some embodiments, the methods comprise administering to the HSV seronegative subject at least or about 0.01 mg, 0.015 mg, 0.02 mg, 0.025 mg, 0.03 mg, 0.035 mg, or 0.04 mg of ethinyl estradiol, or a salt or solvate thereof. In some cases, emtricitabine is administered 1 time per week, 2 times per week, 3 times per week, 4 times per week, 5 times per week, 6 times per week, 1 time per day, 2 times per day, 3 times per day, 4 times per day, or continuously for a set duration of time. In some cases, tenofovir is administered 1 time per week, 2 times per week, 3 times per week, 4 times per week, 5 times per week, 6 times per week, 1 time per day, 2 times per day, 3 times per day, 4 times per day, or continuously for a set duration of time. In some cases, dosogestrel and ethinyl estradiol are administered in cycles, each cycle comprising administering dosogestrel and ethinyl estradiol daily for 21 days, followed by administering a placebo for 7 days. In some cases, a method of preventing pregnancy and HSV infection in the HSV seronegative subject comprises a) administering to the subject from about 500 to about 1500 mg of valacyclovir, or a salt or solvate thereof, once daily, b) administering to the subject from about 100 mg to about 300 mg of emtricitabine, or a salt or solvate thereof, once daily; c) administering to the subject from about 100 mg to about 400 mg of tenofovir, or a salt or solvate thereof, once daily; and d) administering to the subject from about 0.05 mg to about 0.2 mg dosogestrel, or a salt or solvate thereof, and from about 0.02 mg to about 0.04 mg ethinyl estradiol, or a salt or solvate thereof, once per day for about 21 days, followed by a placebo for about 7 days.

In some embodiments, the compositions useful for preventing pregnancy and HSV infection in seronegative subjects comprising valacyclovir, or a salt or solvate thereof, further comprise tenofovir, lamivudine and one or more contraceptive agents. In some embodiments, the methods for preventing pregnancy and HSV infection in seronegative subjects comprising administering to the subject valacyclovir, or a salt or solvate thereof, further comprise administering to the subject lamivudine, or a salt or solvate thereof; tenofovir, or a salt or solvate thereof; and one or more contraceptive agents. In some cases, the contraceptive agents comprise dosogestrel and ethinyl estradiol. In some embodiments, the methods comprise administering to the HSV seronegative subject at least or about 50 mg, 100 mg, 150 mg, 200 mg, 250 mg, 300 mg, 350 mg, or 400 mg of tenofovir, or a salt or solvate thereof. In some embodiments, the methods comprise administering to the HSV seronegative subject at least or about 50 mg, 100 mg, 150 mg, 200 mg, 250 mg, 300 mg, 350 mg, or 400 mg of lamivudine, or a salt or solvate thereof. In some embodiments, the methods comprise administering to the HSV seronegative subject at least or about 0.05 mg, 0.10 mg, 0.15 mg, 0.2 mg, 0.25 mg or 0.3 mg of dosogestrel, or a salt or solvate thereof. In some embodiments, the methods comprise administering to the HSV seronegative subject at least or about 0.01 mg, 0.015 mg, 0.02 mg, 0.025 mg, 0.03 mg, 0.035 mg, or 0.04 mg of ethinyl estradiol, or a salt or solvate thereof. In some cases, lamivudine is administered 1 time per week, 2 times per week, 3 times per week, 4 times per week, 5 times per week, 6 times per week, 1 time per day, 2 times per day, 3 times per day, 4 times per day, or continuously for a set duration of time. In some cases, tenofovir is administered 1 time per week, 2 times per week, 3 times per week, 4 times per week, 5 times per week, 6 times per week, 1 time per day, 2 times per day, 3 times per day, 4 times per day, or continuously for a set duration of time. In some cases, dosogestrel and ethinyl estradiol are administered in cycles, each cycle comprising administering dosogestrel and ethinyl estradiol daily for 21 days, followed by administering a placebo for 7 days. In some cases, a method of preventing pregnancy and HSV infection in the HSV seronegative subject comprises a) administering to the subject from about 500 to about 1500 mg of valacyclovir, or a salt or solvate thereof, once daily, b) administering to the subject from about 100 mg to about 300 mg of lamivudine, or a salt or solvate thereof, once daily; c) administering to the subject from about 100 mg to about 400 mg of tenofovir, or a salt or solvate thereof, once daily; and d) administering to the subject from about 0.05 mg to about 0.2 mg dosogestrel, or a salt or solvate thereof, and from about 0.02 mg to about 0.04 mg ethinyl estradiol, or a salt or solvate thereof, once per day for about 21 days, followed by a placebo for about 7 days.

In some embodiments, the compositions useful for preventing pregnancy and HSV infection in seronegative subjects comprising valacyclovir, or a salt or solvate thereof, further comprise tenofovir, emtricitabine, glycyrrhizic acid and one or more contraceptive agents. In some embodiments, the methods for preventing pregnancy and HSV infection in seronegative subjects comprising administering to the subject valacyclovir, or a salt or solvate thereof, further comprise administering to the subject emtricitabine, or a salt or solvate thereof; glycyrrhizic acid, or a salt or solvate thereof; tenofovir, or a salt or solvate thereof; and one or more contraceptive agents. In some cases, the contraceptive agents comprise dosogestrel and ethinyl estradiol. In some embodiments, the methods comprise administering to the HSV seronegative subject at least or about 50 mg, 100 mg, 150 mg, 200 mg, 250 mg, 300 mg, 350 mg, or 400 mg of tenofovir, or a salt or solvate thereof. In some embodiments, the methods comprise administering to the HSV seronegative subject at least or about 50 mg, 100 mg, 150 mg, 200 mg, 250 mg, 300 mg, 350 mg, or 400 mg of emtricitabine, or a salt or solvate thereof. In some embodiments, the methods comprise administering to the HSV seronegative subject at least or about 1 mg, 2 mg, 3 mg, 4 mg, 5 mg, 6 mg, 7 mg, 8 mg, 9 mg, 10 mg, 11 mg, 12 mg, 13 mg, 14 mg, 15 mg, or 20 mg of glycyrrhizic acid, or a salt or solvate thereof. In some embodiments, the methods comprise administering to the HSV seronegative subject at least or about 0.05 mg, 0.10 mg, 0.15 mg, 0.2 mg, 0.25 mg or 0.3 mg of dosogestrel, or a salt or solvate thereof. In some embodiments, the methods comprise administering to the HSV seronegative subject at least or about 0.01 mg, 0.015 mg, 0.02 mg, 0.025 mg, 0.03 mg, 0.035 mg, or 0.04 mg of ethinyl estradiol, or a salt or solvate thereof. In some cases, glycyrrhizic acid is administered 1 time per week, 2 times per week, 3 times per week, 4 times per week, 5 times per week, 6 times per week, 1 time per day, 2 times per day, 3 times per day, 4 times per day, or continuously for a set duration of time. In some cases, emtricitabine is administered 1 time per week, 2 times per week, 3 times per week, 4 times per week, 5 times per week, 6 times per week, 1 time per day, 2 times per day, 3 times per day, 4 times per day, or continuously for a set duration of time. In some cases, tenofovir is administered 1 time per week, 2 times per week, 3 times per week, 4 times per week, 5 times per week, 6 times per week, 1 time per day, 2 times per day, 3 times per day, 4 times per day, or continuously for a set duration of time. In some cases, dosogestrel and ethinyl estradiol are administered in cycles, each cycle comprising administering dosogestrel and ethinyl estradiol daily for 21 days, followed by administering a placebo for 7 days. In some cases, a method of preventing pregnancy and HSV infection in the HSV seronegative subject comprises a) administering to the subject from about 500 to about 1500 mg of valacyclovir, or a salt or solvate thereof, once daily, b) administering to the subject from about 1 mg to about 10 mg of glycyrrhizic acid, or a salt or solvate thereof, once daily; c) administering to the subject from about 100 mg to about 400 mg of tenofovir, or a salt or solvate thereof, once daily; d) administering to the subject from about 100 mg to about 300 mg of emtricitabine, or a salt or solvate thereof, once daily; and e) administering to the subject from about 0.05 mg to about 0.2 mg dosogestrel, or a salt or solvate thereof, and from about 0.02 mg to about 0.04 mg ethinyl estradiol, or a salt or solvate thereof, once per day for about 21 days, followed by a placebo for about 7 days.

In some embodiments, the compositions useful for preventing pregnancy and HSV infection in seronegative subjects comprising valacyclovir, or a salt or solvate thereof, further comprise tenofovir, emtricitabine, *Sambucus nigra* and one or more contraceptive agents. In some embodiments, the methods for preventing pregnancy and HSV infection in seronegative subjects comprising administering to the subject valacyclovir, or a salt or solvate thereof, further comprise administering to the subject emtricitabine, or a salt or solvate thereof; *Sambucus nigra*, or a salt or solvate thereof; tenofovir, or a salt or solvate thereof; and one or more contraceptive agents. In some cases, the contraceptive agents comprise dosogestrel and ethinyl estradiol. In some embodiments, the methods comprise administering to the HSV seronegative subject at least or about 50 mg, 100 mg, 150 mg, 200 mg, 250 mg, 300 mg, 350 mg, or 400 mg of tenofovir, or a salt or solvate thereof. In some embodiments, the methods comprise administering to the HSV seronegative subject at least or about 50 mg, 100 mg, 150 mg, 200 mg, 250 mg, 300 mg, 350 mg, or 400 mg of emtricitabine, or a salt or solvate thereof. In some embodiments, the methods comprise administering to the HSV seronegative subject at least or about 50 mg, 100 mg, 150 mg, 200 mg, 250 mg, or 300 mg *sambucus nigra* or a salt or solvate thereof. In some embodiments, the methods comprise administering to the HSV seronegative subject at least or about 0.05 mg, 0.10 mg, 0.15 mg, 0.2 mg, 0.25 mg or 0.3 mg of dosogestrel, or a salt or solvate thereof. In some embodiments, the methods comprise administering to the HSV seronegative subject at least or about 0.01 mg, 0.015 mg, 0.02 mg, 0.025 mg, 0.03 mg, 0.035 mg, or 0.04 mg of ethinyl estradiol, or a salt or solvate thereof. In some cases, *Sambucus nigra* is administered 1 time per week, 2 times per week, 3 times per week, 4 times per week, 5 times per week, 6 times per week, 1 time per day, 2 times per day, 3 times per day, 4 times per day, or continuously for a set duration of time. In some cases, emtricitabine is administered 1 time per week, 2 times per week, 3 times per week, 4 times per week, 5 times per week, 6 times per week, 1 time per day, 2 times per day, 3 times per day, 4 times per day, or continuously for a set duration of time. In some cases, tenofovir is administered 1 time per week, 2 times per week, 3 times per week, 4 times per week, 5 times per week, 6 times per week, 1 time per day, 2 times per day, 3 times per day, 4 times per day, or continuously for a set duration of time. In some cases, dosogestrel and ethinyl estradiol are administered in cycles, each cycle comprising administering dosogestrel and ethinyl estradiol daily for 21 days, followed by administering a placebo for 7 days. In some cases, a method of preventing pregnancy and HSV infection in the HSV seronegative subject comprises a) administering to the subject from about 500 to about 1500 mg of valacyclovir, or a salt or solvate thereof, once daily, b) administering to the subject from about 50 mg to about 200 mg of *Sambucus nigra*, or a salt or solvate thereof, once daily; c) administering to the subject from about 100 mg to about 400 mg of tenofovir, or a salt or solvate thereof, once daily; d) administering to the subject from about 100 mg to about 300 mg of emtricitabine, or a salt or solvate thereof, once daily; and e) administering to the subject from about 0.05 mg to about 0.2 mg dosogestrel, or a salt or solvate thereof, and from about 0.02 mg to about 0.04 mg ethinyl estradiol, or a salt or solvate thereof, once per day for about 21 days, followed by a placebo for about 7 days.

In some embodiments, the compositions useful for preventing pregnancy and HSV infection in seronegative subjects comprising valacyclovir, or a salt or solvate thereof, further comprise tenofovir, emtricitabine, efavirenz and one or more contraceptive agents. In some embodiments, the methods for preventing pregnancy and HSV infection in seronegative subjects comprising administering to the subject valacyclovir, or a salt or solvate thereof, further comprise administering to the subject emtricitabine, or a salt or solvate thereof; efavirenz, or a salt or solvate thereof; tenofovir, or a salt or solvate thereof; and one or more contraceptive agents. In some cases, the contraceptive agents comprise dosogestrel and ethinyl estradiol. In some embodiments, the methods comprise administering to the HSV seronegative subject at least or about 50 mg, 100 mg, 150 mg, 200 mg, 250 mg, 300 mg, 350 mg, or 400 mg of tenofovir, or a salt or solvate thereof. In some embodiments, the methods comprise administering to the HSV seronegative subject at least or about 50 mg, 100 mg, 150 mg, 200 mg, 250 mg, 300 mg, 350 mg, or 400 mg of emtricitabine, or a salt or solvate thereof. In some embodiments, the methods comprise administering to the HSV seronegative subject at least or about 100 mg, 200 mg, 300 mg, 400 mg, 500 mg, 600 mg, 700 mg, or 800 mg efavirenz or a salt or solvate thereof. In some embodiments, the methods comprise administering to the HSV seronegative subject at least or about 0.05 mg, 0.10 mg, 0.15 mg, 0.2 mg, 0.25 mg or 0.3 mg of dosogestrel, or a salt or solvate thereof. In some embodiments, the methods comprise administering to the HSV seronegative subject at least or about 0.01 mg, 0.015 mg, 0.02 mg, 0.025 mg, 0.03 mg, 0.035 mg, or 0.04 mg of ethinyl estradiol, or a salt or solvate thereof. In some cases, efavirenz is administered 1 time per week, 2 times per week, 3 times per week, 4 times per week, 5 times per week, 6 times per week, 1 time per day, 2 times per day, 3 times per day, 4 times per day, or continuously for a set duration of time. In some cases, emtricitabine is administered 1 time per week, 2 times per week, 3 times per week, 4 times per week, 5 times per week, 6 times per week, 1 time per day, 2 times per day, 3 times per day, 4 times per day, or continuously for a set duration of time. In some cases, tenofovir is administered 1 time per week, 2 times per week, 3 times per week, 4 times per week, 5 times per week, 6 times per week, 1 time per day, 2 times per day, 3 times per day, 4 times per day, or continuously for a set duration of time. In some cases, dosogestrel and ethinyl estradiol are administered in cycles, each cycle comprising administering dosogestrel and ethinyl estradiol daily for 21 days, followed by administering a placebo for 7 days. In some cases, a method of preventing pregnancy and HSV infection in the HSV seronegative subject comprises a) administering to the subject from about 500 to about 1500 mg of valacyclovir, or a salt or solvate thereof, once daily, b) administering to the subject from about 400 mg to about 700 mg of efavirenz, or a salt or solvate thereof, once daily; c) administering to the subject from about 100 mg to about 400 mg of tenofovir, or a salt or solvate thereof, once daily; d) administering to the subject from about 100 mg to about 300 mg of emtricitabine, or a salt or solvate thereof, once daily; and e) administering to the subject from about 0.05 mg to about 0.2 mg dosogestrel, or a salt or solvate thereof, and from about 0.02 mg to about 0.04 mg ethinyl estradiol, or a salt or solvate thereof, once per day for about 21 days, followed by a placebo for about 7 days.

In some embodiments, the compositions useful for preventing pregnancy and HSV infection in seronegative subjects comprising valacyclovir, or a salt or solvate thereof, further comprise tenofovir, lamivudine, efavirenz and one or more contraceptive agents. In some embodiments, the methods for preventing pregnancy and HSV infection in seronegative subjects comprising administering to the subject valacyclovir, or a salt or solvate thereof, further comprise administering to the subject lamivudine, or a salt or solvate thereof; efavirenz, or a salt or solvate thereof; tenofovir, or a salt or solvate thereof; and one or more contraceptive agents. In some cases, the contraceptive agents comprise dosogestrel and ethinyl estradiol. In some embodiments, the methods comprise administering to the HSV seronegative subject at least or about 50 mg, 100 mg, 150 mg, 200 mg, 250 mg, 300 mg, 350 mg, or 400 mg of tenofovir, or a salt or solvate thereof. In some embodiments, the methods comprise administering to the HSV seronegative subject at least or about 50 mg, 100 mg, 150 mg, 200 mg, 250 mg, 300 mg, 350 mg, or 400 mg of lamivudine, or a salt or solvate thereof. In some embodiments, the methods comprise administering to the HSV seronegative subject at least or about 100 mg, 200 mg, 300 mg, 400 mg, 500 mg, 600 mg, 700 mg, or 800 mg efavirenz or a salt or solvate thereof. In some embodiments, the methods comprise administering to the HSV seronegative subject at least or about 0.05 mg, 0.10 mg, 0.15 mg, 0.2 mg, 0.25 mg or 0.3 mg of dosogestrel, or a salt or solvate thereof. In some embodiments, the methods comprise administering to the HSV seronegative subject at least or about 0.01 mg, 0.015 mg, 0.02 mg, 0.025 mg, 0.03 mg, 0.035 mg, or 0.04 mg of ethinyl estradiol, or a salt or solvate thereof. In some cases, efavirenz is administered 1 time per week, 2 times per week, 3 times per week, 4 times per week, 5 times per week, 6 times per week, 1 time per day, 2 times per day, 3 times per day, 4 times per day, or continuously for a set duration of time. In some cases, lamivudine is administered 1 time per week, 2 times per week, 3 times per week, 4 times per week, 5 times per week, 6 times per week, 1 time per day, 2 times per day, 3 times per day, 4 times per day, or continuously for a set duration of time. In some cases, tenofovir is administered 1 time per week, 2 times per week, 3 times per week, 4 times per week, 5 times per week, 6 times per week, 1 time per day, 2 times per day, 3 times per day, 4 times per day, or continuously for a set duration of time. In some cases, dosogestrel and ethinyl estradiol are administered in cycles, each cycle comprising administering dosogestrel and ethinyl estradiol daily for 21 days, followed by administering a placebo for 7 days. In some cases, a method of preventing pregnancy and HSV infection in the HSV seronegative subject comprises a) administering to the subject from about 500 to about 1500 mg of valacyclovir, or a salt or solvate thereof, once daily, b) administering to the subject from about 400 mg to about 700 mg of efavirenz, or a salt or solvate thereof, once daily; c) administering to the subject from about 100 mg to about 400 mg of tenofovir, or a salt or solvate thereof, once daily; d) administering to the subject from about 100 mg to about 300 mg of lamivudine, or a salt or solvate thereof, once daily; and e) administering to the subject from about 0.05 mg to about 0.2 mg dosogestrel, or a salt or solvate thereof, and from about 0.02 mg to about 0.04 mg ethinyl estradiol, or a salt or solvate thereof, once per day for about 21 days, followed by a placebo for about 7 days.

In some embodiments, the compositions useful for preventing pregnancy and HSV infection in seronegative subjects comprising valacyclovir, or a salt or solvate thereof, further comprise tenofovir, emtricitabine, efavirenz, glycyrrhizic acid and one or more contraceptive agents. In some embodiments, the methods for preventing pregnancy and HSV infection in seronegative subjects comprising administering to the subject valacyclovir, or a salt or solvate thereof, further comprise administering to the subject emtricitabine, or a salt or solvate thereof; efavirenz, or a salt or solvate thereof; tenofovir, or a salt or solvate thereof; glycyrrhizic acid, or a salt or solvate thereof; and one or more contraceptive agents. In some cases, the contraceptive agents comprise dosogestrel and ethinyl estradiol. In some embodiments, the methods comprise administering to the HSV seronegative subject at least or about 50 mg, 100 mg, 150 mg, 200 mg, 250 mg, 300 mg, 350 mg, or 400 mg of tenofovir, or a salt or solvate thereof. In some embodiments, the methods comprise administering to the HSV seronegative subject at least or about 50 mg, 100 mg, 150 mg, 200 mg, 250 mg, 300 mg, 350 mg, or 400 mg of emtricitabine, or a salt or solvate thereof. In some embodiments, the methods comprise administering to the HSV seronegative subject at least or about 100 mg, 200 mg, 300 mg, 400 mg, 500 mg, 600 mg, 700 mg, or 800 mg efavirenz or a salt or solvate thereof. In some embodiments, the methods comprise administering to the HSV seronegative subject at least or about 1 mg, 2 mg, 3 mg, 4 mg, 5 mg, 6 mg, 7 mg, 8 mg, 9 mg, 10 mg, 11 mg, 12 mg, 13 mg, 14 mg, 15 mg, or 20 mg of glycyrrhizic acid, or a salt or solvate thereof. In some embodiments, the methods comprise administering to the HSV seronegative subject at least or about 0.05 mg, 0.10 mg, 0.15 mg, 0.2 mg, 0.25 mg or 0.3 mg of dosogestrel, or a salt or solvate thereof. In some embodiments, the methods comprise administering to the HSV seronegative subject at least or about 0.01 mg, 0.015 mg, 0.02 mg, 0.025 mg, 0.03 mg, 0.035 mg, or 0.04 mg of ethinyl estradiol, or a salt or solvate thereof. In some cases, efavirenz is administered 1 time per week, 2 times per week, 3 times per week, 4 times per week, 5 times per week, 6 times per week, 1 time per day, 2 times per day, 3 times per day, 4 times per day, or continuously for a set duration of time. In some cases, emtricitabine is administered 1 time per week, 2 times per week, 3 times per week, 4 times per week, 5 times per week, 6 times per week, 1 time per day, 2 times per day, 3 times per day, 4 times per day, or continuously for a set duration of time. In some cases, tenofovir is administered 1 time per week, 2 times per week, 3 times per week, 4 times per week, 5 times per week, 6 times per week, 1 time per day, 2 times per day, 3 times per day, 4 times per day, or continuously for a set duration of time. In some cases, glycyrrhizic acid is administered 1 time per week, 2 times per week, 3 times per week, 4 times per week, 5 times per week, 6 times per week, 1 time per day, 2 times per day, 3 times per day, 4 times per day, or continuously for a set duration of time. In some cases, dosogestrel and ethinyl estradiol are administered in cycles, each cycle comprising administering dosogestrel and ethinyl estradiol daily for 21 days, followed by administering a placebo for 7 days. In some cases, a method of preventing pregnancy and HSV infection in the HSV seronegative subject comprises a) administering to the subject from about 500 to about 1500 mg of valacyclovir, or a salt or solvate thereof, once daily, b) administering to the subject from about 400 mg to about 700 mg of efavirenz, or a salt or solvate thereof, once daily; c) administering to the subject from about 100 mg to about 400 mg of tenofovir, or a salt or solvate thereof, once daily; d) administering to the subject from about 100 mg to about 300 mg of emtricitabine, or a salt or solvate thereof, once daily; e) administering to the subject from about 1 mg to about 10 mg of glycyrrhizic acid, or a salt or solvate thereof, once daily; and f) administering to the subject from about 0.05 mg to about 0.2 mg dosogestrel, or a salt or solvate thereof, and from about 0.02 mg to about 0.04 mg ethinyl estradiol, or a salt or solvate thereof, once per day for about 21 days, followed by a placebo for about 7 days.

In some embodiments, the compositions useful for preventing pregnancy and HSV infection in seronegative subjects comprising valacyclovir, or a salt or solvate thereof, further comprise tenofovir, emtricitabine, efavirenz, *Sambucus nigra* and one or more contraceptive agents. In some embodiments, the methods for preventing pregnancy and HSV infection in seronegative subjects comprising administering to the subject valacyclovir, or a salt or solvate thereof, further comprise administering to the subject emtricitabine, or a salt or solvate thereof; efavirenz, or a salt or solvate thereof; tenofovir, or a salt or solvate thereof; *Sambucus nigra*, or a salt or solvate thereof; and one or more contraceptive agents. In some cases, the contraceptive agents comprise dosogestrel and ethinyl estradiol. In some embodiments, the methods comprise administering to the HSV seronegative subject at least or about 50 mg, 100 mg, 150 mg, 200 mg, 250 mg, 300 mg, 350 mg, or 400 mg of tenofovir, or a salt or solvate thereof. In some embodiments, the methods comprise administering to the HSV seronegative subject at least or about 50 mg, 100 mg, 150 mg, 200 mg, 250 mg, 300 mg, 350 mg, or 400 mg of emtricitabine, or a salt or solvate thereof. In some embodiments, the methods comprise administering to the HSV seronegative subject at least or about 100 mg, 200 mg, 300 mg, 400 mg, 500 mg, 600 mg, 700 mg, or 800 mg efavirenz or a salt or solvate thereof. In some embodiments, the methods comprise administering to the HSV seronegative subject at least or about 50 mg, 100 mg, 150 mg, 200 mg, 250 mg, 300 mg, 350 mg, or 400 mg of *Sambucus nigra*, or a salt or solvate thereof. In some embodiments, the methods comprise administering to the HSV seronegative subject at least or about 0.05 mg, 0.10 mg, 0.15 mg, 0.2 mg, 0.25 mg or 0.3 mg of dosogestrel, or a salt or solvate thereof. In some embodiments, the methods comprise administering to the HSV seronegative subject at least or about 0.01 mg, 0.015 mg, 0.02 mg, 0.025 mg, 0.03 mg, 0.035 mg, or 0.04 mg of ethinyl estradiol, or a salt or solvate thereof. In some cases, efavirenz is administered 1 time per week, 2 times per week, 3 times per week, 4 times per week, 5 times per week, 6 times per week, 1 time per day, 2 times per day, 3 times per day, 4 times per day, or continuously for a set duration of time. In some cases, emtricitabine is administered 1 time per week, 2 times per week, 3 times per week, 4 times per week, 5 times per week, 6 times per week, 1 time per day, 2 times per day, 3 times per day, 4 times per day, or continuously for a set duration of time. In some cases, tenofovir is administered 1 time per week, 2 times per week, 3 times per week, 4 times per week, 5 times per week, 6 times per week, 1 time per day, 2 times per day, 3 times per day, 4 times per day, or continuously for a set duration of time. In some cases, *Sambucus nigra* is administered 1 time per week, 2 times per week, 3 times per week, 4 times per week, 5 times per week, 6 times per week, 1 time per day, 2 times per day, 3 times per day, 4 times per day, or continuously for a set duration of time. In some cases, dosogestrel and ethinyl estradiol are administered in cycles, each cycle comprising administering dosogestrel and ethinyl estradiol daily for 21 days, followed by administering a placebo for 7 days. In some cases, a method of preventing pregnancy and HSV infection in the HSV seronegative subject comprises a) administering to the subject from about 500 to about 1500 mg of valacyclovir, or a salt or solvate thereof, once daily, b) administering to the subject from about 400 mg to about 700 mg of efavirenz, or a salt or solvate thereof, once daily; c) administering to the subject from about 100 mg to about 400 mg of tenofovir, or a salt or solvate thereof, once daily; d) administering to the subject from about 100 mg to about 300 mg of emtricitabine, or a salt or solvate thereof, once daily; e) administering to the subject from about 50 mg to about 300 mg of *Sambucus nigra*, or a salt or solvate thereof, once daily; and f) administering to the subject from about 0.05 mg to about 0.2 mg dosogestrel, or a salt or solvate thereof, and from about 0.02 mg to about 0.04 mg ethinyl estradiol, or a salt or solvate thereof, once per day for about 21 days, followed by a placebo for about 7 days.

In some embodiments, the compositions useful for preventing pregnancy and HSV infection in seronegative subjects comprising valacyclovir, or a salt or solvate thereof, further comprise tenofovir, emtricitabine, dolutegravir and one or more contraceptive agents. In some embodiments, the methods for preventing pregnancy and HSV infection in seronegative subjects comprising administering to the subject valacyclovir, or a salt or solvate thereof, further comprise administering to the subject emtricitabine, or a salt or solvate thereof; dolutegravir, or a salt or solvate thereof; tenofovir, or a salt or solvate thereof; and one or more contraceptive agents. In some cases, the contraceptive agents comprise dosogestrel and ethinyl estradiol. In some embodiments, the methods comprise administering to the HSV seronegative subject at least or about 50 mg, 100 mg, 150 mg, 200 mg, 250 mg, 300 mg, 350 mg, or 400 mg of tenofovir, or a salt or solvate thereof. In some embodiments, the methods comprise administering to the HSV seronegative subject at least or about 50 mg, 100 mg, 150 mg, 200 mg, 250 mg, 300 mg, 350 mg, or 400 mg of emtricitabine, or a salt or solvate thereof. In some embodiments, the methods comprise administering to the HSV seronegative subject at least or about 20 mg, 30 mg, 40 mg, 50 mg, 60 mg, 70 mg, 80 mg, 90 mg or 100 mg of dolutegravir or a salt or solvate thereof. In some embodiments, the methods comprise administering to the HSV seronegative subject at least or about 0.05 mg, 0.10 mg, 0.15 mg, 0.2 mg, 0.25 mg or 0.3 mg of dosogestrel, or a salt or solvate thereof. In some embodiments, the methods comprise administering to the HSV seronegative subject at least or about 0.01 mg, 0.015 mg, 0.02 mg, 0.025 mg, 0.03 mg, 0.035 mg, or 0.04 mg of ethinyl estradiol, or a salt or solvate thereof. In some cases, dolutegravir is administered 1 time per week, 2 times per week, 3 times per week, 4 times per week, 5 times per week, 6 times per week, 1 time per day, 2 times per day, 3 times per day, 4 times per day, or continuously for a set duration of time. In some cases, emtricitabine is administered 1 time per week, 2 times per week, 3 times per week, 4 times per week, 5 times per week, 6 times per week, 1 time per day, 2 times per day, 3 times per day, 4 times per day, or continuously for a set duration of time. In some cases, tenofovir is administered 1 time per week, 2 times per week, 3 times per week, 4 times per week, 5 times per week, 6 times per week, 1 time per day, 2 times per day, 3 times per day, 4 times per day, or continuously for a set duration of time. In some cases, dosogestrel and ethinyl estradiol are administered in cycles, each cycle comprising administering dosogestrel and ethinyl estradiol daily for 21 days, followed by administering a placebo for 7 days. In some cases, a method of preventing pregnancy and HSV infection in the HSV seronegative subject comprises a) administering to the subject from about 500 to about 1500 mg of valacyclovir, or a salt or solvate thereof, once daily, b) administering to the subject from about 20 mg to about 70 mg of dolutegravir, or a salt or solvate thereof, once daily; c) administering to the subject from about 100 mg to about 400 mg of tenofovir, or a salt or solvate thereof, once daily; d) administering to the subject from about 100 mg to about 300 mg of emtricitabine, or a salt or solvate thereof, once daily; and e) administering to the subject from about 0.05 mg to about 0.2 mg dosogestrel, or a salt or solvate thereof, and from about 0.02 mg to about 0.04 mg ethinyl estradiol, or a salt or solvate thereof, once per day for about 21 days, followed by a placebo for about 7 days.

In some embodiments, the compositions useful for preventing pregnancy and HSV infection in seronegative subjects comprising valacyclovir, or a salt or solvate thereof, further comprise tenofovir, lamivudine, dolutegravir and one or more contraceptive agents. In some embodiments, the methods for preventing pregnancy and HSV infection in seronegative subjects comprising administering to the subject valacyclovir, or a salt or solvate thereof, further comprise administering to the subject lamivudine, or a salt or solvate thereof; dolutegravir, or a salt or solvate thereof; tenofovir, or a salt or solvate thereof; and one or more contraceptive agents. In some cases, the contraceptive agents comprise dosogestrel and ethinyl estradiol. In some embodiments, the methods comprise administering to the HSV seronegative subject at least or about 50 mg, 100 mg, 150 mg, 200 mg, 250 mg, 300 mg, 350 mg, or 400 mg of tenofovir, or a salt or solvate thereof. In some embodiments, the methods comprise administering to the HSV seronegative subject at least or about 50 mg, 100 mg, 150 mg, 200 mg, 250 mg, 300 mg, 350 mg, or 400 mg of lamivudine, or a salt or solvate thereof. In some embodiments, the methods comprise administering to the HSV seronegative subject at least or about 20 mg, 30 mg, 40 mg, 50 mg, 60 mg, 70 mg, 80 mg, 90 mg or 100 mg of dolutegravir or a salt or solvate thereof. In some embodiments, the methods comprise administering to the HSV seronegative subject at least or about 0.05 mg, 0.10 mg, 0.15 mg, 0.2 mg, 0.25 mg or 0.3 mg of dosogestrel, or a salt or solvate thereof. In some embodiments, the methods comprise administering to the HSV seronegative subject at least or about 0.01 mg, 0.015 mg, 0.02 mg, 0.025 mg, 0.03 mg, 0.035 mg, or 0.04 mg of ethinyl estradiol, or a salt or solvate thereof. In some cases, dolutegravir is administered 1 time per week, 2 times per week, 3 times per week, 4 times per week, 5 times per week, 6 times per week, 1 time per day, 2 times per day, 3 times per day, 4 times per day, or continuously for a set duration of time. In some cases, lamivudine is administered 1 time per week, 2 times per week, 3 times per week, 4 times per week, 5 times per week, 6 times per week, 1 time per day, 2 times per day, 3 times per day, 4 times per day, or continuously for a set duration of time. In some cases, tenofovir is administered 1 time per week, 2 times per week, 3 times per week, 4 times per week, 5 times per week, 6 times per week, 1 time per day, 2 times per day, 3 times per day, 4 times per day, or continuously for a set duration of time. In some cases, dosogestrel and ethinyl estradiol are administered in cycles, each cycle comprising administering dosogestrel and ethinyl estradiol daily for 21 days, followed by administering a placebo for 7 days. In some cases, a method of preventing pregnancy and HSV infection in the HSV seronegative subject comprises a) administering to the subject from about 500 to about 1500 mg of valacyclovir, or a salt or solvate thereof, once daily, b) administering to the subject from about 20 mg to about 70 mg of dolutegravir, or a salt or solvate thereof, once daily; c) administering to the subject from about 100 mg to about 400 mg of tenofovir, or a salt or solvate thereof, once daily; d) administering to the subject from about 100 mg to about 300 mg of lamivudine, or a salt or solvate thereof, once daily; and e) administering to the subject from about 0.05 mg to about 0.2 mg dosogestrel, or a salt or solvate thereof, and from about 0.02 mg to about 0.04 mg ethinyl estradiol, or a salt or solvate thereof, once per day for about 21 days, followed by a placebo for about 7 days.

In some embodiments, the compositions useful for preventing pregnancy and HSV infection in seronegative subjects comprising valacyclovir, or a salt or solvate thereof, further comprise tenofovir, emtricitabine, dolutegravir, glycyrrhizic acid and one or more contraceptive agents. In some embodiments, the methods for preventing pregnancy and HSV infection in seronegative subjects comprising administering to the subject valacyclovir, or a salt or solvate thereof, further comprise administering to the subject emtricitabine, or a salt or solvate thereof; dolutegravir, or a salt or solvate thereof; tenofovir, or a salt or solvate thereof; glycyrrhizic acid, or a salt or solvate thereof; and one or more contraceptive agents. In some cases, the contraceptive agents comprise dosogestrel and ethinyl estradiol. In some embodiments, the methods comprise administering to the HSV seronegative subject at least or about 50 mg, 100 mg, 150 mg, 200 mg, 250 mg, 300 mg, 350 mg, or 400 mg of tenofovir, or a salt or solvate thereof. In some embodiments, the methods comprise administering to the HSV seronegative subject at least or about 50 mg, 100 mg, 150 mg, 200 mg, 250 mg, 300 mg, 350 mg, or 400 mg of emtricitabine, or a salt or solvate thereof. In some embodiments, the methods comprise administering to the HSV seronegative subject at least or about 10 mg, 20 mg, 30 mg, 40 mg, 50 mg, 60 mg, 70 mg, 80 mg, 90 mg, or 100 mg of dolutegravir or a salt or solvate thereof. In some embodiments, the methods comprise administering to the HSV seronegative subject at least or about 1 mg, 2 mg, 3 mg, 4 mg, 5 mg, 6 mg, 7 mg, 8 mg, 9 mg, 10 mg, 11 mg, 12 mg, 13 mg, 14 mg, 15 mg, or 20 mg of glycyrrhizic acid, or a salt or solvate thereof. In some embodiments, the methods comprise administering to the HSV seronegative subject at least or about 0.05 mg, 0.10 mg, 0.15 mg, 0.2 mg, 0.25 mg or 0.3 mg of dosogestrel, or a salt or solvate thereof. In some embodiments, the methods comprise administering to the HSV seronegative subject at least or about 0.01 mg, 0.015 mg, 0.02 mg, 0.025 mg, 0.03 mg, 0.035 mg, or 0.04 mg of ethinyl estradiol, or a salt or solvate thereof. In some cases, dolutegravir is administered 1 time per week, 2 times per week, 3 times per week, 4 times per week, 5 times per week, 6 times per week, 1 time per day, 2 times per day, 3 times per day, 4 times per day, or continuously for a set duration of time. In some cases, emtricitabine is administered 1 time per week, 2 times per week, 3 times per week, 4 times per week, 5 times per week, 6 times per week, 1 time per day, 2 times per day, 3 times per day, 4 times per day, or continuously for a set duration of time. In some cases, tenofovir is administered 1 time per week, 2 times per week, 3 times per week, 4 times per week, 5 times per week, 6 times per week, 1 time per day, 2 times per day, 3 times per day, 4 times per day, or continuously for a set duration of time. In some cases, glycyrrhizic acid is administered 1 time per week, 2 times per week, 3 times per week, 4 times per week, 5 times per week, 6 times per week, 1 time per day, 2 times per day, 3 times per day, 4 times per day, or continuously for a set duration of time. In some cases, dosogestrel and ethinyl estradiol are administered in cycles, each cycle comprising administering dosogestrel and ethinyl estradiol daily for 21 days, followed by administering a placebo for 7 days. In some cases, a method of preventing pregnancy and HSV infection in the HSV seronegative subject comprises a) administering to the subject from about 500 to about 1500 mg of valacyclovir, or a salt or solvate thereof, once daily, b) administering to the subject from about 20 mg to about 70 mg of dolutegravir, or a salt or solvate thereof, once daily; c) administering to the subject from about 100 mg to about 400 mg of tenofovir, or a salt or solvate thereof, once daily; d) administering to the subject from about 100 mg to about 300 mg of emtricitabine, or a salt or solvate thereof, once daily; e) administering to the subject from about 1 mg to about 10 mg of glycyrrhizic acid, or a salt or solvate thereof, once daily; and f) administering to the subject from about 0.05 mg to about 0.2 mg dosogestrel, or a salt or solvate thereof, and from about 0.02 mg to about 0.04 mg ethinyl estradiol, or a salt or solvate thereof, once per day for about 21 days, followed by a placebo for about 7 days.

In some embodiments, the compositions useful for preventing pregnancy and HSV infection in seronegative subjects comprising valacyclovir, or a salt or solvate thereof, further comprise tenofovir, emtricitabine, dolutegravir, Sambucus nigra and one or more contraceptive agents. In some embodiments, the methods for preventing pregnancy and HSV infection in seronegative subjects comprising administering to the subject valacyclovir, or a salt or solvate thereof, further comprise administering to the subject emtricitabine, or a salt or solvate thereof; dolutegravir, or a salt or solvate thereof; tenofovir, or a salt or solvate thereof; Sambucus nigra, or a salt or solvate thereof; and one or more contraceptive agents. In some cases, the contraceptive agents comprise dosogestrel and ethinyl estradiol. In some embodiments, the methods comprise administering to the HSV seronegative subject at least or about 50 mg, 100 mg, 150 mg, 200 mg, 250 mg, 300 mg, 350 mg, or 400 mg of tenofovir, or a salt or solvate thereof. In some embodiments, the methods comprise administering to the HSV seronegative subject at least or about 50 mg, 100 mg, 150 mg, 200 mg, 250 mg, 300 mg, 350 mg, or 400 mg of emtricitabine, or a salt or solvate thereof. In some embodiments, the methods comprise administering to the HSV seronegative subject at least or about 10 mg, 20 mg, 30 mg, 40 mg, 50 mg, 60 mg, 70 mg, 80 mg, 90 mg, or 100 mg of dolutegravir or a salt or solvate thereof. In some embodiments, the methods comprise administering to the HSV seronegative subject at least or about 50 mg, 100 mg, 10 mg, 200 mg, 250 mg, or 300 mg of Sambucus nigra, or a salt or solvate thereof. In some embodiments, the methods comprise administering to the HSV seronegative subject at least or about 0.05 mg, 0.10 mg, 0.15 mg, 0.2 mg, 0.25 mg or 0.3 mg of dosogestrel, or a salt or solvate thereof. In some embodiments, the methods comprise administering to the HSV seronegative subject at least or about 0.01 mg, 0.015 mg, 0.02 mg, 0.025 mg, 0.03 mg, 0.035 mg, or 0.04 mg of ethinyl estradiol, or a salt or solvate thereof. In some cases, dolutegravir is administered 1 time per week, 2 times per week, 3 times per week, 4 times per week, 5 times per week, 6 times per week, 1 time per day, 2 times per day, 3 times per day, 4 times per day, or continuously for a set duration of time. In some cases, emtricitabine is administered 1 time per week, 2 times per week, 3 times per week, 4 times per week, 5 times per week, 6 times per week, 1 time per day, 2 times per day, 3 times per day, 4 times per day, or continuously for a set duration of time. In some cases, tenofovir is administered 1 time per week, 2 times per week, 3 times per week, 4 times per week, 5 times per week, 6 times per week, 1 time per day, 2 times per day, 3 times per day, 4 times per day, or continuously for a set duration of time. In some cases, Sambucus nigra is administered 1 time per week, 2 times per week, 3 times per week, 4 times per week, 5 times per week, 6 times per week, 1 time per day, 2 times per day, 3 times per day, 4 times per day, or continuously for a set duration of time. In some cases, dosogestrel and ethinyl estradiol are administered in cycles, each cycle comprising administering dosogestrel and ethinyl estradiol daily for 21 days, followed by administering a placebo for 7 days. In some cases, a method of preventing pregnancy and HSV infection in the HSV seronegative subject comprises a) administering to the subject from about 500 to about 1500 mg of valacyclovir, or a salt or solvate thereof, once daily, b) administering to the subject from about 20 mg to about 70 mg of dolutegravir, or a salt or solvate thereof, once daily; c) administering to the subject from about 100 mg to about 400 mg of tenofovir, or a salt or solvate thereof, once daily; d) administering to the subject from about 100 mg to about 300 mg of emtricitabine, or a salt or solvate thereof, once daily; e) administering to the subject from about 50 mg to about 200 mg of Sambucus nigra, or a salt or solvate thereof, once daily; and f) administering to the subject from about 0.05 mg to about 0.2 mg dosogestrel, or a salt or solvate thereof, and from about 0.02 mg to about 0.04 mg ethinyl estradiol, or a salt or solvate thereof, once per day for about 21 days, followed by a placebo for about 7 days.

Non-Limiting Antiviral Compositions for Preventing HSV Infection

In some embodiments, provided herein are methods of preventing HSV infection in an HSV seronegative subject comprising administering to the subject from about 200 mg to about 2,500 mg of valacyclovir, or a salt or solvate thereof, once per day. In some cases, valacyclovir is administered prior to exposure to HSV. In some cases, valacyclovir is administered after exposure to HSV. In some cases, valacyclovir is administered both prior to and after exposure to HSV. In some cases, valacyclovir is administered with one or more additional active agents, e.g., one or more additional antiviral agents, one or more contraceptive agents, or one or more additional antiviral agents and one or more contraceptive agents. In some embodiments, the methods further prevent infection of one or more additional infectious diseases, for example, HIV. In some embodiments, wherein the HSV seronegative subject is further administered one or more contraceptive agents, the methods further prevent pregnancy. In some embodiments, the methods further comprise administering to an HSV seropositive partner of the HSV seronegative subject one or more antiviral agents, for example, one or more HSV antiviral agents, one or more HIV antiviral agents, and/or any antiviral agent described herein. In some cases, the methods comprise administering to the HSV seronegative subject about 400 mg, 500 mg, 600 mg, 700 mg, 800 mg, 900 mg, 1000 mg, 1100 mg, 1200 mg, 1300 mg, 1400 mg, 1500 mg, 1600 mg, 1700 mg, 1800 mg, 1900 mg, 2000 mg, 2100 mg, 2200 mg, 2300 mg, 2400 mg, or 2500 mg of valacyclovir, or a salt or solvate thereof, once per day. In some cases, the methods comprise administering to the HSV seronegative subject from about 400 mg to about 2000 mg, from about 400 mg to about 1000 mg, or from about 1000 mg to about 2000 mg valacyclovir, or a salt or solvate thereof, once per day. In some embodiments, the additional antiviral agents include tenofovir, emtricitabine, lamivudine, efavirenz, raltegravir, dolutegravir, maravoric, rilpirivine, Atripla®, and salts, solvates and/or combinations thereof. In some embodiments, one of the one or more additional antiviral agents is tenofovir and the methods further comprise administering to the HSV seronegative subject from about 50 mg to about 500 mg of tenofovir once per day, e.g., about 50 mg, 100 mg, 150 mg, 200 mg, 250 mg, 300 mg, 350 mg, 400 mg or 500 mg of tenofovir per day. In some embodiments, one of the one or more additional antiviral agents is emtricitabine and the methods further comprise administering to the HSV seronegative subject from about 50 mg to about 300 mg of emtricitabine once per day, e.g., about 50 mg, 100 mg, 150 mg, 200 mg, 250 mg, or 300 mg of emtricitabine per day. In some embodiments, one of the one of more additional antiviral agents is lamivudine and the methods further comprise administering to the HSV seronegative subject from about 50 mg to about 400 mg of lamivudine once per day, e.g., about 50 mg, 100 mg, 150 mg, 200 mg, 250 mg, 300 mg, 350 mg or 400 mg of lamivudine per day. In some embodiments, one of the one of more additional antiviral agents is efavirenz and the methods further comprise administering to the HSV seronegative subject from about 300 mg to about 900 mg of efavirenz once per day, e.g., about 300 mg, 400 mg, 500 mg, 600 mg, 700 mg, 800 mg, or 900 mg of efavirenz per day. In some embodiments, one of the one of more additional antiviral agents is raltegravir and the methods further comprise administering to the HSV seronegative subject from about 200 mg to about 600 mg of raltegravir twice per day, e.g., about 200 mg, 300 mg, 400 mg, 500 mg, or 600 mg of raltegravir twice per day. In some embodiments, one of the one of more additional antiviral agents is dolutegravir and the methods further comprise administering to the HSV seronegative subject from about 10 mg to about 100 mg of dolutegravir once per day, e.g., about 10 mg, 20 mg, 30 mg, 40 mg, 50 mg, 60 mg, 70 mg, 80 mg, 90 mg or 100 mg of dolutegravir per day. In some embodiments, one of the one of more additional antiviral agents is maravoric and the methods further comprise administering to the HSV seronegative subject from about 100 mg to about 400 mg of maravoric twice per day, e.g., about 100 mg, 150 mg, 200 mg, 250 mg, 300 mg, 350 mg or 400 mg of maravoric twice per day. In some embodiments, one of the one of more additional antiviral agents is rilpirivine and the methods further comprise administering to the HSV seronegative subject from about 10 mg to about 50 mg of rilpirivine once per day, e.g., about 10 mg, 20 mg, 25 mg, 30 mg, 40 mg, or 50 mg of rilpirivine per day. In some embodiments, a) one of the one or more additional antiviral agents is emtricitabine and the methods further comprise administering to the HSV seronegative subject from about 50 mg to about 300 mg of emtricitabine once per day, e.g., about 50 mg, 100 mg, 150 mg, 200 mg, 250 mg, or 300 mg of emtricitabine per day; b) one of the one of more additional antiviral agents is efavirenz and the methods further comprise administering to the HSV seronegative subject from about 300 mg to about 900 mg of efavirenz once per day, e.g., about 300 mg, 400 mg, 500 mg, 600 mg, 700 mg, 800 mg, or 900 mg of efavirenz per day; and c) one of the one or more additional antiviral agents is tenofovir and the methods further comprise administering to the HSV seronegative subject from about 50 mg to about 500 mg of tenofovir once per day, e.g., about 50 mg, 100 mg, 150 mg, 200 mg, 250 mg, 300 mg, 350 mg, 400 mg or 500 mg of tenofovir per day. In some cases, the one or more additional antiviral agents are administered prior to, after, or both prior to and after the HSV seronegative subject is exposed to HSV. In some embodiments, the contraceptive agent comprises levonorgestrel, estradiol, dosogestrel, ethinyl estradiol, norethindrone acetate, norgestimate, or salts, solvates or combinations thereof. In some cases, a contraceptive comprises levonorgestrel and estradiol and the methods further comprise administering to the HSV seronegative subject about 0.10 mg of levonorgestrel and about 0.02 mg of estradiol. In some cases, a contraceptive comprises dosogestrel and ethinyl estradiol and the methods further comprise administering to the HSV seronegative subject about 0.15 mg of dosogestrel and about 0.03 mg of ethinyl estradiol. In some cases, a contraceptive comprises norethindrone acetate and ethinyl estradiol and the methods further comprise administering to the HSV seronegative subject about 1 mg of norethindrone acetate and about 20 ug of ethinyl estradiol. In some cases, a contraceptive comprises norgestimate and ethinyl estradiol and the methods further comprise administering to the HSV seronegative subject about 0.18 mg or about 0.25 mg of norgestimate and about 35 ug or about 25 ug of ethinyl estradiol. In some embodiments, the contraceptive agent(s) are administered prior to, after, or both prior to and after the subject is exposed to HSV. In some cases, a contraceptive comprises levonorgestrel and the methods further comprise administering to the HSV seronegative subject about 0.75 mg of levonorgestrel; wherein the 0.75 mg of levonorgestrel is administered to the subject once per day for two days following sexual conduct that could result in pregnancy. In some cases, one or more of the contraceptive agents are available over the counter to a subject who is over the age of 14, 15, 16, 17 or 18 years.

In some embodiments, provided herein are methods of preventing HSV infection in an HSV seronegative subject comprising administering to the subject from about 200 mg to about 2,000 mg of acyclovir, or a salt or solvate thereof, twice per day. In some cases, acyclovir is administered prior to exposure to HSV. In some cases, acyclovir is administered after exposure to HSV. In some cases, acyclovir is administered both prior to and after exposure to HSV. In some cases, acyclovir is administered with one or more additional active agents, e.g., one or more additional antiviral agents, one or more contraceptive agents, or one or more additional antiviral agents and one or more contraceptive agents. In some embodiments, the methods further prevent infection of one or more additional infectious diseases, for example, HIV. In some embodiments, wherein the HSV seronegative subject is further administered one or more contraceptive agents, the methods further prevent pregnancy. In some embodiments, the methods further comprise administering to an HSV seropositive partner of the HSV seronegative subject one or more antiviral agents, for example, one or more HSV antiviral agents, one or more HIV antiviral agents, and/or any antiviral agent described herein. In some cases, the methods comprise administering to the HSV seronegative subject about 400 mg, 500 mg, 600 mg, 700 mg, 800 mg, 900 mg, 1000 mg, 1100 mg, 1200 mg, 1300 mg, 1400 mg, 1500 mg, or 1600 mg of acyclovir, or a salt or solvate thereof, twice per day. In some cases, the methods comprise administering to the HSV seronegative subject from about 400 mg to about 800 mg, from about 800 mg to about 1000 mg, or from about 1000 mg to about 1600 mg of acyclovir, or a salt or solvate thereof, twice per day. In some embodiments, the additional antiviral agents include tenofovir, emtricitabine, lamivudine, efavirenz, raltegravir, dolutegravir, maravoric, rilpirivine, Atripla®, and salts, solvates and/or combinations thereof. In some embodiments, one of the one or more additional antiviral agents is tenofovir and the methods further comprise administering to the HSV seronegative subject from about 50 mg to about 500 mg of tenofovir once per day, e.g., about 50 mg, 100 mg, 150 mg, 200 mg, 250 mg, 300 mg, 350 mg, 400 mg or 500 mg of tenofovir per day. In some embodiments, one of the one or more additional antiviral agents is emtricitabine and the methods further comprise administering to the HSV seronegative subject from about 50 mg to about 300 mg of emtricitabine once per day, e.g., about 50 mg, 100 mg, 150 mg, 200 mg, 250 mg, or 300 mg of emtricitabine per day. In some embodiments, one of the one of more additional antiviral agents is lamivudine and the methods further comprise administering to the HSV seronegative subject from about 50 mg to about 400 mg of lamivudine once per day, e.g., about 50 mg, 100 mg, 150 mg, 200 mg, 250 mg, 300 mg, 350 mg or 400 mg of lamivudine per day. In some embodiments, one of the one of more additional antiviral agents is efavirenz and the methods further comprise administering to the HSV seronegative subject from about 300 mg to about 900 mg of efavirenz once per day, e.g., about 300 mg, 400 mg, 500 mg, 600 mg, 700 mg, 800 mg, or 900 mg of efavirenz per day. In some embodiments, one of the one of more additional antiviral agents is raltegravir and the methods further comprise administering to the HSV seronegative subject from about 200 mg to about 600 mg of raltegravir twice per day, e.g., about 200 mg, 300 mg, 400 mg, 500 mg, or 600 mg of raltegravir twice per day. In some embodiments, one of the one of more additional antiviral agents is dolutegravir and the methods further comprise administering to the HSV seronegative subject from about 10 mg to about 100 mg of dolutegravir once per day, e.g., about 10 mg, 20 mg, 30 mg, 40 mg, 50 mg, 60 mg, 70 mg, 80 mg, 90 mg or 100 mg of dolutegravir per day. In some embodiments, one of the one of more additional antiviral agents is maravoric and the methods further comprise administering to the HSV seronegative subject from about 100 mg to about 400 mg of maravoric twice per day, e.g., about 100 mg, 150 mg, 200 mg, 250 mg, 300 mg, 350 mg or 400 mg of maravoric twice per day. In some embodiments, one of the one of more additional antiviral agents is rilpirivine and the methods further comprise administering to the HSV seronegative subject from about 10 mg to about 50 mg of rilpirivine once per day, e.g., about 10 mg, 20 mg, 25 mg, 30 mg, 40 mg, or 50 mg of rilpirivine per day. In some embodiments, a) one of the one or more additional antiviral agents is emtricitabine and the methods further comprise administering to the HSV seronegative subject from about 50 mg to about 300 mg of emtricitabine once per day, e.g., about 50 mg, 100 mg, 150 mg, 200 mg, 250 mg, or 300 mg of emtricitabine per day; b) one of the one of more additional antiviral agents is efavirenz and the methods further comprise administering to the HSV seronegative subject from about 300 mg to about 900 mg of efavirenz once per day, e.g., about 300 mg, 400 mg, 500 mg, 600 mg, 700 mg, 800 mg, or 900 mg of efavirenz per day; and c) one of the one or more additional antiviral agents is tenofovir and the methods further comprise administering to the HSV seronegative subject from about 50 mg to about 500 mg of tenofovir once per day, e.g., about 50 mg, 100 mg, 150 mg, 200 mg, 250 mg, 300 mg, 350 mg, 400 mg or 500 mg of tenofovir per day. In some cases, the one or more additional antiviral agents are administered prior to, after, or both prior to and after the HSV seronegative subject is exposed to HSV. In some embodiments, the contraceptive agent comprises levonorgestrel, estradiol, dosogestrel, ethinyl estradiol, norethindrone acetate, norgestimate, or salts, solvates or combinations thereof. In some cases, a contraceptive comprises levonorgestrel and estradiol and the methods further comprise administering to the HSV seronegative subject about 0.10 mg of levonorgestrel and about 0.02 mg of estradiol. In some cases, a contraceptive comprises dosogestrel and ethinyl estradiol and the methods further comprise administering to the HSV seronegative subject about 0.15 mg of dosogestrel and about 0.03 mg of ethinyl estradiol. In some cases, a contraceptive comprises norethindrone acetate and ethinyl estradiol and the methods further comprise administering to the HSV seronegative subject about 1 mg of norethindrone acetate and about 20 ug of ethinyl estradiol. In some cases, a contraceptive comprises norgestimate and ethinyl estradiol and the methods further comprise administering to the HSV seronegative subject about 0.18 mg or about 0.25 mg of norgestimate and about 35 ug or about 25 ug of ethinyl estradiol. In some embodiments, the contraceptive agent(s) are administered prior to, after, or both prior to and after the subject is exposed to HSV. In some cases, a contraceptive comprises levonorgestrel and the methods further comprise administering to the HSV seronegative subject about 0.75 mg of levonorgestrel; wherein the 0.75 mg of levonorgestrel is administered to the subject once per day for two days following sexual conduct that could result in pregnancy. In some cases, one or more of the contraceptive agents are available over the counter to a subject who is over the age of 14, 15, 16, 17 or 18 years.

In some embodiments, provided herein are methods of preventing HSV infection in an HSV seronegative subject comprising administering to the subject from about 5 mg to about 80 mg of pritelivir, or a salt or solvate thereof, once per day. In some cases, pritelivir is administered prior to exposure to HSV. In some cases, pritelivir is administered after exposure to HSV. In some cases, pritelivir is administered both prior to and after exposure to HSV. In some cases, pritelivir is administered with one or more additional active agents, e.g., one or more additional antiviral agents, one or more contraceptive agents, or one or more additional antiviral agents and one or more contraceptive agents. In some embodiments, the methods further prevent infection of one or more additional infectious diseases, for example, HIV. In some embodiments, wherein the HSV seronegative subject is further administered one or more contraceptive agents, the methods further prevent pregnancy. In some embodiments, the methods further comprise administering to an HSV seropositive partner of the HSV seronegative subject one or more antiviral agents, for example, one or more HSV antiviral agents, one or more HIV antiviral agents, and/or any antiviral agent described herein. In some cases, the methods comprise administering to the HSV seronegative subject about 5 mg, 10 mg, 20 mg, 30 mg, 40 mg, 50 mg, 60 mg, 70 mg, or 80 mg of pritelivir, or a salt or solvate thereof, once per day. In some cases, the methods comprise administering to the HSV seronegative subject from about 5 mg to about 20 mg, from about 20 mg to about 50 mg, or from about 50 mg to about 80 mg of pritelivir, or a salt or solvate thereof, once per day. In some embodiments, the additional antiviral agents include tenofovir, emtricitabine, lamivudine, efavirenz, raltegravir, dolutegravir, maravoric, rilpirivine, Atripla®, and salts, solvates and/or combinations thereof. In some embodiments, one of the one or more additional antiviral agents is tenofovir and the methods further comprise administering to the HSV seronegative subject from about 50 mg to about 500 mg of tenofovir once per day, e.g., about 50 mg, 100 mg, 150 mg, 200 mg, 250 mg, 300 mg, 350 mg, 400 mg or 500 mg of tenofovir per day. In some embodiments, one of the one or more additional antiviral agents is emtricitabine and the methods further comprise administering to the HSV seronegative subject from about 50 mg to about 300 mg of emtricitabine once per day, e.g., about 50 mg, 100 mg, 150 mg, 200 mg, 250 mg, or 300 mg of emtricitabine per day. In some embodiments, one of the one of more additional antiviral agents is lamivudine and the methods further comprise administering to the HSV seronegative subject from about 50 mg to about 400 mg of lamivudine once per day, e.g., about 50 mg, 100 mg, 150 mg, 200 mg, 250 mg, 300 mg, 350 mg or 400 mg of lamivudine per day. In some embodiments, one of the one of more additional antiviral agents is efavirenz and the methods further comprise administering to the HSV seronegative subject from about 300 mg to about 900 mg of efavirenz once per day, e.g., about 300 mg, 400 mg, 500 mg, 600 mg, 700 mg, 800 mg, or 900 mg of efavirenz per day. In some embodiments, one of the one of more additional antiviral agents is raltegravir and the methods further comprise administering to the HSV seronegative subject from about 200 mg to about 600 mg of raltegravir twice per day, e.g., about 200 mg, 300 mg, 400 mg, 500 mg, or 600 mg of raltegravir twice per day. In some embodiments, one of the one of more additional antiviral agents is dolutegravir and the methods further comprise administering to the HSV seronegative subject from about 10 mg to about 100 mg of dolutegravir once per day, e.g., about 10 mg, 20 mg, 30 mg, 40 mg, 50 mg, 60 mg, 70 mg, 80 mg, 90 mg or 100 mg of dolutegravir per day. In some embodiments, one of the one of more additional antiviral agents is maravoric and the methods further comprise administering to the HSV seronegative subject from about 100 mg to about 400 mg of maravoric twice per day, e.g., about 100 mg, 150 mg, 200 mg, 250 mg, 300 mg, 350 mg or 400 mg of maravoric twice per day. In some embodiments, one of the one of more additional antiviral agents is rilpirivine and the methods further comprise administering to the HSV seronegative subject from about 10 mg to about 50 mg of rilpirivine once per day, e.g., about 10 mg, 20 mg, 25 mg, 30 mg, 40 mg, or 50 mg of rilpirivine per day. In some embodiments, a) one of the one or more additional antiviral agents is emtricitabine and the methods further comprise administering to the HSV seronegative subject from about 50 mg to about 300 mg of emtricitabine once per day, e.g., about 50 mg, 100 mg, 150 mg, 200 mg, 250 mg, or 300 mg of emtricitabine per day; b) one of the one of more additional antiviral agents is efavirenz and the methods further comprise administering to the HSV seronegative subject from about 300 mg to about 900 mg of efavirenz once per day, e.g., about 300 mg, 400 mg, 500 mg, 600 mg, 700 mg, 800 mg, or 900 mg of efavirenz per day; and c) one of the one or more additional antiviral agents is tenofovir and the methods further comprise administering to the HSV seronegative subject from about 50 mg to about 500 mg of tenofovir once per day, e.g., about 50 mg, 100 mg, 150 mg, 200 mg, 250 mg, 300 mg, 350 mg, 400 mg or 500 mg of tenofovir per day. In some cases, the one or more additional antiviral agents are administered prior to, after, or both prior to and after the HSV seronegative subject is exposed to HSV. In some embodiments, the contraceptive agent comprises levonorgestrel, estradiol, dosogestrel, ethinyl estradiol, norethindrone acetate, norgestimate, or salts, solvates or combinations thereof. In some cases, a contraceptive comprises levonorgestrel and estradiol and the methods further comprise administering to the HSV seronegative subject about 0.10 mg of levonorgestrel and about 0.02 mg of estradiol. In some cases, a contraceptive comprises dosogestrel and ethinyl estradiol and the methods further comprise administering to the HSV seronegative subject about 0.15 mg of dosogestrel and about 0.03 mg of ethinyl estradiol. In some cases, a contraceptive comprises norethindrone acetate and ethinyl estradiol and the methods further comprise administering to the HSV seronegative subject about 1 mg of norethindrone acetate and about 20 ug of ethinyl estradiol. In some cases, a contraceptive comprises norgestimate and ethinyl estradiol and the methods further comprise administering to the HSV seronegative subject about 0.18 mg or about 0.25 mg of norgestimate and about 35 ug or about 25 ug of ethinyl estradiol. In some embodiments, the contraceptive agent(s) are administered prior to, after, or both prior to and after the subject is exposed to HSV. In some cases, a contraceptive comprises levonorgestrel and the methods further comprise administering to the HSV seronegative subject about 0.75 mg of levonorgestrel; wherein the 0.75 mg of levonorgestrel is administered to the subject once per day for two days following sexual conduct that could result in pregnancy. In some cases, one or more of the contraceptive agents are available over the counter to a subject who is over the age of 14, 15, 16, 17 or 18 years.

In some embodiments, provided herein are methods of preventing HSV infection in an HSV seronegative subject comprising administering to the subject from about 200 mg to about 500 mg of famciclovir, or a salt or solvate thereof, twice per day. In some cases, famciclovir is administered prior to exposure to HSV. In some cases, famciclovir is administered after exposure to HSV. In some cases, famciclovir is administered both prior to and after exposure to HSV. In some cases, famciclovir is administered with one or more additional active agents, e.g., one or more additional antiviral agents, one or more contraceptive agents, or one or more additional antiviral agents and one or more contraceptive agents. In some embodiments, the methods further prevent infection of one or more additional infectious diseases, for example, HIV. In some embodiments, wherein the HSV seronegative subject is further administered one or more contraceptive agents, the methods further prevent pregnancy. In some embodiments, the methods further comprise administering to an HSV seropositive partner of the HSV seronegative subject one or more antiviral agents, for example, one or more HSV antiviral agents, one or more HIV antiviral agents, and/or any antiviral agent described herein. In some cases, the methods comprise administering to the HSV seronegative subject about 200 mg, 225 mg, 250 mg, 275 mg, 300 mg, 350 mg, 400 mg, 450 mg, or 500 mg of famciclovir, or a salt or solvate thereof, twice per day. In some cases, the methods comprise administering to the HSV seronegative subject from about 225 mg to about 300 mg, from about 300 mg to about 400 mg, or from about 400 mg to about 500 mg of famciclovir, or a salt or solvate thereof, twice per day. In some embodiments, the additional antiviral agents include tenofovir, emtricitabine, lamivudine, efavirenz, raltegravir, dolutegravir, maravoric, rilpirivine, Atripla®, and salts, solvates and/or combinations thereof. In some embodiments, one of the one or more additional antiviral agents is tenofovir and the methods further comprise administering to the HSV seronegative subject from about 50 mg to about 500 mg of tenofovir once per day, e.g., about 50 mg, 100 mg, 150 mg, 200 mg, 250 mg, 300 mg, 350 mg, 400 mg or 500 mg of tenofovir per day. In some embodiments, one of the one or more additional antiviral agents is emtricitabine and the methods further comprise administering to the HSV seronegative subject from about 50 mg to about 300 mg of emtricitabine once per day, e.g., about 50 mg, 100 mg, 150 mg, 200 mg, 250 mg, or 300 mg of emtricitabine per day. In some embodiments, one of the one of more additional antiviral agents is lamivudine and the methods further comprise administering to the HSV seronegative subject from about 50 mg to about 400 mg of lamivudine once per day, e.g., about 50 mg, 100 mg, 150 mg, 200 mg, 250 mg, 300 mg, 350 mg or 400 mg of lamivudine per day. In some embodiments, one of the one of more additional antiviral agents is efavirenz and the methods further comprise administering to the HSV seronegative subject from about 300 mg to about 900 mg of efavirenz once per day, e.g., about 300 mg, 400 mg, 500 mg, 600 mg, 700 mg, 800 mg, or 900 mg of efavirenz per day. In some embodiments, one of the one of more additional antiviral agents is raltegravir and the methods further comprise administering to the HSV seronegative subject from about 200 mg to about 600 mg of raltegravir twice per day, e.g., about 200 mg, 300 mg, 400 mg, 500 mg, or 600 mg of raltegravir twice per day. In some embodiments, one of the one of more additional antiviral agents is dolutegravir and the methods further comprise administering to the HSV seronegative subject from about 10 mg to about 100 mg of dolutegravir once per day, e.g., about 10 mg, 20 mg, 30 mg, 40 mg, 50 mg, 60 mg, 70 mg, 80 mg, 90 mg or 100 mg of dolutegravir per day. In some embodiments, one of the one of more additional antiviral agents is maravoric and the methods further comprise administering to the HSV seronegative subject from about 100 mg to about 400 mg of maravoric twice per day, e.g., about 100 mg, 150 mg, 200 mg, 250 mg, 300 mg, 350 mg or 400 mg of maravoric twice per day. In some embodiments, one of the one of more additional antiviral agents is rilpirivine and the methods further comprise administering to the HSV seronegative subject from about 10 mg to about 50 mg of rilpirivine once per day, e.g., about 10 mg, 20 mg, 25 mg, 30 mg, 40 mg, or 50 mg of rilpirivine per day. In some embodiments, a) one of the one or more additional antiviral agents is emtricitabine and the methods further comprise administering to the HSV seronegative subject from about 50 mg to about 300 mg of emtricitabine once per day, e.g., about 50 mg, 100 mg, 150 mg, 200 mg, 250 mg, or 300 mg of emtricitabine per day; b) one of the one of more additional antiviral agents is efavirenz and the methods further comprise administering to the HSV seronegative subject from about 300 mg to about 900 mg of efavirenz once per day, e.g., about 300 mg, 400 mg, 500 mg, 600 mg, 700 mg, 800 mg, or 900 mg of efavirenz per day; and c) one of the one or more additional antiviral agents is tenofovir and the methods further comprise administering to the HSV seronegative subject from about 50 mg to about 500 mg of tenofovir once per day, e.g., about 50 mg, 100 mg, 150 mg, 200 mg, 250 mg, 300 mg, 350 mg, 400 mg or 500 mg of tenofovir per day. In some cases, the one or more additional antiviral agents are administered prior to, after, or both prior to and after the HSV seronegative subject is exposed to HSV. In some embodiments, the contraceptive agent comprises levonorgestrel, estradiol, dosogestrel, ethinyl estradiol, norethindrone acetate, norgestimate, or salts, solvates or combinations thereof. In some cases, a contraceptive comprises levonorgestrel and estradiol and the methods further comprise administering to the HSV seronegative subject about 0.10 mg of levonorgestrel and about 0.02 mg of estradiol. In some cases, a contraceptive comprises dosogestrel and ethinyl estradiol and the methods further comprise administering to the HSV seronegative subject about 0.15 mg of dosogestrel and about 0.03 mg of ethinyl estradiol. In some cases, a contraceptive comprises norethindrone acetate and ethinyl estradiol and the methods further comprise administering to the HSV seronegative subject about 1 mg of norethindrone acetate and about 20 ug of ethinyl estradiol. In some cases, a contraceptive comprises norgestimate and ethinyl estradiol and the methods further comprise administering to the HSV seronegative subject about 0.18 mg or about 0.25 mg of norgestimate and about 35 ug or about 25 ug of ethinyl estradiol. In some embodiments, the contraceptive agent(s) are administered prior to, after, or both prior to and after the subject is exposed to HSV. In some cases, a contraceptive comprises levonorgestrel and the methods further comprise administering to the HSV seronegative subject about 0.75 mg of levonorgestrel; wherein the 0.75 mg of levonorgestrel is administered to the subject once per day for two days following sexual conduct that could result in pregnancy. In some cases, one or more of the contraceptive agents are available over the counter to a subject who is over the age of 14, 15, 16, 17 or 18 years.

In some embodiments, provided herein are methods of preventing HSV infection in an HSV seronegative subject comprising administering to the subject from about 200 mg to about 400 mg of tenofovir, or a salt or solvate thereof, once per day. In some cases, tenofovir is administered prior to exposure to HSV. In some cases, tenofovir is administered after exposure to HSV. In some cases, tenofovir is administered both prior to and after exposure to HSV. In some cases, tenofovir is administered with one or more additional active agents, e.g., one or more additional antiviral agents, one or more contraceptive agents, or one or more additional antiviral agents and one or more contraceptive agents. In some embodiments, the methods further prevent infection of one or more additional infectious diseases, for example, HIV. In some embodiments, wherein the HSV seronegative subject is further administered one or more contraceptive agents, the methods further prevent pregnancy. In some embodiments, the methods further comprise administering to an HSV seropositive partner of the HSV seronegative subject one or more antiviral agents, for example, one or more HSV antiviral agents, one or more HIV antiviral agents, and/or any antiviral agent described herein. In some cases, the methods comprise administering to the HSV seronegative subject about 200 mg, 225 mg, 250 mg, 275 mg, 300 mg, 325 mg, 350 mg, 375 mg, or 400 mg of tenofovir, or a salt or solvate thereof, once per day. In some cases, the methods comprise administering to the HSV seronegative subject from about 200 mg to about 250 mg, from about 250 mg to about 350 mg, or from about 350 mg to about 400 mg of tenofovir, or a salt or solvate thereof, once per day. In some embodiments, the additional antiviral agents include tenofovir, emtricitabine, lamivudine, efavirenz, raltegravir, dolutegravir, maravoric, rilpirivine, Atripla®, and salts, solvates and/or combinations thereof. In some embodiments, one of the one or more additional antiviral agents is tenofovir and the methods further comprise administering to the HSV seronegative subject from about 50 mg to about 500 mg of tenofovir once per day, e.g., about 50 mg, 100 mg, 150 mg, 200 mg, 250 mg, 300 mg, 350 mg, 400 mg or 500 mg of tenofovir per day. In some embodiments, one of the one or more additional antiviral agents is emtricitabine and the methods further comprise administering to the HSV seronegative subject from about 50 mg to about 300 mg of emtricitabine once per day, e.g., about 50 mg, 100 mg, 150 mg, 200 mg, 250 mg, or 300 mg of emtricitabine per day. In some embodiments, one of the one of more additional antiviral agents is lamivudine and the methods further comprise administering to the HSV seronegative subject from about 50 mg to about 400 mg of lamivudine once per day, e.g., about 50 mg, 100 mg, 150 mg, 200 mg, 250 mg, 300 mg, 350 mg or 400 mg of lamivudine per day. In some embodiments, one of the one of more additional antiviral agents is efavirenz and the methods further comprise administering to the HSV seronegative subject from about 300 mg to about 900 mg of efavirenz once per day, e.g., about 300 mg, 400 mg, 500 mg, 600 mg, 700 mg, 800 mg, or 900 mg of efavirenz per day. In some embodiments, one of the one of more additional antiviral agents is raltegravir and the methods further comprise administering to the HSV seronegative subject from about 200 mg to about 600 mg of raltegravir twice per day, e.g., about 200 mg, 300 mg, 400 mg, 500 mg, or 600 mg of raltegravir twice per day. In some embodiments, one of the one of more additional antiviral agents is dolutegravir and the methods further comprise administering to the HSV seronegative subject from about 10 mg to about 100 mg of dolutegravir once per day, e.g., about 10 mg, 20 mg, 30 mg, 40 mg, 50 mg, 60 mg, 70 mg, 80 mg, 90 mg or 100 mg of dolutegravir per day. In some embodiments, one of the one of more additional antiviral agents is maravoric and the methods further comprise administering to the HSV seronegative subject from about 100 mg to about 400 mg of maravoric twice per day, e.g., about 100 mg, 150 mg, 200 mg, 250 mg, 300 mg, 350 mg or 400 mg of maravoric twice per day. In some embodiments, one of the one of more additional antiviral agents is rilpirivine and the methods further comprise administering to the HSV seronegative subject from about 10 mg to about 50 mg of rilpirivine once per day, e.g., about 10 mg, 20 mg, 25 mg, 30 mg, 40 mg, or 50 mg of rilpirivine per day. In some embodiments, a) one of the one or more additional antiviral agents is emtricitabine and the methods further comprise administering to the HSV seronegative subject from about 50 mg to about 300 mg of emtricitabine once per day, e.g., about 50 mg, 100 mg, 150 mg, 200 mg, 250 mg, or 300 mg of emtricitabine per day; b) one of the one of more additional antiviral agents is efavirenz and the methods further comprise administering to the HSV seronegative subject from about 300 mg to about 900 mg of efavirenz once per day, e.g., about 300 mg, 400 mg, 500 mg, 600 mg, 700 mg, 800 mg, or 900 mg of efavirenz per day; and c) one of the one or more additional antiviral agents is tenofovir and the methods further comprise administering to the HSV seronegative subject from about 50 mg to about 500 mg of tenofovir once per day, e.g., about 50 mg, 100 mg, 150 mg, 200 mg, 250 mg, 300 mg, 350 mg, 400 mg or 500 mg of tenofovir per day. In some cases, the one or more additional antiviral agents are administered prior to, after, or both prior to and after the HSV seronegative subject is exposed to HSV. In some embodiments, the contraceptive agent comprises levonorgestrel, estradiol, dosogestrel, ethinyl estradiol, norethindrone acetate, norgestimate, or salts, solvates or combinations thereof. In some cases, a contraceptive comprises levonorgestrel and estradiol and the methods further comprise administering to the HSV seronegative subject about 0.10 mg of levonorgestrel and about 0.02 mg of estradiol. In some cases, a contraceptive comprises dosogestrel and ethinyl estradiol and the methods further comprise administering to the HSV seronegative subject about 0.15 mg of dosogestrel and about 0.03 mg of ethinyl estradiol. In some cases, a contraceptive comprises norethindrone acetate and ethinyl estradiol and the methods further comprise administering to the HSV seronegative subject about 1 mg of norethindrone acetate and about 20 ug of ethinyl estradiol. In some cases, a contraceptive comprises norgestimate and ethinyl estradiol and the methods further comprise administering to the HSV seronegative subject about 0.18 mg or about 0.25 mg of norgestimate and about 35 ug or about 25 ug of ethinyl estradiol. In some embodiments, the contraceptive agent(s) are administered prior to, after, or both prior to and after the subject is exposed to HSV. In some cases, a contraceptive comprises levonorgestrel and the methods further comprise administering to the HSV seronegative subject about 0.75 mg of levonorgestrel; wherein the 0.75 mg of levonorgestrel is administered to the subject once per day for two days following sexual conduct that could result in pregnancy. In some cases, one or more of the contraceptive agents are available over the counter to a subject who is over the age of 14, 15, 16, 17 or 18 years.

In some embodiments, provided herein are methods of preventing HSV infection in an HSV seronegative subject comprising administering to the subject from about 500 mg to about 1500 mg of ganciclovir, or a salt or solvate thereof, three times per day. In some cases, ganciclovir is administered prior to exposure to HSV. In some cases, ganciclovir is administered after exposure to HSV. In some cases, ganciclovir is administered both prior to and after exposure to HSV. In some cases, ganciclovir is administered with one or more additional active agents, e.g., one or more additional antiviral agents, one or more contraceptive agents, or one or more additional antiviral agents and one or more contraceptive agents. In some embodiments, the methods further prevent infection of one or more additional infectious diseases, for example, HIV. In some embodiments, wherein the HSV seronegative subject is further administered one or more contraceptive agents, the methods further prevent pregnancy. In some embodiments, the methods further comprise administering to an HSV seropositive partner of the HSV seronegative subject one or more antiviral agents, for example, one or more HSV antiviral agents, one or more HIV antiviral agents, and/or any antiviral agent described herein. In some cases, the methods comprise administering to the HSV seronegative subject about 500 mg, 600 mg, 700 mg, 800 mg, 900 mg, 1000 mg, 1100 mg, 1200 mg, 1300 mg, 1400 mg, or 1500 mg of ganciclovir, or a salt or solvate thereof, three times per day. In some cases, the methods comprise administering to the HSV seronegative subject from about 500 mg to about 800 mg, from about 800 mg to about 1200 mg, or from about 1200 mg to about 1500 mg of ganciclovir, or a salt or solvate thereof, three times per day. In some embodiments, the additional antiviral agents include tenofovir, emtricitabine, lamivudine, efavirenz, raltegravir, dolutegravir, maravoric, rilpirivine, Atripla®, and salts, solvates and/or combinations thereof. In some embodiments, one of the one or more additional antiviral agents is tenofovir and the methods further comprise administering to the HSV seronegative subject from about 50 mg to about 500 mg of tenofovir once per day, e.g., about 50 mg, 100 mg, 150 mg, 200 mg, 250 mg, 300 mg, 350 mg, 400 mg or 500 mg of tenofovir per day. In some embodiments, one of the one or more additional antiviral agents is emtricitabine and the methods further comprise administering to the HSV seronegative subject from about 50 mg to about 300 mg of emtricitabine once per day, e.g., about 50 mg, 100 mg, 150 mg, 200 mg, 250 mg, or 300 mg of emtricitabine per day. In some embodiments, one of the one of more additional antiviral agents is lamivudine and the methods further comprise administering to the HSV seronegative subject from about 50 mg to about 400 mg of lamivudine once per day, e.g., about 50 mg, 100 mg, 150 mg, 200 mg, 250 mg, 300 mg, 350 mg or 400 mg of lamivudine per day. In some embodiments, one of the one of more additional antiviral agents is efavirenz and the methods further comprise administering to the HSV seronegative subject from about 300 mg to about 900 mg of efavirenz once per day, e.g., about 300 mg, 400 mg, 500 mg, 600 mg, 700 mg, 800 mg, or 900 mg of efavirenz per day. In some embodiments, one of the one of more additional antiviral agents is raltegravir and the methods further comprise administering to the HSV seronegative subject from about 200 mg to about 600 mg of raltegravir twice per day, e.g., about 200 mg, 300 mg, 400 mg, 500 mg, or 600 mg of raltegravir twice per day. In some embodiments, one of the one of more additional antiviral agents is dolutegravir and the methods further comprise administering to the HSV seronegative subject from about 10 mg to about 100 mg of dolutegravir once per day, e.g., about 10 mg, 20 mg, 30 mg, 40 mg, 50 mg, 60 mg, 70 mg, 80 mg, 90 mg or 100 mg of dolutegravir per day. In some embodiments, one of the one of more additional antiviral agents is maravoric and the methods further comprise administering to the HSV seronegative subject from about 100 mg to about 400 mg of maravoric twice per day, e.g., about 100 mg, 150 mg, 200 mg, 250 mg, 300 mg, 350 mg or 400 mg of maravoric twice per day. In some embodiments, one of the one of more additional antiviral agents is rilpirivine and the methods further comprise administering to the HSV seronegative subject from about 10 mg to about 50 mg of rilpirivine once per day, e.g., about 10 mg, 20 mg, 25 mg, 30 mg, 40 mg, or 50 mg of rilpirivine per day. In some embodiments, a) one of the one or more additional antiviral agents is emtricitabine and the methods further comprise administering to the HSV seronegative subject from about 50 mg to about 300 mg of emtricitabine once per day, e.g., about 50 mg, 100 mg, 150 mg, 200 mg, 250 mg, or 300 mg of emtricitabine per day; b) one of the one of more additional antiviral agents is efavirenz and the methods further comprise administering to the HSV seronegative subject from about 300 mg to about 900 mg of efavirenz once per day, e.g., about 300 mg, 400 mg, 500 mg, 600 mg, 700 mg, 800 mg, or 900 mg of efavirenz per day; and c) one of the one or more additional antiviral agents is tenofovir and the methods further comprise administering to the HSV seronegative subject from about 50 mg to about 500 mg of tenofovir once per day, e.g., about 50 mg, 100 mg, 150 mg, 200 mg, 250 mg, 300 mg, 350 mg, 400 mg or 500 mg of tenofovir per day. In some cases, the one or more additional antiviral agents are administered prior to, after, or both prior to and after the HSV seronegative subject is exposed to HSV. In some embodiments, the contraceptive agent comprises levonorgestrel, estradiol, dosogestrel, ethinyl estradiol, norethindrone acetate, norgestimate, or salts, solvates or combinations thereof. In some cases, a contraceptive comprises levonorgestrel and estradiol and the methods further comprise administering to the HSV seronegative subject about 0.10 mg of levonorgestrel and about 0.02 mg of estradiol. In some cases, a contraceptive comprises dosogestrel and ethinyl estradiol and the methods further comprise administering to the HSV seronegative subject about 0.15 mg of dosogestrel and about 0.03 mg of ethinyl estradiol. In some cases, a contraceptive comprises norethindrone acetate and ethinyl estradiol and the methods further comprise administering to the HSV seronegative subject about 1 mg of norethindrone acetate and about 20 ug of ethinyl estradiol. In some cases, a contraceptive comprises norgestimate and ethinyl estradiol and the methods further comprise administering to the HSV seronegative subject about 0.18 mg or about 0.25 mg of norgestimate and about 35 ug or about 25 ug of ethinyl estradiol. In some embodiments, the contraceptive agent(s) are administered prior to, after, or both prior to and after the subject is exposed to HSV. In some cases, a contraceptive comprises levonorgestrel and the methods further comprise administering to the HSV seronegative subject about 0.75 mg of levonorgestrel; wherein the 0.75 mg of levonorgestrel is administered to the subject once per day for two days following sexual conduct that could result in pregnancy. In some cases, one or more of the contraceptive agents are available over the counter to a subject who is over the age of 14, 15, 16, 17 or 18 years.

In some embodiments, provided herein are methods of preventing HSV infection in an HSV seronegative subject comprising administering to the subject from about 1 mg to about 20 mg of glycyrrhizic acid, or a salt or solvate thereof, once per day. In some cases, glycyrrhizic acid is administered prior to exposure to HSV. In some cases, glycyrrhizic acid is administered after exposure to HSV. In some cases, glycyrrhizic acid is administered both prior to and after exposure to HSV. In some cases, glycyrrhizic acid is administered with one or more additional active agents, e.g., one or more additional antiviral agents, one or more contraceptive agents, or one or more additional antiviral agents and one or more contraceptive agents. In some embodiments, the methods further prevent infection of one or more additional infectious diseases, for example, HIV. In some embodiments, wherein the HSV seronegative subject is further administered one or more contraceptive agents, the methods further prevent pregnancy. In some embodiments, the methods further comprise administering to an HSV seropositive partner of the HSV seronegative subject one or more antiviral agents, for example, one or more HSV antiviral agents, one or more HIV antiviral agents, and/or any antiviral agent described herein. In some cases, the methods comprise administering to the HSV seronegative subject about 1 mg, 2 mg, 3 mg, 4 mg, 5 mg, 6 mg, 7 mg, 8 mg, 9 mg, 10 mg, 11 mg, 12 mg, 13 mg, 14 mg, 15 mg, 16 mg, 17 mg, 18 mg, 19 mg or 20 mg of glycyrrhizic acid, or a salt or solvate thereof, once per day. In some cases, the methods comprise administering to the HSV seronegative subject from about 1 mg to about 5 mg, from about 5 mg to about 10 mg, or from about 10 mg to about 15 mg of glycyrrhizic acid, or a salt or solvate thereof, once per day. In some embodiments, the additional antiviral agents include tenofovir, emtricitabine, lamivudine, efavirenz, raltegravir, dolutegravir, maravoric, rilpirivine, Atripla®, and salts, solvates and/or combinations thereof. In some embodiments, one of the one or more additional antiviral agents is tenofovir and the methods further comprise administering to the HSV seronegative subject from about 50 mg to about 500 mg of tenofovir once per day, e.g., about 50 mg, 100 mg, 150 mg, 200 mg, 250 mg, 300 mg, 350 mg, 400 mg or 500 mg of tenofovir per day. In some embodiments, one of the one or more additional antiviral agents is emtricitabine and the methods further comprise administering to the HSV seronegative subject from about 50 mg to about 300 mg of emtricitabine once per day, e.g., about 50 mg, 100 mg, 150 mg, 200 mg, 250 mg, or 300 mg of emtricitabine per day. In some embodiments, one of the one of more additional antiviral agents is lamivudine and the methods further comprise administering to the HSV seronegative subject from about 50 mg to about 400 mg of lamivudine once per day, e.g., about 50 mg, 100 mg, 150 mg, 200 mg, 250 mg, 300 mg, 350 mg or 400 mg of lamivudine per day. In some embodiments, one of the one of more additional antiviral agents is efavirenz and the methods further comprise administering to the HSV seronegative subject from about 300 mg to about 900 mg of efavirenz once per day, e.g., about 300 mg, 400 mg, 500 mg, 600 mg, 700 mg, 800 mg, or 900 mg of efavirenz per day. In some embodiments, one of the one of more additional antiviral agents is raltegravir and the methods further comprise administering to the HSV seronegative subject from about 200 mg to about 600 mg of raltegravir twice per day, e.g., about 200 mg, 300 mg, 400 mg, 500 mg, or 600 mg of raltegravir twice per day. In some embodiments, one of the one of more additional antiviral agents is dolutegravir and the methods further comprise administering to the HSV seronegative subject from about 10 mg to about 100 mg of dolutegravir once per day, e.g., about 10 mg, 20 mg, 30 mg, 40 mg, 50 mg, 60 mg, 70 mg, 80 mg, 90 mg or 100 mg of dolutegravir per day. In some embodiments, one of the one of more additional antiviral agents is maravoric and the methods further comprise administering to the HSV seronegative subject from about 100 mg to about 400 mg of maravoric twice per day, e.g., about 100 mg, 150 mg, 200 mg, 250 mg, 300 mg, 350 mg or 400 mg of maravoric twice per day. In some embodiments, one of the one of more additional antiviral agents is rilpirivine and the methods further comprise administering to the HSV seronegative subject from about 10 mg to about 50 mg of rilpirivine once per day, e.g., about 10 mg, 20 mg, 25 mg, 30 mg, 40 mg, or 50 mg of rilpirivine per day. In some embodiments, a) one of the one or more additional antiviral agents is emtricitabine and the methods further comprise administering to the HSV seronegative subject from about 50 mg to about 300 mg of emtricitabine once per day, e.g., about 50 mg, 100 mg, 150 mg, 200 mg, 250 mg, or 300 mg of emtricitabine per day; b) one of the one of more additional antiviral agents is efavirenz and the methods further comprise administering to the HSV seronegative subject from about 300 mg to about 900 mg of efavirenz once per day, e.g., about 300 mg, 400 mg, 500 mg, 600 mg, 700 mg, 800 mg, or 900 mg of efavirenz per day; and c) one of the one or more additional antiviral agents is tenofovir and the methods further comprise administering to the HSV seronegative subject from about 50 mg to about 500 mg of tenofovir once per day, e.g., about 50 mg, 100 mg, 150 mg, 200 mg, 250 mg, 300 mg, 350 mg, 400 mg or 500 mg of tenofovir per day. In some cases, the one or more additional antiviral agents are administered prior to, after, or both prior to and after the HSV seronegative subject is exposed to HSV. In some embodiments, the contraceptive agent comprises levonorgestrel, estradiol, dosogestrel, ethinyl estradiol, norethindrone acetate, norgestimate, or salts, solvates or combinations thereof. In some cases, a contraceptive comprises levonorgestrel and estradiol and the methods further comprise administering to the HSV seronegative subject about 0.10 mg of levonorgestrel and about 0.02 mg of estradiol. In some cases, a contraceptive comprises dosogestrel and ethinyl estradiol and the methods further comprise administering to the HSV seronegative subject about 0.15 mg of dosogestrel and about 0.03 mg of ethinyl estradiol. In some cases, a contraceptive comprises norethindrone acetate and ethinyl estradiol and the methods further comprise administering to the HSV seronegative subject about 1 mg of norethindrone acetate and about 20 ug of ethinyl estradiol. In some cases, a contraceptive comprises norgestimate and ethinyl estradiol and the methods further comprise administering to the HSV seronegative subject about 0.18 mg or about 0.25 mg of norgestimate and about 35 ug or about 25 ug of ethinyl estradiol. In some embodiments, the contraceptive agent(s) are administered prior to, after, or both prior to and after the subject is exposed to HSV. In some cases, a contraceptive comprises levonorgestrel and the methods further comprise administering to the HSV seronegative subject about 0.75 mg of levonorgestrel; wherein the 0.75 mg of levonorgestrel is administered to the subject once per day for two days following sexual conduct that could result in pregnancy. In some cases, one or more of the contraceptive agents are available over the counter to a subject who is over the age of 14, 15, 16, 17 or 18 years.

In some embodiments, provided herein are methods of preventing HSV infection in an HSV seronegative subject comprising administering to the subject from about 50 mg to about 400 mg of *Sambucus nigra*, or a salt or solvate thereof, once per day. In some cases, *Sambucus nigra* is administered prior to exposure to HSV. In some cases, *Sambucus nigra* is administered after exposure to HSV. In some cases, *Sambucus nigra* is administered both prior to and after exposure to HSV. In some cases, *Sambucus nigra* is administered with one or more additional active agents, e.g., one or more additional antiviral agents, one or more contraceptive agents, or one or more additional antiviral agents and one or more contraceptive agents. In some embodiments, the methods further prevent infection of one or more additional infectious diseases, for example, HIV. In some embodiments, wherein the HSV seronegative subject is further administered one or more contraceptive agents, the methods further prevent pregnancy. In some embodiments, the methods further comprise administering to an HSV seropositive partner of the HSV seronegative subject one or more antiviral agents, for example, one or more HSV antiviral agents, one or more HIV antiviral agents, and/or any antiviral agent described herein. In some cases, the methods comprise administering to the HSV seronegative subject about 50 mg, 75 mg, 100 mg, 125 mg, 150 mg, 175 mg, 200 mg, 225 mg, 250 mg, 275 mg, 300 mg, 325 mg, 350 mg, 375 mg, or 400 mg of *Sambucus nigra*, or a salt or solvate thereof, once per day. In some cases, the methods comprise administering to the HSV seronegative subject from about 50 mg to about 100 mg, from about 100 mg to about 250 mg, or from about 250 mg to about 400 mg of *Sambucus nigra*, or a salt or solvate thereof, once per day. In some embodiments, the additional antiviral agents include tenofovir, emtricitabine, lamivudine, efavirenz, raltegravir, dolutegravir, maravoric, rilpirivine, Atripla®, and salts, solvates and/or combinations thereof. In some embodiments, one of the one or more additional antiviral agents is tenofovir and the methods further comprise administering to the HSV seronegative subject from about 50 mg to about 500 mg of tenofovir once per day, e.g., about 50 mg, 100 mg, 150 mg, 200 mg, 250 mg, 300 mg, 350 mg, 400 mg or 500 mg of tenofovir per day. In some embodiments, one of the one or more additional antiviral agents is emtricitabine and the methods further comprise administering to the HSV seronegative subject from about 50 mg to about 300 mg of emtricitabine once per day, e.g., about 50 mg, 100 mg, 150 mg, 200 mg, 250 mg, or 300 mg of emtricitabine per day. In some embodiments, one of the one of more additional antiviral agents is lamivudine and the methods further comprise administering to the HSV seronegative subject from about 50 mg to about 400 mg of lamivudine once per day, e.g., about 50 mg, 100 mg, 150 mg, 200 mg, 250 mg, 300 mg, 350 mg or 400 mg of lamivudine per day. In some embodiments, one of the one of more additional antiviral agents is efavirenz and the methods further comprise administering to the HSV seronegative subject from about 300 mg to about 900 mg of efavirenz once per day, e.g., about 300 mg, 400 mg, 500 mg, 600 mg, 700 mg, 800 mg, or 900 mg of efavirenz per day. In some embodiments, one of the one of more additional antiviral agents is raltegravir and the methods further comprise administering to the HSV seronegative subject from about 200 mg to about 600 mg of raltegravir twice per day, e.g., about 200 mg, 300 mg, 400 mg, 500 mg, or 600 mg of raltegravir twice per day. In some embodiments, one of the one of more additional antiviral agents is dolutegravir and the methods further comprise administering to the HSV seronegative subject from about 10 mg to about 100 mg of dolutegravir once per day, e.g., about 10 mg, 20 mg, 30 mg, 40 mg, 50 mg, 60 mg, 70 mg, 80 mg, 90 mg or 100 mg of dolutegravir per day. In some embodiments, one of the one of more additional antiviral agents is maravoric and the methods further comprise administering to the HSV seronegative subject from about 100 mg to about 400 mg of maravoric twice per day, e.g., about 100 mg, 150 mg, 200 mg, 250 mg, 300 mg, 350 mg or 400 mg of maravoric twice per day. In some embodiments, one of the one or more additional antiviral agents is rilpirivine and the methods further comprise administering to the HSV seronegative subject from about 10 mg to about 50 mg of rilpirivine once per day, e.g., about 10 mg, 20 mg, 25 mg, 30 mg, 40 mg, or 50 mg of rilpirivine per day. In some embodiments, a) one of the one or more additional antiviral agents is emtricitabine and the methods further comprise administering to the HSV seronegative subject from about 50 mg to about 300 mg of emtricitabine once per day, e.g., about 50 mg, 100 mg, 150 mg, 200 mg, 250 mg, or 300 mg of emtricitabine per day; b) one of the one of more additional antiviral agents is efavirenz and the methods further comprise administering to the HSV seronegative subject from about 300 mg to about 900 mg of efavirenz once per day, e.g., about 300 mg, 400 mg, 500 mg, 600 mg, 700 mg, 800 mg, or 900 mg of efavirenz per day; and c) one of the one or more additional antiviral agents is tenofovir and the methods further comprise administering to the HSV seronegative subject from about 50 mg to about 500 mg of tenofovir once per day, e.g., about 50 mg, 100 mg, 150 mg, 200 mg, 250 mg, 300 mg, 350 mg, 400 mg or 500 mg of tenofovir per day. In some cases, the one or more additional antiviral agents are administered prior to, after, or both prior to and after the HSV seronegative subject is exposed to HSV. In some embodiments, the contraceptive agent comprises levonorgestrel, estradiol, dosogestrel, ethinyl estradiol, norethindrone acetate, norgestimate, or salts, solvates or combinations thereof. In some cases, a contraceptive comprises levonorgestrel and estradiol and the methods further comprise administering to the HSV seronegative subject about 0.10 mg of levonorgestrel and about 0.02 mg of estradiol. In some cases, a contraceptive comprises dosogestrel and ethinyl estradiol and the methods further comprise administering to the HSV seronegative subject about 0.15 mg of dosogestrel and about 0.03 mg of ethinyl estradiol. In some cases, a contraceptive comprises norethindrone acetate and ethinyl estradiol and the methods further comprise administering to the HSV seronegative subject about 1 mg of norethindrone acetate and about 20 ug of ethinyl estradiol. In some cases, a contraceptive comprises norgestimate and ethinyl estradiol and the methods further comprise administering to the HSV seronegative subject about 0.18 mg or about 0.25 mg of norgestimate and about 35 ug or about 25 ug of ethinyl estradiol. In some embodiments, the contraceptive agent(s) are administered prior to, after, or both prior to and after the subject is exposed to HSV. In some cases, a contraceptive comprises levonorgestrel and the methods further comprise administering to the HSV seronegative subject about 0.75 mg of levonorgestrel; wherein the 0.75 mg of levonorgestrel is administered to the subject once per day for two days following sexual conduct that could result in pregnancy. In some cases, one or more of the contraceptive agents are available over the counter to a subject who is over the age of 14, 15, 16, 17 or 18 years.

In some embodiments, provided herein are methods of preventing HSV infection in an HSV seronegative subject comprising administering to the subject from about 500 mg to about 1500 mg of valganciclovir, or a salt or solvate thereof, once per day. In some cases, valganciclovir is administered prior to exposure to HSV. In some cases, valganciclovir is administered after exposure to HSV. In some cases, valganciclovir is administered both prior to and after exposure to HSV. In some cases, valganciclovir is administered with one or more additional active agents, e.g., one or more additional antiviral agents, one or more contraceptive agents, or one or more additional antiviral agents and one or more contraceptive agents. In some embodiments, the methods further prevent infection of one or more additional infectious diseases, for example, HIV. In some embodiments, wherein the HSV seronegative subject is further administered one or more contraceptive agents, the methods further prevent pregnancy. In some embodiments, the methods further comprise administering to an HSV seropositive partner of the HSV seronegative subject one or more antiviral agents, for example, one or more HSV antiviral agents, one or more HIV antiviral agents, and/or any antiviral agent described herein. In some cases, the methods comprise administering to the HSV seronegative subject about 500 mg, 600 mg, 700 mg, 800 mg, 900 mg, 1000 mg, 1100 mg, 1200 mg, 1300 mg, 1400 mg, or 1500 mg of valganciclovir, or a salt or solvate thereof, once per day. In some cases, the methods comprise administering to the HSV seronegative subject from about 500 mg to about 800 mg, from about 800 mg to about 1200 mg, or from about 1200 mg to about 1500 mg of valganciclovir, or a salt or solvate thereof, once per day. In some embodiments, the additional antiviral agents include tenofovir, emtricitabine, lamivudine, efavirenz, raltegravir, dolutegravir, maravoric, rilpirivine, Atripla®, and salts, solvates and/or combinations thereof. In some embodiments, one of the one or more additional antiviral agents is tenofovir and the methods further comprise administering to the HSV seronegative subject from about 50 mg to about 500 mg of tenofovir once per day, e.g., about 50 mg, 100 mg, 150 mg, 200 mg, 250 mg, 300 mg, 350 mg, 400 mg or 500 mg of tenofovir per day. In some embodiments, one of the one or more additional antiviral agents is emtricitabine and the methods further comprise administering to the HSV seronegative subject from about 50 mg to about 300 mg of emtricitabine once per day, e.g., about 50 mg, 100 mg, 150 mg, 200 mg, 250 mg, or 300 mg of emtricitabine per day. In some embodiments, one of the one of more additional antiviral agents is lamivudine and the methods further comprise administering to the HSV seronegative subject from about 50 mg to about 400 mg of lamivudine once per day, e.g., about 50 mg, 100 mg, 150 mg, 200 mg, 250 mg, 300 mg, 350 mg or 400 mg of lamivudine per day. In some embodiments, one of the one of more additional antiviral agents is efavirenz and the methods further comprise administering to the HSV seronegative subject from about 300 mg to about 900 mg of efavirenz once per day, e.g., about 300 mg, 400 mg, 500 mg, 600 mg, 700 mg, 800 mg, or 900 mg of efavirenz per day. In some embodiments, one of the one of more additional antiviral agents is raltegravir and the methods further comprise administering to the HSV seronegative subject from about 200 mg to about 600 mg of raltegravir twice per day, e.g., about 200 mg, 300 mg, 400 mg, 500 mg, or 600 mg of raltegravir twice per day. In some embodiments, one of the one of more additional antiviral agents is dolutegravir and the methods further comprise administering to the HSV seronegative subject from about 10 mg to about 100 mg of dolutegravir once per day, e.g., about 10 mg, 20 mg, 30 mg, 40 mg, 50 mg, 60 mg, 70 mg, 80 mg, 90 mg or 100 mg of dolutegravir per day. In some embodiments, one of the one of more additional antiviral agents is maravoric and the methods further comprise administering to the HSV seronegative subject from about 100 mg to about 400 mg of maravoric twice per day, e.g., about 100 mg, 150 mg, 200 mg, 250 mg, 300 mg, 350 mg or 400 mg of maravoric twice per day. In some embodiments, one of the one of more additional antiviral agents is rilpirivine and the methods further comprise administering to the HSV seronegative subject from about 10 mg to about 50 mg of rilpirivine once per day, e.g., about 10 mg, 20 mg, 25 mg, 30 mg, 40 mg, or 50 mg of rilpirivine per day. In some embodiments, a) one of the one or more additional antiviral agents is emtricitabine and the methods further comprise administering to the HSV seronegative subject from about 50 mg to about 300 mg of emtricitabine once per day, e.g., about 50 mg, 100 mg, 150 mg, 200 mg, 250 mg, or 300 mg of emtricitabine per day; b) one of the one or more additional antiviral agents is efavirenz and the methods further comprise administering to the HSV seronegative subject from about 300 mg to about 900 mg of efavirenz once per day, e.g., about 300 mg, 400 mg, 500 mg, 600 mg, 700 mg, 800 mg, or 900 mg of efavirenz per day; and c) one of the one or more additional antiviral agents is tenofovir and the methods further comprise administering to the HSV seronegative subject from about 50 mg to about 500 mg of tenofovir once per day, e.g., about 50 mg, 100 mg, 150 mg, 200 mg, 250 mg, 300 mg, 350 mg, 400 mg or 500 mg of tenofovir per day. In some cases, the one or more additional antiviral agents are administered prior to, after, or both prior to and after the HSV seronegative subject is exposed to HSV. In some embodiments, the contraceptive agent comprises levonorgestrel, estradiol, dosogestrel, ethinyl estradiol, norethindrone acetate, norgestimate, or salts, solvates or combinations thereof. In some cases, a contraceptive comprises levonorgestrel and estradiol and the methods further comprise administering to the HSV seronegative subject about 0.10 mg of levonorgestrel and about 0.02 mg of estradiol. In some cases, a contraceptive comprises dosogestrel and ethinyl estradiol and the methods further comprise administering to the HSV seronegative subject about 0.15 mg of dosogestrel and about 0.03 mg of ethinyl estradiol. In some cases, a contraceptive comprises norethindrone acetate and ethinyl estradiol and the methods further comprise administering to the HSV seronegative subject about 1 mg of norethindrone acetate and about 20 ug of ethinyl estradiol. In some cases, a contraceptive comprises norgestimate and ethinyl estradiol and the methods further comprise administering to the HSV seronegative subject about 0.18 mg or about 0.25 mg of norgestimate and about 35 ug or about 25 ug of ethinyl estradiol. In some embodiments, the contraceptive agent(s) are administered prior to, after, or both prior to and after the subject is exposed to HSV. In some cases, a contraceptive comprises levonorgestrel and the methods further comprise administering to the HSV seronegative subject about 0.75 mg of levonorgestrel; wherein the 0.75 mg of levonorgestrel is administered to the subject once per day for two days following sexual conduct that could result in pregnancy. In some cases, one or more of the contraceptive agents are available over the counter to a subject who is over the age of 14, 15, 16, 17 or 18 years.

Pre-Exposure Compositions and Methods

In some aspects, described herein are compositions for administration to an HSV seronegative subject, the compositions comprising a low dose of a first antiviral agent; wherein the composition is administered to the subject prior to physical contact with a partner who is either infected with HSV or has unknown HSV status. In some embodiments, the composition is a pre-exposure composition. In some embodiments, the first antiviral agent is an HSV antiviral agent. In some embodiments, the first antiviral agent comprises valacyclovir, acyclovir, famciclovir, pritelivir, penciclovir, ganciclovir, valganciclovir, cidofovir, foscarnet, darunavir, glycyrrhizic acid, glutamine, FV-100, ASP2151, me-609, ASP2151, topical VDO, PEG-formulation (Devirex AG), vidarabine, cidofovir, crofelemer (SP-303T), EPB-348, CMX001, V212, NB-001, squaric acid, ionic zinc, sorivudine (ARYS-01), trifluridine, 882C87, merlin (ethanol and glycolic acid mixture), vitamin C, AIC316, versabase gel with *Sarracenia purpurea*, UB-621, lysine, edoxudine, brivudine, cytarabine, docosanol, tromantadine, resiquimod (R-848), imiquimod, resiquimod, tenofovir, tenofovir disoproxil fumarate, tenofovir alafenamide fumarate, or salts, solvates, or combinations thereof. In some embodiments, the composition and/or antiviral agent is useful for the prevention of HSV infection in the seronegative subject when the composition and/or antiviral agent is administered to the subject at least prior to exposure to HSV. In some cases, the composition and/or first antiviral agent is useful for the prevention of HSV infection in the seronegative subject when the composition and/or antiviral agent is administered to the subject prior to and after exposure to HSV. In some embodiments, the composition and/or antiviral agent is useful to suppress HSV replication in the subject when the composition and/or antiviral agent is administered to the subject prior to exposure to HSV. In some cases, the composition and/or antiviral agent is useful to suppress HSV replication in the subject when the composition and/or antiviral agent is administered to the subject prior to and after exposure to HSV. In some embodiments, the composition and/or antiviral agent is useful to suppress HSV activation in the subject when the composition and/or antiviral agent is administered to the subject prior to exposure to HSV. In some cases, the composition and/or antiviral agent is useful to suppress HSV activation in the subject when the composition and/or antiviral agent is administered to the subject prior to and after exposure to HSV.

In some embodiments, the composition is useful to reduce the risk of HSV infection in the subject when the composition is administered to the subject prior to exposure to HSV. In some embodiments, the risk of HSV infection is reduced by at least about 10%, 20%, 30%, 40%, 50%, 60%, 70%, 80%, 90%, or 100%, as compared to the risk of HSV infection without administration of the composition.

In some embodiments, the low dose of the first antiviral agent is from about 50 mg to about 1 g. In some embodiments, the low dose of the first antiviral agent is less than about 1,000 mg, less than about 900 mg, less than about 800 mg, less than about 700 mg, less than about 600 mg, less than about 500 mg, less than about 480 mg, less than about 460 mg, less than about 440 mg, less than about 420 mg, less than about 400 mg, less than about 380 mg, less than about 360 mg, less than about 340 mg, less than about 320 mg, less than about 300 mg, less than about 280 mg, less than about 260 mg, less than about 240 mg, less than about 220 mg, less than about 200 mg, less than about 180 mg, less than about 160 mg, less than about 140 mg, less than about 120 mg, less than about 100 mg, less than about 90 mg, less than about 80 mg, less than about 70 mg, less than about 60 mg, less than about 50 mg, less than about 40 mg, less than about 30 mg, less than about 20 mg, less than about 10 mg, less than about 5 mg, or less than about 1 mg. In some cases, the low dose of the first antiviral agent is between about 50 mg and about 500 mg, between about 50 mg and about 480 mg, between about 50 mg and about 460 mg, between about 50 mg and about 440 mg, between about 50 mg and about 420 mg, between about 50 mg and about 400 mg, between about 50 mg and about 380 mg, between about 50 mg and about 360 mg, between about 50 mg and about 340 mg, between about 50 mg and about 320 mg, between about 50 mg and about 300 mg, between about 50 mg and about 280 mg, between about 50 mg and about 260 mg, between about 50 mg and about 240 mg, between about 50 mg and about 220 mg, or between about 50 mg and about 200 mg. In some embodiments, the low dose of the first antiviral agent is an amount similar to an amount of the first antiviral agent useful for suppression treatment in an HSV seropositive subject. In some embodiments, the low dose of the first antiviral agent is configured for administration to the subject between about once per 5 years to about twice daily. For example, the antiviral is administered every year, 6 months, 5 months, 4 months, 3 months, 2 months, 1 month, 3 weeks, 2 weeks, 1 week, twice a week, daily, or twice daily. In some embodiments, the composition is administered to the subject at least about 1 day, 2 days, 3 days, 4 days, 5 days, 6 days, 7 days, 8 days, 9 days, 10 days, 11 days, 12 days, 13 days, 14 days, 15 days, 16 days, 17 days, 18 days, 19 days, 20 days, 21 days, 22 days, 23 days, 24 days, 25 days, 26 days, 27 days, 28 days, 29 days, 30 days, 1 month, 2 months, or 3 months prior to HSV exposure (time points are not limited to whether it is the first HSV exposure or any subsequent HSV exposure).

In some embodiments, the first antiviral agent is formulated for administration by a long-acting drug delivery mechanism using a long-acting drug delivery device. In some embodiments, the long-acting delivery device is an intravaginal ring. In some embodiments, the long-acting delivery device is a transdermal patch. In some embodiments, the long-acting delivery device is an injection device.

In some embodiments, the composition further comprises a second, third, fourth, or fifth antiviral agent. In alternative or additional embodiments, the composition is configured for administration with a second, third, fourth, or fifth antiviral agent. In some embodiments, the second, third, fourth, and/or fifth antiviral agent is present in the composition at a second lose dose. In some cases, the second, third, fourth, and/or fifth antiviral agent comprises the same or different active agent as the first antiviral agent. In some embodiments, the second, third, fourth, and/or fifth antiviral agent comprises valacyclovir, acyclovir, famciclovir, pritelivir, penciclovir, ganciclovir, valganciclovi, cidofovir, foscarnet, darunavir, glycyrrhizic acid, glutamine, FV-100, ASP2151, me-609, ASP2151, topical VDO, PEG-formulation (Devirex AG), vidarabine, cidofovir, crofelemer (SP-303T), EPB-348, CMX001, V212, NB-001, squaric acid, ionic zinc, sorivudine (ARYS-01), trifluridine, 882C87, merlin (ethanol and glycolic acid mixture), vitamin C, AIC316, versabase gel with *Sarracenia purpurea*, UB-621, lysine, edoxudine, brivudine, cytarabine, docosanol, tromantadine, resiquimod (R-848), imiquimod, resiquimod, tenofovir, tenofovir disoproxil fumarate, tenofovir alafenamide fumarate, include GSK208141 (gD2t, GSK glycoprotein D (gD)-Alum/3-deacylated form of monophosphoryl lipid A), Herpes Zoster GSK 1437173A, gD2-AS04, Havrix™ gD-Alum, Zostavax/Zoster vaccine (V211, V212, V210), HSV529, HerpV (AG-707 rh-Hsc70 polyvalent peptide complex), VCL-HB01, VCL-HM01, pPJV7630, GEN-003, SPL7013 gel (VivaGel™), GSK324332A, GSK1492903A, VariZIG™, and Varivax, maraviroc, enfuvirtide, vicriviroc, cenicriviroc, lbalizumab, fostemsavir (BMS-663068), ibalizumab (TMB-355, TNX-355), PRO 140, b12 antibody, DCM205, DARPins, caprine antibody, VIR-576, enfuvirtide (T-20), AMD11070, PR0542, SCH-C, T-1249, cyanovirin, griffithsen, lectins, pentafuside, dolutegravir, elvitegravir, raltegravir, globoidnan A, MK-2048, BI224436, cabotegravir, GSK 1265744, GSK-572, MK-0518, abacavir, didanosine, emtrictabine, lamivudine, stavudine, tenofovir, tenofovir disoporoxil fumarate, zidovudine, apricitabine, stampidine, elvucitabine, racivir, amdoxovir, stavudine, zalcitabine, festinavir, dideoxycytidine ddC, azidothymidine, tenofovir alafenamide fumarate, entecavir, delavirdine, efavirenz, etravirine (TMC-125), nevirapine, rilpivirine, doravirine, Calanolide A, capravirine, epivir, adefovir, dapivirine, lersivirine, alovudine, elvucitabine, TMC-278, DPC-083, amdoxovir, (−)-beta-D-2,6-diamino-purine dioxolane, MIV-210 (FLG), DFC (dexelvucitabine), dioxolane thymidine, L697639, atevirdine (U87201E), MIV-150, GSK-695634, GSK-678248, TMC-278, KP1461, KP-1212, lodenosine (FddA), 5-[(3,5-dichlorophenyl)thio]-4-isopropyl-1-(4-pyridylmethyl)imidazole-2-methanol carbamic acid, (−)-I2-D-2,6-diaminopurine dioxolane, AVX-754, BCH-13520, BMS-56190 ((4S)-6-chloro-4-[(1E)-cyclopropylethenyl]-3,-4-dihydro-4-trifluoromethyl-2 (1H)-quinazolinone), TMC-120, L697639, atazanavir, darunavir, fosamprenavir, indinavir, nelfinavir, ritonavir, saquinavir, tipranavir, lopinavir, amprenavir, telinavir (SC-52151), droxinavir, emtriva, invirase, agenerase, TMC-126, mozenavir (DMP-450), JE-2147 (AG1776), L-756423, KNI-272, DPC-681, DPC-684, BMS 186318, droxinavir (SC-55389a), DMP-323, KNI-227, 1-[(2-hydroxyethoxy)methyl]-6-(phenylthio)-thymine, AG-1859, RO-033-4649, R-944, DMP-850, DMP-851, brecanavir (GW640385), nonoxynol-9, sodium dodecyl sulfate, Savvy (1.0% C31G), BufferGel®, carrageenans, VivaGel®, PRO-2000, also known as PRO 2000/5, naphthalene 2-sulfonate polymer, or polynaphthalene sulphonate, amphotericin B, sulfamethoxazole, trimethoprim, clarithromycin, daunorubicin, fluconazole, doxorubicin, anidulafungin, immune globulin, gamma globulin, dronabinol, megestrol acetate, atovaquone, rifabutin, pentamidine, trimetrexate glucuronate, leucovorin, alitretinoin gel, erythropoeetin, calcium hydroxylapatite, poly-L-lactic acid, somatropin rDNA, itraconazole, paclitaxel, voriconazole, cidofovir, fomivirsen, azithromycin, ruxolitinib, tocilizumab, beviramat, TRIM5alpha, Tat antagonists, trichosanthin, abzyme, calanolide A, ceragenin, cyanovirin-N, diarylpyrimidines, epigallocatechin gallate (EGCG), foscarnet, griffithsin, hydroxycarbamide, miltefosine, portmanteau inhibitors, scytovirin, seliciclib, synergistic enhancers, tre recombinase, zinc finger protein transcription factor, KP-1461, BIT225, aplaviroc, atevirdine, brecanavir, capravirine, dexelvucitabine, emivirine, lersivirine, lodenosine, loviride, fomivirsen, glycyrrhizic acid (anti-inflammatory, inhibits 1 lbeta-hydroxysteroid dehydrogenase), zinc salts, cellulose sulfate, cyclodextrins, dextrin-2-sulfate, NCP7 inhibitors, AMD-3100, BMS-806, BMS-793, C31G, carrageenan, CD4-IgG2, cellulose acetate phthalate, mAb 2G12, mAb b12, Merck 167, plant lectins, poly naphthalene sulfate, poly sulfo-styrene, PRO2000, PSC-Rantes, SCH-C, SCH-D, T-20, TMC-125, UC-781, UK-427, UK-857, Carraguard (PC-515), brincidofovir (CMX001), zidovudine, virus-specific cytotoxic T cells, idoxuridine, podophyllotoxin, rifampicin, metisazone, interferon alfa 2b (Intron-A), peginterferon alfa-2a, ribavirin, moroxydine, pleconaril, BCX4430, taribavirin (viramidine, ICN 3142), favipiravir, rintatolimod, ibacitabine, (5-iodo-2'-deoxycytidine), methisazone (metisazone), ampligen, arbidol, Atripla®, combivir, imunovir, nexavir, trizivir, truvada, lamivudine, dideoxyadenosine, floxuridine, idozuridine, inosine pranobex, 2'-deoxy-5-(methylamino)uridine, digoxin, imiquimod, interferon type III, interferon type II, interferon type I, tea tree oil, glycyrrhizic acid, fialuridine, telbivudine, adefovir, etecavir, lamivudine, clevudine, asunaprevir, boceprevir, faldaprevir, grazoprevir, paritaprevir, ritonavir, telaprevir, simeprevir, sofosbuvir, ACH-3102, daclatasvir, deleobuvir, elbasvir, ledipasvir, MK-3682, MK-8408, samatasvir, ombitasvir, entecavir, elderberry *sambucus*, umifenovir, amantadine, rimantadine, oseltamivir, zanamivir, peramivir, laninamivir, pyrrole polyamides, lopinavir, or salts, solvates, and/or combinations thereof.

In some embodiments, the second, third, fourth, and/or fifth antiviral agent is an HIV antiviral comprising maraviroc, enfuvirtide, vicriviroc, cenicriviroc, lbalizumab, fostemsavir (BMS-663068), ibalizumab (TMB-355, TNX-355), PRO 140, b12 antibody, DCM205, DARPins, caprine antibody, VIR-576, enfuvirtide (T-20), AMD11070, PR0542, SCH-C, T-1249, cyanovirin, griffithsen, lectins, pentafuside, dolutegravir, elvitegravir, raltegravir, globoidnan A, MK-2048, BI224436, cabotegravir, GSK 1265744, GSK-572, MK-0518, abacavir, didanosine, emtricitabine, lamivudine, stavudine, tenofovir, tenofovir disoporoxil fumarate, zidovudine, apricitabine, stampidine, elvucitabine, racivir, amdoxovir, stavudine, zalcitabine, festinavir, dideoxycytidine ddC, azidothymidine, tenofovir alafenamide fumarate, entecavir, delavirdine, efavirenz, etravirine (TMC-125), nevirapine, rilpivirine, doravirine, Calanolide A, capravirine, epivir, adefovir, dapivirine, lersivirine, alovudine, elvucitabine, TMC-278, DPC-083, amdoxovir, (−)-beta-D-2,6-diamino-purine dioxolane, MIV-210 (FLG), DFC (dexelvucitabine), dioxolane thymidine, L697639, atevirdine (U87201E), MIV-150, GSK-695634, GSK-678248, TMC-278, KP1461, KP-1212, lodenosine (FddA), 5-[(3,5-dichlorophenyl)thio]-4-isopropyl-1-(4-pyridylmethyl)imidazole-2-methanol carbamic acid, (−)-I2-D-2,6-diaminopurine dioxolane, AVX-754, BCH-13520, BMS-56190 ((4S)-6-chloro-4-[(1E)-cyclopropylethenyl]-3,-4-dihydro-4-trifluoromethyl-2 (1H)-quinazolinone), TMC-120, L697639, atazanavir, darunavir, fosamprenavir, indinavir, nelfinavir, ritonavir, saquinavir, tipranavir, lopinavir, amprenavir, telinavir (SC-52151), droxinavir, emtriva, invirase, agenerase, TMC-126, mozenavir (DMP-450), JE-2147 (AG1776), L-756423, KNI-272, DPC-681, DPC-684, BMS 186318, droxinavir (SC-55389a), DMP-323, KNI-227, 1-[(2-hydroxyethoxy)methyl]-6-(phenylthio)-thymine, AG-1859, RO-033-4649, R-944, DMP-850, DMP-851, brecanavir (GW640385), or salts, solvates or combinations thereof.

In some embodiments, the second, third, fourth, and/or fifth low dose of a second, third, fourth, and/or fifth antiviral agent is from about 50 mg to about 1 g. In some embodiments, the low dose of the second, third, fourth, and/or fifth antiviral agent is less than about 1,000 mg, less than about 900 mg, less than about 800 mg, less than about 700 mg, less than about 600 mg, less than about 500 mg, less than about 480 mg, less than about 460 mg, less than about 440 mg, less than about 420 mg, less than about 400 mg, less than about 380 mg, less than about 360 mg, less than about 340 mg, less than about 320 mg, less than about 300 mg, less than about 280 mg, less than about 260 mg, less than about 240 mg, less than about 220 mg, less than about 200 mg, less than about 180 mg, less than about 160 mg, less than about 140 mg, less than about 120 mg, less than about 100 mg, less than about 90 mg, less than about 80 mg, less than about 70 mg, less than about 60 mg, less than about 50 mg, less than about 40 mg, less than about 30 mg, less than about 20 mg, less than about 10 mg, less than about 5 mg, or less than about 1 mg. In some cases, the low dose of the second, third, fourth, and/or fifth antiviral agent is between about 50 mg and about 500 mg, between about 50 mg and about 480 mg, between about 50 mg and about 460 mg, between about 50 mg and about 440 mg, between about 50 mg and about 420 mg, between about 50 mg and about 400 mg, between about 50 mg and about 380 mg, between about 50 mg and about 360 mg, between about 50 mg and about 340 mg, between about 50 mg and about 320 mg, between about 50 mg and about 300 mg, between about 50 mg and about 280 mg, between about 50 mg and about 260 mg, between about 50 mg and about 240 mg, between about 50 mg and about 220 mg, or between about 50 mg and about 200 mg.

In various embodiments, the compositions described herein further comprise or are administered with one or more contraceptive agents. In some embodiments, the contraceptive agent comprises 17a-ethinyl-levonorgestrel-17b-hydroxy-estra-4,9,11-trien-3-one, estradiol, ethinyl estradiol, levonorgestrel, medroxyprogesterone acetate, nestorone, norethindrone, ethynodiol diacetate, RU486, N9, mifepristone, mifegyne, mifeprex, 17a-ethinyl-levongestrel, 17b-hydroxy-estra-4,9,11-trien-3-one, estradiol, norgestrienone, progesterone, etonogestril (3-keto-desogestrel), progestin, megestrol, etono-progestin alonegestrel, and 17-acetoxy-16-methylene-19-norprogesterone, and salts, solvates, and/or combinations thereof.

In some aspects, described herein are methods for preventing HSV infection in an HSV seronegative subject, the methods comprising the administration of a composition comprising a low dose of a first antiviral agent to the subject prior to physical contact (e.g., sexual contact) with a partner who is either infected with HSV or has unknown HSV status. In some embodiments, the physical contact occurs during one sexual incident. In some embodiments, the physical contact occurs during two or more sexual incidents. In some embodiments, the physical contact occurs with a single partner. In some embodiments, the physical contact occurs with two or more partners. In various instances, the subject has a risk of exposure to HSV during physical contact with the partner. In some methods, the subject is exposed to HSV. In some embodiments, the methods further comprise administration of the composition after exposure to HSV. In some embodiments, the composition is a pre-exposure composition as described above.

In some embodiments, the subject is at risk for exposure to HSV because the subject is or will be in an ongoing sexual relationship with a partner who is seropositive for HSV. In some embodiments, the seropositive partner is undergoing HSV suppression therapy. In some cases, the HSV suppression therapy comprises the administration of a low dose of an additional antiviral agent to the partner. In some cases, this additional antiviral agent comprises a same active agent as the first antiviral agent. In some cases, the additional antiviral agent comprises a different active agent as the first antiviral agent. In some cases, the subject and the seropositive partner use a physical barrier such as a condom during sexual contact. In some instances, the subject is exposed to HSV from the seropositive partner. In such instances, the administered composition suppresses HSV replication in the subject. In some instances, the administered composition suppresses HSV activation in the subject. In some instances, the administered composition reduces the risk of HSV infection to the subject. In some embodiments, the risk of HSV infection due to the administered composition is reduced by at least about 10%, 20%, 30%, 40%, 50%, 60%, 70%, 80%, 90%, or 100%, as compared to the risk of HSV infection without administration of the composition. In some embodiments, the composition administered to the subject and the suppressive therapy in the partner reduces the risk of HSV infection in the seronegative subject by at least about 10%, 20%, 30%, 40%, 50%, 60%, 70%, 80%, 90%, or 100%.

In some embodiments, the subject is at risk for exposure to HSV because the subject is not or will not be in a mutually-monogamous sexual relationship. In some instances, the subject is exposed to HSV during sexual contact within the non-mutual monogamous sexual relationship. In such instances, the administered composition suppresses HSV replication in the subject. In some instances, the administered composition suppresses HSV activation in the subject. In some instances, the administered composition reduces the risk of HSV infection to the subject. In some embodiments, the risk of HSV infection due to the administered composition is reduced by at least about 10%, 20%, 30%, 40%, 50%, 60%, 70%, 80%, 90%, or 100%, as compared to the risk of HSV infection without administration of the composition.

In some embodiments, the subject is at risk for exposure to HSV because the subject has or will have physical contact with a partner of unknown HSV status. In some cases, the partner of unknown HSV status is undergoing HSV treatment comprising the administration of a low dose of an additional antiviral agent to the partner, as described above. In some cases, the additional antiviral agent comprises a same active agent as the first antiviral agent. In some cases, the additional antiviral agent comprises a different active agent than the first antiviral agent. In some cases, the physical contact is sexual contact. In some instances, the subject and the partner of unknown HSV status use physical barrier, such as a condom during sexual contact.

In some embodiments, the subject is at risk for exposure to HSV because the subject has or will have physical contact with an HSV seropositive partner. In some cases, the partner is undergoing HSV treatment comprising the administration of a low dose of an additional antiviral agent to the partner, as described above. In some cases, the additional antiviral agent comprises a same active agent as the first antiviral agent. In some cases, the additional antiviral agent comprises a different active agent than the first antiviral agent. In some cases, the physical contact is sexual contact. In some instances, the subject and the partner of unknown HSV status use physical barrier, such as a condom during sexual contact. In some instances, the subject is exposed to HSV from the partner known to have HSV. In such instances, the administered composition suppresses HSV replication in the subject. In some instances, the administered composition suppresses HSV activation in the subject. In some instances, the administered composition reduces the risk of HSV infection to the subject. In some embodiments, the risk of HSV infection due to the administered composition is reduced by at least about 10%, 20%, 30%, 40%, 50%, 60%, 70%, 80%, 90%, or 100%, as compared to the risk of HSV infection without administration of the composition. In some embodiments, the composition administered to the subject and the suppressive therapy in the partner reduces the risk of HSV infection in the seronegative subject by at least about 10%, 20%, 30%, 40%, 50%, 60%, 70%, 80%, 90%, or 100%.

In various embodiments, the composition administered to the subject further comprises one or more contraceptive agents. In some embodiments, the methods further comprise administering to the subject one or more contraceptive agents. In some embodiments, the contraceptive agent comprises 17a-ethinyl-levonorgestrel-17b-hydroxy-estra-4,9,11-trien-3-one, estradiol, ethinyl estradiol, levonorgestrel, medroxyprogesterone acetate, nestorone, norethindrone, ethynodiol diacetate, RU486, N9, mifepristone, mifegyne, mifeprex, 17a-ethinyl-levongestrel, 17b-hydroxy-estra-4,9,11-trien-3-one, estradiol, norgestrienone, progesterone, etonogestril (3-keto-desogestrel), progestin, megestrol, etono-progestin alonegestrel, and 17-acetoxy-16-methylene-19-norprogesterone, and salts, solvates, and/or combinations thereof. In some embodiments, the contraceptive agent comprises a condom, cervical cap, female condom, diaphragm, intrauterine device, spermicide (e.g., nonoxynol, octoxynol), or other contraceptives known in the art.

In some embodiments, the compositions are used in conjunction with condoms, to enhance the risk-reducing effectiveness of condoms and provide maximum protection. In some cases, the composition is coated onto condoms during manufacture, and enclosed within conventional watertight plastic or foil packages that contain one condom per package, or it can be manually applied by a user to either the inside or the outside of a condom, immediately before use.

In some embodiments, the methods further comprise determining if the subject is in a risk category for exposure to HSV. In some embodiments, the methods further comprise determining the low dose of the composition for administration to the subject. In some instances, provided that the subject is in a risk category for exposure to HSV, the method further comprises using the risk category to determine the low dose of the composition for administration to the subject. In some embodiments, the methods further comprise determining the identity of the first antiviral agent. In some instances, provided that the subject is in a risk category for exposure to HSV, the method further comprises using the risk category to determine the identity of the first antiviral agent. In some instances, the methods further comprise determining a delivery device for the administration of the composition to the subject. In some cases, the delivery device is a long-acting delivery device. In some cases, the long-acting delivery device is an intravaginal ring. In some cases, the long-acting delivery device is an injection device. In some instances, the long-acting delivery device is a transdermal patch.

An exemplary method of delivery of an antiviral composition described herein for the prevention of HSV infection in a seronegative subject is through a sustained release system via an intravaginal ring. In some embodiments, the intravaginal ring comprises a silicone elastomer. In some embodiments, the intravaginal ring comprises ethylene vinyl acetate. In some embodiments, the intravaginal ring is latex free. In some embodiments, the intravaginal ring comprises polyurethane. In some cases, the polyurethane is a polyesterurethane. In some cases, the intravaginal ring is biodegradable. In some embodiments, the intravaginal ring further comprises one or more active agents as a contraceptive. In some cases, the contraceptive agent is an estrogenic compound, a progestational compound, and/or a gonadotropin releasing hormone or its peptide or non-peptide agonists or antagonist analogues. In some embodiments, the method comprises inserting delivery device intravaginally and maintaining the device intravaginally for about 1 to about 180 days. In some embodiments, the delivery device is an intravaginal ring and the release rate of the antiviral agent is from about 1 ug/day to about 10 mg/day. In some cases, the intravaginal ring further comprises a contraceptive agent and the contraceptive agent is released from the ring from about 1 ug/day to about 10 mg/day.

Post-Exposure Compositions and Methods

In some aspects, described herein are compositions for administration to an HSV seronegative subject, the compositions comprising a very dose of a first antiviral agent; wherein the composition is administered to the subject after exposure to HSV. In some embodiments, the composition is a post-exposure composition. In some embodiments, the first antiviral agent is an HSV antiviral agent. In some embodiments, the first antiviral agent comprises valacyclovir, acyclovir, famciclovir, pritelivir, penciclovir, ganciclovir, valganciclovi, cidofovir, foscarnet, darunavir, glycyrrhizic acid, glutamine, FV-100, ASP2151, me-609, ASP2151, topical VDO, PEG-formulation (Devirex AG), vidarabine, cidofovir, crofelemer (SP-303T), EPB-348, CMX001, V212, NB-001, squaric acid, ionic zinc, sorivudine (ARYS-01), trifluridine, 882C87, merlin (ethanol and glycolic acid mixture), vitamin C, AIC316, versabase gel with *Sarracenia purpurea*, UB-621, lysine, edoxudine, brivudine, cytarabine, docosanol, tromantadine, resiquimod (R-848), imiquimod, resiquimod, tenofovir, tenofovir disoproxil fumarate, tenofovir alafenamide fumarate, or salts, solvates, or combinations thereof. In some embodiments, the composition and/or first antiviral agent is useful for the prevention of HSV infection in the seronegative subject when the composition and/or first antiviral agent is administered to the subject after exposure to HSV. In some cases, the composition and/or first viral agent is useful for the prevention of HSV infection in the seronegative subject when the composition and/or first viral agent is administered to the subject prior to and after exposure to HSV. In some embodiments, the composition and/or antiviral agent is useful to suppress HSV replication in the subject when the composition and/or antiviral agent is administered to the subject after exposure to HSV. In some cases, the composition and/or antiviral agent is useful to suppress HSV replication in the subject when the composition and/or antiviral agent is administered to the subject prior to and after exposure to HSV. In some embodiments, the composition and/or antiviral agent is useful to suppress HSV activation in the subject when the composition and/or antiviral agent is administered to the subject after exposure to HSV. In some cases, the composition and/or antiviral agent is useful to suppress HSV activation in the subject when the composition is administered to the subject prior to and after exposure to HSV.

In some embodiments, the composition is useful to reduce the risk of HSV infection in the subject when the composition is administered to the subject after exposure to HSV. In some embodiments, the risk of HSV infection is reduced by at least about 10%, 20%, 30%, 40%, 50%, 60%, 70%, 80%, 90%, or 100%, as compared to the risk of HSV infection without administration of the composition.

In some embodiments, the very high dose of the first antiviral agent is from about 500 mg to about 5,000 mg. In some embodiments, the very high dose of the first antiviral agent is greater than about 500 mg, greater than about 600 mg, greater than about 700 mg, greater than about 800 mg, greater than about 900 mg, greater than about 1,000 mg, greater than about 1,100 mg, greater than about 1,200 mg, greater than about 1,300 mg, greater than about 1,400 mg, greater than about 1,500 mg, greater than about 1,600 mg, greater than about 1,700 mg, greater than about 1,800 mg, greater than about 1,900 mg, greater than about 2,000 mg, greater than about 2,100 mg, greater than about 2,200 mg, greater than about 2,300 mg, greater than about 2,400 mg, greater than about 2,500 mg, greater than about 2,600 mg, greater than about 2,700 mg, greater than about 2,800 mg, greater than about 2,900 mg, greater than about 3,000 mg, greater than about 3,500 mg, greater than about 4,000 mg, greater than about 4,500 mg, or greater than about 5,000 mg. In some cases, the very high dose of the first antiviral agent is between about 500 mg and about 5,000 mg, between about 600 mg and about 5,000 mg, between about 700 mg and about 5,000 mg, between about 800 mg and about 5,000 mg, between about 900 mg and about 5,000 mg, between about 1,000 mg and about 5,000 mg, between about 1,200 mg and about 5,000 mg, between about 1,400 mg and about 5,000 mg, between about 1,600 mg and about 5,000 mg, between about 1,800 mg and about 5,000 mg, between about 2,000 mg and about 5,000 mg, between about 2,200 mg and about 5,000 mg, between about 2,400 mg and about 5,000 mg, between about 2,600 mg and about 5,000 mg, between about 2,800 mg and about 5,000 mg, between about 3,000 mg and about 5,000 mg, or between about 3,200 mg and about 5,000 mg. In some embodiments, the very high dose of the first antiviral agent is an amount greater than an amount of the first antiviral agent useful for treatment of an outbreak in an HSV seropositive subject. In some embodiments, the very high dose of the first antiviral agent is configured for administration to the subject within 1 hour, 2 hours, 3 hours, 4 hours, 5 hours, 6 hours, 7 hours, 8 hours, 9 hours, 10 hours, 11 hours, 12 hours, 13 hours, 14 hours, 15 hours, 16 hours, 17 hours, 18 hours, 19 hours, 20 hours, 21 hours, 22 hours, 23 hours, 24 hours, 1 day, 36 hours, 2 days, 60 hours, 3 days, 4 days, 5 days, 6 days, 1 week, 2 weeks or 1 month of HSV exposure. In some embodiments, the very high dose is administered once a month, once every 3 weeks, once every 2 weeks, once every week, 6 times a week, 5 times a week, 4 times a week, 3 times a week, 2 times a week, 3 times per day, 2 times per day or once per day.

In some embodiments, the first antiviral agent is formulated for administration by a long-acting drug delivery mechanism using a long-acting drug delivery device. In some embodiments, the long-acting delivery device is an intravaginal ring. In some embodiments, the long-acting delivery device is a transdermal patch. In some embodiments, the long-acting delivery device is an injection device.

In some embodiments, the composition further comprises a second, third, fourth, or fifth antiviral agent. In alternative or additional embodiments, the composition is configured for administration with a second, third, fourth, and/or fifth antiviral agent. In some embodiments, the second, third, fourth, and/or fifth antiviral agent is present in the composition at a second, third, fourth, and/or fifth very high dose. In some cases, the second, third, fourth, and/or fifth antiviral agent comprises the same or different active agent as the first antiviral agent. In some embodiments, the second, third, fourth, and/or fifth antiviral agent comprises valacyclovir, acyclovir, famciclovir, pritelivir, penciclovir, ganciclovir, valganciclovi, cidofovir, foscarnet, darunavir, glycyrrhizic acid, glutamine, FV-100, ASP2151, me-609, ASP2151, topical VDO, PEG-formulation (Devirex AG), vidarabine, cidofovir, crofelemer (SP-303T), EPB-348, CMX001, V212, NB-001, squaric acid, ionic zinc, sorivudine (ARYS-01), trifluridine, 882C87, merlin (ethanol and glycolic acid mixture), vitamin C, AIC316, versabase gel with *Sarracenia purpurea*, UB-621, lysine, edoxudine, brivudine, cytarabine, docosanol, tromantadine, resiquimod (R-848), imiquimod, resiquimod, tenofovir, tenofovir disoproxil fumarate, tenofovir alafenamide fumarate, include GSK208141 (gD2t, GSK glycoprotein D (gD)-Alum/3-deacylated form of monophosphoryl lipid A), Herpes Zoster GSK 1437173A, gD2-AS04, Havrix™, gD-Alum, Zostavax/Zoster vaccine (V211, V212, V210), HSV529, HerpV (AG-707 rh-Hsc70 polyvalent peptide complex), VCL-HB01, VCL-HM01, pPJV7630, GEN-003, SPL7013 gel (VivaGel™), GSK324332A, GSK1492903A, VariZIG™, and Varivax, maraviroc, enfuvirtide, vicriviroc, cenicriviroc, lbalizumab, fostemsavir (BMS-663068), ibalizumab (TMB-355, TNX-355), PRO 140, b12 antibody, DCM205, DARPins, caprine antibody, VIR-576, enfuvirtide (T-20), AMD11070, PRO542, SCH-C, T-1249, cyanovirin, griffithsen, lectins, pentafuside, dolutegravir, elvitegravir, raltegravir, globoidnan A, MK-2048, BI224436, cabotegravir, GSK 1265744, GSK-572, MK-0518, abacavir, didanosine, emtricitabine, lamivudine, stavudine, tenofovir, tenofovir disoporoxil fumarate, zidovudine, apricitabine, stampidine, elvucitabine, racivir, amdoxovir, stavudine, zalcitabine, festinavir, dideoxycytidine ddC, azidothymidine, tenofovir alafenamide fumarate, entecavir, delavirdine, efavirenz, etravirine (TMC-125), nevirapine, rilpivirine, doravirine, Calanolide A, capravirine, epivir, adefovir, dapivirine, lersivirine, alovudine, elvucitabine, TMC-278, DPC-083, amdoxovir, (−)-beta-D-2,6-diamino-purine dioxolane, MIV-210 (FLG), DFC (dexelvucitabine), dioxolane thymidine, L697639, atevirdine (U87201E), MIV-150, GSK-695634, GSK-678248, TMC-278, KP1461, KP-1212, lodenosine (FddA), 5-[(3,5-dichlorophenyl)thio]-4-isopropyl-1-(4-pyridylmethyl)imidazole-2-methanol carbamic acid, (−)-I2-D-2,6-diaminopurine dioxolane, AVX-754, BCH-13520, BMS-56190 ((4S)-6-chloro-4-[(1E)-cyclopropylethenyl]-3,-4-dihydro-4-trifluoromethyl-2 (1H)-quinazolinone), TMC-120, L697639, atazanavir, darunavir, fosamprenavir, indinavir, nelfinavir, ritonavir, saquinavir, tipranavir, lopinavir, amprenavir, telinavir (SC-52151), droxinavir, emtriva, invirase, agenerase, TMC-126, mozenavir (DMP-450), JE-2147 (AG1776), L-756423, KNI-272, DPC-681, DPC-684, BMS 186318, droxinavir (SC-55389a), DMP-323, KNI-227, 1-[(2-hydroxyethoxy)methyl]-6-(phenylthio)-thymine, AG-1859, RO-033-4649, R-944, DMP-850, DMP-851, brecanavir (GW640385), nonoxynol-9, sodium dodecyl sulfate, Savvy (1.0% C31G), BufferGel®, carrageenans, VivaGel®, PRO-2000, also known as PRO 2000/5, naphthalene 2-sulfonate polymer, or polynaphthalene sulphonate, amphotericin B, sulfamethoxazole, trimethoprim, clarithromycin, daunorubicin, fluconazole, doxorubicin, anidulafungin, immune globulin, gamma globulin, dronabinol, megestrol acetate, atovaquone, rifabutin, pentamidine, trimetrexate glucuronate, leucovorin, alitretinoin gel, erythropoeetin, calcium hydroxylapatite, poly-L-lactic acid, somatropin rDNA, itraconazole, paclitaxel, voriconazole, cidofovir, fomivirsen, azithromycin, ruxolitinib, tocilizumab, bevirimat, TRIM5alpha, Tat antagonists, trichosanthin, abzyme, calanolide A, ceragenin, cyanovirin-N, diarylpyrimidines, epigallocatechin gallate (EGCG), foscarnet, griffithsin, hydroxycarbamide, miltefosine, portmanteau inhibitors, scytovirin, seliciclib, synergistic enhancers, tre recombinase, zinc finger protein transcription factor, KP-1461, BIT225, aplaviroc, atevirdine, brecanavir, capravirine, dexelvucitabine, emivirine, lersivirine, lodenosine, loviride, fomivirsen, glycyrrhizic acid (anti-inflammatory, inhibits 1 lbeta-hydroxysteroid dehydrogenase), zinc salts, cellulose sulfate, cyclodextrins, dextrin-2-sulfate, NCP7 inhibitors, AMD-3100, BMS-806, BMS-793, C31G, carrageenan, CD4-IgG2, cellulose acetate phthalate, mAb 2G12, mAb b12, Merck 167, plant lectins, poly naphthalene sulfate, poly sulfo-styrene, PRO2000, PSC-Rantes, SCH-C, SCH-D, T-20, TMC-125, UC-781, UK-427, UK-857, Carraguard (PC-515), brincidofovir (CMX001), zidovudine, virus-specific cytotoxic T cells, idoxuridine, podophyllotoxin, rifampicin, metisazone, interferon alfa 2b (Intron-A), peginterferon alfa-2a, ribavirin, moroxydine, pleconaril, BCX4430, taribavirin (viramidine, ICN 3142), favipiravir, rintatolimod, ibacitabine, (5-iodo-2'-deoxycytidine), methisazone (metisazone), ampligen, arbidol, Atripla®, combivir, imunovir, nexavir, trizivir, truvada, larnivudine, dideoxyadenosine, floxuridine, idozuridine, inosine pranobex, 2'-deoxy-5-(methylamino)uridine, digoxin, imiquimod, interferon type III, interferon type II, interferon type I, tea tree oil, glycyrrhizic acid, fialuridine, telbivudine, adefovir, etecavir, lamivudine, clevudine, asunaprevir, boceprevir, faldaprevir, grazoprevir, paritaprevir, ritonavir, telaprevir, simeprevir, sofosbuvir, ACH-3102, daclatasvir, deleobuvir, elbasvir, ledipasvir, MK-3682, MK-8408, samatasvir, ombitasvir, entecavir, elderberry *sambucus*, umifenovir, amantadine, rimantadine, oseltamivir, zanamivir, peramivir, laninamivir, pyrrole polyamides, lopinavir, or salts, solvates, and/or combinations thereof.

In some embodiments, the second, third, fourth, and/or fifth antiviral agent is an HIV antiviral comprising maraviroc, enfuvirtide, vicriviroc, cenicriviroc, lbalizumab, fostemsavir (BMS-663068), ibalizumab (TMB-355, TNX-355), PRO 140, b12 antibody, DCM205, DARPins, caprine antibody, VIR-576, enfuvirtide (T-20), AMD11070, PR0542, SCH-C, T-1249, cyanovirin, griffithsen, lectins, pentafuside, dolutegravir, elvitegravir, raltegravir, globoidnan A, MK-2048, BI224436, cabotegravir, GSK 1265744, GSK-572, MK-0518, abacavir, didanosine, emtrictabine, lamivudine, stavudine, tenofovir, tenofovir disoporoxil fumarate, zidovudine, apricitabine, stampidine, elvucitabine, racivir, amdoxovir, stavudine, zalcitabine, festinavir, dideoxycytidine ddC, azidothymidine, tenofovir alafenamide fumarate, entecavir, delavirdine, efavirenz, etravirine (TMC-125), nevirapine, rilpivirine, doravirine, Calanolide A, capravirine, epivir, adefovir, dapivirine, lersivirine, alovudine, elvucitabine, TMC-278, DPC-083, amdoxovir, (−)-beta-D-2,6-diamino-purine dioxolane, MIV-210 (FLG), DFC (dexelvucitabine), dioxolane thymidine, L697639, atevirdine (U87201E), MIV-150, GSK-695634, GSK-678248, TMC-278, KP1461, KP-1212, lodenosine (FddA), 5-[(3,5-dichlorophenyl)thio]-4-isopropyl-1-(4-pyridylmethyl)imidazole-2-methanol carbamic acid, (−)-I2-D-2,6-diaminopurine dioxolane, AVX-754, BCH-13520, BMS-56190 ((4S)-6-chloro-4-[(1E)-cyclopropylethenyl]-3,-4-dihydro-4-trifluoromethyl-2 (1H)-quinazolinone), TMC-120, L697639, atazanavir, darunavir, fosamprenavir, indinavir, nelfinavir, ritonavir, saquinavir, tipranavir, lopinavir, amprenavir, telinavir (SC-52151), droxinavir, emtriva, invirase, agenerase, TMC-126, mozenavir (DMP-450), JE-2147 (AG1776), L-756423, KNI-272, DPC-681, DPC-684, BMS 186318, droxinavir (SC-55389a), DMP-323, KNI-227, 1-[(2-hydroxyethoxy)methyl]-6-(phenylthio)-thymine, AG-1859, RO-033-4649, R-944, DMP-850, DMP-851, brecanavir (GW640385), or salts, solvates or combinations thereof.

In some embodiments, the second, third, fourth, and/or fifth very high dose of a second antiviral agent is from about 500 mg to about 5,000 mg. In some embodiments, the very high dose of the second, third, fourth, and/or fifth antiviral agent is greater than about 500 mg, greater than about 600 mg, greater than about 700 mg, greater than about 800 mg, greater than about 900 mg, greater than about 1,000 mg, greater than about 1,100 mg, greater than about 1,200 mg, greater than about 1,300 mg, greater than about 1,400 mg, greater than about 1,500 mg, greater than about 1,600 mg, greater than about 1,700 mg, greater than about 1,800 mg, greater than about 1,900 mg, greater than about 2,000 mg, greater than about 2,100 mg, greater than about 2,200 mg, greater than about 2,300 mg, greater than about 2,400 mg, greater than about 2,500 mg, greater than about 2,600 mg, greater than about 2,700 mg, greater than about 2,800 mg, greater than about 2,900 mg, greater than about 3,000 mg, greater than about 3,500 mg, greater than about 4,000 mg, greater than about 4,500 mg, or greater than about 5,000 mg. In some cases, the very high dose of the second, third, fourth, and/or fifth antiviral agent is between about 500 mg and about 5,000 mg, between about 600 mg and about 5,000 mg, between about 700 mg and about 5,000 mg, between about 800 mg and about 5,000 mg, between about 900 mg and about 5,000 mg, between about 1,000 mg and about 5,000 mg, between about 1,200 mg and about 5,000 mg, between about 1,400 mg and about 5,000 mg, between about 1,600 mg and about 5,000 mg, between about 1,800 mg and about 5,000 mg, between about 2,000 mg and about 5,000 mg, between about 2,200 mg and about 5,000 mg, between about 2,400 mg and about 5,000 mg, between about 2,600 mg and about 5,000 mg, between about 2,800 mg and about 5,000 mg, between about 3,000 mg and about 5,000 mg, or between about 3,200 mg and about 5,000 mg. In some embodiments, the very high dose of the second, third, fourth, and/or fifth antiviral agent is an amount greater than an amount of the first antiviral agent useful for treatment of an outbreak in an HSV seropositive subject. In some embodiments, the very high dose of the second, third, fourth, and/or fifth antiviral agent is configured for administration to the subject within 1 hour, 2 hours, 3 hours, 4 hours, 5 hours, 6 hours, 7 hours, 8 hours, 9 hours, 10 hours, 11 hours, 12 hours, 13 hours, 14 hours, 15 hours, 16 hours, 17 hours, 18 hours, 19 hours, 20 hours, 21 hours, 22 hours, 23 hours, 24 hours, 1 day, 36 hours, 2 days, 60 hours, 3 days, 4 days, 5 days, 6 days, 1 week, 2 weeks or 1 month of HSV exposure. In some embodiments, the very high dose is administered once a month, once every 3 weeks, once every 2 weeks, once every week, 6 times a week, 5 times a week, 4 times a week, 3 times a week, 2 times a week, 3 times per day, 2 times per day or once per day.

In various embodiments, the compositions described herein further comprise or are administered with one or more contraceptive agents. In some embodiments, the contraceptive agent comprises 17a-ethinyl-levonorgestrel-17b-hydroxy-estra-4,9,11-trien-3-one, estradiol, ethinyl estradiol, levonorgestrel, medroxyprogesterone acetate, nestorone, norethindrone, ethynodiol diacetate, RU486, N9, mifepristone, mifegyne, mifeprex, 17a-ethinyl-levongestrel, 17b-hydroxy-estra-4,9,11-trien-3-one, estradiol, norgestrienone, progesterone, etonogestril (3-keto-desogestrel), progestin, megestrol, etono-progestin alonegestrel, and 17-acetoxy-16-methylene-19-norprogesterone, and salts, solvates, and/or combinations thereof.

In some aspects, described herein are methods for preventing HSV infection in an HSV seronegative subject, the methods comprising the administration of a composition comprising a very high dose of a first antiviral agent to the subject after the subject is exposed to HSV. In some embodiments, the HSV exposure occurs during one sexual incident between the HSV seronegative subject and an HSV seropositive partner. In some embodiments, HSV exposure occurs during two or more sexual incidents. In some embodiments, HSV exposure is from a single partner. In some embodiments, HSC exposure occurs from two or more partners. In some embodiments, the composition is a post-exposure composition as described above. In some embodiments, the methods further comprise administering to the subject a pre-exposure composition as previously described.

In some embodiments, the subject is exposed to HSV from physical contact (e.g., sexual contact) with a partner who is seropositive for HSV, wherein the subject and the partner are in a mutually monogamous relationship. In some instances, the partner is aware of their seropositive status. In some instances, the partner is not aware of their seropositive status. In some cases, the subject is aware the HSV seropositive status of the partner. In some cases, the subject is not aware of the HSV seropositive status of the partner. In some embodiments, the seropositive partner is undergoing HSV suppression therapy. In some cases, the HSV suppression therapy comprises the administration of a low dose of an additional antiviral agent to the partner. In some cases, this additional antiviral agent comprises a same active agent as the first antiviral agent. In some cases, the additional antiviral agent comprises a different active agent as the first antiviral agent. In some cases, the subject and the seropositive partner use a physical barrier such as a condom during sexual contact. In some instances, the administered composition suppresses HSV replication in the subject. In some instances, the administered composition suppresses HSV activation in the subject. In some instances, the administered composition reduces the risk of HSV infection to the subject. In some embodiments, the risk of HSV infection due to the administered composition is reduced by at least about 10%, 20%, 30%, 40%, 50%, 60%, 70%, 80%, 90%, or 100%, as compared to the risk of HSV infection without administration of the composition. In some embodiments, the composition administered to the subject and the suppressive therapy in the partner reduces the risk of HSV infection in the seronegative subject by at least about 10%, 20%, 30%, 40%, 50%, 60%, 70%, 80%, 90%, or 100%.

In some embodiments, the subject is exposed to HSV from physical contact (e.g., sexual contact) with an HSV seropositive partner, wherein the subject and the partner are not in a mutually monogamous relationship. In some instances, the partner is aware of their seropositive status. In some instances, the partner is not aware of their seropositive status. In some cases, the subject is aware the HSV seropositive status of the partner. In some cases, the subject is not aware of the HSV seropositive status of the partner. In some embodiments, the seropositive partner is undergoing HSV suppression therapy. In some cases, the HSV suppression therapy comprises the administration of a low dose of an additional antiviral agent to the partner. In some cases, this additional antiviral agent comprises a same active agent as the first antiviral agent. In some cases, the additional antiviral agent comprises a different active agent as the first antiviral agent. In some cases, the subject and the seropositive partner use a physical barrier such as a condom during sexual contact. In some instances, the administered composition suppresses HSV replication in the subject. In some instances, the administered composition suppresses HSV activation in the subject. In some instances, the administered composition reduces the risk of HSV infection to the subject. In some embodiments, the risk of HSV infection due to the administered composition is reduced by at least about 10%, 20%, 30%, 40%, 50%, 60%, 70%, 80%, 90%, or 100%, as compared to the risk of HSV infection without administration of the composition. In some embodiments, the composition administered to the subject and the suppressive therapy in the partner reduces the risk of HSV infection in the seronegative subject by at least about 10%, 20%, 30%, 40%, 50%, 60%, 70%, 80%, 90%, or 100%.

In various embodiments, the composition administered to the subject further comprises one or more contraceptive agents. In some embodiments, the methods further comprise administering to the subject one or more contraceptive agents. In some embodiments, the contraceptive agent comprises 17a-ethinyl-levonorgestrel-17b-hydroxy-estra-4,9,11-trien-3-one, estradiol, ethinyl estradiol, levonorgestrel, medroxyprogesterone acetate, nestorone, norethindrone, ethynodiol diacetate, RU486, N9, mifepristone, mifegyne, mifeprex, 17a-ethinyl-levongestrel, 17b-hydroxy-estra-4,9, 11-trien-3-one, estradiol, norgestrienone, progesterone, etonogestril (3-keto-desogestrel), progestin, megestrol, etono-progestin alonegestrel, and 17-acetoxy-16-methylene-19-norprogesterone, and salts, solvates, and/or combinations thereof. In some embodiments, the contraceptive agent comprises a condom, cervical cap, female condom, diaphragm, intrauterine device, spermicide (e.g., nonoxynol, octoxynol), or other contraceptives known in the art. In some embodiments, the contraceptive is an emergency contraceptive. Non-limiting examples of emergency contraceptive agents include levonorgestrel, combinations of estrogen and progestin, progestin, antiprogestin (e.g., ulipristal acetate, mifepristone), and salts, solvates or combinations thereof.

In some embodiments, the compositions are used in conjunction with condoms, to enhance the risk-reducing effectiveness of condoms and provide maximum protection. In some cases, the composition is coated onto condoms during manufacture, and enclosed within conventional watertight plastic or foil packages that contain one condom per package, or it can be manually applied by a user to either the inside or the outside of a condom, immediately before use.

In some embodiments, the methods further comprise determining the very high dose of the composition for administration to the subject. In some embodiments, the methods further comprise determining the identity of the first antiviral agent. In some instances, the methods further comprise determining a delivery device for the administration of the composition to the subject. In some cases, the delivery device is a long-acting delivery device. In some cases, the long-acting delivery device is an intravaginal ring. In some cases, the long-acting delivery device is an injection device. In some instances, the long-acting delivery device is a transdermal patch.

An exemplary method of delivery of an antiviral composition described herein for the prevention of HSV infection in a seronegative subject is through a sustained release system via an intravaginal ring. In some embodiments, the intravaginal ring comprises a silicone elastomer. In some embodiments, the intravaginal ring comprises ethylene vinyl acetate. In some embodiments, the intravaginal ring is latex free. In some embodiments, the intravaginal ring comprises polyurethane. In some cases, the polyurethane is a polyesterurethane. In some cases, the intravaginal ring is biodegradable. In some embodiments, the intravaginal ring further comprises one or more active agents as a contraceptive. In some cases, the contraceptive agent is an estrogenic compound, a progestational compound, and/or a gonadotropin releasing hormone or its peptide or non-peptide agonists or antagonist analogues. In some embodiments, the method comprises inserting delivery device intravaginally and maintaining the device intravaginally for about 1 to about 180 days. In some embodiments, the delivery device is an intravaginal ring and the release rate of the antiviral agent is from about 1 ug/day to about 10 mg/day. In some cases, the intravaginal ring further comprises a contraceptive agent and the contraceptive agent is released from the ring from about 1 ug/day to about 10 mg/day.

Pharmaceutical Compositions and Formulations

Provided herein, in various aspects, are compositions comprising one or more active agents, for example, antiviral agents and contraceptive agents, formulated with one or more pharmaceutically acceptable excipients, diluents, carriers and/or adjuvants. In addition, compositions of the disclosure include active agents formulated with one or more pharmaceutically acceptable auxiliary substances. Auxiliary substances, such as pH adjusting and buffering agents, tonicity adjusting agents, stabilizers, wetting agents and the like are readily available to the public. Suitable excipient vehicles for a composition include, for example, water, saline, dextrose, glycerol, ethanol and/or combinations thereof. In addition, the vehicle may comprise auxiliary substances such as wetting or emulsifying agents or pH buffering agents.

In many embodiments, the active agent is formulated into a pharmaceutical composition by combination with appropriate, pharmaceutically acceptable carriers or diluents, into solid, semi-solid, liquid or gaseous forms, such as tablets, capsules, powders, granules, ointments, solutions, suppositories, injections, inhalants and aerosols. For oral preparations, the active agent may be used alone or in combination with appropriate additives to make tablets, powders, granules or capsules, for example, with conventional additives, such as lactose, mannitol, corn starch, or potato starch; with binders such as crystalline cellulose, cellulose derivatives, acacia, corn starch or gelatins; with disintegrators, such as corn starch, potato starch, or sodium carboxymethylcellulose; with lubricants, such as talc or magnesium stearate; and/or if desired, with diluents, buffering agents, moistening agents, preservatives and/or flavoring agents. Suitable pharmaceutically acceptable carriers include, without limitation, water, dextrose, glycerol, saline, ethanol, and/or combinations thereof.

In some embodiments, an active agent of a composition herein is formulated into a preparation for injection by dissolving, suspending or emulsifying the agent in an aqueous or non-aqueous solvent, such as vegetable or other similar oils, synthetic aliphatic acid glycerides, esters of high aliphatic acids, or propylene glycol; and if desired, with conventional additives such as solubilizers, isotonic agents, suspending agents, emulsifying agents, stabilizers and preservatives.

In some embodiments, an active agent of a composition herein is utilized in an aerosol formulation to be administered via inhalation. As examples, the agent is formulated into a pressurized acceptable propellant such as dichlorodifluoromethane, propane and nitrogen.

In some embodiments, an active agent of a composition herein is made into a suppository by mixing with a base, such as an emulsifying base or water-soluble base. In some instances, an active agent is administered rectally via a suppository. The suppository may include vehicles such as cocoa butter, carbowaxes and polyethylene glycols, which melt at body temperature, yet are solidified at room temperature.

In some embodiments, an active agent of a composition is formulation in an injectable composition. Typically, injectable compositions are prepared as liquid solutions or suspensions. In some instances, a solid form is provided which is suitable for solubilization or suspension in a liquid vehicle prior to injection. In other embodiments, an active agent is emulsified or the active agent is encapsulated in a liposome vehicle.

In some embodiments, unit dosage forms for oral or rectal administration, such as syrups, elixirs and suspensions are provided wherein each dosage unit (e.g., teaspoonful, tablespoonful, table, suppository) comprises a predetermined amount of the composition comprising one or more active agents. In some embodiments, unit dosage forms for injection or intravenous administration comprises the active agent in a composition as a solution in sterile water, normal saline or other pharmaceutically acceptable carrier.

In some embodiments, an active agent of a composition herein is formulated for delivery by a continuous or controlled delivery system. Examples include the use of continuous or controlled delivery devices in combination with catheters, injection devices and the like. In other or additional embodiments, the composition is delivered using a pump, including mechanical and electromechanical infusion pumps. In general, pumps provide consistent and/or controlled release of the composition over time. In some embodiments, the active agent is in a liquid formulation in a drug-impermeable reservoir, and is delivered in a continuous or controlled manner to a patient. In some embodiments, a drug delivery system is at least partially implantable. An implantable device can be implanted at any suitable implantation site using methods and devices well known in the art. Implantation sites include, but are not limited to, a subdermal, subcutaneous, intramuscular or other suitable site within a subject's body. Subcutaneous implantation sites are used in some embodiments for convenience in implantation and removal of the drug delivery device. In some embodiments, the active agent is delivered in a controlled release system. In exemplary embodiments, the active agent is administered using intravenous infusion, implantable osmotic pump, transdermal patch or liposomes.

In some embodiments, compositions suitable for transdermal administration employ transdermal delivery devices and transdermal delivery patches. In some cases, the compositions are formulated as lipophilic emulsions or buffered aqueous solutions, dissolved and/or dispersed in a polymer or an adhesive. Such patches are constructed for continuous, pulsatile, or on demand delivery of active agents. In some cases, transdermal delivery is accomplished by means of iontophoretic patches and the like. In some cases, transdermal patches provide controlled delivery. The rate of absorption can be slowed by using rate-controlling membranes or by trapping an active agent within a polymer matrix or gel. Conversely, absorption enhancers can be used to increase absorption. An absorption enhancer or carrier includes absorbable pharmaceutically acceptable solvents to assist passage through the skin. In an exemplary embodiment, transdermal devices are in the form of a bandage comprising a backing member, a reservoir containing active agents and optional carriers, a rate controlling barrier to deliver the agents to the skin of the subject at a controlled and predetermined rate over a prolonged period of time, and adhesives to secure the device to the skin.

In other embodiments, an active agent of a composition described herein is formulated into absorptive materials, such as sutures, bandages and gauze; or coated onto the surface of solid phase materials, such as surgical staples, zippers and catheters to deliver the agent.

Compositions described herein, in various implementations, comprise an immediate release form, a sustained-release form, a controlled release form, or a combination thereof. In some embodiments, an immediate release formulation is formulated to allow the active agents to act rapidly. Non-limiting examples of immediate release formulations include readily dissolvable formulations. In some embodiments, a controlled release formulation is a pharmaceutical formulation that has been adapted such that active agent release rates and release profiles can be matched to physiological and therapeutic requirements or, alternatively, is formulated to effect release of an active agent at a programmed rate. Non-limiting examples of controlled release formulations include granules, delayed release granules, hydrogels (e.g., of synthetic or natural origin), other gelling agents (e.g., gel-forming dietary fibers), matrix-based formulations (e.g., formulations comprising a polymeric material having at least one active ingredient dispersed through), granules within a matrix, polymeric mixtures, granular masses, and the like. In some embodiments, a controlled release formulation is a delayed release form, wherein a delayed release form is formulated to delay action of an active agent for an extended period of time (e.g., for about 4, about 8, about 12, about 16, or about 24 hours).

In some embodiments, the active agents may be used in conjunction with other treatments that use sustained-release formulations. A sustained-release matrix, in many instances, is a matrix made of materials, usually polymers, which are degradable by enzymatic or acid-based hydrolysis or by dissolution. Once inserted into the body, the matrix may be acted upon by enzymes and body fluids. Examples of sustained-release matrix materials include, without limitation, liposomes, polylactides (polylactic acid), polyglycolide (polymer of glycolic acid), polylactide co-glylide (copolymers of lactic acid and glycolic acid), polyanhydrides, poly(ortho)esters, polypeptides, hyaluronic acid, collagen, chondroitin sulfate, carboxcylic acids, fatty acids, phospholipids, polysaccharides, nucleic acids, polyamino acids, amino acids (e.g., phenylalanine, tyrosine, isoleucine), polynucleotides, polyvinyl propylene, polyvinylpyrrolidone and silicone. Illustrative biodegradable matrices include a polylactide matrix, a polyglycolide matrix and a polylactide co-glycolide (co-polymers of lactic acid and glycolic acid) matrix.

The compositions used in the disclosed methods of treatment may be administered topically and can be incorporated into a delivery device. For example, a delivery device may be coated with or comprise the compositions disclosed herein. In some cases, the delivery device is a condom.

In some embodiments, the compositions and active agents described herein are delivered via vaginal devices which include, without limitation, intravaginal rings, vaginal tampons, vaginal strips, vaginal capsules, vaginal tablets, vaginal pessarys, vaginal cups, vaginal films, and vaginal sponges. In some embodiments, the compositions and active agents described herein are applied to the vagina of a subject in a number of forms including aerosols, foams, sprays, pastes, gels, jellies, creams, or suppositories. In some cases, the compositions are formulated for immediate release. In some embodiments, the compositions are formulated for long-acting, sustained release.

In various embodiments, intravaginal rings are designed to deliver a relatively constant dose of an active agent to the vagina, usually over a period of weeks to months. In some embodiments, the vaginal rings are made of a silicone elastomer and comprise an active agent released by diffusion through the elastomer. In some embodiments, the intravaginal ring comprises ethylene vinyl acetate. In some embodiments, the intravaginal ring is latex free. In some embodiments, the intravaginal ring comprises polyurethane. In some cases, the polyurethane is a polyesterurethane. In some cases, the intravaginal ring is biodegradable. In some embodiments, a vaginal ring comprises separate reservoirs containing different active agents. In some embodiments, a vaginal ring is a drug delivery device that is in the shape of a ring, a wafer, or suppository and is suitable for placement and retention inside a vagina. In some cases, the delivery device has an overall diameter of from about 10 mm to about 100 mm, and a cross-sectional diameter of from about 1 mm to about 15 mm.

In some embodiments, a composition described herein is in the form of a cream, lotion, gel, or foam that is applied to the affected skin or epithelial cavity, and preferably spread over the entire skin or epithelial surface which is at risk of contact with bodily fluids. Such formulations, which are suitable for vaginal or rectal administration, may be present as aqueous or oily suspensions, solutions or emulsions (liquid formulations) comprising active agents, such as antivirals, and optionally carriers.

In some embodiments, an active agent of a composition described herein is packaged into a biological compartment. Biological compartments can include, but are not limited to, viruses (lentivirus, adenovirus), nanospheres, liposomes, quantum dots, nanoparticles, microparticles, nanocapsules, vesicles, polyethylene glycol particles, hydrogels, and micelles. For example, a biological compartment can comprise a liposome. A liposome can be a self-assembling structure comprising one or more lipid bilayers, each of which can comprise two monolayers containing oppositely oriented amphipathic lipid molecules. Amphipathic lipids can comprise a polar (hydrophilic) headgroup covalently linked to one or two or more non-polar (hydrophobic) acyl or alkyl chains. Energetically unfavorable contacts between the hydrophobic acyl chains and a surrounding aqueous medium induce amphipathic lipid molecules to arrange themselves such that polar headgroups can be oriented towards the bilayer's surface and acyl chains are oriented towards the interior of the bilayer, effectively shielding the acyl chains from contact with the aqueous environment. Non-limiting examples of amphipathic compounds used in liposomes include phosphoglycerides and sphingolipids, representative examples of which include phosphatidylcholine, phosphatidylethanolamine, phosphatidylserine, phosphatidylinositol, phosphatidic acid, phoasphatidylglycerol, palmitoyloleoyl phosphatidylcholine, lysophosphatidylcholine, lysophosphatidylethanolamine, dimyristoylphosphatidylcholine (DMPC), dipalmitoylphosphatidylcholine (DPPC), dioleoylphosphatidylcholine, distearoylphosphatidylcholine (DSPC), dilinoleoylphosphatidylcholine and egg sphingomyelin, or any combination thereof.

In some embodiments, a biological compartment comprises a nanoparticle. In some cases, a nanoparticle comprises a diameter of from about 40 nanometers to about 1.5 micrometers, from about 50 nanometers to about 1.2 micrometers, from about 60 nanometers to about 1 micrometer, from about 70 nanometers to about 800 nanometers, from about 80 nanometers to about 600 nanometers, from about 90 nanometers to about 400 nanometers, from about 100 nanometers to about 200 nanometers. In some instances, as the size of the nanoparticle increases, the release rate can be slowed or prolonged and as the size of the nanoparticle decreases, the release rate can be increased. In some cases, the amount of albumin in the nanoparticles ranges from about 5% to about 85% albumin (v/v), from about 10% to about 80%, from about 15% to about 80%, from about 20% to about 70% albumin (v/v), from about 25% to about 60%, from about 30% to about 50%, or from about 35% to about 40%. In some cases, a pharmaceutical composition comprises up to 30, 40, 50, 60, 70 or 80% or more of the nanoparticle. In some instances, active agents of the disclosure are be bound to the surface of the nanoparticle.

Dosing and Treatment Regimens

The compositions comprising one or more active agents described herein may be administered to a patient in one or more doses. In some embodiments, a composition comprises two or more active agents. In some embodiments, a composition comprising one or more active agents is administered with one or more addition compositions, each comprising one or more additional active agents. In some instances, a patient is administered one dose of one active agent and another dose of another active agent. In some embodiments, one or more active agents is an antiviral agent. In some embodiments, one or more active agents is a contraceptive.

In various embodiments, the compositions containing the one or more active agents described herein are administered for prophylactic and/or therapeutic treatments. In some prophylactic applications, the compositions are administered to a subject at risk for exposure to a virus. In some prophylactic applications, the compositions are administered to a subject exposed to a virus. In some prophylactic applications, the compositions are administered to a subject prior to and after exposure to a virus. In some embodiments, prophylactic compositions prevent or reduce the risk of viral infection in a seronegative individual. In some prophylactic applications, compositions containing the one or more active agents described herein are administered to a patient susceptible to or otherwise at risk of a particular disease, disorder or condition. Such an amount is defined to be a prophylactically effective amount or dose. In this use, the precise amounts also depend on the patient's state of health, weight, and the like. When used in patients, effective amounts for this use will depend on the severity and course of the disease, disorder or condition, previous therapy, the patient's health status and response to the drugs, and the judgment of the treating physician. In some embodiments, the disease is an infectious disease caused by a virus. In some cases, the virus is HSV. In some cases, the virus is HIV.

In some therapeutic applications, the compositions are administered to a patient already suffering from a disease or condition, in an amount sufficient to cure or at least partially arrest at least one of the symptoms of the disease or condition. Amounts effective for this use depend on the severity and course of the disease or condition, previous therapy, the patient's health status, weight, and response to the drugs, and the judgment of the treating physician. Therapeutically effective amounts are optionally determined by methods including, but not limited to, a dose escalation and/or dose ranging clinical trial. In some embodiments, the disease is an infectious disease caused by a virus. In some cases, the virus is HSV. In some cases, the virus is HIV.

In certain embodiments wherein the patient's condition does not improve, upon the doctor's discretion the administration of composition comprising the one or more active agents is administered chronically, that is, for an extended period of time, including throughout the duration of the patient's life in order to ameliorate or otherwise control or limit the symptoms of the patient's disease or condition.

In certain embodiments wherein a patient's status does improve, the dose of active agent(s) being administered is temporarily reduced or temporarily suspended for a certain length of time (i.e., a drug holiday). In some embodiments, the length of the drug holiday is between 2 days and 1 year, including by way of example only, 2 days, 3 days, 4 days, 5 days, 6 days, 7 days, 10 days, 12 days, 15 days, 20 days, 28 days, or more than 28 days. The dose reduction during a drug holiday is, for example, by 10%-100%, including only 10%, 15%, 20%, 25%, 30%, 35%, 40%, 45%, 50%, 55%, 60%, 65%, 70%, 75%, 80%, 85%, 90%, 95%, and 100%.

Once improvement of the patient's conditions has occurred, a maintenance dose is administered if necessary. Subsequently, in specific embodiments, the dosage or the frequency of administration, or both, is reduced, as a function of the symptoms, to a level at which the improved disease, disorder or condition is retained. In certain embodiments, however, the patient requires intermittent treatment on a long-term basis upon any recurrence of symptoms.

In some embodiments, the dose of an active agent administered to a patient varies depending on factors such as time point during therapy, identity of active agent or combination of active agents, identity of disease, disease condition/severity, identity of patient (e.g., age, weight, sex), and route of administration.

In some embodiments, a composition described herein comprises a low dose of an active agent, such as an antiviral agent. In some embodiments, the low dose of the antiviral agent is from about 50 mg to about 1 g. In some embodiments, the low dose of the antiviral agent is less than about 1,000 mg, less than about 900 mg, less than about 800 mg, less than about 700 mg, less than about 600 mg, less than about 500 mg, less than about 480 mg, less than about 460 mg, less than about 440 mg, less than about 420 mg, less than about 400 mg, less than about 380 mg, less than about 360 mg, less than about 340 mg, less than about 320 mg, less than about 300 mg, less than about 280 mg, less than about 260 mg, less than about 240 mg, less than about 220 mg, less than about 200 mg, less than about 180 mg, less than about 160 mg, less than about 140 mg, less than about 120 mg, less than about 100 mg, less than about 90 mg, less than about 80 mg, less than about 70 mg, less than about 60 mg, less than about 50 mg, less than about 40 mg, less than about 30 mg, less than about 20 mg, less than about 10 mg, less than about 5 mg, or less than about 1 mg. In some cases, the low dose of the antiviral agent is between about 50 mg and about 500 mg, between about 50 mg and about 480 mg, between about 50 mg and about 460 mg, between about 50 mg and about 440 mg, between about 50 mg and about 420 mg, between about 50 mg and about 400 mg, between about 50 mg and about 380 mg, between about 50 mg and about 360 mg, between about 50 mg and about 340 mg, between about 50 mg and about 320 mg, between about 50 mg and about 300 mg, between about 50 mg and about 280 mg, between about 50 mg and about 260 mg, between about 50 mg and about 240 mg, between about 50 mg and about 220 mg, or between about 50 mg and about 200 mg. In some embodiments, the low dose of the antiviral agent is an amount similar to an amount of the antiviral agent useful for suppression treatment in an individual seropositive for the virus targeted by the antiviral agent. In some embodiments, the antiviral agent is an HSV antiviral agent. In some embodiments, the antiviral agent is an HIV antiviral agent.

In some embodiments, a composition described herein comprises a very high dose of an active agent, such as an antiviral agent. In some embodiments, the very high dose of the antiviral agent is from about 500 mg to about 5,000 mg. In some embodiments, the very high dose of the antiviral agent is greater than about 500 mg, greater than about 600 mg, greater than about 700 mg, greater than about 800 mg, greater than about 900 mg, greater than about 1,000 mg, greater than about 1,100 mg, greater than about 1,200 mg, greater than about 1,300 mg, greater than about 1,400 mg, greater than about 1,500 mg, greater than about 1,600 mg, greater than about 1,700 mg, greater than about 1,800 mg, greater than about 1,900 mg, greater than about 2,000 mg, greater than about 2,100 mg, greater than about 2,200 mg, greater than about 2,300 mg, greater than about 2,400 mg, greater than about 2,500 mg, greater than about 2,600 mg, greater than about 2,700 mg, greater than about 2,800 mg, greater than about 2,900 mg, greater than about 3,000 mg, greater than about 3,500 mg, greater than about 4,000 mg, greater than about 4,500 mg, or greater than about 5,000 mg. In some cases, the very high dose of the antiviral agent is between about 500 mg and about 5,000 mg, between about 600 mg and about 5,000 mg, between about 700 mg and about 5,000 mg, between about 800 mg and about 5,000 mg, between about 900 mg and about 5,000 mg, between about 1,000 mg and about 5,000 mg, between about 1,200 mg and about 5,000 mg, between about 1,400 mg and about 5,000 mg, between about 1,600 mg and about 5,000 mg, between about 1,800 mg and about 5,000 mg, between about 2,000 mg and about 5,000 mg, between about 2,200 mg and about 5,000 mg, between about 2,400 mg and about 5,000 mg, between about 2,600 mg and about 5,000 mg, between about 2,800 mg and about 5,000 mg, between about 3,000 mg and about 5,000 mg, or between about 3,200 mg and about 5,000 mg. In some embodiments, the very high dose of the antiviral agent is an amount greater than an amount of the antiviral agent useful for treatment of an outbreak in a seropositive individual infected with the virus targeted by the antiviral agent. In some embodiments, the antiviral agent is an HSV antiviral agent. In some embodiments, the antiviral agent is an HIV antiviral agent.

In some embodiments, an active agent is administered in about a 50 mg dosage. In some embodiments, an active agent is administered in about a 100 mg dosage. In some embodiments, an active agent is administered in about a 200 mg dosage. In some embodiments, an active agent is administered in about a 300 mg dosage. In some embodiments, an active agent is administered in about a 400 mg dosage. In some embodiments, an active agent is administered in about a 500 mg dosage. In some embodiments, an active agent is administered in about a 50 mg dosage. In some embodiments, an active agent is administered in about a 600 mg dosage. In some embodiments, an active agent is administered in about a 700 mg dosage. In some embodiments, an active agent is administered in about a 800 mg dosage. In some embodiments, an active agent is administered in about a 900 mg dosage. In some embodiments, an active agent is administered in about a 1,000 mg dosage. In some embodiments, an active agent is administered in about a 1,100 mg dosage. In some embodiments, an active agent is administered in about a 1,200 mg dosage. In some embodiments, an active agent is administered in about a 1,300 mg dosage. In some embodiments, an active agent is administered in about a 1,400 mg dosage. In some embodiments, an active agent is administered in about a 1,500 mg dosage. In some embodiments, an active agent is administered in about a 1,600 mg dosage. In some embodiments, an active agent is administered in about a 1,100 mg dosage. In some embodiments, an active agent is administered in about a 1,700 mg dosage. In some embodiments, an active agent is administered in about a 1,800 mg dosage. In some embodiments, an active agent is administered in about a 1,900 mg dosage. In some embodiments, an active agent is administered in about a 2,000 mg dosage. In some embodiments, an active agent is administered in about a 2,100 mg dosage. In some embodiments, an active agent is administered in about a 2,200 mg dosage. In some embodiments, an active agent is administered in about a 2,300 mg dosage. In some embodiments, an active agent is administered in about a 2,400 mg dosage. In some embodiments, an active agent is administered in about a 2,500 mg dosage. In some embodiments, an active agent is administered in about a 2,600 mg dosage. In some embodiments, an active agent is administered in about a 2,700 mg dosage. In some embodiments, an active agent is administered in about a 2,800 mg dosage. In some embodiments, an active agent is administered in about a 2,900 mg dosage. In some embodiments, an active agent is administered in about a 3,000 mg dosage. In some embodiments, an active agent is administered in about a 4,000 mg dosage. In some embodiments, an active agent is administered in about a 5,000 mg dosage. In some embodiments, the active agent is an antiviral agent. In some embodiments, the dosage is a very low dose. In some embodiments, the dosage is a very high dose. In some embodiments, the antiviral agent is an HSV antiviral agent. In some embodiments, the antiviral agent is an HIV antiviral agent.

In some embodiments, a composition described herein comprises 1, 2, 3, 4, 5 or more active agents. In some embodiments, 1, 2, 3, 4 or 5 of the active agents are antiviral agents. In some embodiments, one antiviral agent is administered at a low dosage (as described above, e.g., from about 50 mg to about 1 g) and one or more additional antiviral agents are administered at a second low dosage (as described above, e.g., from about 50 mg to about 1 g). In some embodiments, one antiviral agent is administered at a low dosage (as described above, e.g., from about 50 mg to about 1 g) and one or more additional antiviral agents are administered at a very high dosage (as described above, e.g., from about 500 mg to about 5,000 mg).

In many implementations of the disclosure, the amount of active agent per dose is determined on a per body weight basis. For example, in an embodiment, the active agent is administered in an amount of about 0.5 mg/kg body weight to about 100 mg/kg body weight. Those of skill will readily appreciate that dose levels often vary as a function of the specific active agent administered and the susceptibility of the subject to side effects. Preferred dosage forms of a given active agent are readily determinable by those of skill in the art. In some embodiments, the dosage or the amount of active agent in the dosage form are lower or higher than the ranges indicated herein, based on a number of variables in regard to an individual treatment regime. In various embodiments, the unit dosages are altered depending on a number of variables including, but not limited to, the activity of the agent, the mode of administration, the requirements of the individual subject, the condition of the patient (e.g., seronegative pre-exposure, seronegative post-exposure, seropositive), and/or the judgment of the practitioner.

In various embodiments, the dose of an active agent in a composition described herein is administered multiple times. The frequency of administration, in some instances, is dependent on the method of use, for example, for pre-exposure or post-exposure compositions. In some embodiments, an active agent is administered once per month, twice per month, three times per month, every other week, once per week, twice per week, three times per week, four times per week, five times per week, six times per week, every other day, daily, twice a day, three times a day, four times a day, five times a day, six times a day or more. In some embodiments, an active agent is administered continuously.

The duration of administration of the active agent (period of time over which the agent is administered), in many instances, varies depending on a number of factors. Examples of such factors include, without limitation, patient response, severity of symptoms, and disease type (e.g., virus type). In an example, an active agent is administered over a period of time of about one day to about one week, about one week to about two weeks, about two weeks to about four weeks, about one month to about two months, about two months to about four months, about four months to about six months, about six months to about eight months, about eight months to about 1 year, about 1 year to about 2 years or more.

In some embodiments, pharmaceutical compositions described herein are in unit dosage forms suitable for single administration of precise dosages. In some cases, in unit dosage form, the formulation is divided into unit doses containing appropriate quantities of one or more active agents. In some cases, the unit dosage is in the form of a package containing discrete quantities of the formulation. Non-limiting examples include packaged tablets or capsules, and powders in vials or ampoules. Aqueous suspension compositions can be packaged in single-dose non-reclosable containers. Multiple-dose reclosable containers can be used, for example, in combination with a preservative. Formulations for parenteral injection can be presented in unit dosage form, for example, in ampoules, or in multi-dose containers with a preservative.

In some embodiments, an active agent described herein is present in a composition in a range of from about 1 mg to about 5,000 mg, from about 5 mg to about 5,000 mg, from about 10 mg to about 5,000 mg, from about 20 mg to about 5,000 mg, from about 30 mg to about 5,000 mg, from about 40 mg to about 5,000 mg, from about 50 mg to about 5,000 mg, from about 60 mg to about 5,000 mg, from about 70 mg to about 5,000 mg, from about 80 mg to about 5,000 mg, from about 90 mg to about 5,000 mg, from about 100 mg to about 5,000 mg, from about 120 mg to about 5,000 mg, from about 140 mg to about 5,000 mg, from about 160 mg to about 5,000 mg, from about 180 mg to about 5,000 mg, from about 200 mg to about 5,000 mg, from about 250 mg to about 5,000 mg, from about 300 mg to about 5,000 mg, from about 350 mg to about 5,000 mg, from about 400 mg to about 5,000 mg, from about 500 mg to about 5,000 mg, from about 1,000 mg to about 5,000 mg, or from about 2,000 mg to about 5,000 mg. In some embodiments, the active agent is present in a composition deliverable with an intravaginal ring. In some embodiments, the active agent is an antiviral agent. In some embodiments, the active agent is an HSV antiviral agent. In some embodiments, the active agent is an HIV antiviral agent. In some embodiments, the active agent is a contraceptive agent.

Kits

In some applications, an HSV prophylaxis and/or treatment kit is provided that includes an antiviral agent to be given to a subject in an effective amount such that HSV replication is suppressed, HSV activation is suppressed, or both; a delivery mechanism for the antiviral agent; dosage information specific to the antiviral agent; and use instructions specific to the delivery mechanism. In some instances, a kit can be used by a seronegative person or a seropositive person.

In certain instances, the drug delivery mechanism is a long-lasting drug delivery mechanism, which can include, for example, injection devices, intravaginal rings, or transdermal patches. The use instructions can include timing information on when to begin therapy, such as one to three weeks in advance of entering a demographic risk category, and may also include instructions on interval timing for maintaining the drug delivery mechanism. In some cases, the use instructions and dosage information can be provided via the internet.

In some embodiments, the kit comprises a composition as described herein. In some embodiments, the composition is a pre-exposure composition. In some embodiments, the composition is a post-exposure composition. In some embodiments, the composition is a composition for suppression therapy. In some embodiments, the kit comprises one, two or more active agents. In some embodiments, the active agents are formulated together. In other embodiments, the active agents are formulated separately. In some embodiments, the kit comprises a means to administrate a composition comprising one or more active agents as described herein.

In some embodiments, the kit comprises suitable instructions in order to perform the methods of the kit. The instructions may provide information of performing any of the methods disclosed herein, whether or not the methods may be performed using only the reagents provided in the kit. The kit and instructions may require additional reagents or systems.

In some embodiments, a kit provided herein includes a carrier means being compartmentalized to receive in close confinement one or more containers such as vials, tubes, and the like, each of the containers comprising one of the separate elements to be used in a method provided herein.

The following examples are provided to further illustrate the advantages and features of the present disclosure, but are not intended to limit the scope of the disclosure. While they are typical of those that might be used, other procedures, methodologies, or techniques known to those skilled in the art may alternatively be used.

EXAMPLES

Example 1: Intravaginal Ring for Prevention of HSV Infection in a Seronegative Subject Intravaginal rings are produced from an ethylene acetate polymer and compounded with valacyclovir such that the effective dose is similar to the oral dose ranging from 500 mg to 2,000 mg per ring. The amount of valacyclovir released each day over a period of at least 14 days is measured in vitro. In vitro daily release profiles are determined using experimental conditions in vitro that effectively simulate the active drug diffusion that occurs in vivo.

Vaginal rings releasing low doses of valacyclovir are selected as candidates for clinical trials for the prevention of HSV infection in seronegative subjects at risk for exposure to HSV. Optionally, vaginal rings releasing high doses of valacyclovir are selected as candidates for clinical trials for the prevention of HSV infection in seronegative subjects exposed to HSV. The rings comprise silicone, polyether urethane or polyurethane.

Example 2: Safety of HSV Intravaginal Ring

Purpose:
The purpose of the study is to assess the safety of vaginal rings releasing low to high doses of valacyclovir.
Intervention:
Participants receive an intravaginal ring having valacyclovir or an intravaginal ring having a placebo.
Description:
Participants are instructed to insert a vaginal ring comprising valacyclovir or placebo every 30 days for the duration of the study. The dosages of valacyclovir within each intravaginal ring are optionally varied in different arms of the intervention to range from 500 mg to 2,000 mg of valacyclovir.
Primary Outcome Measures:
Safety as determined by the proportion of women in each arm experiencing protocol-specified events, including adverse events, laboratory abnormalities, cervico-vaginal abnormalities, and/or abnormal vaginal flora/pH during the study.
Secondary Outcome Measures:
Adherence to the protocol-specific product regimen as determined by self-report and clinician observation at each study visit.
Inclusion Criteria:
Women between 18 and 45 years of age who can provide informed consent.
HSV and HIV negative.
Currently on contraception and willing to continue contraception at least 3 months prior to enrollment
Willing to refrain from use of vaginal products or objects for duration of the study.
Willing to refrain from coitus for duration of the study.
Exclusion Criteria:
Currently pregnant or last pregnancy within 3 months prior to enrollment.
Currently breast-feeding.
Treatment with an antiviral within the past 12 months.
Presence of any abnormal physical finding on the vulva, vaginal walls or cervix during pelvic examination.

Example 3: Safety and Effectiveness of HSV Pre-Exposure Intravaginal Ring in the Prevention of HSV Infection in Seronegative Women in Discordant Relationships Purpose:
The purpose of the study is to assess the safety and effectiveness of an intravaginal ring releasing low-doses of valacyclovir in preventing HSV-2 infection in HSV seronegative women in a monogamous sexual relationship with an HSV seropositive partner.
Intervention:
Arm 1: Seronegative women participants are intravaginally fitted with an intravaginal ring having valacyclovir or a placebo. Women use their assigned ring type for the entirety of the study.
Arm 2: Seronegative women participants are intravaginally fitted with an intravaginal ring having valacyclovir or a placebo intravaginal ring. Women use their assigned ring type for the entirety of the study. Seropositive partners take 500 mg of valacyclovir once daily.
Description:
Seronegative participants are instructed to insert a first intravaginal ring having valacyclovir or a placebo intravaginally at least seven days prior to coitus. Seronegative participants will replace the first intravaginal ring with a second assigned intravaginal ring after 30 days. Alternatively, participants are fitted with the first intravaginal ring by a medical practitioner during enrollment.

In the second arm, HSV seropositive participants are administered 500 mg of valacyclovir once a day for the duration of the study. Treatment of symptomatic episodes in the HSV seropositive participants during the duration of the study optionally involve increasing the dosage of valacyclovir to 500 mg bid×5 days.

Participants attend study visits during the course of enrollment. Study visits include behavioral assessments, adherence assessments, physical examinations, blood collection, urine collection, and pelvic specimen collection. Participants receive initial and ongoing HSV and sexually transmitted disease risk-reduction counseling, male condoms, diagnosis and treatment of sexually transmitted infections, pregnancy testing and family planning services, and treatment or referrals for medical conditions. Initially seronegative women who test positive for HSV or HIV during the study immediately stop using the ring and are referred to local health facilities for care and treatment, with an option to enroll in a follow-up study to assess the ring's impact, if any, on HSV or HIV treatment outcomes.
Eligibility and Inclusion Criteria:
HSV seronegative female subjects who were female at birth that are 18 years to 45 years of age and are in a monogamous sexual relationship with an HSV seropositive partner.

Use of an effective method of contraception at enrollment and continued use of the effective method for the duration of study participation. Effective methods include hormonal methods (except contraceptive IVRs), intrauterine device inserted at least 28 days prior to enrollment, and sterilized (self or partner).

Seropositive partner does not have a history of frequent symptomatic episodes (>9 episodes/year).

Exclusion Criteria:

Patients with a psychiatric disorder that might cause difficulty in obtaining informed consent or in conducting the trial.

Pregnant or nursing.

HIV seropositive.

History of adverse reactions to any of the components of the intravaginal ring.

Pre-exposure prophylaxis for HSV or HIV prevention within the 6 months prior to enrollment.

Post-exposure prophylaxis for HSV or HIV prevention within the 6 months prior to enrollment.

Treatment with antivirals within the 6 months prior to enrollment.

Primary Outcome Measures:

Incidence of genital herpes caused by HSV infection. Genital herpes disease is defined as signs (swelling, papules, vesicles, ulcers, crusts, fissures, erythema, or vaginal discharge) and/or symptoms (pain, burning, itching, tingling, dysuria) which developed on the skin or mucosa of the anogenital region and/or buttocks and laboratory confirmation of HSV-1 or 2 infection (either concomitant positive HSV culture or HSV seroconversion within 6 months after onset of signs and/or symptoms. Seroconversion to HSV-1 and/or HSV-2 is defined as a positive HSV-1 and/or HSV-2 Western blot in a subject with a previously negative Western blot result for the corresponding HSV type.

Efficacy as determined by HSV seroconversion rate per person-months of product use, measured at the end of the investigational product use period.

Percentage of subjects infected with HSV who used the vaginal ring as directed. Use as directed is monitored by patient self-reporting and/or measurement of valacyclovir drug in their system during treatment.

Percentage of subjects infected with HSV who used the vaginal ring as directed and had partners who took the valacyclovir as directed.

Percentage of subjects infected with HSV who used the vaginal ring as directed and had partners who did not take the valacyclovir as directed.

Percentage of subjects infected with HSV who had detectable levels of drug in their system during treatment.

Secondary Outcome Measures:

Safety and tolerability by adverse event assessment.

HSV incidence after removal of intravaginal ring.

Pharmacokinetics: assessment of concentration of active agents in plasma and vaginal fluids before, during and after trial period.

Adherence to the protocol-specific product regimen as determined by self-reported questionnaires.

Incidence of sexually transmitted disease.

Incidence of pregnancy.

Viral shedding of at least a subset of partners with daily swabs for study duration.

Example 4: Safety and Effectiveness of HSV Pre-Exposure Intravaginal Ring in the Prevention of HSV Infection in Women at Risk for Exposure to HSV Purpose:

The purpose of the study is to assess the safety and effectiveness of an intravaginal ring releasing low-doses of valacyclovir in preventing HSV-2 infection in HSV seronegative women at risk for sexual contact with a partner who is HSV seropositive or has an unknown HSV sero-status for the duration of the study. Sexual contact includes one or more incidents of sexual contact with one or more partners.

Intervention:

Participants are intravaginally fitted with an intravaginal ring having valacyclovir or a placebo. Women use their assigned ring type for the entirety of the study.

Description:

Participants are instructed to insert a first intravaginal ring having valacyclovir or a placebo intravaginally at least seven days prior to coitus with a partner seropositive for HSV or with unknown HSV sero-status. Participants will replace the first intravaginal ring with a second assigned intravaginal ring after 30 days. Alternatively, participants are fitted with the first intravaginal ring by a medical practitioner during enrollment.

Participants attend study visits during the course of enrollment. Study visits include behavioral assessments, adherence assessments, physical examinations, blood collection, urine collection, and pelvic specimen collection. Participants receive initial and ongoing HSV and sexually transmitted disease risk-reduction counseling, male condoms, diagnosis and treatment of sexually transmitted infections, pregnancy testing and family planning services, and treatment or referrals for medical conditions. Women who test positive for HSV or HIV immediately stop using the ring and are referred to local health facilities for care and treatment, with an option to enroll in a follow-up study to assess the ring's impact, if any, on HSV or HIV treatment outcomes.

Eligibility and Inclusion Criteria:

HSV seronegative female subjects who were female at birth that are 18 years to 45 years of age and expect to have at least one incident of sexual contact with a partner with HSV seropositive status or unknown HSV sero-status.

Use of an effective method of contraception at enrollment and continued use of the effective method for the duration of study participation. Effective methods include hormonal methods (except contraceptive IVRs), intrauterine device inserted at least 28 days prior to enrollment, and sterilized (self or partner).

Exclusion Criteria:

Patients with a psychiatric disorder that might cause difficulty in obtaining informed consent or in conducting the trial.

Pregnant or nursing.

HIV or HSV seropositive.

History of adverse reactions to any of the components of the intravaginal ring.

Pre-exposure prophylaxis for HSV or HIV prevention within the 6 months prior to enrollment.

Post-exposure prophylaxis for HSV or HIV prevention within the 6 months prior to enrollment.

Treatment with antivirals within the 6 months prior to enrollment.

Primary Outcome Measures:

Incidence of genital herpes caused by HSV infection. Genital herpes disease is defined as signs (swelling, papules, vesicles, ulcers, crusts, fissures, erythema, or vaginal discharge) and/or symptoms (pain, burning, itching, tingling, dysuria) which developed on the skin or mucosa of the anogenital region and/or buttocks and laboratory confirmation of HSV-1 or 2 infection (either concomitant positive HSV culture or HSV seroconversion within 6 months after onset of signs and/or symptoms. Seroconversion to HSV-1 and/or HSV-2 is defined as a positive HSV-1 and/or HSV-2 Western blot in a subject with a previously negative Western blot result for the corresponding HSV type.

Efficacy as determined by HSV seroconversion rate per person-months of product use, measured at the end of the investigational product use period.

Percentage of subjects infected with HSV who used the vaginal ring as directed. Use as directed is monitored by patient self-reporting and/or measurement of valacyclovir drug in their system during treatment.

Percentage of subjects infected with HSV who had detectable levels of drug in their system during treatment.

Secondary Outcome Measures:

Safety and tolerability by adverse event assessment.

HSV incidence after removal of intravaginal ring.

Pharmacokinetics: assessment of concentration of active agents in plasma and vaginal fluids before, during and after trial period.

Adherence to the protocol-specific product regimen as determined by self-reported questionnaires.

Incidence of sexually transmitted disease.

Incidence of pregnancy.

Number of sexual contact incidents during study duration.

Number of sexual partners during study duration.

HSV sero-status of sexual partners during study duration as reported by study participant. HSV sero-status of partners reported include: known HSV seropositive, unknown HSV sero-status, and known HSV seronegative.

Example 5: Effectiveness of HSV Pre-Exposure Treatment in the Prevention of HSV Infection in Seronegatives in Discordant Relationships Purpose:

The purpose of the study is to assess the effectiveness of oral administration of valacyclovir in preventing HSV-2 infection in HSV seronegative partner in a monogamous sexual relationship with an HSV seropositive partner.

Intervention:

Arm 1: Seronegative participants are administered 650 mg of valacyclovir or a placebo once daily.

Arm 2: Seronegative participants are administered 650 mg of valacyclovir or a placebo once daily. Seropositive partners are administered 500 mg of valacyclovir once daily.

Description:

Seronegative participants are administered 650 mg of valacyclovir or a placebo once daily for at least seven days prior to coitus. In the second arm, HSV seropositive participants are administered 500 mg of valacyclovir once daily beginning at least seven days prior to coitus and for the duration of the study. Treatment of symptomatic episodes in the HSV seropositive participants during the duration of the study optionally involve increasing the dosage of valacyclovir to 500 mg bid×3 days.

HSV seronegative and seropositive participants attend study visits during the course of enrollment. Study visits include behavioral assessments, adherence assessments, physical examinations, blood collection, urine collection, and pelvic specimen collection. Participants receive initial and ongoing HSV and sexually transmitted disease risk-reduction counseling, male condoms, diagnosis and treatment of sexually transmitted infections, pregnancy testing and family planning services, and treatment or referrals for medical conditions. Initially seronegative women who test positive for HSV or HIV immediately stop using the ring and are referred to local health facilities for care and treatment, with an option to enroll in a follow-up study to assess the impact of prophylactic treatment with valacyclovir, if any, on HSV or HIV treatment outcomes.

Eligibility and Inclusion Criteria:

HSV seronegative subjects in a monogamous sexual relationship with an HSV seropositive partner.

Use of an effective method of contraception at enrollment and continued use of the effective method for the duration of study participation. Effective methods include physical barriers such as condoms and diaphragms, hormonal methods, intrauterine device inserted at least 28 days prior to enrollment, and sterilized (self or partner).

Seropositive partner does not have a history of frequent symptomatic episodes (>9 episodes/year).

Exclusion Criteria:

Patients with a psychiatric disorder that might cause difficulty in obtaining informed consent or in conducting the trial.

Pregnant or nursing.

HIV seropositive.

Pre-exposure prophylaxis for HSV or HIV prevention within the 6 months prior to enrollment.

Post-exposure prophylaxis for HSV or HIV prevention within the 6 months prior to enrollment.

Treatment with antivirals within the 6 months prior to enrollment.

Primary Outcome Measures:

Incidence of genital herpes caused by HSV infection. Genital herpes disease is defined as signs (swelling, papules, vesicles, ulcers, crusts, fissures, erythema, or vaginal discharge) and/or symptoms (pain, burning, itching, tingling, dysuria) which developed on the skin or mucosa of the anogenital region and/or buttocks and laboratory confirmation of HSV-1 or 2 infection (either concomitant positive HSV culture or HSV seroconversion within 6 months after onset of signs and/or symptoms. Seroconversion to HSV-1 and/or HSV-2 is defined as a positive HSV-1 and/or HSV-2 Western blot in a subject with a previously negative Western blot result for the corresponding HSV type.

Efficacy as determined by HSV seroconversion rate per person-months of product use, measured at the end of the investigational product use period.

Percentage of subjects infected with HSV who adhered to the treatment regimen as monitored by self-reporting and/or measurement of valacyclovir drug in the subjects' system during treatment.

Percentage of subjects infected with HSV who adhered to the treatment regimen and had partners who took the valacyclovir as directed.

Percentage of subjects infected with HSV who adhered to the treatment regimen and had partners who did not take the valacyclovir as directed.

Percentage of subjects infected with HSV who had detectable levels of drug in their system during treatment.

Secondary Outcome Measures:

Safety and tolerability by adverse event assessment.

HSV incidence after study completion.

Pharmacokinetics: assessment of concentration of active agents in plasma before, during and after trial period.

Adherence to the protocol-specific product regimen as determined by self-reported questionnaires.

Incidence of sexually transmitted disease.

Incidence of pregnancy.

Viral shedding of at least a subset of partners with daily swabs for study duration.

Example 6: Effectiveness of HSV Pre-Exposure Treatment in the Prevention of HSV Infection in Seronegatives at Risk for Exposure to HSV Purpose:

The purpose of the study is to assess the effectiveness of oral administration of valacyclovir in preventing HSV-2 infection in HSV seronegatives at risk for sexual contact with a partner who is HSV seropositive or has an unknown HSV sero-status for the duration of the study. Sexual contact includes one or more incidents of sexual contact with one or more partners.

Intervention:

Participants are administered 650 mg of valacyclovir or a placebo once daily.

Description:

Participants are instructed to begin administration of 650 mg of valacyclovir or placebo at least seven days prior to coitus with any partner. Participants attend study visits during the course of enrollment. Study visits include behavioral assessments, adherence assessments, physical examinations, blood collection, urine collection, and pelvic specimen collection. Women receive initial and ongoing HSV and sexually transmitted disease risk-reduction counseling, male condoms, diagnosis and treatment of sexually transmitted infections, pregnancy testing and family planning services, and treatment or referrals for medical conditions. Women who test positive for HSV or HIV immediately stop using the drug and are referred to local health facilities for care and treatment, with an option to enroll in a follow-up study to assess the drugs impact, if any, on HSV or HIV treatment outcomes.

Eligibility and Inclusion Criteria:

HSV seronegative female subjects who were female at birth that are 18 years to 45 years of age and expect to have at least one incident of sexual contact with a partner with HSV seropositive status or unknown HSV sero-status.

Use of an effective method of contraception at enrollment and continued use of the effective method for the duration of study participation. Effective methods include physical barriers such as condoms or diaphragms, hormonal methods, intrauterine device inserted at least 28 days prior to enrollment, and sterilized (self or partner).

Exclusion Criteria:

Patients with a psychiatric disorder that might cause difficulty in obtaining informed consent or in conducting the trial.

Pregnant or nursing.

HIV or HSV seropositive.

Pre-exposure prophylaxis for HSV or HIV prevention within the 6 months prior to enrollment.

Post-exposure prophylaxis for HSV or HIV prevention within the 6 months prior to enrollment.

Treatment with antivirals within the 6 months prior to enrollment.

Primary Outcome Measures:

Incidence of genital herpes caused by HSV infection. Genital herpes disease is defined as signs (swelling, papules, vesicles, ulcers, crusts, fissures, erythema, or vaginal discharge) and/or symptoms (pain, burning, itching, tingling, dysuria) which developed on the skin or mucosa of the anogenital region and/or buttocks and laboratory confirmation of HSV-1 or 2 infection (either concomitant positive HSV culture or HSV seroconversion within 6 months after onset of signs and/or symptoms. Seroconversion to HSV-1 and/or HSV-2 is defined as a positive HSV-1 and/or HSV-2 Western blot in a subject with a previously negative Western blot result for the corresponding HSV type.

Efficacy as determined by HSV seroconversion rate per person-months of product use, measured at the end of the investigational product use period.

Percentage of subjects infected with HSV who took the prophylaxis treatment as directed.

Percentage of subjects infected with HSV who had detectable levels of drug in their system during treatment.

Secondary Outcome Measures:

Safety and tolerability by adverse event assessment.

HSV incidence after completion of a dosing regimen of valacyclovir or placebo.

Pharmacokinetics: assessment of concentration of active agents in plasma before, during and after trial period.

Adherence to the protocol-specific product regimen as determined by self-reported questionnaires.

Incidence of sexually transmitted disease.

Incidence of pregnancy.

Number of sexual contact incidents during study duration.

Number of sexual partners during study duration.

HSV sero-status of sexual partners during study duration as reported by study participant. HSV sero-status of partners reported include: known HSV seropositive, unknown HSV sero-status, and known HSV seronegative.

Example 7: HSV Treatment Kit

An HSV prophylaxis kit for treatment of HSV. The kit has an oral formulation comprising a low dosage of valacyclovir (650 mg or less) and instructions having information on how to administer the composition. The instructions include dosing information useful for administration of the composition to an HSV seronegative subject to prevent HSV infection prior to HSV exposure. The HSV prophylaxis kit also includes dosing information and instructions for administration of the composition to an HSV seropositive subject to suppress HSV activation and viral shedding. The packing of the kit is designed to market to both HSV seronegative and HSV seropositive subjects.

Example 8: HSV Treatment Kit Comprising an Antiviral Transdermal Patch

An HSV prophylaxis kit for treatment of HSV using a transdermal patch. The kit has a composition comprising valacyclovir within a transdermal patch for sustained drug release, and instructions having information on how to affix the transdermal patch onto the skin of the subject. The instructions include dosing information useful for application of the patch to an HSV seronegative subject to prevent HSV infection prior to HSV exposure. The HSV prophylaxis kit optionally includes dosing information and instructions for application of the patch to an HSV seropositive subject to suppress HSV activation and viral shedding. The packing of the kit is optionally designed to market to both HSV seronegative and HSV seropositive subjects.

Example 9: HSV Treatment Kit Comprising an Antiviral Intravaginal Ring

An HSV prophylaxis kit for treatment of HSV using an intravaginal ring. The kit has a composition comprising valacyclovir within an intravaginal ring for sustained drug release, and instructions having information on how to insert the intravaginal ring into the vagina of a subject. The instructions include dosing and application information useful for the prevention of HSV infection in a seronegative subject prior to HSV exposure. The HSV prophylaxis kit optionally includes instructions on how to suppress HSV activation and viral shedding in an HSV seropositive subject using the intravaginal ring. The packing of the kit is optionally designed to market to both HSV seronegative and HSV seropositive subjects.

Example 10: HSV Treatment Kit Having a High Dosage of Antiviral

An HSV prophylaxis kit for treatment of HSV. The kit has an oral formulation comprising a high dosage of valacyclovir (2 g or more) and instructions having information on how to administer the composition. The instructions include dosing information useful for administration of the composition to an HSV seronegative subject to prevent HSV infection after HSV exposure. The HSV prophylaxis kit also includes dosing information and instructions for administration of the composition to an HSV seropositive subject after an outbreak of genital herpes or cold sore. The packing of the kit is designed to market to both HSV seronegative and HSV seropositive subjects.

Example 11: HSV Treatment Kit Comprising a High Dosage Antiviral Transdermal Patch An HSV prophylaxis kit for treatment of HSV using a transdermal patch. The kit has a transdermal patch that releases sustained high doses of valacyclovir and instructions having information on how to affix the transdermal patch onto the skin of the subject. The instructions include dosing information useful for application of the patch to an HSV seronegative subject after HSV exposure to prevent HSV infection. The HSV prophylaxis kit optionally includes dosing information and instructions for application of the patch to an HSV seropositive subject after an outbreak of genital herpes or cold sore. The packing of the kit is optionally designed to market to both HSV seronegative and HSV seropositive subjects.

Example 12: HSV Treatment Kit Comprising a High Dosage Antiviral Intravaginal Ring An HSV prophylaxis kit for treatment of HSV using an intravaginal ring. The kit has a composition comprising valacyclovir within an intravaginal ring, wherein the valacyclovir is released at sustained high doses in use, and instructions having information on how to insert the intravaginal ring into the vagina of a subject. The instructions include dosing and application information useful for the prevention of HSV infection in a seronegative subject after HSV exposure. The HSV prophylaxis kit optionally includes instructions on how to treat an outbreak of genital herpes or cold sores in an HSV seropositive subject using the intravaginal ring. The packing of the kit is optionally designed to market to both HSV seronegative and HSV seropositive subjects.

Example 13: Safety and Effectiveness of HSV Intravaginal Ring in the Prevention of HSV Infection in Women Exposed to HSV Purpose:

The purpose of the study is to assess the safety and effectiveness of an intravaginal ring releasing high-doses of valacyclovir in preventing HSV-2 infection in HSV seronegative women exposed to HSV.

Intervention:

Participants are intravaginally fitted with an intravaginal ring having valacyclovir or a placebo. Women use their assigned ring type for the entirety of the study.

Description:

Participants are instructed to insert an intravaginal ring having valacyclovir or a placebo intravaginally within 24 hours of exposure to HSV, ideally within several hours. Participants will remove the intravaginal ring after a prescribed duration of time, usually 30 days.

Participants attend study visits during the course of enrollment. Study visits include behavioral assessments, adherence assessments, physical examinations, blood collection, urine collection, and pelvic specimen collection. Participants receive initial and ongoing HSV and sexually transmitted disease risk-reduction counseling, male condoms, diagnosis and treatment of sexually transmitted infections, pregnancy testing and family planning services, and treatment or referrals for medical conditions. Women who test positive for HSV or HIV immediately stop using the ring and are referred to local health facilities for care and treatment, with an option to enroll in a follow-up study to assess the ring's impact, if any, on HSV or HIV treatment outcomes.

Eligibility and Inclusion Criteria:

HSV seronegative female subjects who were female at birth that are 18 years to 45 years of age and expect to have at least one incident of sexual contact with a partner with HSV seropositive status during the study duration. The partner can be a monogamous partner or not a monogamous partner. The sexual contact can include any number of sexual occasions with any number of sexual partners for the study duration.

Use of an effective method of contraception at enrollment and continued use of the effective method for the duration of study participation. Effective methods include hormonal methods (except contraceptive IVRs), intrauterine device inserted at least 28 days prior to enrollment, and sterilized (self or partner).

Exclusion Criteria:

Patients with a psychiatric disorder that might cause difficulty in obtaining informed consent or in conducting the trial.

Pregnant or nursing.

HIV or HSV seropositive.

History of adverse reactions to any of the components of the intravaginal ring.

Pre-exposure prophylaxis for HSV or HIV prevention within the 6 months prior to enrollment.

Post-exposure prophylaxis for HSV or HIV prevention within the 6 months prior to enrollment.

Treatment with antivirals within the 6 months prior to enrollment.

Renal insufficiency defined as CrCl<50 mL/min

Primary Outcome Measures:

Incidence of genital herpes caused by HSV infection. Genital herpes disease is defined as signs (swelling, papules, vesicles, ulcers, crusts, fissures, erythema, or vaginal discharge) and/or symptoms (pain, burning, itching, tingling, dysuria) which developed on the skin or mucosa of the anogenital region and/or buttocks and laboratory confirmation of HSV-1 or 2 infection (either concomitant positive HSV culture or HSV seroconversion within 6 months after onset of signs and/or symptoms. Seroconversion to HSV-1 and/or HSV-2 is defined as a positive HSV-1 and/or HSV-2 Western blot in a subject with a previously negative Western blot result for the corresponding HSV type.

Efficacy as determined by HSV seroconversion rate at the end of the investigational product use period.

Percentage of subjects infected with HSV who used the vaginal ring as directed after exposure to HSV. Use as directed is monitored by patient self-reporting and/or measurement of valacyclovir drug in their system during treatment.

Percentage of subjects infected with HSV who had detectable levels of drug in their system during treatment.

Secondary Outcome Measures:
Safety and tolerability by adverse event assessment.
HSV incidence after removal of intravaginal ring.
Pharmacokinetics: assessment of concentration of active agents in plasma and vaginal fluids before, during and after trial period.
Adherence to the protocol-specific product regimen as determined by self-reported questionnaires.
Incidence of sexually transmitted disease.
Incidence of pregnancy.
Number of sexual contact incidents during study duration.
Number of sexual partners during study duration.
Number of HSV exposures during study duration.

Example 14: Effectiveness of HSV Post-Exposure Treatment in the Prevention of HSV Infection in Seronegatives Exposed to HSV Purpose:
The purpose of the study is to assess the effectiveness of oral administration of valacyclovir in preventing HSV-2 infection in HSV seronegatives exposed to HSV.

Intervention:
Participants are administered 1,250 mg of valacyclovir or a placebo twice daily for ten days, with the first dose administered within 24 hours of exposure to HSV, ideally within several hours.

Description:
Participants are instructed to take 1,250 mg of valacyclovir twice daily for 10 days within 24 hours of exposure to HSV. Participants attend study visits during the course of enrollment. Study visits include behavioral assessments, adherence assessments, physical examinations, blood collection, urine collection, and pelvic specimen collection. Participants receive initial and ongoing HSV and sexually transmitted disease risk-reduction counseling, male condoms, diagnosis and treatment of sexually transmitted infections, pregnancy testing and family planning services, and treatment or referrals for medical conditions. Women who test positive for HSV or HIV are referred to local health facilities for care and treatment, with an option to enroll in a follow-up study to assess the impact of treatment, if any, on HSV or HIV treatment outcomes.

Eligibility and Inclusion Criteria:
HSV seronegative subjects who expect to have at least one incident of sexual contact with a partner with HSV seropositive status during the study duration. The partner can be a monogamous partner or not a monogamous partner. The sexual contact can include any number of sexual occasions with any number of sexual partners for the study duration.

Use of an effective method of contraception at enrollment and continued use of the effective method for the duration of study participation. Effective methods include hormonal methods, intrauterine device inserted at least 28 days prior to enrollment, and sterilized (self or partner).

Exclusion Criteria:
Patients with a psychiatric disorder that might cause difficulty in obtaining informed consent or in conducting the trial.
Pregnant or nursing.
HIV or HSV seropositive.
Pre-exposure prophylaxis for HSV or HIV prevention within the 6 months prior to enrollment.
Post-exposure prophylaxis for HSV or HIV prevention within the 6 months prior to enrollment.
Treatment with antivirals within the 6 months prior to enrollment.
Renal insufficiency defined as CrCl<50 mL/min Primary Outcome Measures:
Incidence of genital herpes caused by HSV infection. Genital herpes disease is defined as signs (swelling, papules, vesicles, ulcers, crusts, fissures, erythema, or vaginal discharge) and/or symptoms (pain, burning, itching, tingling, dysuria) which developed on the skin or mucosa of the anogenital region and/or buttocks and laboratory confirmation of HSV-1 or 2 infection (either concomitant positive HSV culture or HSV seroconversion within 6 months after onset of signs and/or symptoms. Seroconversion to HSV-1 and/or HSV-2 is defined as a positive HSV-1 and/or HSV-2 Western blot in a subject with a previously negative Western blot result for the corresponding HSV type.

Efficacy as determined by HSV seroconversion rate at the end of the investigational product use period.

Percentage of subjects infected with HSV who following the treatment regimen after exposure to HSV. Treatment adherence is monitored by patient self-reporting and/or measurement of valacyclovir drug in their system during treatment.

Percentage of subjects infected with HSV who had detectable levels of drug in their system during treatment.

Secondary Outcome Measures:
Safety and tolerability by adverse event assessment.
Pharmacokinetics: assessment of concentration of active agents in plasma and vaginal fluids before, during and after trial period.
Adherence to the protocol-specific product regimen as determined by self-reported questionnaires.
Incidence of sexually transmitted disease.
Incidence of pregnancy.
Number of sexual contact incidents during study duration.
Number of sexual partners during study duration.
Number of HSV exposures during study duration.

Example 15: Intravaginal Rings for the Prevention of HSV and HIV Infection in Seronegative Subjects Intravaginal rings are produced using hollow hydrophilic polyether urethane (HPEU) elastomeric tubes filled with valacyclovir ranging from 500 mg to 2,000 mg per ring and tenofovir ranging from 200 mg to 500 mg per ring and emtricitabine ranging from 150 mg to 150 mg per ring. The amount of valacyclovir and tenofovir released each day over a period of at least 14 days is measured in vitro. In vitro daily release profiles are determined using experimental conditions in vitro that effectively simulate the active drug diffusion that occurs in vivo.

Vaginal rings releasing low doses of valacyclovir and tenofovir are selected as candidates for clinical trials for the prevention of HSV and/or HIV infection in seronegative subjects at risk for exposure to HSV and/or HIV. Optionally, vaginal rings releasing high doses of valacyclovir, tenofovir and emtricitabine are selected as candidates for clinical trials for the prevention of HSV and/or HIV infection in seronegative subjects exposed to HSV and/or HIV. Vaginal rings will comprise silicone.

Example 16: Safety of Antiviral Combination Intravaginal Ring

Purpose:

The purpose of the study is to assess the safety of vaginal rings releasing low or high doses of valacyclovir, tenofovir and emtricitabine.

Intervention:

Arm 1: Participants receive an intravaginal ring having valacyclovir, tenofovir and emtricitabine in combination.

Arm 2: Participants receive an intravaginal ring having valacyclovir.

Arm 3: Participants receive an intravaginal ring having tenofovir and emtricitabine.

Arm 4: Participants receive an intravaginal ring having a placebo.

Description:

Participants are instructed to insert a vaginal ring comprising valacyclovir, tenofovir/emtricitabine, valacyclovir/tenofovir/emtricitabine, or placebo every 30 days for the duration of the study. The dosages of valacyclovir within each intravaginal ring are optionally varied to range from 500 mg to 2,000 mg of each drug. Doses of tenofovir are 300 mg/day and doses of emtricitabine are 200 mg/day.

Primary Outcome Measures:

Safety as determined by the proportion of women in each arm experiencing protocol-specified events, including adverse events, laboratory abnormalities, cervico-vaginal abnormalities, and/or abnormal vaginal flora/pH during the study.

Secondary Outcome Measures:

Adherence to the protocol-specific product regimen as determined by self-report and clinician observation at each study visit.

Inclusion Criteria:

Women between 18 and 45 years of age who can provide informed consent.

HSV and HIV negative.

Currently on contraception and willing to continue contraception at least 3 months prior to enrollment.

Willing to refrain from use of vaginal products or objects for duration of the study.

Willing to refrain from coitus for duration of the study.

Exclusion Criteria:

Currently pregnant or last pregnancy within 3 months prior to enrollment.

Currently breast-feeding.

Treatment with an antiviral within the past 12 months.

Presence of any abnormal physical finding on the vulva, vaginal walls or cervix during pelvic examination.

Example 17: Safety and Effectiveness of Antiviral Combination Intravaginal Ring in the Prevention of HSV and HIV Infection in Seronegative Women in Discordant Relationships Purpose:

The purpose of the study is to assess the safety and effectiveness of an intravaginal ring releasing low-doses of valacyclovir and tenofovir in preventing HSV-2 or HIV infection in HSV and HIV seronegative women in a monogamous sexual relationship with an HSV seropositive partner or an HIV seropositive partner.

Intervention:

Arm 1: Seronegative women participants are intravaginally fitted with an intravaginal ring having valacyclovir, tenofovir, valacyclovir, emtricitabine and tenofovir, or a placebo. Women use their assigned ring type for the entirety of the study.

Arm 2: HIV/HSV seronegative women participants are intravaginally fitted with an intravaginal ring having valacyclovir, tenofovir/emtricitabine, valacyclovir and tenofovir/emtricitabine, or a placebo intravaginal ring. Women use their assigned ring type for the entirety of the study. HSV seropositive partners take 500 mg of valacyclovir once daily. HIV seropositive partners take their usual prescribed anti-retrovirals (anti-HIV medications).

Description:

Seronegative participants are instructed to insert a first assigned intravaginal ring intravaginally at least seven days prior to coitus. Seronegative participants will replace the first intravaginal ring with a second assigned intravaginal ring for a prescribed dosing cycle. Alternatively, participants are fitted with the first intravaginal ring by a medical practitioner during enrollment.

In the second arm, HSV seropositive partners are administered 500 mg of valacyclovir once a day for the duration of the study and HIV seropositive partners take their usual prescribed anti-HIV medications daily.

HSV/HIV seronegative and seropositive participants attend study visits during the course of enrollment. Study visits include behavioral assessments, adherence assessments, physical examinations, blood collection, urine collection, and pelvic specimen collection. Participants receive initial and ongoing sexually transmitted disease risk-reduction counseling, male condoms, diagnosis and treatment of sexually transmitted infections, pregnancy testing and family planning services, and treatment or referrals for medical conditions. Initially HSV/HIV seronegative women who test positive for HSV or HIV immediately stop using the ring and are referred to local health facilities for care and treatment, with an option to enroll in a follow-up study to assess the ring's impact, if any, on HSV or HIV treatment outcomes.

Eligibility and Inclusion Criteria:

HSV and HIV seronegative female subjects who were female at birth that are 18 years to 45 years of age and are in a monogamous sexual relationship with an HSV or HIV seropositive partner.

Use of an effective method of contraception at enrollment and continued use of the effective method for the duration of study participation. Effective methods include hormonal methods (except contraceptive IVRs), intrauterine device inserted at least 28 days prior to enrollment, and sterilized (self or partner).

HSV Seropositive partner does not have a history of frequent symptomatic episodes (>9 episodes/year).

Exclusion Criteria:

Patients with a psychiatric disorder that might cause difficulty in obtaining informed consent or in conducting the trial.

Pregnant or nursing.

History of adverse reactions to any of the components of the intravaginal ring.

Pre-exposure prophylaxis for HSV or HIV prevention within the 6 months prior to enrollment.

Post-exposure prophylaxis for HSV or HIV prevention within the 6 months prior to enrollment.

Treatment with HSV antivirals within the 6 months prior to enrollment.

Drug resistance to any agent in the treatment regimen.

Primary Outcome Measures:

Incidence of genital herpes caused by HSV infection. Genital herpes disease is defined as signs (swelling, papules, vesicles, ulcers, crusts, fissures, erythema, or vaginal discharge) and/or symptoms (pain, burning, itching, tingling, dysuria) which developed on the skin or mucosa of the anogenital region and/or buttocks and laboratory confirmation of HSV-1 or 2 infection (either concomitant positive HSV culture or HSV seroconversion within 6 months after onset of signs and/or symptoms. Seroconversion to HSV-1 and/or HSV-2 is defined as a positive HSV-1 and/or HSV-2 Western blot in a subject with a previously negative Western blot result for the corresponding HSV type.

Efficacy as determined by HSV seroconversion rate per person-months of product use, measured at the end of the investigational product use period.

Percentage of subjects infected with HSV who used the vaginal ring as directed. Use as directed is monitored by patient self-reporting and/or measurement of drug(s) in their system during treatment.

Percentage of subjects infected with HSV who used the vaginal ring as directed and had partners who took the valacyclovir as directed.

Percentage of subjects infected with HSV who used the vaginal ring as directed and had partners who did not take the valacyclovir as directed.

Percentage of subjects infected with HSV who had detectable levels of drug(s) in their system during treatment.

Efficacy as determined by HIV-1 seroconversion rate per person-months of product use, measured at the end of the investigational product use period. The primary endpoint is HIV-1 seroconversion measured by immunoassay-based HIV blood tests. Endpoint confirmation of HIV infection is by Western blot.

Percentage of subjects infected with HIV who used the vaginal ring as directed. Use as directed is monitored by patient self-reporting and/or measurement of drug(s) in their system during treatment.

Percentage of subjects infected with HIV who used the vaginal ring as directed and had partners who took their anti-HIV medications as directed.

Percentage of subjects infected with HIV who used the vaginal ring as directed and had partners who did not take their anti-HIV medications as directed.

Percentage of subjects infected with HIV who had detectable levels of drug(s) in their system during treatment.

Secondary Outcome Measures:

Safety as determined by grade 3 and 4 adverse events, clinically significant grade 2 laboratory findings (based on DAIDS grading) and all serious adverse events.

HSV incidence after removal of intravaginal ring.

HIV incidence after removal of intravaginal ring.

Pharmacokinetics: assessment of concentration of active agents in plasma and vaginal fluids before, during and after trial period.

Adherence to the protocol-specific product regimen as determined by self-reported questionnaires.

Incidence of sexually transmitted disease.

Incidence of pregnancy.

Example 18: Safety and Effectiveness of Antiviral Combination Intravaginal Ring in the Prevention of HSV and HIV Infection in Seronegative Women at Risk for Exposure to HSV and HIV Purpose:

The purpose of the study is to assess the safety and effectiveness of an intravaginal ring releasing low-doses of valacyclovir and tenofovir in preventing HSV-2 and/or HIV infection in HSV and HIV seronegative women at risk for sexual contact with a partner who is HSV or HIV seropositive or has unknown HSV or HIV sero-status during study duration. Sexual contact includes one or more incidents of sexual contact with one or more partners.

Intervention:

Seronegative women participants are intravaginally fitted with an intravaginal ring having valacyclovir, tenofovir, valacyclovir, emtricitabine and tenofovir, or a placebo. Women use their assigned ring type for the entirety of the study.

Description:

Seronegative participants are instructed to insert a first assigned intravaginal ring intravaginally at least seven days prior to coitus. Seronegative participants will replace the first intravaginal ring with a second assigned intravaginal ring for a prescribed dosing cycle. Alternatively, participants are fitted with the first intravaginal ring by a medical practitioner during enrollment.

Participants attend study visits during the course of enrollment. Study visits include behavioral assessments, adherence assessments, physical examinations, blood collection, urine collection, and pelvic specimen collection. Participants receive initial and ongoing sexually transmitted disease risk-reduction counseling, male condoms, diagnosis and treatment of sexually transmitted infections, pregnancy testing and family planning services, and treatment or referrals for medical conditions. Initially seronegative women who test positive for HSV or HIV are referred to local health facilities for care and treatment, with an option to enroll in a follow-up study to assess treatment impact, if any, on HSV or HIV outcomes.

Eligibility and Inclusion Criteria:

HSV and HIV seronegative female subjects who were female at birth that are 18 years to 45 years of age and expect to have at least one incident of sexual contact with a partner with HSV or HIV seropositive status, or unknown HSV or HIV sero-status.

Use of an effective method of contraception at enrollment and continued use of the effective method for the duration of study participation. Effective methods include hormonal methods (except contraceptive IVRs), intrauterine device inserted at least 28 days prior to enrollment, and sterilized (self or partner).

Exclusion Criteria:

Patients with a psychiatric disorder that might cause difficulty in obtaining informed consent or in conducting the trial.

Pregnant or nursing.

History of adverse reactions to any of the components of the intravaginal ring.

Pre-exposure prophylaxis for HSV or HIV prevention within the 6 months prior to enrollment.

Post-exposure prophylaxis for HSV or HIV prevention within the 6 months prior to enrollment.

Treatment with HSV antivirals within the 6 months prior to enrollment.

Primary Outcome Measures:

Incidence of genital herpes caused by HSV infection. Genital herpes disease is defined as signs (swelling, papules, vesicles, ulcers, crusts, fissures, erythema, or vaginal discharge) and/or symptoms (pain, burning, itching, tingling, dysuria) which developed on the skin or mucosa of the anogenital region and/or buttocks and laboratory confirmation of HSV-1 or 2 infection (either concomitant positive HSV culture or HSV seroconversion within 6 months after onset of signs and/or symptoms. Seroconversion to HSV-1 and/or HSV-2 is defined as a positive HSV-1 and/or HSV-2 Western blot in a subject with a previously negative Western blot result for the corresponding HSV type.

Efficacy as determined by HSV seroconversion rate per person-months of product use, measured at the end of the investigational product use period.

Percentage of subjects infected with HSV who used the vaginal ring as directed. Use as directed is monitored by patient self-reporting and/or measurement of drug(s) in their system during treatment.

Percentage of subjects infected with HSV who had detectable levels of drug(s) in their system during treatment.

Efficacy as determined by HIV-1 seroconversion rate per person-months of product use, measured at the end of the investigational product use period. The primary endpoint is HIV-1 seroconversion measured by immunoassay-based HIV blood tests. Endpoint confirmation of HIV infection is by Western blot.

Percentage of subjects infected with HIV who used the vaginal ring as directed. Use as directed is monitored by patient self-reporting and/or measurement of drug(s) in their system during treatment.

Percentage of subjects infected with HIV who had detectable levels of drug(s) in their system during treatment.

Secondary Outcome Measures:

Safety as determined by grade 3 and 4 adverse events, clinically significant grade 2 laboratory findings (based on DAIDS grading) and all serious adverse events.

HSV incidence after removal of intravaginal ring.

HIV incidence after removal of intravaginal ring.

Pharmacokinetics: assessment of concentration of active agents in plasma and vaginal fluids before, during and after trial period.

Adherence to the protocol-specific product regimen as determined by self-reported questionnaires.

Incidence of sexually transmitted disease.

Incidence of pregnancy.

Example 19: Effectiveness of Antiviral Combination Pre-Exposure Treatment in the Prevention of HSV and HIV Infection in HSV/HIV Seronegatives in Discordant Relationships Purpose:

The purpose of the study is to assess the safety and effectiveness of oral administration of valacyclovir and tenofovir in preventing HSV or HIV infection in HSV and HIV seronegative women in a monogamous sexual relationship with an HSV seropositive partner or an HIV seropositive partner.

Intervention:

Arm 1: Seronegative participants are administered valacyclovir, HSV seropositive partners are administered 500 mg valacyclovir. HIV seropositive partners continue on their usual prescribed anti-HIV regimen.

Arm 2: Seronegative participants are administered tenofovir and emtricitabine. HIV seropositive partners continue on their usual prescribed anti-HIV regimen.

Arm 3: Seronegative participants are administered valacyclovir, tenofovir, and emtricitabine, HSV seropositive partners are administered 500 mg valacyclovir. HIV seropositive partners continue on their usual prescribed anti-HIV regimen.

Arm 4: Seronegative participants are administered a placebo. HIV seropositive partners continue on their usual prescribed anti-HIV regimen.

Description:

Seronegative participants are administered 650 mg of valacyclovir, HSV seropositive subjects are offered 500 mg valacyclovir once daily at least seven days prior to coitus in the first arm. HIV seropositive participants continue on their usual standard of care anti-HIV regimen. In the second arm, HSV seronegative participants are administered tenofovir and emtricitabine. HIV seropositive partners continue on their usual prescribed anti-HIV regimen. In the third arm, HSV seronegatives are administered valacyclovir, tenofovir, and emtricitabine, HSV seropositive partners are administered 500 mg valacyclovir. HIV seropositive partners continue on their usual prescribed anti-HIV regimen. In the fourth arm, Seronegative participants are administered a placebo. HIV seropositive partners continue on their usual prescribed anti-HIV regimen. Treatment of symptomatic episodes in the HSV seropositive participants during the duration of the study optionally involve increasing the dosage of valacyclovir to 500 mg bid×5 days.

Participants attend study visits during the course of enrollment. Study visits include behavioral assessments, adherence assessments, physical examinations, blood collection, urine collection, and pelvic specimen collection. Participants receive initial and ongoing sexually transmitted disease risk-reduction counseling, male condoms, diagnosis and treatment of sexually transmitted infections, pregnancy testing and family planning services, and treatment or referrals for medical conditions. Initially seronegative women who test positive for HSV or HIV are referred to local health facilities for care and treatment, with an option to enroll in a follow-up study to assess the impact of prophylactic treatment, if any, on HSV or HIV treatment outcomes.

Eligibility and Inclusion Criteria:

HSV and HIV seronegatives who are in a monogamous sexual relationship with an HSV or HIV seropositive partner.

Use of an effective method of contraception at enrollment and continued use of the effective method for the duration of study participation. Effective methods include physical barriers such as condoms or diaphragms, hormonal methods, intrauterine device inserted at least 28 days prior to enrollment, and sterilized (self or partner).

HSV Seropositive partner does not have a history of frequent symptomatic episodes (>9 episodes/year).

Exclusion Criteria:

Patients with a psychiatric disorder that might cause difficulty in obtaining informed consent or in conducting the trial.

Pregnant or nursing.

Pre-exposure prophylaxis for HSV or HIV prevention within the 6 months prior to enrollment.

Post-exposure prophylaxis for HSV or HIV prevention within the 6 months prior to enrollment.

Treatment with antivirals within the 6 months prior to enrollment.

Drug resistance to any of the treatment antivirals.

Primary Outcome Measures:

Incidence of genital herpes caused by HSV infection. Genital herpes disease is defined as signs (swelling, papules, vesicles, ulcers, crusts, fissures, erythema, or vaginal discharge) and/or symptoms (pain, burning, itching, tingling, dysuria) which developed on the skin or mucosa of the anogenital region and/or buttocks and laboratory confirmation of HSV-1 or 2 infection (either concomitant positive HSV culture or HSV seroconversion within 6 months after onset of signs and/or symptoms. Seroconversion to HSV-1 and/or HSV-2 is defined as a positive HSV-1 and/or HSV-2 Western blot in a subject with a previously negative Western blot result for the corresponding HSV type.

Efficacy as determined by HSV seroconversion rate per person-months of product use, measured at the end of the investigational product use period.

Percentage of subjects infected with HSV who adhered to study guidelines as monitored by patient self-reporting and/or measurement of drug(s) in their system during treatment.

Percentage of subjects infected with HSV who adhered to study guidelines and had partners who took the valacyclovir as directed.

Percentage of subjects infected with HSV who adhered to study guidelines and had partners who did not take the valacyclovir as directed.

Percentage of subjects infected with HSV who had detectable levels of drug(s) in their system during treatment.

Efficacy as determined by HIV-1 seroconversion rate per person-months of product use, measured at the end of the investigational product use period. The primary endpoint is HIV-1 seroconversion measured by immunoassay-based HIV blood tests. Endpoint confirmation of HIV infection is by Western blot.

Percentage of subjects infected with HIV who adhered to study guidelines as monitored by patient self-reporting and/or measurement of drug(s) in their system during treatment.

Percentage of subjects infected with HIV who adhered to study guidelines and had partners who took their anti-HIV medications as directed.

Percentage of subjects infected with HIV who adhered to study guidelines and had partners who did not take their anti-HIV medications as directed.

Percentage of subjects infected with HIV who had detectable levels of drug(s) in their system during treatment.

Secondary Outcome Measures:

Safety as determined by grade 3 and 4 adverse events, clinically significant grade 2 laboratory findings (based on DAIDS grading) and all serious adverse events.

HSV incidence after completion of course of antivirals.

HIV incidence after completion of course of antivirals.

Pharmacokinetics: assessment of concentration of active agents in plasma before, during and after trial period.

Adherence to the protocol-specific product regimen as determined by self-reported questionnaires.

Incidence of sexually transmitted disease.

Incidence of pregnancy.

Example 20: Effectiveness of Antiviral Combination Pre-Exposure Treatment in the Prevention of HSV and HIV Infection in Seronegatives at Risk for Exposure to HSV and HIV Purpose:

The purpose of the study is to assess the safety and effectiveness of oral administration of valacyclovir, tenofovir, and emtricitabine in preventing HSV-2 and/or HIV infection in HSV and HIV seronegatives at risk for sexual contact with a partner who is HSV or HIV seropositive or has unknown HSV or HIV sero-status during study duration. Sexual contact includes one or more incidents of sexual contact with one or more partners.

Intervention:

Seronegative participants are administered valacyclovir, tenofovir/emtricitabine, valacyclovir and tenofovir/emtricitabine, or a placebo.

Description:

Seronegative participants are administered 650 mg of valacyclovir, 300 mg of tenofovir and 200 mg of emtricitabine per day, 500 mg of valacyclovir 300 mg of tenofovir and 200 mg of emtricitabine, or a placebo once daily starting at least seven days prior to coitus.

Participants attend study visits during the course of enrollment. Study visits include behavioral assessments, adherence assessments, physical examinations, blood collection, urine collection, and pelvic specimen collection. Participants receive initial and ongoing sexually transmitted disease risk-reduction counseling, male condoms, diagnosis and treatment of sexually transmitted infections, pregnancy testing and family planning services, and treatment or referrals for medical conditions. Initially seronegative women who test positive for HSV or HIV are referred to local health facilities for care and treatment, with an option to enroll in a follow-up study to assess treatment impact, if any, on HSV or HIV outcomes.

Eligibility and Inclusion Criteria:

HSV and HIV seronegative female subjects who were female at birth that are 18 years to 45 years of age and expect to have at least one incident of sexual contact with a partner with HSV or HIV seropositive status, or unknown HSV or HIV sero-status.

Use of an effective method of contraception at enrollment and continued use of the effective method for the duration of study participation. Effective methods include physical barriers such as condoms or diaphragms, hormonal methods, intrauterine device inserted at least 28 days prior to enrollment, and sterilized (self or partner).

Exclusion Criteria:

Patients with a psychiatric disorder that might cause difficulty in obtaining informed consent or in conducting the trial.

Pregnant or nursing.

Pre-exposure prophylaxis for HSV or HIV prevention within the 6 months prior to enrollment.

Post-exposure prophylaxis for HSV or HIV prevention within the 6 months prior to enrollment.

Treatment with HSV antivirals within the 6 months prior to enrollment.

Drug Resistance to one or more agents in the HIV treatment arms

Primary Outcome Measures:

Incidence of genital herpes caused by HSV infection. Genital herpes disease is defined as signs (swelling, papules, vesicles, ulcers, crusts, fissures, erythema, or vaginal discharge) and/or symptoms (pain, burning, itching, tingling, dysuria) which developed on the skin or mucosa of the anogenital region and/or buttocks and laboratory confirmation of HSV-1 or 2 infection (either concomitant positive HSV culture or HSV seroconversion within 6 months after onset of signs and/or symptoms. Seroconversion to HSV-1 and/or HSV-2 is defined as a positive HSV-1 and/or HSV-2 Western blot in a subject with a previously negative Western blot result for the corresponding HSV type.

Efficacy as determined by HSV seroconversion rate per person-months of product use, measured at the end of the investigational product use period.

Percentage of subjects infected with HSV who adhered to study guidelines as monitored by patient self-reporting and/or measurement of drug(s) in their system during treatment.

Percentage of subjects infected with HSV who had detectable levels of drug(s) in their system during treatment.

Efficacy as determined by HIV-1 seroconversion rate per person-months of product use, measured at the end of the investigational product use period. The primary endpoint is HIV-1 seroconversion measured by immunoassay-based HIV blood tests. Endpoint confirmation of HIV infection is by Western blot.

Percentage of subjects infected with HIV who adhered to study guidelines as monitored by patient self-reporting and/or measurement of drug(s) in their system during treatment.

Percentage of subjects infected with HIV who had detectable levels of drug(s) in their system during treatment.

Secondary Outcome Measures:

Safety as determined by grade 3 and 4 adverse events, clinically significant grade 2 laboratory findings (based on DAIDS grading) and all serious adverse events.

HSV incidence after completion of course of antivirals.

HIV incidence after completion of course of antivirals.

Pharmacokinetics: assessment of concentration of active agents in plasma before, during and after trial period.

Adherence to the protocol-specific product regimen as determined by self-reported questionnaires.

Incidence of sexually transmitted disease.

Incidence of pregnancy.

Example 21: HSV and HIV Treatment Kit

An HSV and HIV prophylaxis kit for treatment of HSV and HIV. The kit has an oral formulation comprising a low dosage of valacyclovir (650 mg or less), a standard dosage of tenofovir (300 mg), a standard dosage of emtricitabine (200 mg), and instructions having information on how to administer the composition. The instructions include dosing information useful for administration of the composition to an HSV and HIV seronegative subject to prevent HSV and/or HIV infection prior to HSV and/or HIV exposure. The HSV and HIV prophylaxis kit optionally includes dosing information and instructions for administration of the composition to an HSV seropositive subject to suppress HSV activation and viral shedding. The packing of the kit is optionally designed to market to HIV seronegative, HSV seronegative, and HSV seropositive subjects.

Example 22: HSV and HIV Treatment Kit Comprising an Antiviral Transdermal Patch

An HSV and HIV prophylaxis kit for treatment of HSV and HIV using a transdermal patch. The kit has a composition comprising valacyclovir and tenofovir within a transdermal patch and instructions having information on how to affix the transdermal patch onto the skin of the subject. The instructions include dosing information useful for application of the patch to an HSV and HIV seronegative subject to prevent HSV and/or HIV infection prior to HSV and/or HIV exposure. The HSV and HIV prophylaxis kit optionally includes dosing information and instructions for application of the patch to an HSV seropositive subject to suppress HSV activation and viral shedding. The packing of the kit is optionally designed to market to HSV seronegative, HIV seronegative, and HSV seropositive subjects.

Example 23: HSV and HIV Treatment Kit Comprising an Antiviral Intravaginal Ring

An HSV and HIV prophylaxis kit for treatment of HSV and HIV using an intravaginal ring. The kit has a composition comprising valacyclovir and tenofovir/emtricitabine within an intravaginal ring and instructions having information on how to insert the intravaginal ring into the vagina of a subject. The instructions include dosing and application information useful for the prevention of HSV and/or HIV infection in a seronegative subject. The HSV and HIV prophylaxis kit optionally includes instructions on how to suppress HSV activation and viral shedding in an HSV seropositive subject using the intravaginal ring. The packing of the kit is optionally designed to market to HSV seronegative, HIV seronegative, and HSV seropositive subjects.

Example 24: HSV and HIV Treatment Kit for Post-Viral Exposure Administration

An HSV and HIV prophylaxis kit for treatment of HSV and HIV. The kit has an oral formulation comprising high dosages of valacyclovir (2 g in a twice daily dosing regimen), tenofovir (300 mg/day), emtricitabine (200 mg/day) and raltegravir (400 mg twice per day); and instructions having information on how to administer the composition. The instructions include dosing information useful for administration of the composition to an HSV and HIV seronegative subject to prevent HSV and/or HIV infection after possible HSV and/or HIV exposure, but within 72 hours after possible exposure. The HSV and HIV prophylaxis kit optionally includes dosing information and instructions for administration of the composition to an HSV seropositive subject after an outbreak of genital herpes or cold sore. The packing of the kit is optionally designed to market to HSV seronegative, HIV seronegative, and HSV seropositive subjects.

Example 25: HSV and HIV Treatment Kit Comprising a Transdermal Patch for Post-Viral Exposure Administration An HSV and HIV prophylaxis kit for treatment of HSV and HIV using a transdermal patch. The kit has a transdermal patch that releases sustained high doses of valacyclovir, tenofovir, emtricitabine, and raltegravir and instructions having information on how to affix the transdermal patch onto the skin of a subject. The instructions include dosing information useful for application of the patch to an HSV and HIV seronegative subject after HSV and/or HIV exposure to prevent HSV and/or HIV infection. The HSV prophylaxis kit optionally includes dosing information and instructions for application of the patch to an HSV seropositive subject after an outbreak of genital herpes or cold sore. The packing of the kit is optionally designed to market to HSV seronegative, HIV seronegative, and HSV seropositive subjects.

Example 26: HSV and HIV Treatment Kit Comprising an Intravaginal Ring for Post-Viral Exposure Administration An HSV and HIV prophylaxis kit for treatment of HSV and HIV using an intravaginal ring. The kit has a composition comprising valacyclovir and tenofovir within an intravaginal ring, wherein the valacyclovir, tenofovir, emtricitabine and raltegravir active agents are released at sustained high doses in use, and instructions having information on how to insert the intravaginal ring into the vagina of a subject. The instructions include dosing and application information useful for the prevention of HSV and/or HIV infection in a seronegative subject after HSV and/or within 72 hours of HIV exposure. The HSV and HIV prophylaxis kit optionally includes instructions on how to treat an outbreak of genital herpes or cold sores in an HSV seropositive subject using the intravaginal ring. The packing of the kit is optionally designed to market to HSV seronegative, HIV seronegative, and HSV seropositive subjects.

Example 27: Intravaginal Rings for Contraception and Prevention of HSV Infection Intravaginal rings are produced from ethylene vinylacetate copolymers and magnesium stearate and contain the active drugs etonogestrel (11.7 mg), ethinyl estradiol (2.7 mg), and valacyclovir (50 mg to 2,000 mg). The amount of drugs released each day over a period of at least 14 days is measured in vitro. In vitro daily release profiles are determined using experimental conditions in vitro that effectively simulate the active drug diffusion that occurs in vivo.

Vaginal rings releasing ethinyl estradiol/etonogestrel and low doses of valacyclovir are selected as candidates for clinical trials for the prevention of pregnancy and HSV infection in seronegative subjects at risk for exposure to HSV. Optionally, vaginal rings releasing ethinyl estradiol/etonogestrel and high doses of valacyclovir are selected as candidates for clinical trials for the prevention of pregnancy and HSV in seronegative subjects exposed to HSV. The vaginal ring will comprise silicone.

Example 28: Evaluation of Intravaginal Ring Contraceptive with HSV Antiviral Purpose:
The purpose of the study is to assess the safety of vaginal rings releasing contraceptives and valacyclovir.
Intervention:
Arm 1: Participants receive an intravaginal ring having valacyclovir, ethinyl estradiol and etonogestrel.
Arm 2: Participants receive an intravaginal ring having valacyclovir.
Arm 3: Participants receive an intravaginal ring having ethinyl estradiol and etonogestrel.
Arm 4: Participants receive an intravaginal ring having a placebo.
Description:
Participants are instructed to insert an assigned vaginal ring every 30 days for the duration of the study. The dosages of valacyclovir within each intravaginal ring are optionally varied in different arms of the intervention to range from 500 mg to 2,000 mg of each drug.
Primary Outcome Measures:
Safety as determined by the proportion of women in each arm experiencing protocol-specified events, including adverse events, laboratory abnormalities, cervico-vaginal abnormalities, and/or abnormal vaginal flora/pH during the study.
Etonogestrel and ethinyl estradiol concentrations of participants in arms 1 and 3 at given time points throughout the study.
Valacyclovir pharmacokinetics of participants in arms 1 and 2.
Secondary Outcome Measures:
Adherence to the protocol-specific product regimen as determined by self-report and clinician observation at each study visit.
Inclusion Criteria:
Women between 18 and 45 years of age who can provide informed consent.
HSV and HIV negative.
Willing to refrain from use of vaginal products or objects for duration of the study.
Willing to refrain from coitus for duration of the study.
Exclusion Criteria:
Currently pregnant or last pregnancy within 3 months prior to enrollment.
Currently breast-feeding.
Treatment with an antiviral within the past 12 months.
Treatment with hormonal birth control within the past 3 months.
Presence of any abnormal physical finding on the vulva, vaginal walls or cervix during pelvic examination.

Example 29: Safety and Effectiveness of Intravaginal Ring Contraceptive with HSV Antiviral for the Prevention of HSV Infection in Seronegative Women in Discordant Relationships Purpose:
The purpose of the study is to assess the safety and effectiveness of a contraceptive intravaginal ring releasing a low-dose of valacyclovir in preventing pregnancy and/or HSV-2 infection in HSV seronegative women in a monogamous sexual relationship with an HSV seropositive partner.
Intervention:
Arm 1: Seronegative women participants are intravaginally fitted with an intravaginal ring having valacyclovir and ethinyl estradiol and etonogestrel; Women use their assigned ring type for the entirety of the study. HSV seropositive partners take 500 mg of valacyclovir once daily.
Arm 2: Seronegative women participants are intravaginally fitted with an intravaginal ring having ethinyl estradiol and etonogestrel and a placebo. Women use their assigned ring type for the entirety of the study.
Description:
Seronegative participants are instructed to insert a first assigned intravaginal ring intravaginally at least seven days prior to an initial sexual incident. Seronegative participants will replace the first intravaginal ring with a second assigned intravaginal ring for a prescribed dosing cycle, 30 days Alternatively, participants are fitted with the first intravaginal ring by a medical practitioner during enrollment.

In the first arm, HSV seropositive partners are administered 500 mg of valacyclovir once a day for the duration of the study. In the second arm, there is only placebo treatment for HSV.

Participants attend study visits during the course of enrollment. Study visits include behavioral assessments, adherence assessments, physical examinations, blood collection, urine collection, and pelvic specimen collection. Participants receive initial and ongoing sexually transmitted disease risk-reduction counseling, male condoms, diagnosis and treatment of sexually transmitted infections, pregnancy testing and family planning services, and treatment or referrals for medical conditions. Initially seronegative women who test positive for HSV immediately stop using the ring and are referred to local health facilities for care and treatment, with an option to enroll in a follow-up study to assess the ring's impact, if any, on HSV treatment outcomes.

Eligibility and Inclusion Criteria:

HSV and HIV seronegative female subjects who were female at birth that are 18 years to 45 years of age and are in a monogamous sexual relationship with an HSV seropositive partner.

HSV seropositive partner does not have a history of frequent symptomatic episodes (>9 episodes/year) and is not HIV seropositive.

Exclusion Criteria:

Patients with a psychiatric disorder that might cause difficulty in obtaining informed consent or in conducting the trial.

Pregnant or nursing.

History of adverse reactions to any of the components of the intravaginal ring.

Pre-exposure prophylaxis for HSV or HIV prevention within the 6 months prior to enrollment.

Post-exposure prophylaxis for HSV or HIV prevention within the 6 months prior to enrollment.

Treatment with antivirals within the 6 months prior to enrollment.

Primary Outcome Measures:

Incidence of pregnancy.

Incidence of genital herpes caused by HSV infection. Genital herpes disease is defined as signs (swelling, papules, vesicles, ulcers, crusts, fissures, erythema, or vaginal discharge) and/or symptoms (pain, burning, itching, tingling, dysuria) which developed on the skin or mucosa of the anogenital region and/or buttocks and laboratory confirmation of HSV-1 or 2 infection (either concomitant positive HSV culture or HSV seroconversion within 6 months after onset of signs and/or symptoms. Seroconversion to HSV-1 and/or HSV-2 is defined as a positive HSV-1 and/or HSV-2 Western blot in a subject with a previously negative Western blot result for the corresponding HSV type.

Efficacy as determined by HSV seroconversion rate per person-months of product use, measured at the end of the investigational product use period.

Percentage of subjects infected with HSV who used the vaginal ring as directed. Use as directed is monitored by patient self-reporting and/or measurement of active drug(s) in their system during treatment.

Percentage of subjects infected with HSV who used the vaginal ring as directed and had partners who took the valacyclovir as directed.

Percentage of subjects infected with HSV who used the vaginal ring as directed and had partners who did not take the valacyclovir as directed.

Percentage of subjects infected with HSV who had detectable levels of drug(s) in their system during treatment.

Secondary Outcome Measures:

HSV incidence after removal of intravaginal ring.

Pharmacokinetics: assessment of concentration of active agents in plasma and vaginal fluids before, during and after trial period.

Adherence to the protocol-specific product regimen as determined by self-reported questionnaires.

Incidence of sexually transmitted disease.

Example 30: Safety and Effectiveness of Intravaginal Ring Contraceptive with HSV Antiviral for the Prevention of HSV Infection in Seronegative Women at Risk for Exposure to HSV Purpose:

The purpose of the study is to assess the safety and effectiveness of a contraceptive intravaginal ring releasing a low-doses of valacyclovir in preventing HSV-2 and/or pregnancy in HSV and HIV seronegative women at risk for sexual contact with a partner who is HSV seropositive or has unknown HSV sero-status during study duration. Sexual contact includes one or more incidents of sexual contact with one or more partners.

Intervention:

Seronegative women participants are intravaginally fitted with an intravaginal ring having valacyclovir and ethinyl estradiol and etonogestrel; or ethinyl estradiol and etonogestrel and a placebo. Women use their assigned ring type for the entirety of the study.

Description:

Seronegative participants are instructed to insert a first assigned intravaginal ring intravaginally at least seven days prior to coitus. Seronegative participants will replace the first intravaginal ring with a second assigned intravaginal ring for a prescribed dosing cycle. Alternatively, participants are fitted with the first intravaginal ring by a medical practitioner during enrollment.

Participants attend study visits during the course of enrollment. Study visits include behavioral assessments, adherence assessments, physical examinations, blood collection, urine collection, and pelvic specimen collection. Participants receive initial and ongoing sexually transmitted disease risk-reduction counseling, male condoms, diagnosis and treatment of sexually transmitted infections, pregnancy testing and family planning services, and treatment or referrals for medical conditions. Initially seronegative women who test positive for HSV or HIV are referred to local health facilities for care and treatment, with an option to enroll in a follow-up study to assess treatment impact, if any, on HSV or HIV outcomes.

Eligibility and Inclusion Criteria:

HSV and HIV seronegative female subjects who were female at birth that are 18 years to 45 years of age and expect to have at least one incident of sexual contact with a partner with HSV seropositive status, or unknown HSV sero-status.

Exclusion Criteria:

Patients with a psychiatric disorder that might cause difficulty in obtaining informed consent or in conducting the trial.

Pregnant or nursing.

History of adverse reactions to any of the components of the intravaginal ring.

Pre-exposure prophylaxis for HSV or HIV prevention within the 6 months prior to enrollment.

Post-exposure prophylaxis for HSV or HIV prevention within the 6 months prior to enrollment.

Treatment with antivirals within the 6 months prior to enrollment.

Treatment with hormonal contraceptives within the 6 months prior to enrollment.

Primary Outcome Measures:

Incidence of pregnancy.

Incidence of genital herpes caused by HSV infection. Genital herpes disease is defined as signs (swelling, papules, vesicles, ulcers, crusts, fissures, erythema, or vaginal discharge) and/or symptoms (pain, burning, itching, tingling, dysuria) which developed on the skin or mucosa of the anogenital region and/or buttocks and laboratory confirmation of HSV-1 or 2 infection (either concomitant positive HSV culture or HSV seroconversion within 6 months after onset of signs and/or symptoms. Seroconversion to HSV-1 and/or HSV-2 is defined as a positive HSV-1 and/or HSV-2 Western blot in a subject with a previously negative Western blot result for the corresponding HSV type.

Efficacy as determined by HSV seroconversion rate per person-months of product use, measured at the end of the investigational product use period.

Percentage of subjects infected with HSV who used the vaginal ring as directed. Use as directed is monitored by patient self-reporting and/or measurement of drug(s) in their system during treatment.

Percentage of subjects infected with HSV who had detectable levels of drug(s) in their system during treatment.

Secondary Outcome Measures:

Safety as determined by adverse events.

HSV incidence after removal of intravaginal ring.

Pharmacokinetics: assessment of concentration of active agents in plasma and vaginal fluids before, during and after trial period.

Adherence to the protocol-specific product regimen as determined by self-reported questionnaires.

Incidence of sexually transmitted disease.

Example 31: Contraceptive and HSV Treatment Kit

An HSV prophylaxis kit for contraception and treatment of HSV. The kit has an oral formulation comprising a low dosage of valacyclovir (500 mg), ethinyl estradiol and norgestimate, and instructions having information on how to administer the composition. The instructions include dosing information useful for administration of the composition to an HSV seronegative subject to prevent both pregnancy and HSV infection prior to HSV exposure. The HSV prophylaxis kit optionally includes dosing information and instructions for administration of the composition to an HSV seropositive subject to suppress HSV activation and viral shedding while preventing pregnancy. The packing of the kit is optionally designed to market to HSV seronegative and HSV seropositive subjects, as well as women in need of a contraceptive.

Example 32: Contraceptive and HSV Treatment Kit Comprising an Antiviral Transdermal Patch An HSV prophylaxis kit for contraception and treatment of HSV using a transdermal patch. The kit has a composition comprising valacyclovir within a contraceptive transdermal patch and instructions having information on how to affix the transdermal patch onto the skin of the subject. The instructions include dosing information useful for application of the patch to an HSV seronegative subject to prevent HSV infection prior to HSV exposure. The HSV prophylaxis kit optionally includes dosing information and instructions for application of the patch to an HSV seropositive subject to suppress HSV activation and viral shedding. The packing of the kit is optionally designed to market to HSV seronegative and HSV seropositive subjects, as well as women in need of a contraceptive.

Example 33: Contraceptive and HSV Treatment Kit Comprising an Antiviral Intravaginal Ring An HSV prophylaxis kit for contraception and treatment of HSV using an intravaginal ring. The kit has a composition comprising valacyclovir, ethinyl estradiol and etonogestrel within an intravaginal ring and instructions having information on how to insert the intravaginal ring into the vagina of a subject. The instructions include dosing and application information useful for the prevention of HSV infection in a seronegative subject. The HSV prophylaxis kit optionally includes instructions on how to suppress HSV activation and viral shedding in an HSV seropositive subject using the intravaginal ring. The packing of the kit is optionally designed to market to HSV seronegative and HSV seropositive subjects, as well as women in need of a contraceptive.

Example 34: Contraceptive and Antiviral Treatment Kit

An antiviral prophylaxis kit for contraception and treatment of viral disease. The kit has an oral formulation comprising a combination of antiviral agents (valacyclovir 2 g total taken twice per day, 300 mg tenofovir, 200 mg emtricitabine, and 400 mg raltegravir taken twice daily, levonorgestrel 75 mg per day over 2 days, and instructions having information on how to administer the composition. The instructions include dosing information useful for administration of the composition to an HSV and HIV seronegative subject to prevent both pregnancy and viral infection prior to viral exposure, for example, HSV and/or HIV exposure.

Example 35: Contraceptive and Antiviral Treatment Kit Comprising an Antiviral Transdermal Patch An antiviral prophylaxis kit for contraception and treatment of viral disease using a transdermal patch. The kit has a composition comprising a combination of antiviral agents within a contraceptive transdermal patch comprising estrogen and progestin, and instructions having information on how to affix the transdermal patch onto the skin of the subject. The instructions include dosing information useful for application of the patch to an HSV and HIV seronegative subject to prevent viral infection prior to viral exposure, for example, exposure to HSV and/or HIV.

Example 36: Contraceptive and Antiviral Treatment Kit Comprising an Antiviral Intravaginal Ring An antiviral prophylaxis kit for contraception and treatment of viral disease using an intravaginal ring. The kit has a composition comprising a combination of antiviral agents, ethinyl estradiol and etonogestrel within an intravaginal ring, and instructions having information on how to insert the intravaginal ring into the vagina of a subject. The instructions include dosing and application information useful for the prevention of viral infection in an HSV and HIV seronegative subject.

What is claimed is:

1. A method of preventing herpes simplex virus (HSV) infection in a subject in need thereof, the method comprising orally administering to the subject a pharmaceutical composition comprising: a therapeutically effective amount of (a) valacyclovir or a salt or solvate thereof, and (b) famciclovir or a salt or solvate thereof; and pharmaceutically acceptable excipient(s), diluent(s), carrier(s) and/or adjuvant(s);
  wherein the subject is HSV seronegative, the preventing is pre-exposure prophylaxis against HSV infection, and whereby the risk of HSV infection in the subject is reduced.

2. The method of claim 1, wherein the pharmaceutical composition comprises 0.5 mg/kg body weight to about 100 mg/kg body weight of (a) and 0.5 mg/kg body weight to about 100 mg/kg body weight of (b).

3. The method of claim 1, wherein the pharmaceutical composition comprises about 1 mg to about 5000 mg of valacyclovir or a salt or solvate thereof and about 1 mg to about 5000 mg famciclovir or a salt or solvate thereof.

4. The method of claim 1, wherein the pharmaceutical composition comprises about 250 mg to about 1000 mg of valacyclovir or a salt or solvate thereof and about 250 mg to about 1000 mg famciclovir or a salt or solvate thereof.

5. The method of claim 1, wherein the pharmaceutical composition is formulated for oral administration.

6. The method of claim 1, wherein the pharmaceutical composition comprises an oral tablet, oral capsule, or oral solution.

7. The method of claim 1, comprising administration of the pharmaceutical composition once daily or twice daily.

8. The method of claim 1, wherein the pharmaceutical composition is formulated in sustained-release form.

9. The method of claim 1, comprising parenteral or intravenous administration of the pharmaceutical composition.

10. The method of claim 1, additionally comprising administering a therapeutically effective amount of an HIV antiviral agent.

11. The method of claim 1, wherein the subject is a female and the method additionally comprises administering a therapeutically effective amount of a contraceptive.

12. The method of claim 1, wherein the method additionally comprises administering a therapeutically effective amount of an additional antiviral agent.

13. The method of claim 12, wherein the additional antiviral agent comprises a helicase-primase inhibitor, tenofovir, emtricitabine, lamivudine, interfereon, ribavirin, boceprevir, telaprevir, simeprevir, sofosbuvir, ledipasvir, ombitasvir, paritaprevir, pritelivir, brincidofovir, cidofovir, ganciclovir, valganciclovir, or ritonavir.

14. The method of claim 1, wherein (a) comprises valacyclovir and (b) comprises famciclovir.

15. The method of claim 1, wherein the administering begins after physical contact with a partner who is seropositive for HSV.

16. The method of claim 1, wherein the administering begins prior to physical contact with an HSV seropositive partner.

17. The method of claim 16, further comprising administering the composition to the HSV seropositive partner.

18. The method of claim 1, wherein the HSV is HSV-1, HSV-2, varicella-zoster (chicken pox, shingles, human herpes virus 3), Epstein-Barr virus (human herpes virus 4), cytomegalovirus (human herpes virus 5), roseolovirus (human herpes virus 6 and 7), or Karposi's sarcoma-associated herpes virus (human herpes virus 8).

19. The method of claim 1, wherein the pharmaceutical composition comprises about 750 mg valacyclovir or a salt or solvate thereof and about 200 mg famciclovir or a salt or solvate thereof.

20. The method of claim 1, wherein the pharmaceutical composition comprises about 250 mg to about 1500 mg valacyclovir or a salt or solvate thereof and about 60 mg to about 400 mg famciclovir.

21. The method of claim 19, wherein the pharmaceutical composition is formulated for oral administration.

22. The method of claim 19, wherein the pharmaceutical composition comprises an oral tablet.

23. The method of claim 22, wherein the oral tablet is formulated for immediate-release of the valacyclovir and the famciclovir.

24. The method of claim 20, wherein the pharmaceutical composition is formulated for oral administration.

25. The method of claim 20, wherein the pharmaceutical composition comprises an oral tablet.

26. The method of claim 25, wherein the oral tablet is formulated for immediate-release of the valacyclovir and the famciclovir.

27. The method of claim 11, wherein the contraceptive comprises levonorgestrel, estradiol, dosogestrel, ethinyl, estradiol, norethindrone acetate, norgestimate, or salts, solvates or combinations thereof.

28. The method of claim 27, wherein the contraceptive agent comprises levonorgestrel and estradiol.

29. The method of claim 28, wherein the HSV seronegative subject is administered about 0.10 mg of levonorgestrel and about 0.02 mg of estradiol.

30. The method of claim 11, wherein the contraceptive agent comprises dosogestrel and ethinyl estradiol.

31. The method of claim 30, wherein the HSV seronegative subject is administered about 0.15 mg of dosogestrel and about 0.03 mg of ethinyl estradiol.

32. The method of claim 11, wherein the contraceptive agent comprises norethindrone acetate and ethinyl estradiol.

33. The method of claim 32, wherein the HSV seronegative subject is administered about 1 mg of norethindrone acetate and about 20 µg of ethinyl estradiol.

34. The method of claim 11, wherein the contraceptive agent comprises norgestimate and ethinyl estradiol.

35. The method of claim 34, wherein the HSV seronegative subject is administered about 0.18 mg or about 0.25 mg of norgestimate and about 35 µg or 25 µg of ethinyl estradiol.

36. The method of claim 12, wherein the additional antiviral agent is lamivudine.

37. The method of claim 36, wherein the subject is administered about 50 mg to about 400 mg of lamivudine.

38. The method of claim 16, wherein the physical contact occurs during one sexual incident.

39. The method of claim 16, wherein the physical contact occurs during two or more sexual incidents.

40. The method of claim 16, wherein the pharmaceutical composition is not administered to an HSV seropositive partner.

41. The method of claim 1, wherein the HSV is HSV-1.

42. The method of claim 1, wherein the HSV is HSV-2.

* * * * *